United States Patent
Mallams

(10) Patent No.: US 7,635,697 B2
(45) Date of Patent: Dec. 22, 2009

(54) FARNESYL PROTEIN TRANSFERASE INHIBITORS AND METHODS FOR TREATING PROLIFERATIVE DISEASES

(75) Inventor: Alan K. Mallams, Hackettstown, NJ (US)

(73) Assignee: Schering Corporation, Kenilworth, NJ (US)

( * ) Notice: Subject to any disclaimer, the term of this patent is extended or adjusted under 35 U.S.C. 154(b) by 234 days.

(21) Appl. No.: 11/301,798

(22) Filed: Dec. 13, 2005

(65) Prior Publication Data

US 2006/0211706 A1    Sep. 21, 2006

Related U.S. Application Data

(60) Provisional application No. 60/636,451, filed on Dec. 14, 2004.

(51) Int. Cl.
 *A61K 31/497* (2006.01)
 *C07D 241/04* (2006.01)
 *C07D 295/00* (2006.01)

(52) U.S. Cl. .................. 514/252.12; 544/358

(58) Field of Classification Search ........................ None
 See application file for complete search history.

(56) References Cited

U.S. PATENT DOCUMENTS

| 5,801,175 | A | 9/1998 | Afonso et al. |
| 6,214,827 | B1 | 4/2001 | Afonso et al. |
| 2006/0154937 | A1 | 7/2006 | Rane |
| 2007/0213340 | A1 | 9/2007 | Kelly et al. |

FOREIGN PATENT DOCUMENTS

| WO | WO 98/57960 | 12/1998 |
| WO | WO 00/37458 | 6/2000 |
| WO | WO 00/37459 | 6/2000 |
| WO | WO 02/056884 A2 | 7/2002 |
| WO | WO 02/080895 A2 | 10/2002 |
| WO | WO 03/072549 A1 | 9/2003 |

OTHER PUBLICATIONS

Saba et al. Expert Opinion in Investigational Drugs, 2004, 13(6), 609-29.*
Banerji et al. Expert Opinion in Therapeutic Targets, 2004, 8(3), 221-39.*
PCT International Search Report dated Apr. 4, 2006 for counterpart PCT Application No. PCT/US2005/045019.
Schering-Plough Discontinues Phase III Clinical Study of Sarasar(TM) (Lonafarnib) in Non-Small-Cell Lung Cancer, Schering-Plough Press Release, Feb. 5, 2004.

* cited by examiner

*Primary Examiner*—James O Wilson
*Assistant Examiner*—Noble Jarrell
(74) *Attorney, Agent, or Firm*—Henry C. Jeanette

(57) ABSTRACT

Disclosed are compounds of the Formula:

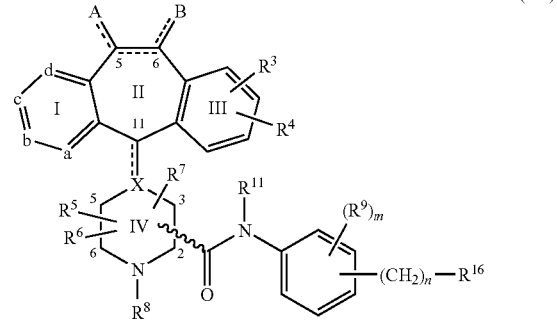

wherein the substituents are as defined herein. Also disclosed are uses of the compounds of formula 1.0 for the manufacture of a medicament for treating cancer and for inhibiting farnesyl protein transferase.

63 Claims, No Drawings

FARNESYL PROTEIN TRANSFERASE INHIBITORS AND METHODS FOR TREATING PROLIFERATIVE DISEASES

REFERENCE TO RELATED APPLICATION

This application claims the benefit of U.S. Provisional Application Ser. No. 60/636,451 filed Dec. 14, 2004.

BACKGROUND

WO 95/10516, published Apr. 20, 1995, WO96/31478, published Oct. 10, 1996, WO 98/57960 published Dec. 23, 1998, U.S. Pat. No. 6,362,188 issued Mar. 26, 2002, U.S. Pat. No. 6,372,747 issued Apr. 16, 2002, and U.S. Pat. No. 6,740,661 issued May 25, 2004, disclose tricyclic compounds useful for inhibiting farnesyl protein transferase.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

In its many embodiments, the invention provides a novel class of farnesyl protein transferase (FPT) inhibitors, methods of preparing such compounds, pharmaceutical compositions comprising one or more such compounds, methods of preparing pharmaceutical formulations comprising one or more such compounds and methods of treatment, prevention, inhibition or amelioration of one or more proliferative diseases such as cancer.

Thus, this invention provides compounds of formula 1.0:

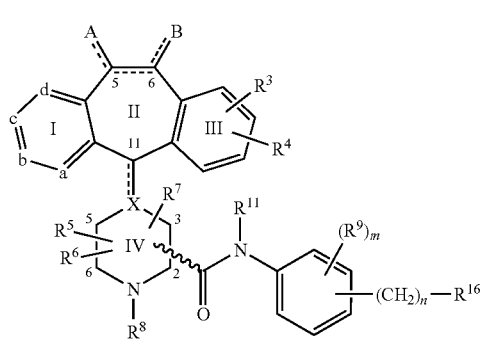

(1.0)

and the pharmaceutically acceptable salts thereof, wherein the substituents are as defined below.

This invention also provides the final compounds of Examples 1 to 47.

This invention also provides compounds selected from the group consisting of: (1.3), (1.4), (2.1), (3.1), (4.1), (4.2), (4.3), (4.4), (5.1), (6.1), (7.1), (8.1), (9.1), (10.1), (11.2), (11.3), (12.1), (12.2), (13.2), (13.3), (14.1), (14.2), (14.3), (15.1), (15.2), (16.1), (17.1), (18.1), (19.1), (20.1), (20.2), (20.3), (20.4), (21.1), (22.1), (24.1), (25.1), (26.1), (27.1), (28.1), (29.1), (30.1), (31.1), (31.2), (32.1), (32.2), (33.1), (33.2), (34.1), (34.2), (35.1), (36.1), (37.1), (38.1), (39.1), (40.1), (40.2), (41.1), (42.1), (43.1), (44.1), (45.1), (46.1), and (47.1).

This invention also provides compounds selected from the group consisting of: (1.3), (1.4), (4.2), (4.3), (5.1), (6.1), (12.1), (12.2), (13.2), (13.3), (14.2), (15.1), (15.2), (16.1), (21.1), (22.1), (26.1), (27.1), (28.1), (29.1), (30.1), (31.1), (31.2), (32.1), (32.2), (45.1) and (47.1).

This invention also provides compounds selected from the group consisting of: (1.3), (1.4), (5.1), (6.1), (15.1), (15.2), (21.1), (22.1), (26.1), (28.1), (29.1), (30.1), (31.1), and (32.1).

This invention also provides compounds selected from the group consisting of: (1.3), (1.4), (15.1), (15.2), (21.1), (22.1), (26.1), (28.1), (29.1), (30.1), (31.1), and (32.1).

This invention also provides compound (1.3).
This invention also provides compound (1.4).
This invention also provides compound (15.1).
This invention also provides compound (15.2).
This invention also provides compound (21.1).
This invention also provides compound (22.1).
This invention also provides compound (26.1).
This invention also provides compound (28.1).
This invention also provides compound (29.1).
This invention also provides compound (30.1).
This invention also provides compound (31.1).
This invention also provides compound (32.1).

This invention also provides a pharmaceutical composition comprising an effective amount of at least one (e.g., 1 or 2, and usually one) compound of formula 1.0 and a pharmaceutically acceptable carrier thereof.

This invention also provides a method of treating proliferative diseases in a patient in need of such treatment, said treatment comprising administering to said patient an effective amount of at least one (e.g., 1 or 2 and usually one) compound of formula 1.0.

This invention also provides a method of inhibiting farnesyl protein transferase in a patient in need of such treatment comprising administering to said patient an effective amount of at least one (e.g., 1 or 2, and usually one) compound of formula 1.0.

This invention also provides methods of treating (or inhibiting) tumors (i.e., cancers) in a patient in need of such treatment comprising administering to said patient an effective amount of at least one (e.g., 1 or 2, and usually one) compound of formula 1.0.

This invention also provides methods of treating (or inhibiting) tumors (i.e., cancers) in a patient in need of such treatment comprising administering to said patient an effective amount of at least one (e.g., 1 or 2, and usually one) compound of formula 1.0 in combination with at least one (e.g., 1 or 2) chemotherapeutic agent (also know in the art as antineoplastic agent or anticancer agent).

This invention also provides methods of treating (or inhibiting) tumors (i.e., cancers) in a patient in need of such treatment comprising administering to said patient an effective amount of at least one (e.g., 1 or 2, and usually one) compound of formula 1.0 in combination with at least one (e.g., 1 or 2, and usually one) chemotherapeutic agent (also know in the art as antineoplastic agent or anticancer agent) and/or radiation.

This invention also provides methods of treating (or inhibiting) tumors (i.e., cancers) in a patient in need of such treatment comprising administering to said patient an effective amount of at least one (e.g., 1 or 2, and usually one) compound of formula 1.0 in combination with at least one signal transduction inhibitor.

This invention provides methods of treating breast cancer (i.e., postmenopausal and premenopausal breast cancer, e.g., hormone.dependent breast cancer) in a patient in need of such treatment wherein said treatment comprises the administration of at least one (e.g., one) compound of formula 1.0 with hormonal therapies (i.e., antihormonal agents).

The methods of this invention include the treatment of hormone.dependent metastatic and advanced breast cancer, adjuvant therapy for hormone.dependent primary and early breast cancer, the treatment of ductal carcinoma in situ, and the treatment of inflammatory breast cancer in situ.

Optionally, neoadjuvant therapy (i.e., the use of chemotherapeutic agents) is used in combination with the compounds of formula 1.0 and hormonal therapies in the methods of this invention.

The methods of this invention can also be used to prevent breast cancer in patients having a high risk of developing breast cancer.

In the methods of this invention the compounds of formula 1.0 can be administered concurrently or sequentially (i.e., consecutively) with the chemotherapeutic agents or the signal transduction inhibitor.

Optionally, radiation treatment can be administered in the methods of this invention.

DETAILED DESCRIPTION OF THE INVENTION

As used herein, the following terms have the following meanings unless otherwise defined:
Bn represent benzyl;
Boc represents tert-butyloxycarbonyl;
Boc-ON represents 1-(tert-butoxycarbonyl)-2-tert-butyl-3-methyl-4-imidazolidinone nitrile;
Bu represents butyl;
$CDCl_3$ represents deuterochloroform;
$CH_2Cl_2$ represents dichloromethane;
CIMS represents chemical ionization mass spectrum;
CSA represents camphor sulfonyl;
DEC represents EDC which represents 1-(3-dimethyl-aminopropyl)-3-ethylcarbodiimide hydrochloride;
DMF represents N,N-dimethylformamide;
FABMS represents fast atom bombardment mass spectra;
HRFABMS represents high resolution fast atom bombardment mass spectrum;
HOBT represents 1-hydroxybenzotriazole hydrate;
LAH represents lithium aluminum hydride;
LDA represents lithium diisopropylamide;
Me represents methyl;
MeOH represents methanol;
$MH^+$ represents the molecular ion plus hydrogen of the molecule in the mass spectrum;
MS (with reference to physical data) represents mass spectroscopy;
Ms (with reference to chemical compounds) represents methanesulfonyl NMM represents N-methylmorpholine;
Ph represents phenyl;
3-PhPr represents a 3-phenylpropyl group;
SA represents soft agar;
TBDMS represents tert-butyidimethylsilyl;
t-Bu represents tertiary-butyl;
TEA represents triethylamine;
THF represents tetrahydrofuran;
Tr represents trityl;
Ts represents a toluenesulfonyl group;
i.m. means intramuscularly;
mpk means milligrams per kilogram (of body weight);
p.o. means by mouth, i.e., orally;
s.c. means subcutaneoulsy;
"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as defined below (and as defined below, the alkyl, alkenyl, alkynyl, cycloalkyl, cycloalkenyl and cycloalkynyl moieties can be substituted); The bond to the parent moiety is through the carbonyl; Preferred acyls contain a lower alkyl; Non-limiting examples of suitable acyl groups include formyl, acetyl, propanoyl, 2-methylpropanoyl, butanoyl and cyclohexanoyl;

"Acylamino" means an acyl-amino- (i.e., acyl-NH—) wherein acyl is as defined above;

"Alkenyl" means an aliphatic hydrocarbon group (chain) comprising at least one carbon to carbon double bond, wherein the chain can be straight or branched, and wherein said group comprises about 2 to about 15 carbon atoms; Preferred alkenyl groups comprise about 2 to about 12 carbon atoms in the chain; and more preferably about 2 to about 6 carbon atoms in the chain; Branched means that one or more lower alkyl groups, such as methyl, ethyl or propyl, are attached to a linear alkenyl chain; "Lower alkenyl" means an alkenyl group comprising about 2 to about 6 carbon atoms in the chain, and the chain can be straight or branched; The term "substituted alkenyl" means that the alkenyl group is substituted by one or more independently selected substituents, and each substituent is independently selected from the group consisting of: halo, alkyl, aryl, cycloalkyl, cyano, alkoxy and —S(alkyl); Non-limiting examples of suitable alkenyl groups include ethenyl, propenyl, n-butenyl, 3-methylbut-2-enyl, n-pentenyl, octenyl and decenyl;

"Alkoxy" means an alkyl-O— group (i.e., the bond to the parent moiety is through the ether oxygen) in which the alkyl group is unsubstituted or substituted as described above; Non-limiting examples of suitable alkoxy groups include methoxy, ethoxy, n-propoxy, isopropoxy, n-butoxy and heptoxy;

"Alkoxycarbonyl" means an alkyl-O—CO— group (i.e., the bond to the parent moiety is through the carbonyl) wherein the alkyl group is unsubstituted or substituted as previously defined; Non-limiting examples of suitable alkoxycarbonyl groups include methoxycarbonyl and ethoxycarbonyl;

"Alkyl" (including the alkyl portions of other moieties, such as trifluoroalkyl and alkyloxy) means an aliphatic hydrocarbon group (chain) that can be straight or branched wherein said group comprises about 1 to about 20 carbon atoms in the chain; Preferred alkyl groups comprise about 1 to about 12 carbon atoms in the chain; More preferred alkyl groups comprise about 1 to about 6 carbon atoms in the chain; Branched means that one or more lower alkyl groups, such as methyl, ethyl or propyl, are attached to a linear alkyl chain; "Lower alkyl" means a group comprising about 1 to about 6 carbon atoms in the chain, and said chain can be straight or branched; The term "substituted alkyl or substituted lower alkyl" means that the alkyl group is substituted by one or more independently selected substituents, and wherein each substituent is independently selected from the group consisting of: halo, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl); Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl;

"Alkylaryl" means an alkyl-aryl-group (i.e., the bond to the parent moiety is through the aryl group) wherein the alkyl group is unsubstituted or substituted as defined above, and the aryl group is unsubstituted or substituted as defined below; Preferred alkylaryls comprise a lower alkyl group; Non-limiting examples of suitable alkylaryl groups include o-tolyl, p-tolyl and xylyl;

"Alkylheteroaryl" means an alkyl-heteroaryl-group (i.e., the bond to the parent moiety is through the heteroaryl group) wherein the alkyl is unsubstituted or substituted as defined above and the heteroaryl group is unsubstituted or substituted as defined below;

"Alkylsulfinyl" means an alkyl-S(O)— group (i.e., the bond to the parent moiety is through the sulfinyl) wherein the alkyl group is unsubstituted or substituted as previously defined; Preferred groups are those in which the alkyl group is lower alkyl;

"Alkylsulfonyl" means an alkyl-S($O_2$)— group (i.e., the bond to the parent moiety is through the sulfonyl) wherein the alkyl group is unsubstituted or substituted as previously defined; Preferred groups are those in which the alkyl group is lower alkyl;

"Alkylthio" means an alkyl-S— group (i.e., the bond to the parent moiety is through the sulfur) wherein the alkyl group is unsubstituted or substituted as previously described; Non-limiting examples of suitable alkylthio groups include methylthio, ethylthio, i-propylthio and heptylthio;

"Alkynyl" means an aliphatic hydrocarbon group (chain) comprising at least one carbon to carbon triple bond, wherein the chain can be straight or branched, and wherein the group comprises about 2 to about 15 carbon atoms in the; Preferred alkynyl groups comprise about 2 to about 12 carbon atoms in the chain; and more preferably about 2 to about 4 carbon atoms in the chain; Branched means that one or more lower alkyl groups, such as methyl, ethyl or propyl, are attached to a linear alkynyl chain; "Lower alkynyl" means an alkynyl group comprising about 2 to about 6 carbon atoms in the chain, and the chain can be straight or branched; Non-limiting examples of suitable alkynyl groups include ethynyl, propynyl, 2-butynyl, 3-methylbutynyl, n-pentynyl, and decynyl; The term "substituted alkynyl" means that the alkynyl group is substituted by one or more independently selected, and each substituent is independently selected from the group consisting of alkyl; aryl and cycloalkyl;

"Amino" means a —$NH_2$ group;

"Aralkenyl" means an aryl-alkenyl-group (i.e., the bond to the parent moiety is through the alkenyl group) wherein the aryl group is unsubstituted or substituted as defined below, and the alkenyl group is unsubstituted or substituted as defined previously; Preferred aralkenyls contain a lower alkenyl group; Non-limiting examples of suitable aralkenyl groups include 2-phenethenyl and 2-naphthylethenyl;

"Aralkyl" or "arylalkyl" means an aryl-alkyl-group (i.e., the bond to the parent moiety is through the alkyl group) wherein the aryl is unsubstituted or substituted as defined below and the alkyl is unsubstituted or substituted as defined above; Preferred aralkyls comprise a lower alkyl group; Non-limiting examples of suitable aralkyl groups include benzyl, 2-phenethyl and naphthalenylmethyl;

"Aralkyloxy" means an aralkyl-O— group (i.e., the bond to the parent moiety is through the ether oxygen) wherein the aralkyl group is unsubstituted or substituted as previously described; Non-limiting examples of suitable aralkyloxy groups include benzyloxy and 1- or 2-naphthalenemethoxy;

"Aralkoxycarbonyl" means an aralkyl-O—C(O)— group (i.e., the bond to the parent moiety is through the carbonyl) wherein the aralkyl group is unsubstituted or substituted as previously defined; A non-limiting example of a suitable aralkoxycarbonyl group is benzyloxycarbonyl;

"Aralkylthio" means an aralkyl-S— group (i.e., the bond to the parent moiety is through the sulfur) wherein the aralkyl group is unsubstituted or substituted as previously described; A non-limiting example of a suitable aralkylthio group is benzylthio;

"Aroyl" means an aryl-C(O)— group (i.e., the bond to the parent moiety is through the carbonyl) wherein the aryl group is unsubstituted or substituted as defined below; Non-limiting examples of suitable groups include benzoyl and 1- and 2-naphthoyl;

"Aryl" (sometimes abbreviated "ar") means an aromatic monocyclic or multicyclic ring system comprising about 6 to about 14 carbon atoms, preferably about 6 to about 10 carbon atoms; The aryl group can be optionally substituted with one or more independently selected "ring system substituents" (defined below); Non-limiting examples of suitable aryl groups include phenyl and naphthyl;

"Aryloxy" means an aryl-O— group (i.e., the bond to the parent moiety is through the ether oxygen) wherein the aryl group is unsubstituted or substituted as defined above; Non-limiting examples of suitable aryloxy groups include phenoxy and naphthoxy;

"Aryloxycarbonyl" means an aryl-O—C(O)— group (i.e., the bond to the parent moiety is through the carbonyl) wherein the aryl group is unsubstituted or substituted as previously defined; Non-limiting examples of suitable aryloxycarbonyl groups include phenoxycarbonyl and naphthoxycarbonyl;

"Arylsulfinyl" means an aryl-S(O)— group (i.e., the bond to the parent moiety is through the sulfinyl) wherein aryl is unsubstituted or substituted as previously defined;

"Arylsulfonyl" means an aryl-S($O_2$)— group (i.e., the bond to the parent moiety is through the sulfonyl) wherein aryl is unsubstituted or substituted as previously defined;

"Arylthio" means an aryl-S— group (i.e., the bond to the parent moiety is through the sulfur) wherein the aryl group is unsubstituted or substituted as previously described; Non-limiting examples of suitable arylthio groups include phenylthio and naphthylthio;

"Cycloalkenyl" means a non-aromatic mono- or multicyclic ring system comprising about 3 to about 10 carbon atoms, preferably about 5 to about 10 carbon atoms that contains at least one carbon-carbon double bond; Preferred cycloalkenyl rings contain about 5 to about 7 ring atoms; The cycloalkenyl can be optionally substituted with one or more independently selected "ring system substituents" (defined below); Non-limiting examples of suitable monocyclic cycloalkenyls include cyclopentenyl, cyclohexenyl, cycloheptenyl, and the like; A non-limiting example of a suitable multicyclic cycloalkenyl is norbornylenyl;

"Cycloalkyl" means a non-aromatic mono- or multicyclic ring system comprising about 3 to about 10 carbon atoms, preferably about 5 to about 10 carbon atoms; Preferred cycloalkyl rings contain about 5 to about 7 ring atoms; The cycloalkyl can be optionally substituted with one or more independently selected "ring system substituents" (defined below); Non-limiting examples of suitable monocyclic cycloalkyls include cyclopropyl, cyclopentyl, cyclohexyl, cycloheptyl and the like; Non-limiting examples of suitable multicyclic cycloalkyls include 1-decalin, norbornyl, adamantyl and the like;

"Halo" means fluoro, chloro, bromo, or iodo groups; Preferred halos are fluoro, chloro or bromo, and more preferred are bromo and chloro;

"Halogen" means fluorine, chlorine, bromine, or iodine; Preferred halogens are fluorine, chlorine and bromine;

"Haloalkyl" means an alkyl, as defined above, wherein one or more hydrogen atoms on the alkyl is replaced by a halo group, as defined above;

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; Preferred heteroaryls comprise about 5 to about 6 ring atoms; The "heteroaryl" can be optionally substituted by one or more independently selected "ring system substituents" (defined below); The prefix aza, oxa or thia before the heteroaryl root name means that at least a nitrogen, oxygen or sulfur atom, respectively, is present as a ring atom; A nitrogen atom of a heteroaryl can be optionally oxidized to the corresponding N-oxide; Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like;

"Heteroaralkyl" means a heteroaryl-alkyl-group (i.e., the bond to the parent moiety is through the alkyl group) in which the heteroaryl is unsubstituted or substituted as defined above, and the alkyl group is unsubstituted or substituted as defined above; Preferred heteroaralkyls comprise an alkyl group that is a lower alkyl group; Non-limiting examples of suitable aralkyl groups include pyridylmethyl, 2-(furan-3-yl)ethyl and quinolin-3-ylmethyl;

"Heteroaralkylthio" means a heteroaralkyl-S— group wherein the heteroaralkyl group is unsubstituted or substituted as defined above;

"Heteroarylsulfinyl" means a heteroaryl-SO— group wherein the heteroaryl group is unsubstituted or substituted as defined above;

"Heteroarylsulfonyl" means a heteroaryl-SO$_2$— group wherein the heteroaryl group is unsubstituted or substituted as defined above;

"Heteroarylthio" means a heteroaryl-S— group wherein the heteroaryl group is unsubstituted or substituted as defined above;

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; There are no adjacent oxygen and/or sulfur atoms present in the ring system; Preferred heterocyclenyl rings contain about 5 to about 6 ring atoms; The prefix aza, oxa or thia before the heterocyclenyl root name means that at least a nitrogen, oxygen or sulfur atom, respectively, is present as a ring atom; The heterocyclenyl can be optionally substituted by one or more independently selected "Ring system substituents" (defined below); The nitrogen or sulfur atom of the heterocyclenyl can be optionally oxidized to the corresponding N-oxide, S-oxide or S,S-dioxide; Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like; Non-limiting examples of suitable oxaheterocyclenyl groups include 3,4-dihydro-2H-pyran, dihydrofuranyl, fluorodihydrofuranyl, and the like; A non-limiting example of a suitable multicyclic oxaheterocyclenyl group is 7-oxabicyclo[2.2.1]heptenyl; Non-limiting examples of suitable monocyclic thiaheterocyclenyl rings include dihydrothiophenyl, dihydrothiopyranyl, and the like;

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; There are no adjacent oxygen and/or sulfur atoms present in the ring system; Preferred heterocyclyls contain about 5 to about 6 ring atoms; The prefix aza, oxa or thia before the heterocyclyl root name means that at least a nitrogen, oxygen or sulfur atom respectively is present as a ring atom; The heterocyclyl can be optionally substituted by one or more independently selected "ring system substituents" (defined below); The nitrogen or sulfur atom of the heterocyclyl can be optionally oxidized to the corresponding N-oxide, S-oxide or S,S-dioxide; Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like;

"Hydroxyalkyl" means a HO-alkyl-group wherein the alkyl group is substituted or unsubstituted as defined above; Preferred hydroxyalkyls comprise a lower alkyl; Non-limiting examples of suitable hydroxyalkyl groups include hydroxymethyl and 2-hydroxyethyl;

"Ring system substituent" means a substituent attached to an aromatic or non-aromatic ring system that, for example, replaces an available hydrogen on the ring system; Ring system substituents are each independently selected from the group consisting of: alkyl, alkenyl, alkynyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, Y$_1$Y$_2$N—, Y$_1$Y$_2$N-alkyl-, Y$_1$Y$_2$NC(O)— and Y$_1$Y$_2$NSO$_2$—, wherein Y$_1$ and Y$_2$ are each independently selected from the group consisting of: hydrogen, alkyl, aryl, and aralkyl; "Ring system substituent" also means a cyclic ring of 3 to 7 ring atoms, wherein 1-2 ring atoms can be heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring; Non-limiting examples include:

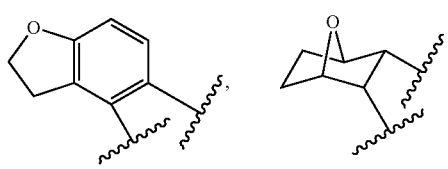

and the like;

"Anti-cancer agent", "chemotherapeutic agent", and "antineoplastic agent" have the same meaning, and these terms represent the drugs (medicaments) used to treat cancer;

"Antineoplastic agent" represents a chemotherapeutic agent effective against cancer;

"At least one" includes, for example, 1, 2 or 3, or 1 or 2, or 1;

"Compound", with reference to the antineoplastic agents, includes the agents that are antibodies;

"Concurrently" represents (1) simultaneously in time (e.g., at the same time); or (2) at different times during the course of a common treatment schedule;

"Consecutively" means one following the other;

"Different", as used in the phrase "different antineoplastic agents", means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound;

"Effective amount" or "therapeutically effective amount" is meant to describe an amount of compound or a composition of the present invention effective in inhibiting or treating the cancer, or effective in inhibiting farnesyl protein transferase; For example, the amount of the compound or composition that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor; Also, for example, a therapeutically effective amount of the FPT inhibitor is that amount which results in the reduction of farnesylation; the reduction in farnesylation may be determined by the analysis of pharmacodynamic markers such as Prelamin A and HDJ-2 (DNAJ-2) using techniques well known in the art;

"One or more" includes, for example, 1, 2 or 3, or 1 or 2, or 1;

"Patient" represents an animal, such as a mammal (e.g., a human being, and preferably a human being);

"Prodrug" represents compounds that are rapidly transformed, for example, by hydrolysis in blood, in vivo to the parent compound, i.e., to the compounds of formula 1.0 or to a salt and/or to a solvate thereof; A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; The scope of this invention includes prodrugs of the novel compounds of this invention;

Sequentially means (1) administration of one component of the method ((a) compound of the invention, or (b) chemotherapeutic agent, signal transduction inhibitor and/or radiation therapy) followed by administration of the other component or components; after administration of one component, the next component can be administered substantially immediately after the first component, or the next component can be administered after an effective time period after the first component; the effective time period is the amount of time given for realization of maximum benefit from the administration of the first component; and "Solvate" means a physical association of a compound of this invention with one or more solvent molecules; This physical association involves varying degrees of ionic and covalent bonding, including hydrogen bonding; In certain instances the solvate will be capable of isolation, for example when one or more solvent molecules are incorporated in the crystal lattice of the crystalline solid; "Solvate" encompasses both solution-phase and isolatable solvates; Non-limiting examples of suitable solvates include ethanolates, methanolates, and the like; "Hydrate" is a solvate wherein the solvent molecule is $H_2O$.

The positions in the tricyclic ring system are:

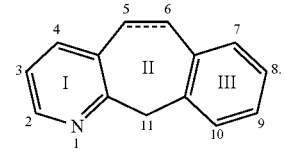

Lines drawn into a ring mean that the indicated bond may be attached to any of the substitutable ring carbon atoms (see, for example, Rings III and IV in formula 1.0).

Thus, this invention provides compounds of formula 1.0:

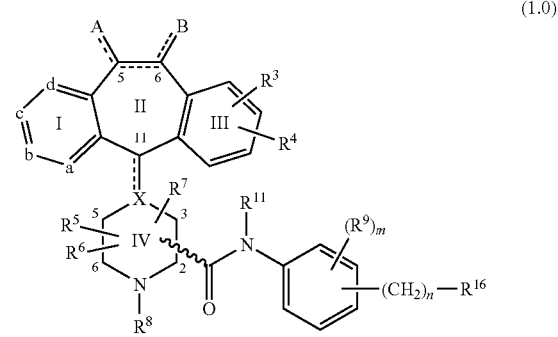

(1.0)

and the pharmaceutically acceptable salts thereof, wherein:
the moiety

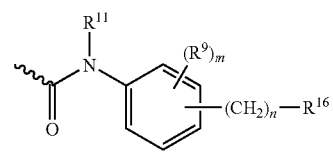

is bound to the 2- or 3-position of Ring IV (wherein the $R^5$, $R^6$, and/or $R^7$ substituents are bound to the remaining 2-, 3-, 5-, and 6-positions of Ring IV);

each a, b, c and d is a $CR^1$ moiety wherein each $R^1$ for each $CR^1$ moiety is independently selected; or one of a, b, c and d represents N or $N^+O^-$, and the remaining groups are $CR^1$ moieties wherein each $R^1$ for each $CR^1$ moiety is independently selected (i.e., one of a, b, c or d represents N, or one of a, b, c, or d represents $N^+O^-$, and the remaining a-d groups are each a $CR^1$ moiety wherein each $R^1$ group for each $CR^1$ moiety is independently selected);

each $R^1$ is independently selected from the group consisting of: H, halo, —$CF_3$, —$OR^{20}$ (e.g., —$OCH_3$), —$COR^{20}$, —$SR^{20}$ (e.g., —$SCH_3$ and —$SCH_2C_6H_5$), —$S(O)_tR^{21}$ (wherein t is 0, 1 or 2, e.g., —$SOCH_3$ and —$SO_2CH_3$), —$N(R^{20})(R^{21})$, —$NO_2$, —$OC(O)R^{20}$, —$CO_2R^{20}$, —$OCO_2R^{21}$, —CN, —$NR^{20}COOR^{21}$, —$SR^{20}C(O)OR^{21}$ (e.g., —$SCH_2CO_2CH_3$), —$SR^{21}N(R^{75})_2$ (provided that $R^{21}$ in —$SR^{21}N(R^{75})_2$ is not —CH$_2$—), alkynyl, alkenyl and alkyl, wherein said alkyl or alkenyl group is optionally substituted with one or more substitutents selected from the group consisting of: halo, —OR$^{20}$ or —CO$_2$R$^{20}$, and wherein each R$^{75}$ is independently selected from H or —C(O)OR$^{21}$ (examples of the —SR$^{21}$N(R$^{75}$)$_2$ moiety include, but are not limited to, —S(CH$_2$)$_2$NHC(O)O-t-butyl and —S(CH$_2$)$_2$NH$_2$);

R$^3$ and R$^4$ are each independently selected from the group consisting of the R$^1$ substituents (i.e., R$^3$ and R$^4$ are defined the same as R$^1$), or R$^3$ and R$^4$ taken together represent a saturated or unsaturated C$_5$-C$_7$ fused ring to the benzene ring (i.e, benzene Ring III);

R$^5$, R$^6$, and R$^7$ are each independently selected from the group consisting of: H, —CF$_3$, —COR$^{20}$, alkyl and aryl, said alkyl or aryl optionally being substituted with one or more substituents selected from the group consisting of: —OR$^{20}$, —SR$^{20}$, —S(O)$_t$R$^{21}$, —NR$^{20}$COOR$^{21}$, —N(R$^{20}$)(R$^{21}$), —NO$_2$, —COR$^{20}$, —OCOR$^{20}$, —OCO$_2$R$^{21}$, and —CO$_2$R$^{20}$, provided that for the groups —OR$^{20}$, —SR$^{20}$ and —N(R$^{20}$)(R$^{21}$), R$^{20}$ and R$^{21}$ are not H; or one of R$^5$ and R$^6$ is =O and the other is H (i.e., R$^5$ and R$^7$ together represent =O, and R$^6$ represents H);

t is 0, 1 or 2;

each dotted line represents an optional bond;

X represents N, CH or C, and when X is C the optional bond to carbon atom 11 is present, and when X is CH or N the optional bond to carbon atom 11 is absent;

when the optional bond between carbon atoms 5 and 6 is present (i.e., there is a double bond between carbon atoms 5 and 6), then the optional bond from carbon atom 5 to A is absent, and the optional bond from carbon atom 6 to B is absent, and A and B are each independently selected from the group consisting of: —R$^{20}$, halo, —OR$^{21}$, —OCO$_2$R$^{21}$ and —OC(O)R$^{20}$;

when the optional bond between carbon atoms 5 and 6 is absent (i.e., there is a single bond between carbon atoms 5 and 6), then the optional bond from carbon atom 5 to A is present, and the optional bond form carbon atom 6 to B is present, and A and B are each independently selected from the group consisting of: =O, =NOR$^{20}$, —O—(CH$_2$)P—O—, the pair H and H, the pair —OR$^{21}$ and —OR$^{21}$, the pair H and halo, the pair halo and halo, the pair alkyl and H, the pair alkyl and alkyl, the pair —H and —OC(O)R$^{20}$, the pair H and —OR$^{20}$, and the pair aryl and H;

p is 2, 3 or 4;

R$^8$, when X is C or CH, is selected from the group consisting of: H, —C(O)—Y—R$^{12}$

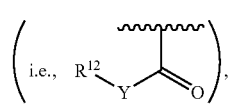

and —SO$_2$R$^{13}$;

R$^8$, when X is N, is selected from the group consisting of: H, —C(O)—Y—R$^{12}$

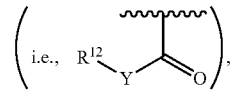

—SO$_2$R$^{13}$, and the tricyclic ring system

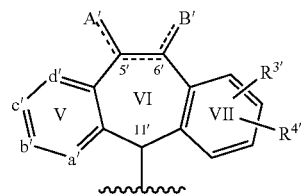

wherein a' is defined the same as a in Ring I, b' is defined the same as b in Ring I, c' is defined the same as c in Ring I, d' is defined the same as d in Ring I, A' is defined the same as A in Ring II, B' is defined the same as B in Ring II, R$^{3'}$ is defined the same as R$^3$ in Ring III, and R$^{4'}$ is defined the same as R$^4$ in Ring III (preferably a' is the same as a, b' is the same as b, c' is the same as c, d' is the same as d, A' is the same as A, B' is the same as B, R$^{3'}$ is the same as R$^3$, and R$^{4'}$ is the same as R$^4$);

Each R$^9$ is independently selected from the group consisting of: halo, alkyl, substituted alkyl, trifluoroalkyl, hydroxy, alkyloxy, amino or acylamino;

R$^{11}$ is selected from the group consisting of: H, alkyl and arylalkyl (examples include, but are not limited to, C$_1$ to C$_4$ alkyl (such as, for example, n-butyl), benzyl and 3-phenylpropyl);

Y is selected from the group consisting of:

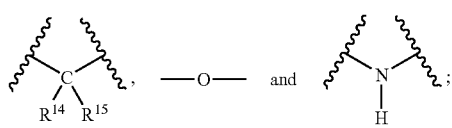

R$^{12}$ is selected from the group consisting of: alkyl, aryl, arylalkyl, cycloalkyl, heterocycloalkyl, heteroaryl or heteroarylalkyl, substituted alkyl, substituted aryl, substituted arylalkyl, substituted cycloalkyl, substituted heterocycloalkyl, substituted heteroaryl and substituted heteroarylalkyl (examples of R$^{12}$ include, but are not limited to, 4-chlorophenyl and 4-cyanophenyl);

R$^{13}$ is selected from the group consisting of: alkyl, substituted alkyl, cycloalkyl, substituted cycloalkyl, aryl, substituted aryl, arylalkyl and substituted arylalkyl R$^{14}$ and R$^{15}$ are each independently selected from the group consisting of: H, and lower alkyl (e.g., C$_1$ to C$_6$ alkyl, or C$_1$ to C$_4$ alkyl, or C$_1$ to C$_2$ alkyl);

$R^{16}$ is selected from the group consisting of:

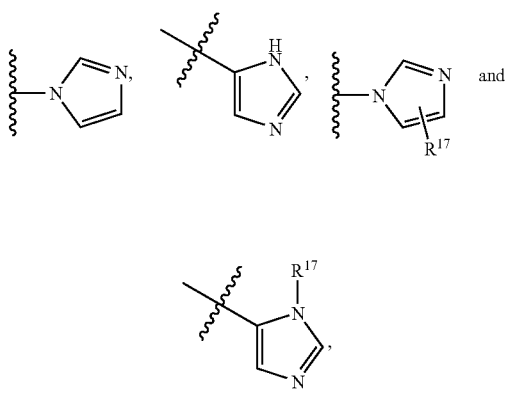

and $R^{16}$ is preferably selected from the group consisting of:

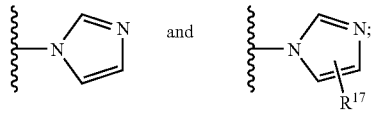

$R^{17}$ is selected from the group consisting of: alkyl (e.g., $C_1$ to $C_4$, such as, for example methyl), and substituted alkyl;

$R^{20}$ represents H, alkyl, aryl, or aralkyl;

$R^{21}$ represents H, alkyl, aryl, or aralkyl;

m is 0 to 4; and n=1, 2, 3 or 4.

One embodiment of this invention is directed to compounds of formula 1.0 having the formula 1.0A:

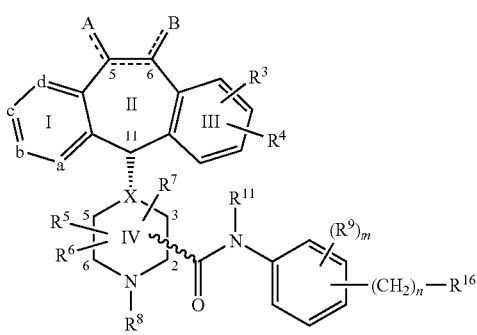

(1.0A)

and the pharmaceutically acceptable salts thereof, wherein X is N and all the other substituents are as defined for formula 1.0.

Another embodiment of this invention is directed to compounds of formula 1.0 having the formula 1.0A and the pharmaceutically acceptable salts thereof, wherein X is CH and all of the other substituents are as defined in formula 1.0.

Another embodiment of this invention is directed to the compounds of formula 1.0 having the formula 1.0B:

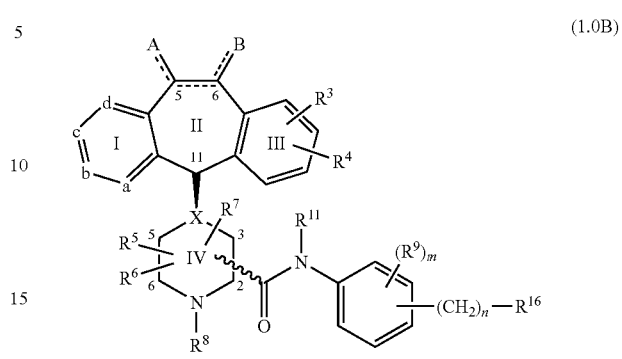

(1.0B)

and the pharmaceutically acceptable salts thereof, wherein X is N and all the other substituents are as defined for formula 1.0.

Another embodiment of this invention is directed to compounds of formula 1.0 having the formula 1.0B and the pharmaceutically acceptable salts thereof, wherein X is CH and all of the other substituents are as defined in formula 1.0.

Another embodiment of this invention is directed to the compounds of formula 1.0 having the formula 1.0C:

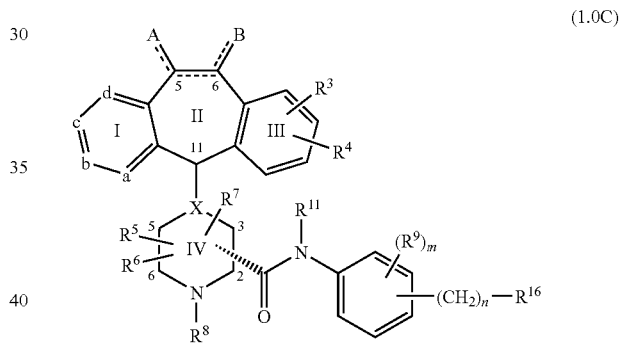

(1.0C)

and the pharmaceutically acceptable salts thereof, wherein X is N and all the other substituents are as defined for formula 1.0.

Another embodiment of this invention is directed to compounds of formula 1.0 having the formula 1.0C and the pharmaceutically acceptable salts thereof, wherein X is CH and all of the other substituents are as defined in formula 1.0.

Another embodiment of this invention is directed to the compounds of formula 1.0 having the formula 1.0D:

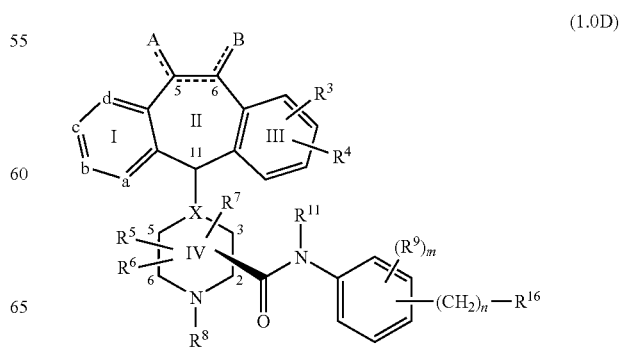

(1.0D)

and the pharmaceutically acceptable salts thereof, wherein X is N and all the other substituents are as defined for formula 1.0.

Another embodiment of this invention is directed to compounds of formula 1.0 having the formula 1.0D and the pharmaceutically acceptable salts thereof, wherein X is CH and all of the other substituents are as defined in formula 1.0.

Another embodiment of this invention is directed to the compounds of formula 1.0 having the formula 1.0E:

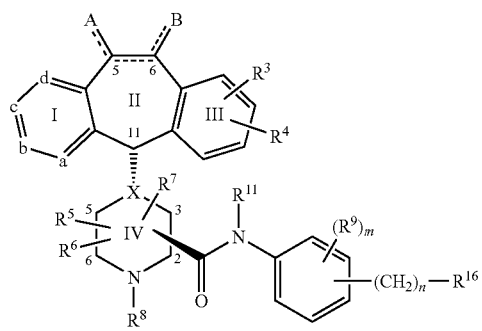

(1.0E)

and the pharmaceutically acceptable salts thereof, wherein X is N and all the other substituents are as defined for formula 1.0.

Another embodiment of this invention is directed to compounds of formula 1.0 having the formula 1.0E and the pharmaceutically acceptable salts thereof, wherein X is CH and all of the other substituents are as defined in formula 1.0.

Another embodiment of this invention is directed to the compounds of formula 1.0 having formula 1.0F:

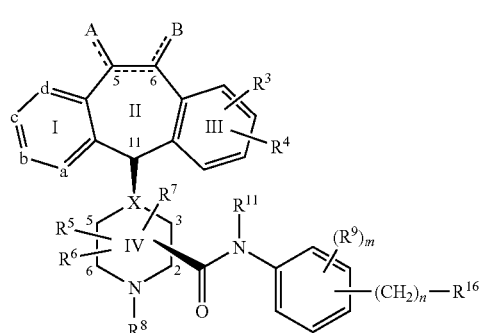

(1.0F)

and the pharmaceutically acceptable salts thereof, wherein X is N and all the other substituents are as defined for formula 1.0.

Another embodiment of this invention is directed to compounds of formula 1.0 having the formula 1.0F and the pharmaceutically acceptable salts thereof, wherein X is CH and all of the other substituents are as defined in formula 1.0.

Another embodiment of this invention is directed to the compounds of formula 1.0 having the formula 1.0G:

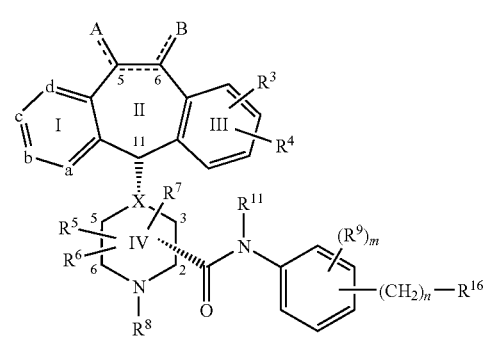

(1.0G)

and the pharmaceutically acceptable salts thereof, wherein X is N and all the other substituents are as defined for formula 1.0.

Another embodiment of this invention is directed to compounds of formula 1.0 having the formula 1.0G and the pharmaceutically acceptable salts thereof, wherein X is CH and all of the other substituents are as defined in formula 1.0.

Another embodiment of this invention is directed to the compounds of formula 1.0 having formula 1.0H:

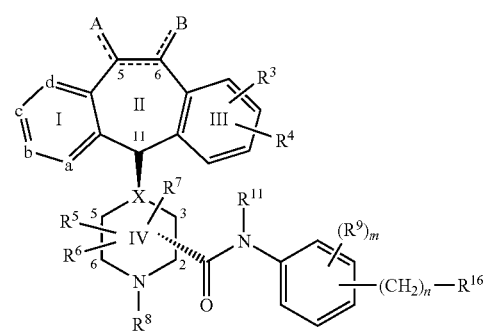

(1.0H)

and the pharmaceutically acceptable salts thereof, wherein X is N and all the other substituents are as defined for formula 1.0.

Another embodiment of this invention is directed to compounds of formula 1.0 having the formula 1.0H and the pharmaceutically acceptable salts thereof, wherein X is CH and all of the other substituents are as defined in formula 1.0.

Another embodiment of the compounds of formula 1.0 is directed to the compounds of formula 2.0:

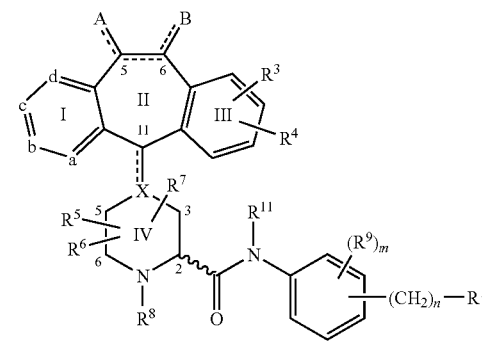

(2.0)

and the pharmaceutically acceptable salts thereof, wherein all substituents are as defined for formula 1.0.

Another embodiment of the compounds of formula 1.0 is directed to the compounds of formula 2.0A:

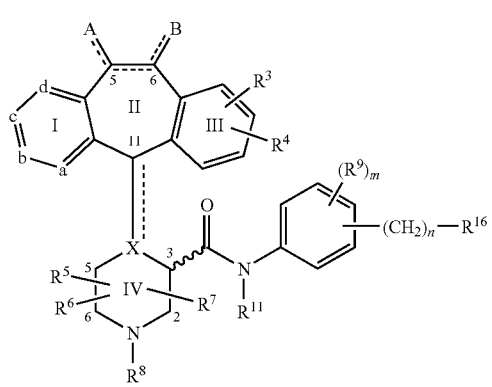

(2.0A)

and the pharmaceutically acceptable salts thereof, wherein all substituents are as defined for formula 1.0.

Another embodiment of the compounds of formula 1.0 is directed to the compounds of formula 3.0:

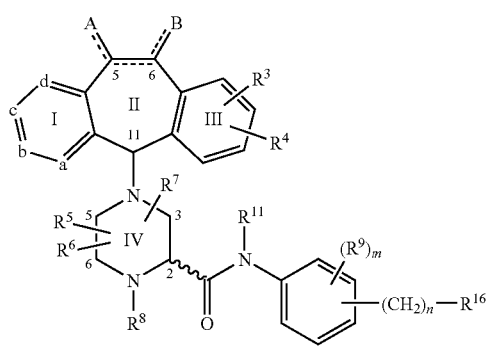

(3.0)

and the pharmaceutically acceptable salts thereof, wherein all substituents are as defined for formula 1.0.

Another embodiment of the compounds of formula 1.0 is directed to the compounds of formula 4.0:

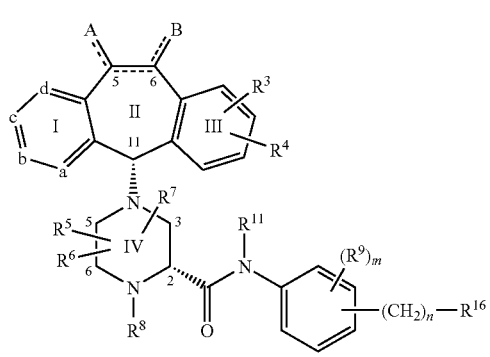

(4.0)

and the pharmaceutically acceptable salts thereof, wherein all substituents are as defined for formula 1.0.

Another embodiment of the compounds of formula 1.0 is directed to the compounds of formula 4.0A:

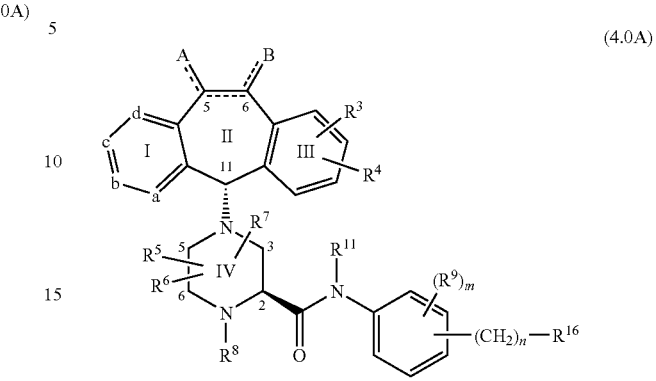

(4.0A)

and the pharmaceutically acceptable salts thereof, wherein all substituents are as defined for formula 1.0.

Another embodiment of the compounds of formula 1.0 is directed to the compounds of formula 5.0:

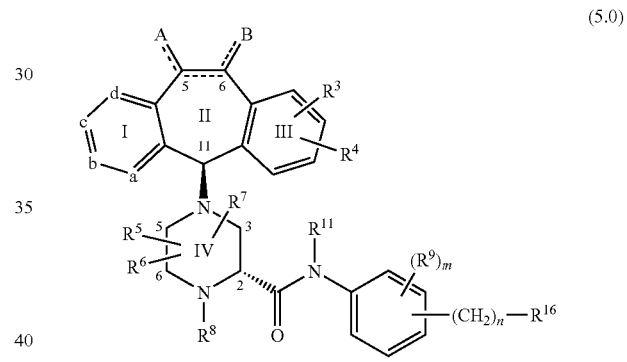

(5.0)

and the pharmaceutically acceptable salts thereof, wherein all substituents are as defined for formula 1.0.

Another embodiment of the compounds of formula 1.0 is directed to the compounds of formula 5.0A:

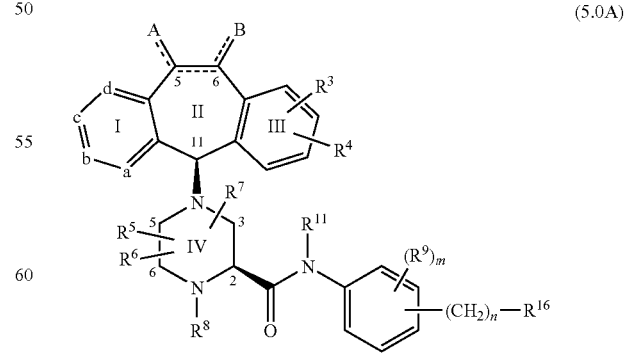

(5.0A)

and the pharmaceutically acceptable salts thereof, wherein all substituents are as defined for formula 1.0.

Another embodiment of the compounds of formula 1.0 is directed to the compounds of formula 6.0:

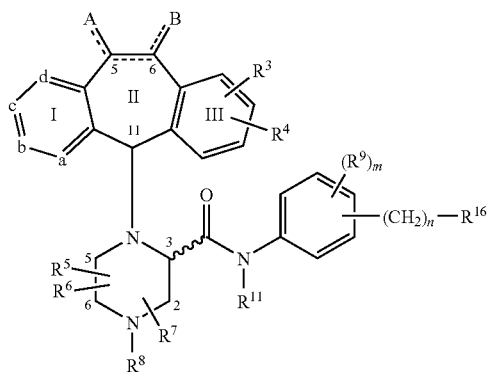

(6.0)

and the pharmaceutically acceptable salts thereof, wherein all substituents are as defined for formula 1.0.

Another embodiment of the compounds of formula 1.0 is directed to the compounds of formula 7.0:

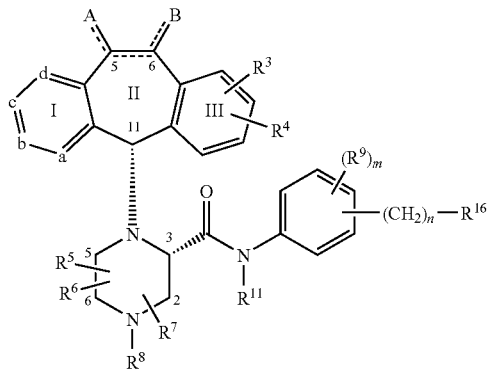

(7.0)

and the pharmaceutically acceptable salts thereof, wherein all substituents are as defined for formula 1.0.

Another embodiment of the compounds of formula 1.0 is directed to the compounds of formula 7.0A:

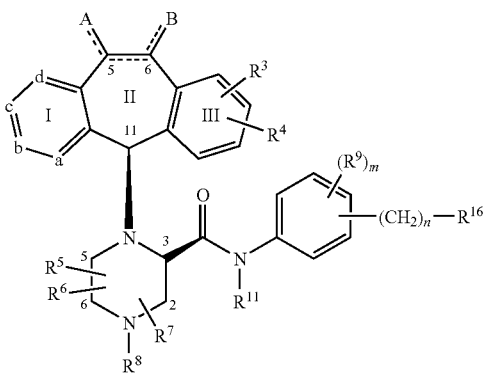

(7.0A)

and the pharmaceutically acceptable salts thereof, wherein all substituents are as defined for formula 1.0.

Another embodiment of the compounds of formula 1.0 is directed to the compounds of formula 7.0B:

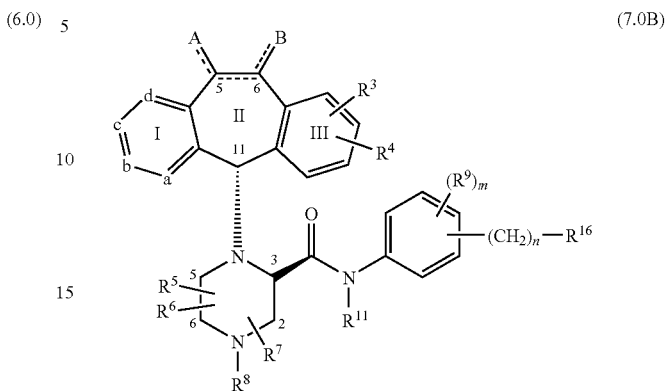

(7.0B)

and the pharmaceutically acceptable salts thereof, wherein all substituents are as defined for formula 1.0.

Another embodiment of the compounds of formula 1.0 is directed to the compounds of formula 7.0C:

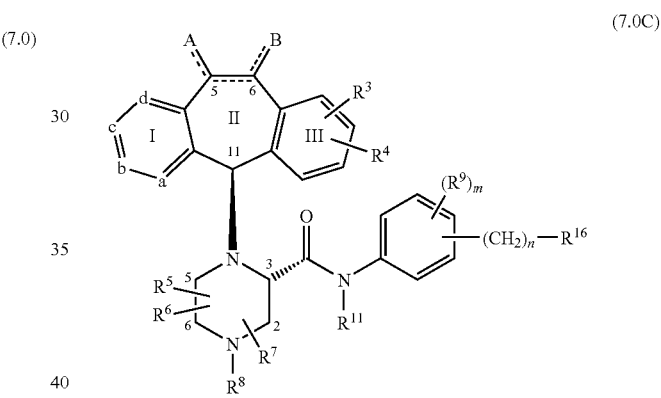

(7.0C)

and the pharmaceutically acceptable salts thereof, wherein all substituents are as defined for formula 1.0.

Another embodiment of the compounds of formula 1.0 is directed to the compounds of formula 8.0:

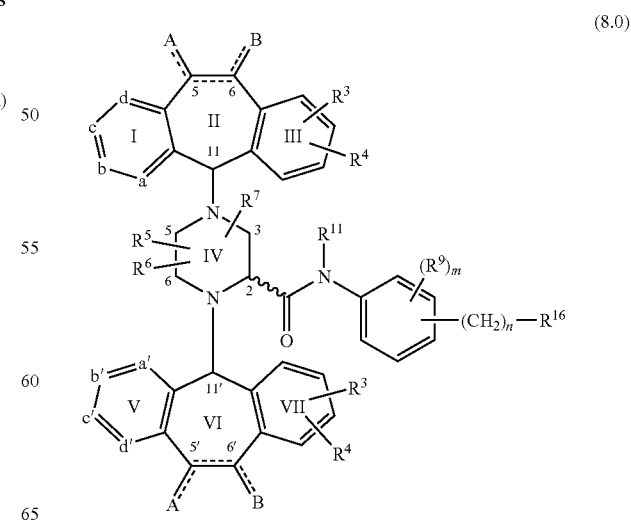

(8.0)

and the pharmaceutically acceptable salts thereof, wherein all substituents are as defined for formula 1.0.

Another embodiment of the compounds of formula 1.0 is directed to the compounds of formula 8.0A:

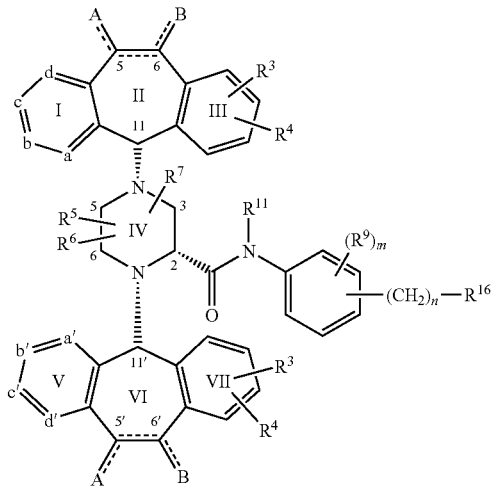

(8.0A)

and the pharmaceutically acceptable salts thereof, wherein all substituents are as defined for formula 1.0.

Another embodiment of the compounds of formula 1.0 is directed to the compounds of formula 8.0B:

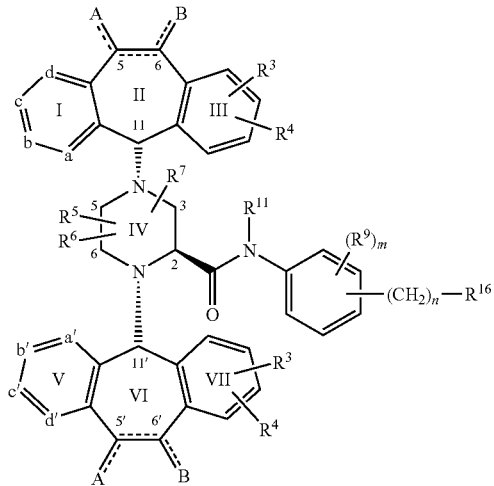

(8.0B)

and the pharmaceutically acceptable salts thereof, wherein all substituents are as defined for formula 1.0.

Another embodiment of the compounds of formula 1.0 is directed to the compounds of formula 8.0C:

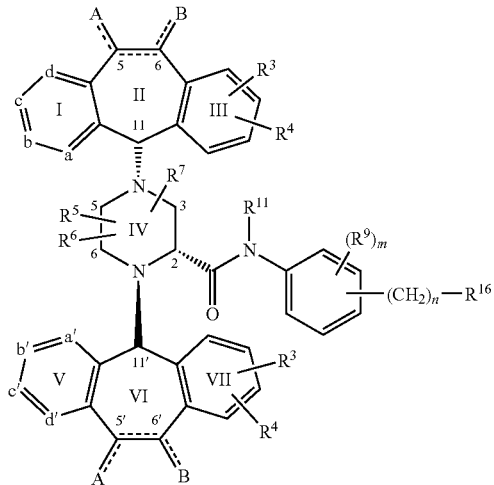

(8.0C)

and the pharmaceutically acceptable salts thereof, wherein all substituents are as defined for formula 1.0.

Another embodiment of the compounds of formula 1.0 is directed to the compounds of formula 8.0D:

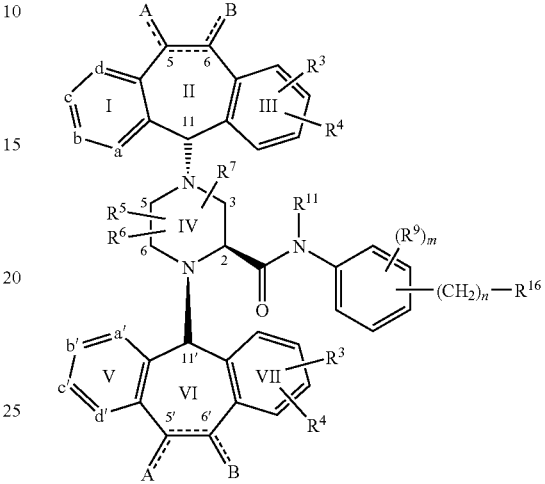

(8.0D)

and the pharmaceutically acceptable salts thereof, wherein all substituents are as defined for formula 1.0.

Another embodiment of the compounds of formula 1.0 is directed to the compounds of formula 8.0E:

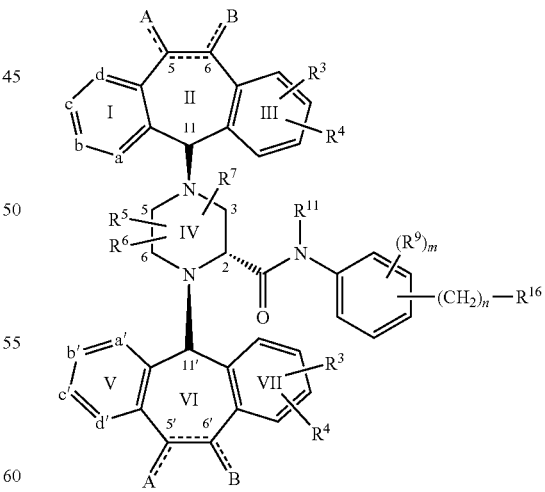

(8.0E)

and the pharmaceutically acceptable salts thereof, wherein all substituents are as defined for formula 1.0.

Another embodiment of the compounds of formula 1.0 is directed to the compounds of formula 8.0F:

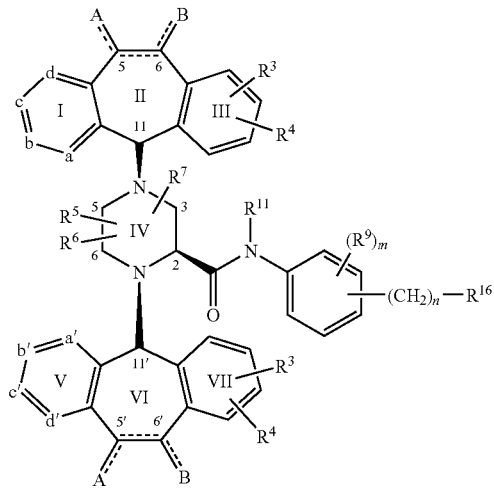

(8.0F)

and the pharmaceutically acceptable salts thereof, wherein all substituents are as defined for formula 1.0.

Another embodiment of the compounds of formula 1.0 is directed to the compounds of formula 8.0G:

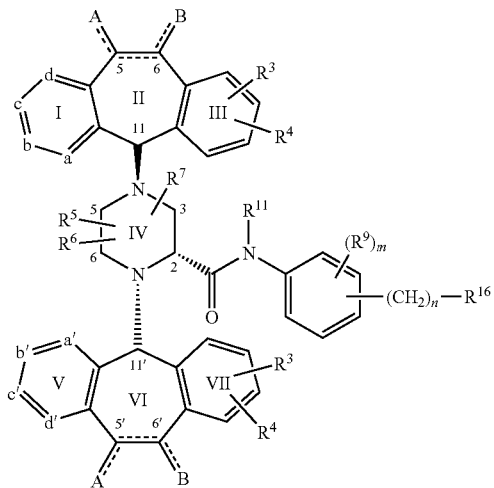

(8.0G)

and the pharmaceutically acceptable salts thereof, wherein all substituents are as defined for formula 1.0.

Another embodiment of the compounds of formula 1.0 is directed to the compounds of formula 8.0H:

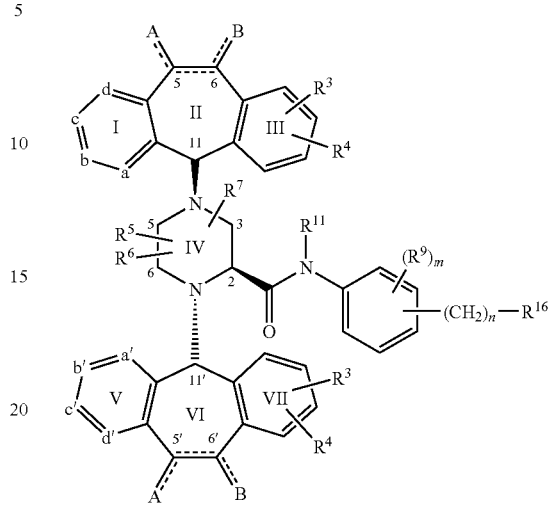

(8.0H)

and the pharmaceutically acceptable salts thereof, wherein all substituents are as defined for formula 1.0.

Another embodiment of the compounds of formula 1.0 is directed to the compounds of formula 8.0I:

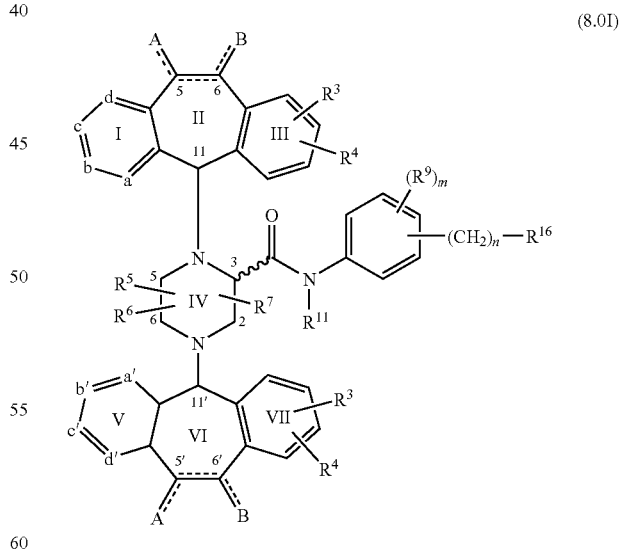

(8.0I)

and the pharmaceutically acceptable salts thereof, wherein all substituents are as defined for formula 1.0.

Another embodiment of the compounds of formula 1.0 is directed to the compounds of formula 8.0J:

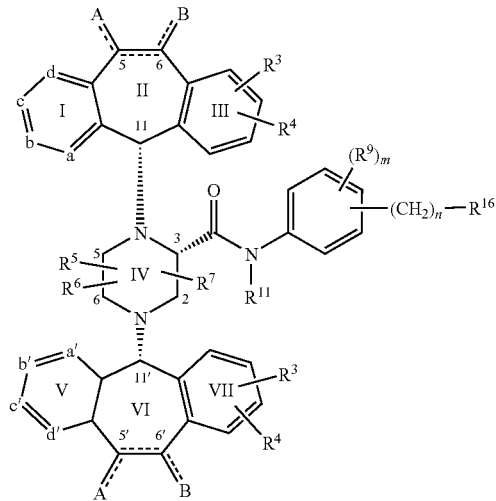

(8.0J)

and the pharmaceutically acceptable salts thereof, wherein all substituents are as defined for formula 1.0.

Another embodiment of the compounds of formula 1.0 is directed to the compounds of formula 8.0K:

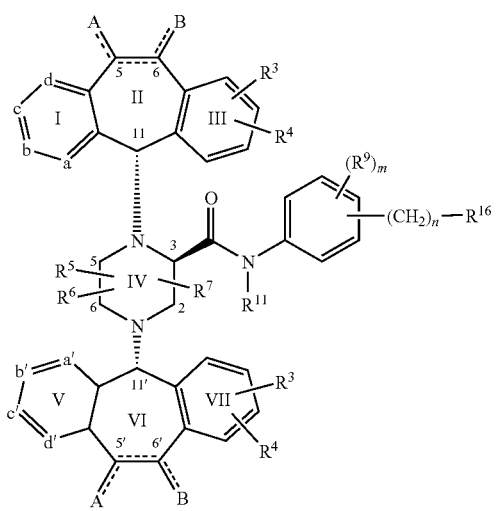

(8.0K)

and the pharmaceutically acceptable salts thereof, wherein all substituents are as defined for formula 1.0.

Another embodiment of the compounds of formula 1.0 is directed to the compounds of formula 8.0L:

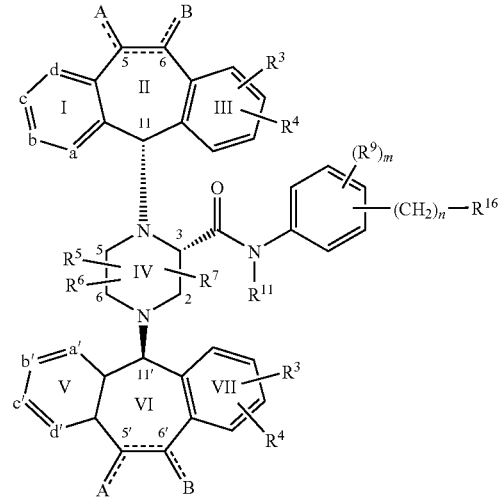

(8.0L)

and the pharmaceutically acceptable salts thereof, wherein all substituents are as defined for formula 1.0.

Another embodiment of the compounds of formula 1.0 is directed to the compounds of formula 8.0M:

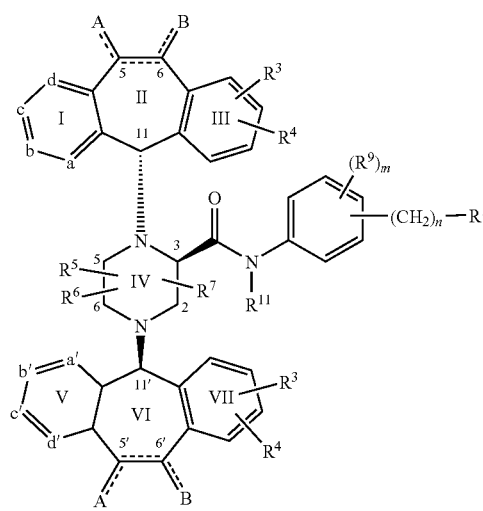

(8.0M)

and the pharmaceutically acceptable salts thereof, wherein all substituents are as defined for formula 1.0.

Another embodiment of the compounds of formula 1.0 is directed to the compounds of formula 8.0N:

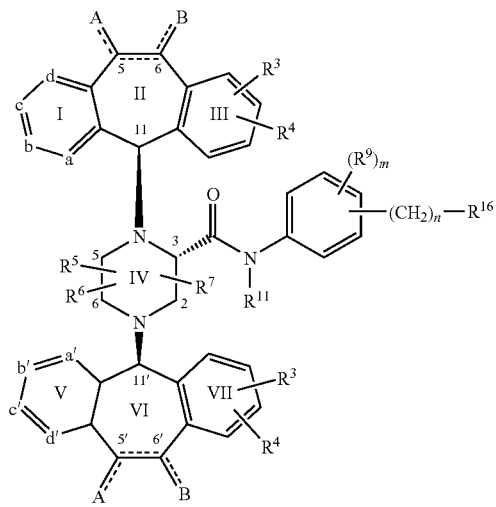

(8.0N)

and the pharmaceutically acceptable salts thereof, wherein all substituents are as defined for formula 1.0.

Another embodiment of the compounds of formula 1.0 is directed to the compounds of formula 8.0P:

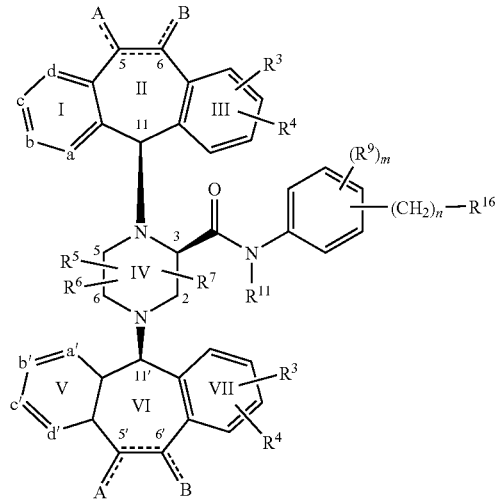

(8.0P)

and the pharmaceutically acceptable salts thereof, wherein all substituents are as defined for formula 1.0.

Another embodiment of the compounds of formula 1.0 is directed to the compounds of formula 8.0Q:

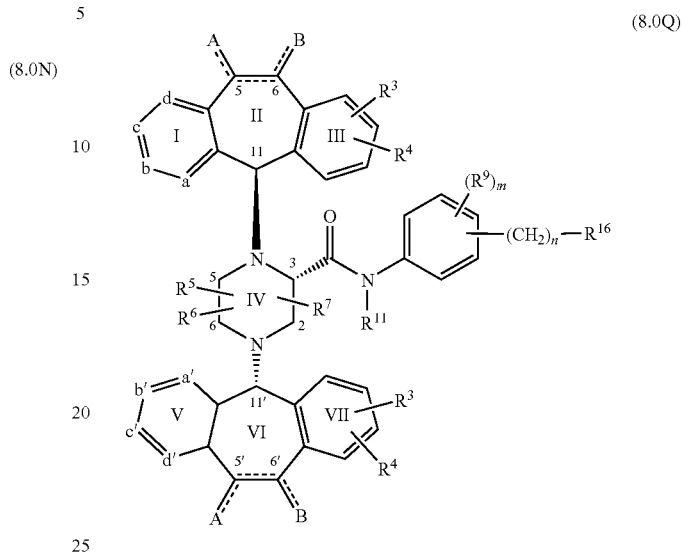

(8.0Q)

and the pharmaceutically acceptable salts thereof, wherein all substituents are as defined for formula 1.0.

Another embodiment of the compounds of formula 1.0 is directed to the compounds of formula 8.0R:

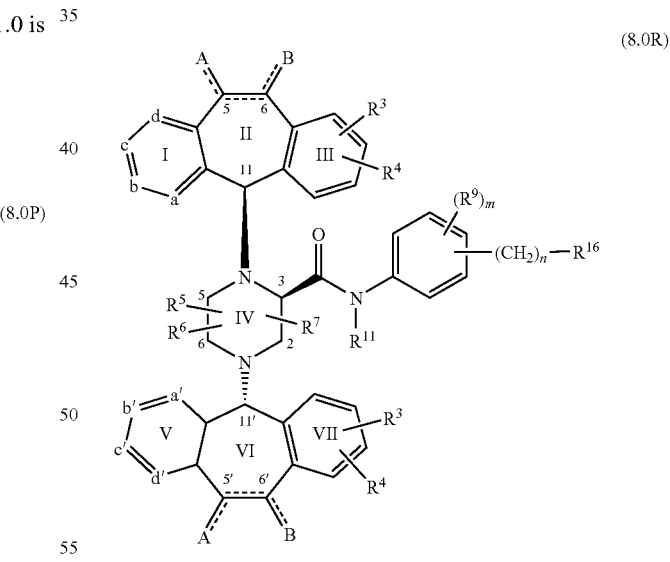

(8.0R)

and the pharmaceutically acceptable salts thereof, wherein all substituents are as defined for formula 1.0.

Preferably, for the compounds of formula 1.0, $R^1$ is selected from the group consisting of H and halo, and most preferably H and Br.

Preferably, for the compounds of formula 1.0, a is N, and b, c and d are $CR^1$. Most preferably, a is N, and b, c, and d are $CR^1$ wherein each $R^1$ is independently selected from the group consisting of H and halo (more preferably H and Br).

Still more preferably, a is N, and b, c, and d are $CR^1$ wherein each $R^1$ is H; or a is N, and one of b, c, and d (even still more preferably c) is $CR^1$ wherein $R^1$ is halo (yet even more preferably Br) and the remaining b, c, and d groups are $CR^1$ wherein $R^1$ is H.

Preferably, for the compounds of formula 1.0, the optional bond between C-5 and C-6 is absent (i.e., there is a single bond between C-5 and C-6), and the optional bond from C-5 to A and the optional bond from C-6 to B are present (i.e., there are two A substituents each being singly bonded to C-5, or there is one A substitutent doubly bonded to C-5, and there are two B substituents each being singly bonded to C-6, or there is one B substituent doubly bonded to C-6), and most preferably there are two A substituents each being singly bonded to C-5 and there are two B substitutents each being singly bonded to C-6, and more preferably A represents two H substituents (i.e., A is $H_2$) and B represents two H substituents (i.e., B is $H_2$).

Preferably for the compounds of formula 1.0, $R^3$ and $R^4$ are independently selected from the group consisting of: H and halo, most preferably $R^3$ and $R^4$ are independently selected from the group consisting of: H and halo wherein at least one of $R^3$ and $R^4$ is halo. More preferably, $R^3$ and $R^4$ are independently selected from the group consisting of: H, Br, F and Cl, and even more preferably $R^3$ and $R^4$ are independently selected from the group consisting of: H, Br and Cl wherein at least one of $R^3$ and $R^4$ is other than H. Still more preferably $R^3$ is halo (yet more preferably Br or Cl) and $R^4$ is selected from the group consisting of H and halo (e.g., Br or Cl) with H being yet still more preferred. Even still more preferably $R^3$ is at the C-8 position and $R^3$ is halo (e.g., Br or Cl, and preferably Cl), and $R^4$ is selected from the group consisting of H and halo (e.g., Br or Cl), and yet still more preferably $R^4$ is H.

Preferably, for the compounds of formula 1.0, X is N.

Preferably, for the compounds of formula 1.0, $R^5$, $R^6$ and $R^7$ are each H.

Preferably, for the compounds of formula 1.0, Y is selected from the group consisting of: —$CH_2$— (i.e., $R^{14}$ and $R^{15}$ are preferably H), —O— and —NH—.

Preferably, for the compounds of formula 1.0, $R^{13}$ is alkyl, and most preferably methyl.

Preferably, for the compounds of formula 1.0, $R^8$ is selected from the group consisting of:

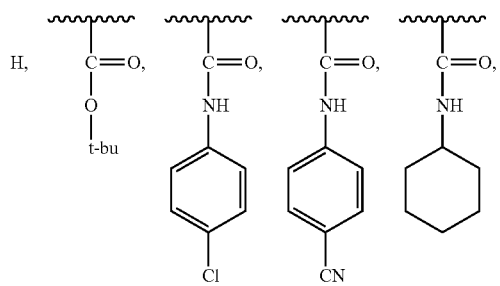

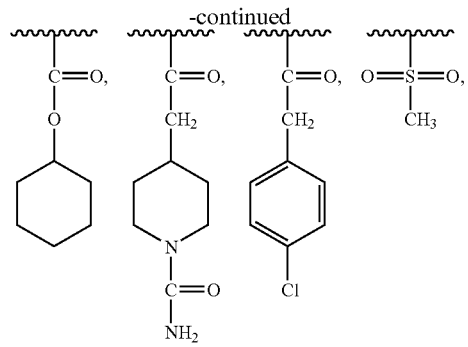

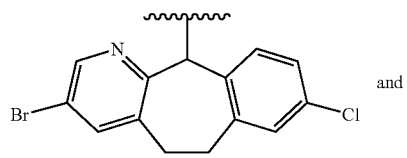

and

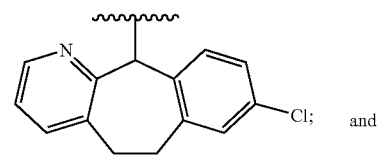

most preferably $R^8$ is selected from the group consisting of:

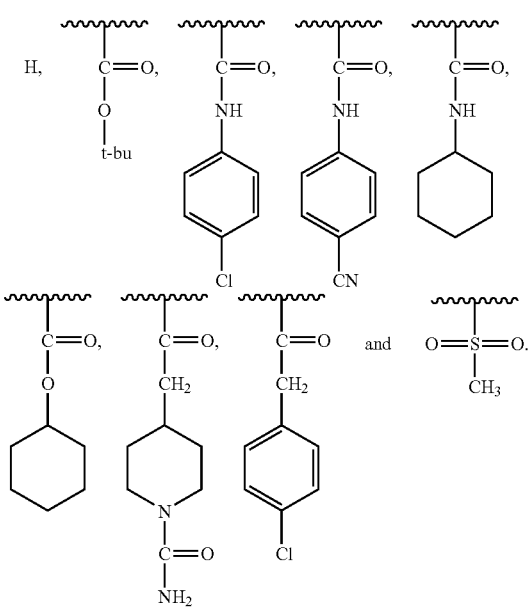

Preferably, for the compounds of formula 1.0, $R^9$ is H.

Preferably, for the compounds of formula 1.0, $R^{11}$ is selected from the group consisting of: H, benzyl, 3-phenylpropyl and n-butyl. Most preferably, $R^{11}$ is H.

Preferably, for the compounds of formula 1.0, n=1 or 2.

Preferably, for the compounds of formula 1.0, $R^{16}$ is

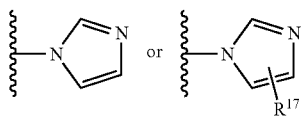

Preferably, for the compounds of formula 1.0, $R^{17}$ is methyl (e.g., methyl bound to the 2-, 4- or 5-position of the imidazolyl).

Thus, in one embodiment of this invention $R^{16}$ is the unsubstituted imidazolyl

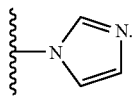

In another embodiment of this invention $R^{16}$ is the substituted imidazolyl

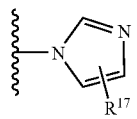

wherein $R^{17}$ is methyl bound to the 2-position of the imidazolyl (i.e., 2-methyl). In another embodiment of this invention $R^{17}$ is methyl bound to the 4-position of the imidazolyl (i.e., 4-methyl). In another embodiment of this invention $R^{17}$ is methyl bound to the 5-position of the imidazolyl (i.e., 5-methyl).

Preferably, for the compounds of formula 1.0, $R^{12}$ is selected from the group consisting of: alkyl (e.g., t-butyl), substituted aryl (e.g., halo substituted aryl (such as mono halo substituted aryl, such as monohalo substituted phenyl, such as chlorophenyl) and cyano substituted aryl (such as cyanophenyl)), cycloalkyl (e.g., cyclohexyl), and substituted heterocycloalkyl (such as piperidinyl substituted on the nitrogen with —C(O)NH₂). Most preferably $R^{12}$ is selected from the group consisting of: $C_1$ to $C_6$ alkyl (e.g., t-butyl), cyclohexyl, piperidinyl substituted on the nitrogen with —C(O)NH₂, halophenyl (e.g., 4-chlorophenyl), and cyanophenyl (e.g., 4-cyanophenyl). More preferably $R^{12}$ is selected from the group consisting of:

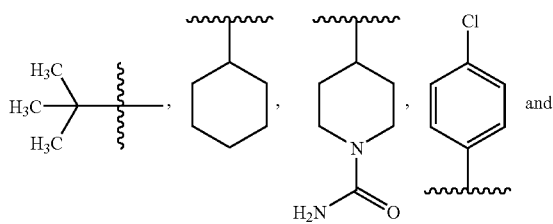

-continued

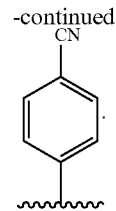

Another embodiment of this invention is directed to compounds of formula 1.0 wherein:
(1) a is N, and b, c and d are $CR^1$, or
  (a) a is N, and b, c, and d are $CR^1$ wherein each $R^1$ is independently selected from the group consisting of H and halo (e.g., H and Br), or
  (b) a is N, and b, c, and d are $CR^1$ wherein $R^1$ is H, or a is N, and one of b, c, and d (e.g., c) is $CR^1$ wherein $R^1$ is halo (e.g., Br) and the remaining b, c, and d groups are $CR^1$ wherein $R^1$ is H,
(2) the optional bond between C-5 and C-6 is absent (i.e., there is a single bond between C-5 and C-6), and the optional bond from C-5 to A and the optional bond from C-6 to B are present (i.e., there are two A substituents each being singly bonded to C-5, or there is one A substitutent doubly bonded to C-5, and there are two B substitutents each being singly bonded to C-6, or there is one B substituent doubly bonded to C-6, or there are two A substituents each being singly bonded to C-5 and there are two B substitutents each being singly bonded to C-6, or A represents two H substituents (i.e., A is H₂) and B represents two H subustituents (i.e., B is H₂),
(3) $R^3$ and $R^4$ are independently selected from the group consisting of: H and halo, or
  (a) $R^3$ and $R^4$ are independently selected from H and halo wherein at least one of $R^3$ and $R^4$ is halo, or
  (b) $R^3$ and $R^4$ are independently selected from the group consisting of: H, Br, F and Cl, or
  (c) $R^3$ and $R^4$ are independently selected from the group consisting of: H, Br and Cl wherein at least one of $R^3$ and $R^4$ is other than H, or
  (d) $R^3$ is halo (e.g., Br or Cl), and $R^4$ is selected from the group consisting of H and halo (e.g., Br or Cl), or $R^4$ is H being yet, or
  (e) $R^3$ is at the C-8 position and $R^3$ is halo (e.g., Br or Cl, and generally Cl), and $R^4$ is selected from the group consisting of H and halo (e.g., Br or Cl), or
  (f) $R^3$ is at the C-8 position and $R^3$ is halo (e.g., Br or Cl, generally Cl), and $R^4$ is selected is H,
(4) $R^5$, $R^6$ and $R^7$ are each H,
(5) Y is selected from the group consisting of: —CH₂ (i.e., $R^{14}$ and $R^{15}$ are H), —O— and —NH—,
(6) $R^{13}$ is alkyl, (e.g., methyl),
(7) $R^{12}$ is selected from the group consisting of: (i) alkyl (e.g., t-butyl), (ii) substituted aryl (e.g., halo substituted aryl (such as mono halo substituted aryl, such as monohalo substituted phenyl, such as chlorophenyl) and cyano substituted aryl (such as cyanophenyl)), (iii) cycloalkyl (e.g., cyclohexyl), and (iv) substituted heterocycloalkyl (such as piperidinyl substituted on the nitrogen with —C(O)NH₂), or
  (a) $R^{12}$ is selected from the group consisting of: $C_1$ to $C_6$ alkyl (e.g., t-butyl), cyclohexyl, piperidinyl substituted on the nitrogen with —C(O)NH₂, halophenyl (e.g., 4-chlorophenyl) and cyanophenyl (e.g., 4-cyanophenyl), or (b) $R^{12}$ is selected from the group consisting of:

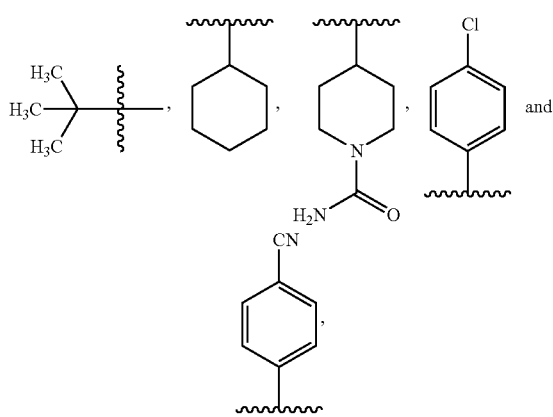

(8) $R^9$ is H,
(9) $R^{11}$ is selected from the group consisting of: H, benzyl, 3-phenylpropyl and n-butyl, or preferably $R^{11}$ is H,
(10) n=1 or 2;
(11) $R^1$ is

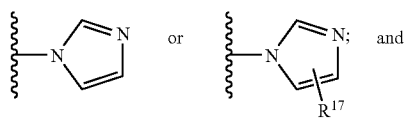

(12) $R^{17}$ is methyl (for example, in one embodiment $R^{16}$ is the unsubstituted imidazolyl ring

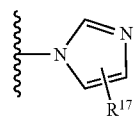

in another embodiment $R^{16}$ is the substituted imidazolyl ring

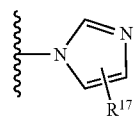

wherein $R^{17}$ is 2-methyl, or in another embodiment $R^{17}$ is 4-methyl, or in another embodiment $R^{17}$ is 5-methyl).

Thus, another embodiment of this invention (referred to hereinafter as the (1)-(13) paragraph embodiment) is directed to compounds of formula 1.0 wherein:

(1) a is N, and b, c and d are $CR^1$, and
  (a) preferably, a is N, and b, c, and d are $CR^1$ wherein each $R^1$ is independently selected from the group consisting of H and halo (most preferably H and Br), and
  (b) most preferably, a is N, and b, c, and d are $CR^1$ wherein $R^1$ is H, or a is N, and one of b, c, and d (more preferably c) is $CR^1$ wherein $R^1$ is halo (still more preferably Br) and the remaining b, c, and d groups are $CR^1$ wherein $R^1$ is H, (2) the optional bond between C-5 and C-6 is absent (i.e., there is a single bond between C-5 and C-6), and the optional bond from C-5 to A and the optional bond from C-6 to B are present (i.e., there are two A substituents each being singly bonded to C-5, or there is one A substitutent doubly bonded to C-5, and there are two B substitutents each being singly bonded to C-6, or there is one B substituent doubly bonded to C-6), and preferably there are two A substituents each being singly bonded to C-5 and there are two B substitutents each being singly bonded to C-6, and most preferably A represents two H substituents (i.e., A is $H_2$) and B represents two H substituents (i.e., B is $H_2$), (3) $R^3$ and $R^4$ are independently selected from the group consisting of: H and halo, and
  (a) preferably $R^3$ and $R^4$ are independently selected from H and halo wherein at least one of $R^3$ and $R^4$ is halo, and
  (b) most preferably, $R^3$ and $R^4$ are independently selected from the group consisting of: H, Br, F and Cl, and
  (c) more preferably $R^3$ and $R^4$ are independently selected from the group consisting of: H, Br and Cl wherein at least one of $R^3$ and $R^4$ is other than H, and
  (d) still more preferably $R^3$ is halo (yet more preferably Br or Cl) and $R^4$ is selected from the group consisting of H and halo (e.g., Br or Cl) with H being yet still more preferred, and
  (e) even still more preferably $R^3$ is at the C-8 position and $R^3$ is halo (e.g., Br or Cl, and preferably Cl), and $R^4$ is selected from the group consisting of H and halo (e.g., Br or Cl), and
  (f) yet still more preferably $R^3$ is at the C-8 position and $R^3$ is halo (e.g., Br or Cl, and preferably Cl), and $R^4$ is selected is H, (4) X is N,
(5) $R^5$, $R^6$ and $R^7$ are each H,
(6) Y is selected from the group consisting of: —$CH_2$— (i.e., $R^{14}$ and $R^{15}$ are preferably H), —O— and —NH—,
(7) $R^{13}$ is alkyl, and most preferably methyl,
(8) $R^{12}$ is selected from the group consisting of: (i) alkyl (e.g., t-butyl), (ii) substituted aryl (e.g., halo substituted aryl (such as mono halo substituted aryl, such as monohalo substituted phenyl, such as chlorophenyl) and cyano substituted aryl (such as cyanophenyl)), (iii) cycloalkyl (e.g., cyclohexyl), and (iv) substituted heterocycloalkyl (such as piperidinyl substituted on the nitrogen with —C(O)$NH_2$), and
  (a) preferably $R^{12}$ is selected from the group consisting of: $C_1$ to $C_6$ alkyl (e.g., t.butyl), cyclohexyl, piperidinyl substituted on the nitrogen with —C(O)$NH_2$, halophenyl (e.g., 4-chlorophenyl) and cyanophenyl (e.g., 4-cycanophenyl), and
  (b) most preferably $R^{12}$ is selected from the group consisting of:

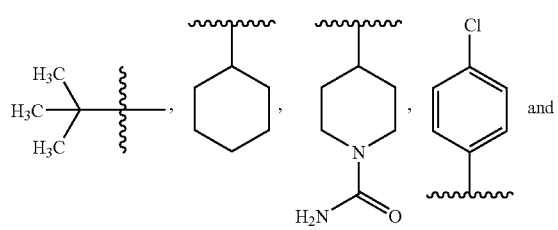

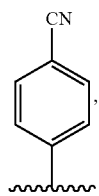

(9) $R^9$ is H,
(10) $R^{11}$ is selected from the group consisting of: H, benzyl, 3-phenylpropyl and n-butyl, and preferably $R^{11}$ is H,
(11) n=1 or 2;
(12) $R^{16}$ is

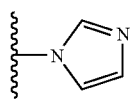 or 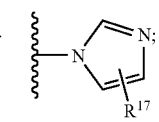 and

(13) $R^{17}$ is methyl (for example, in one embodiment $R^{16}$ is the unsubstituted imidazolyl ring

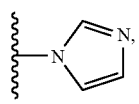

in another embodiment $R^{16}$ is the substituted imidazolyl ring

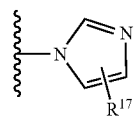

wherein $R^{17}$ is 2-methyl, or in another embodiment $R^{17}$ is 4-methyl, or in another embodiment $R^{17}$ is 5-methyl).

Preferably, for the compounds of formula 1.0 (for example, the (1) to (13) paragraph embodiment described above), $R^8$ is selected from the group consisting of:

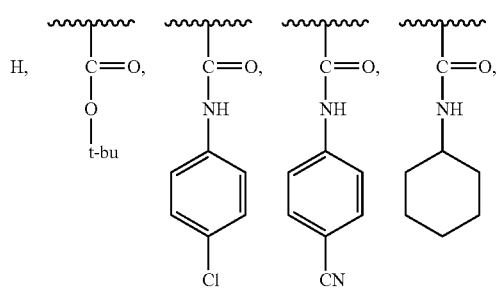

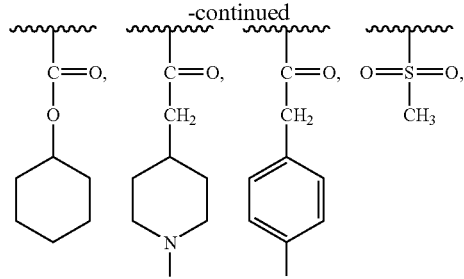

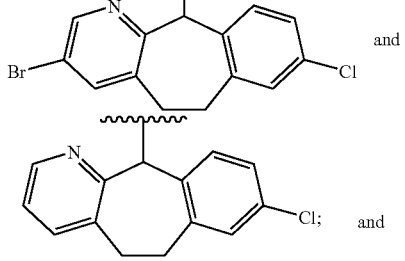

most preferably $R^8$ is selected from the group consisting of:

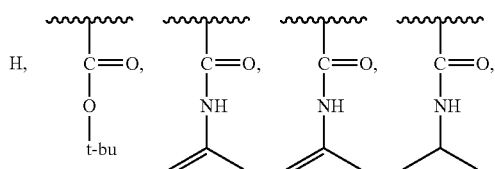

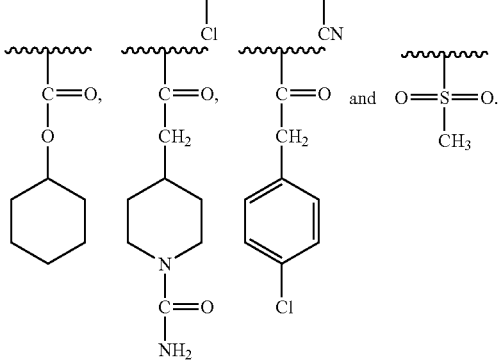

In another embodiment of the compounds of formula 1.0, (e.g., the (1) to (13) paragraph embodiment described above), the

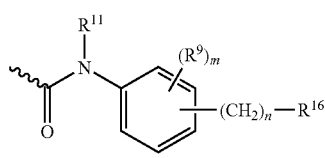

moiety is selected from the group consisting of:
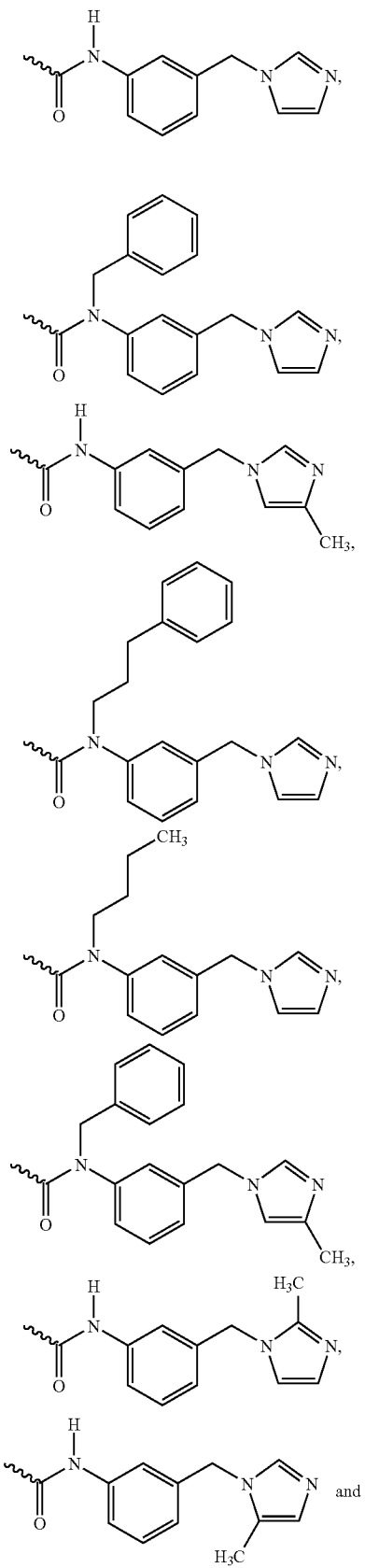
-continued
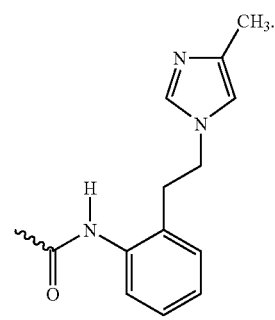
In another embodiment of the compounds of formula 1.0, (e.g., the (1) to (13) paragraph embodiment described above), the
moiety is selected from the group consisting of:

-continued
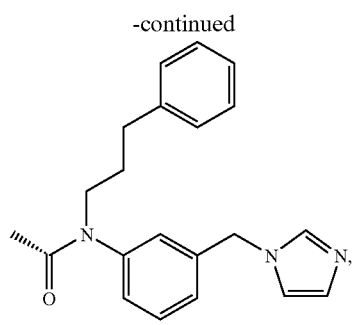
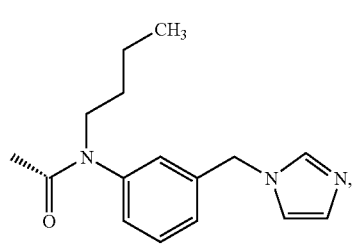
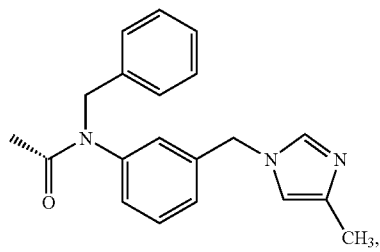
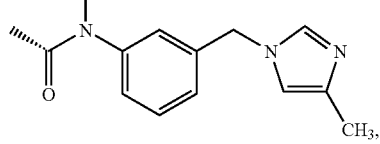
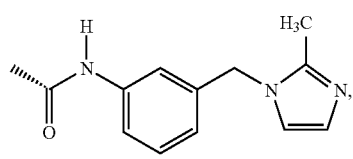, and
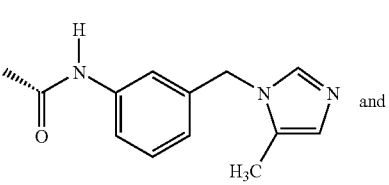
-continued
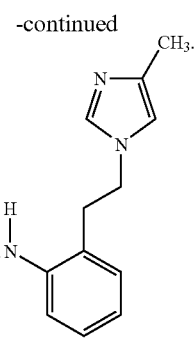
In another embodiment of the compounds of formula 1.0, (e.g., the (1) to (13) paragraph embodiment described above), the
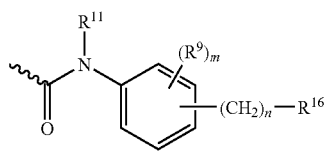
moiety is selected from the group consisting of:
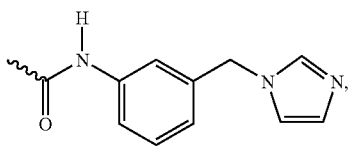
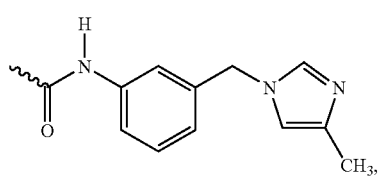
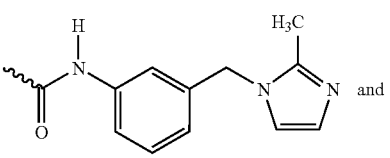 and
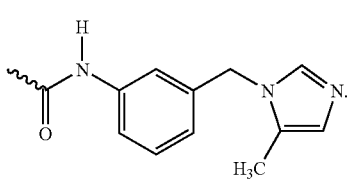

In another embodiment of the compounds of formula 1.0, (e.g., the (1) to (13) paragraph embodiment described above), the

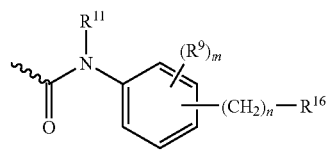

moiety is selected from the group consisting of:

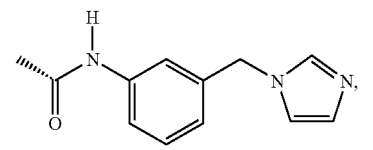

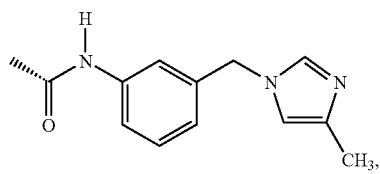

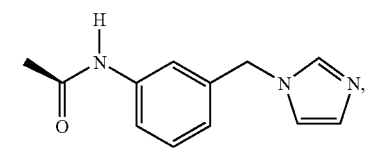

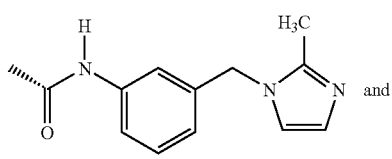

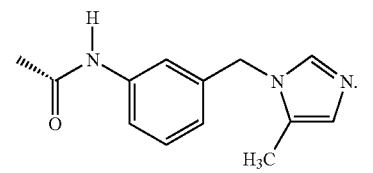

In another embodiment of the compounds of formula 1.0, (e.g., the (1) to (13) paragraph embodiment described above), the

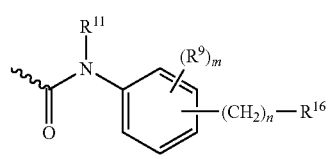

moiety is selected from the group consisting of:

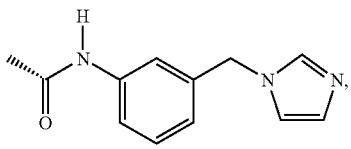

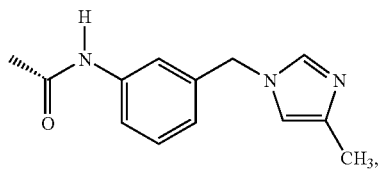

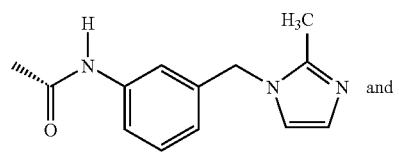

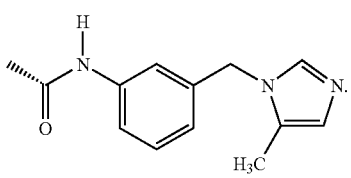

In another embodiment of the compounds of formula 1.0 (for example, the (1) to (13) paragraph embodiment described above), $R^8$ is selected from the group consisting of:

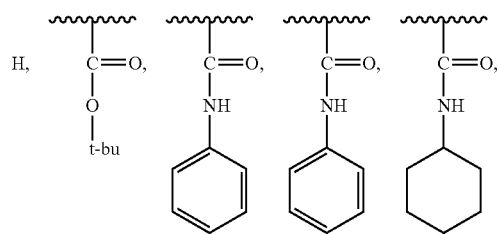

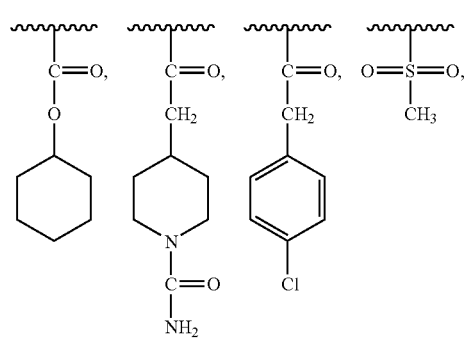

-continued
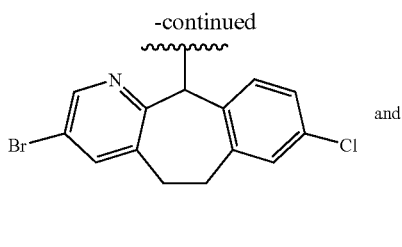
and
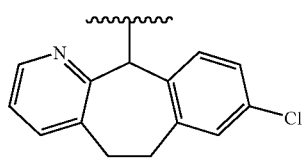
and the
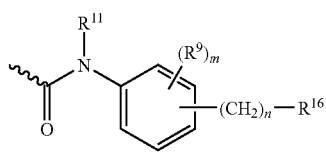
moiety is selected from the group consisting of:
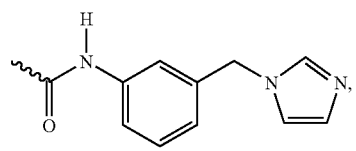
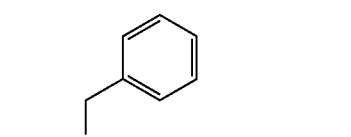
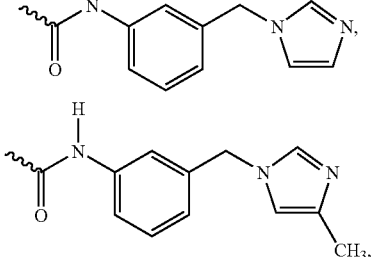
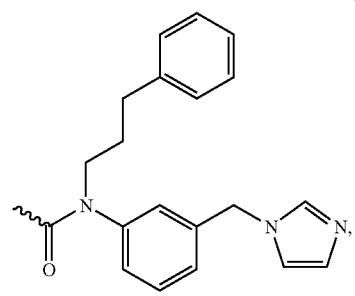
-continued
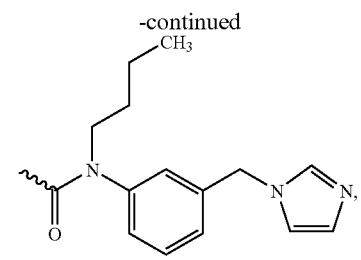
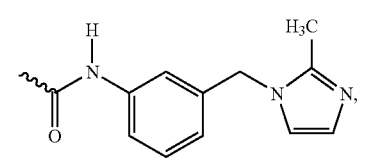
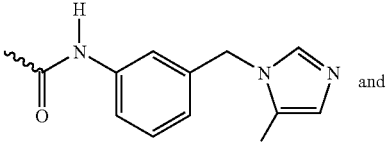
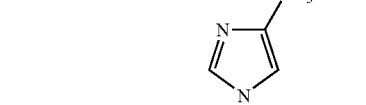
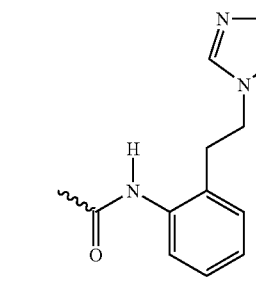
In another embodiment of the compounds of formula 1.0 (for example, the (1) to (13) paragraph embodiment described above), $R^8$ is selected from the group consisting of:
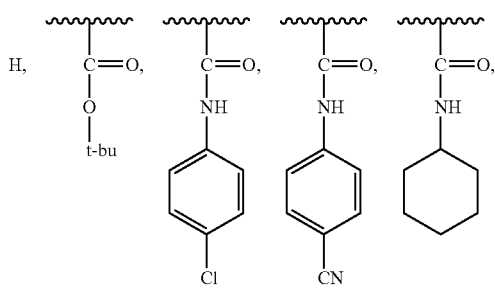

-continued
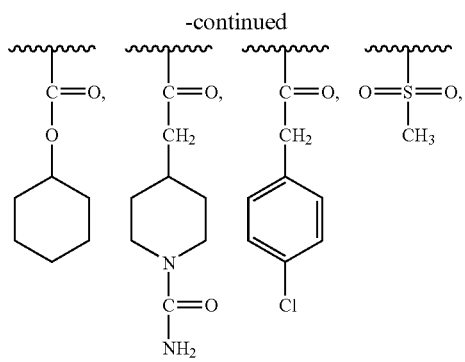
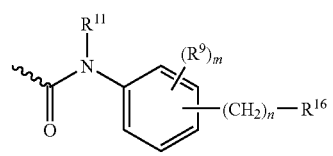
and the
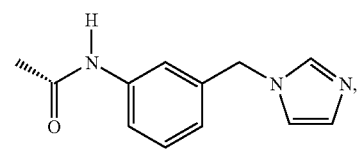
moiety is selected from the group consisting of:
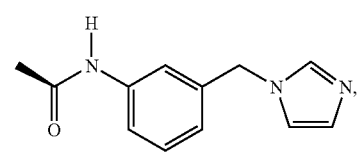
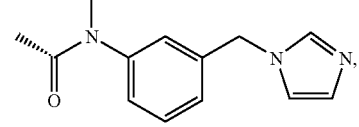
-continued
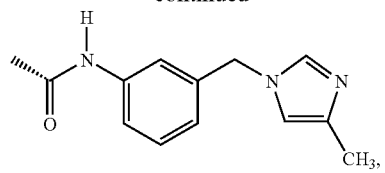
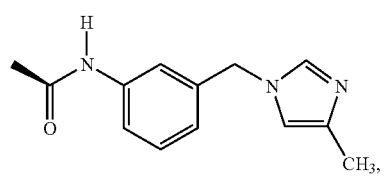
and
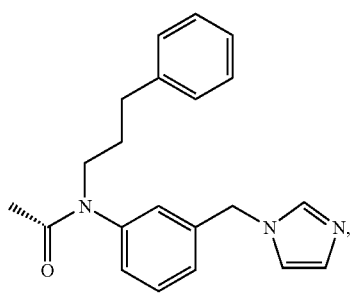
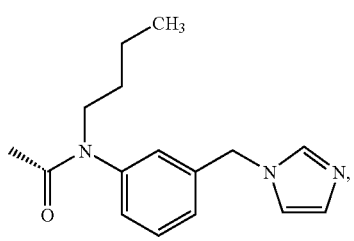
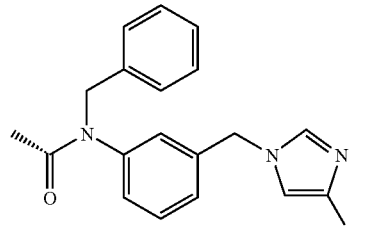
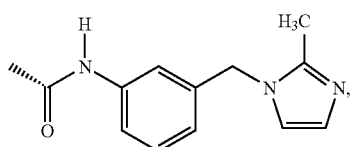
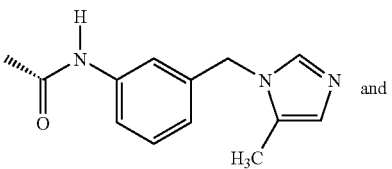
and -continued
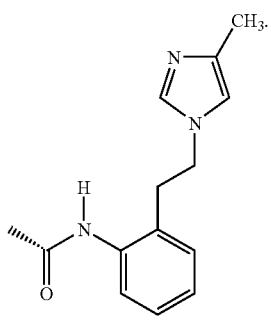
In another embodiment of the compounds of formula 1.0 (for example, the (1) to (13) paragraph embodiment described above), $R^8$ is selected from the group consisting of:
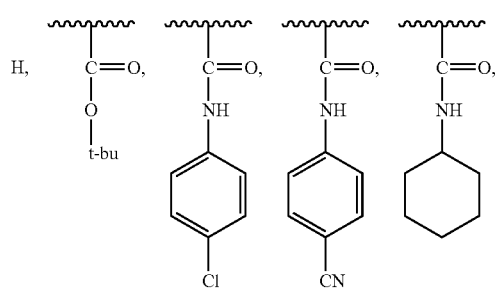
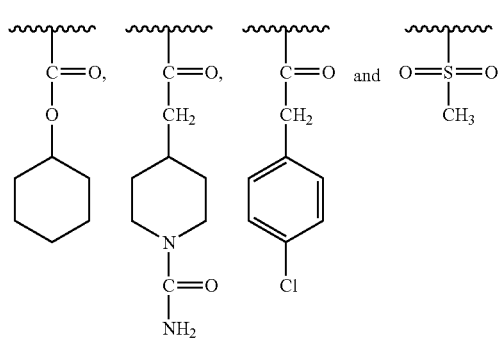
and the
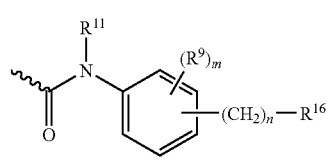
moiety is selected from the group consisting of:
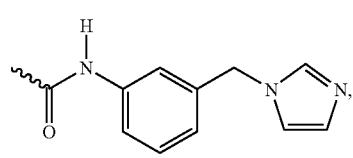
-continued
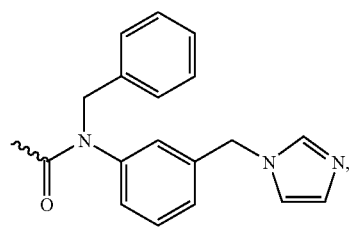
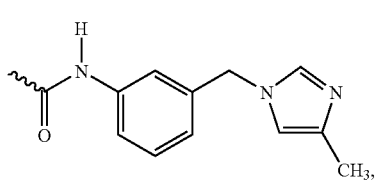
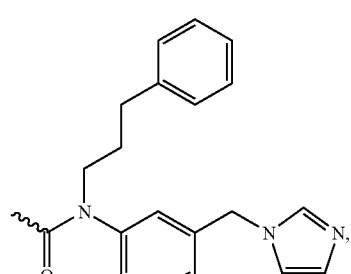
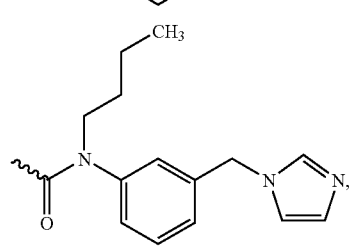
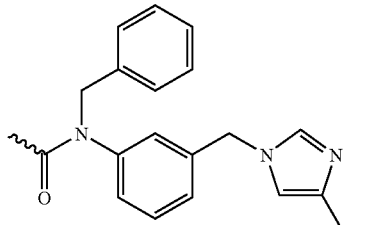
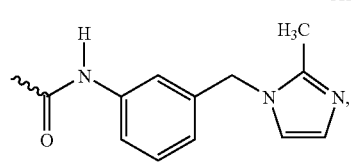
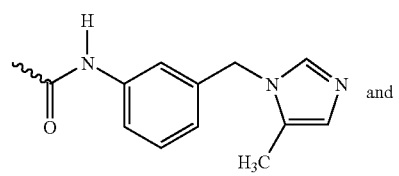 and

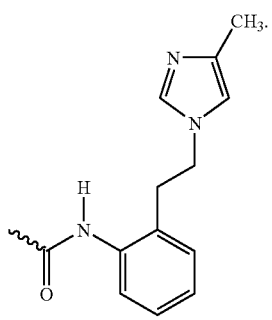
In another embodiment of the compounds of formula 1.0 (for example, the (1) to (13) paragraph embodiment described above), $R^8$ is selected from the group consisting of:
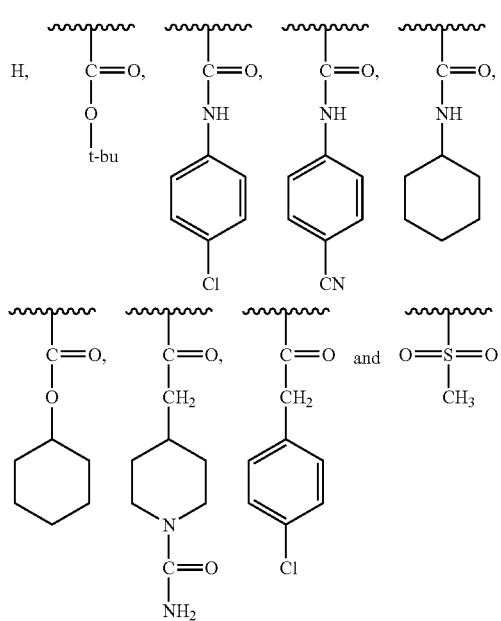
and the
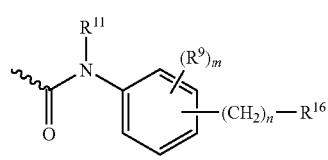
moiety is selected from the group consisting of:
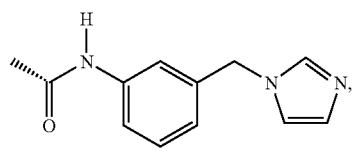
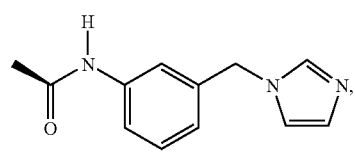
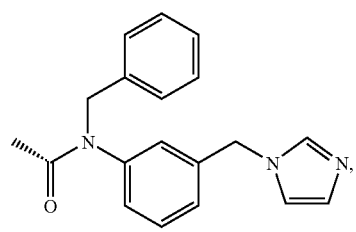
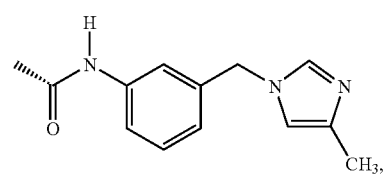
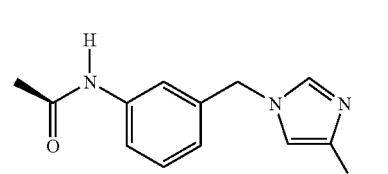
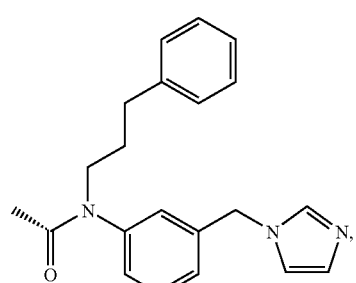
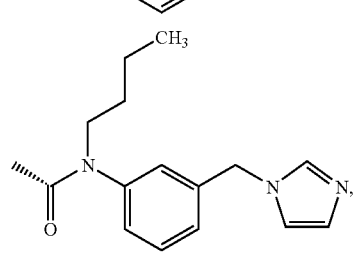
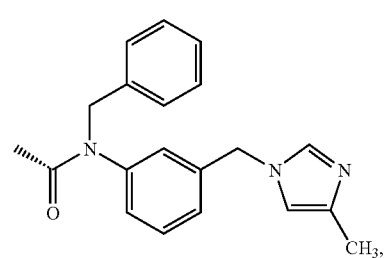

-continued

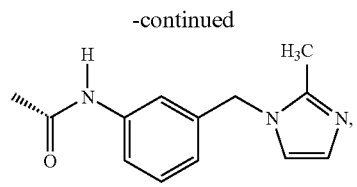

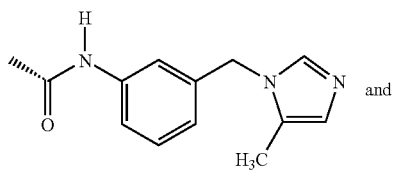

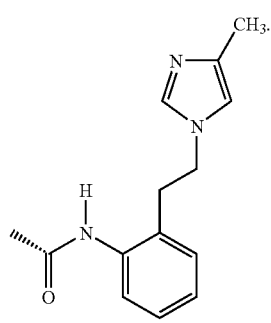

In another embodiment of the compounds of formula 1.0, (e.g., the (1) to (13) paragraph embodiment described above), the

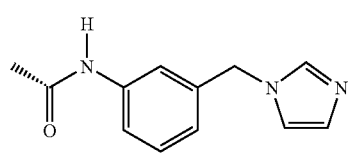

moiety is:

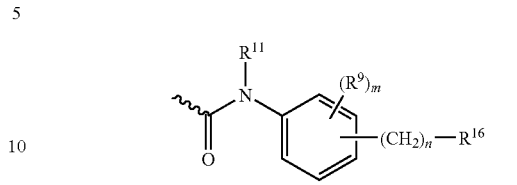

and the compound of formula 1.0 is a compound of formula 4.0.

In another embodiment of the compounds of formula 1.0, (e.g., the (1) to (13) paragraph embodiment described above), the

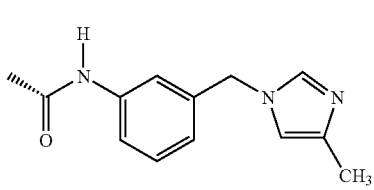

moiety is:

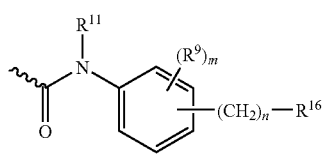

and the compound of formula 1.0 is a compound of formula 4.0.

In another embodiment of the compounds of formula 1.0, (e.g., the (1) to (13) paragraph embodiment described above), the

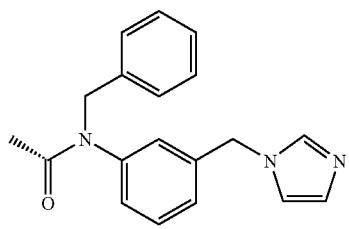

moiety is:

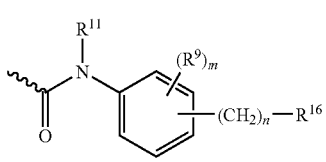

and the compound of formula 1.0 is a compound of formula 4.0.

In another embodiment of the compounds of formula 1.0, (e.g., the (1) to (13) paragraph embodiment described above), the moiety is:

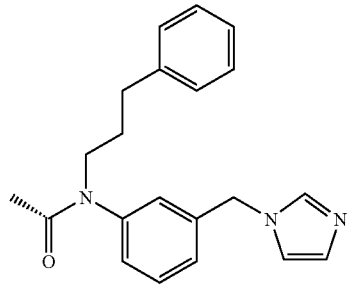

and the compound of formula 1.0 is a compound of formula 4.0.

In another embodiment of the compounds of formula 1.0, (e.g., the (1) to (13) paragraph embodiment described above), the

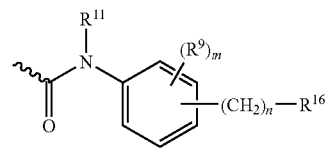

moiety is:

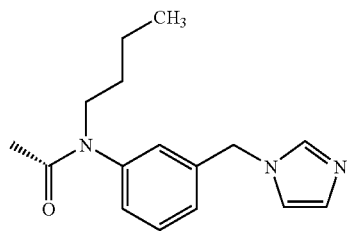

and the compound of formula 1.0 is a compound of formula 4.0.

In another embodiment of the compounds of formula 1.0, (e.g., the (1) to (13) paragraph embodiment described above), the

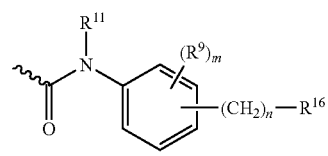

moiety is:

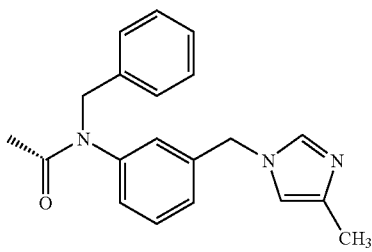

and the compound of formula 1.0 is a compound of formula 4.0.

In another embodiment of the compounds of formula 1.0, (e.g., the (1) to (13) paragraph embodiment described above), the

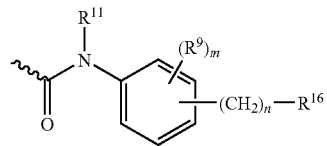

moiety is:

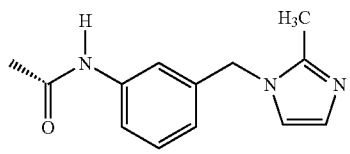

and the compound of formula 1.0 is a compound of formula 4.0.

In another embodiment of the compounds of formula 1.0, (e.g., the (1) to (13) paragraph embodiment described above), the

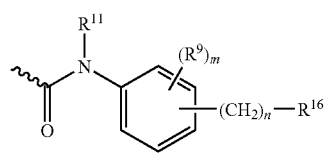

moiety is:

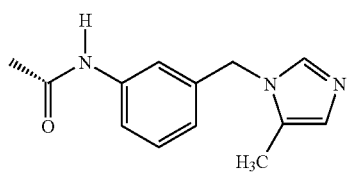

and the compound of formula 1.0 is a compound of formula 4.0.

In another embodiment of the compounds of formula 1.0, (e.g., the (1) to (13) paragraph embodiment described above), the

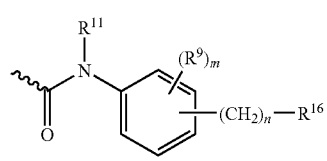

moiety is:

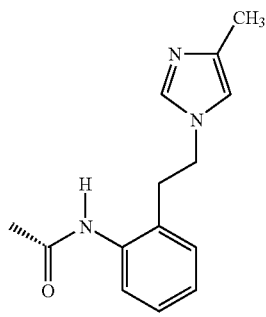

and the compound of formula 1.0 is a compound of formula 4.0.

In another embodiment of the compounds of formula 1.0, (e.g., the (1) to (13) paragraph embodiment described above), the

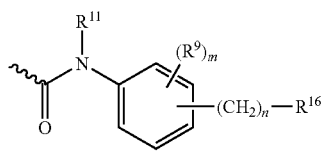

moiety is:

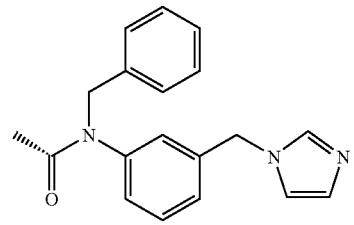

and the compound of formula 1.0 is a compound of formula 5.0.

In another embodiment of the compounds of formula 1.0, (e.g., the (1) to (13) paragraph embodiment described above), the

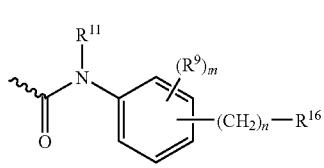

moiety is:

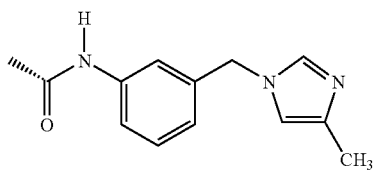

and the compound of formula 1.0 is a compound of formula 5.0.

In another embodiment of the compounds of formula 1.0, (e.g., the (1) to (13) paragraph embodiment described above), the

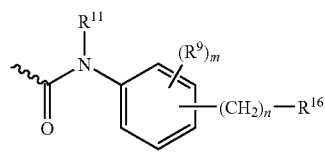

moiety is:

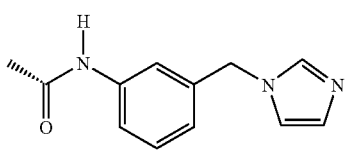

and the compound of formula 1.0 is a compound of formula 5.0.

In another embodiment of the compounds of formula 1.0, (e.g., the (1) to (13) paragraph embodiment described above), the

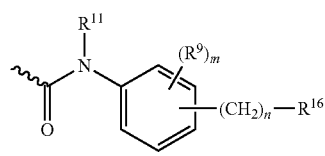

moiety is:

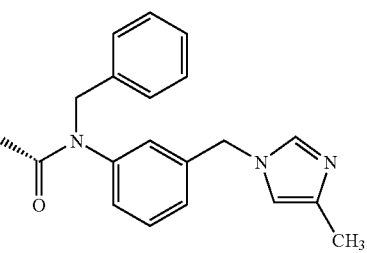

and the compound of formula 1.0 is a compound of formula 5.0.

In another embodiment of the compounds of formula 1.0, (e.g., the (1) to (13) paragraph embodiment described above), the

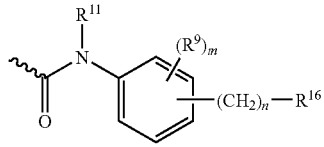

moiety is:

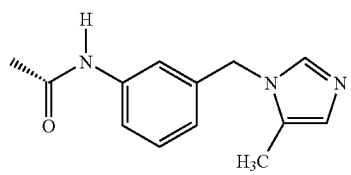

and the compound of formula 1.0 is a compound of formula 5.0.

In another embodiment of the compounds of formula 1.0, (e.g., the (1) to (13) paragraph embodiment described above), the

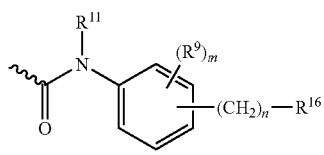

moiety is:

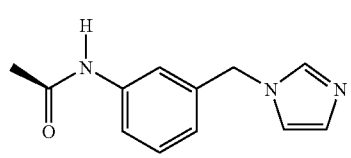

and the compound of formula 1.0 is a compound of formula 4.0A.

In another embodiment of the compounds of formula 1.0, (e.g., the (1) to (13) paragraph embodiment described above), the

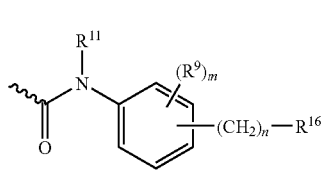

moiety is:

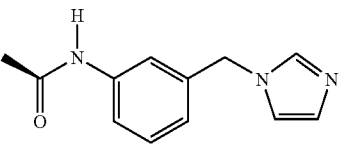

and the compound of formula 1.0 is a compound of formula 5.0A.

In another embodiment of the compounds of formula 1.0, (e.g., the (1) to (13) paragraph embodiment described above), the

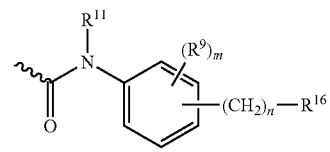

moiety is:

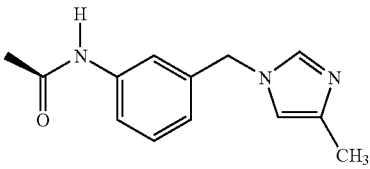

and the compound of formula 1.0 is a compound of formula 7.0A.

In another embodiment of the compounds of formula 1.0, (e.g., the (1) to (13) paragraph embodiment described above), the

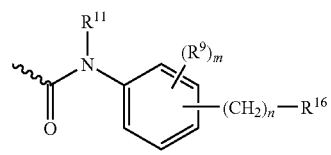

moiety is:

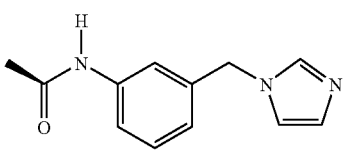

and the compound of formula 1.0 is a compound of formula 7.0A.

In another embodiment of the compounds of formula 1.0, (e.g., the (1) to (13) paragraph embodiment described above), the

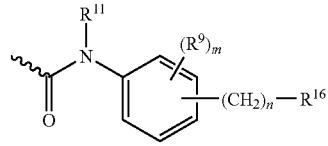

moiety is:

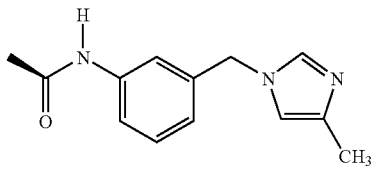

and the compound of formula 1.0 is a compound of formula 7.0B.

In another embodiment of the compounds of formula 1.0, (e.g., the (1) to (13) paragraph embodiment described above), the

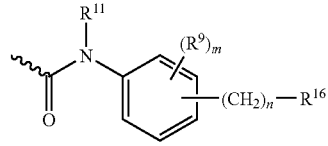

moiety is:

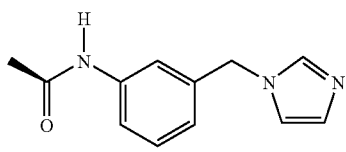

and the compound of formula 1.0 is a compound of formula 7.0B.

In another embodiment of the compounds of formula 1.0, (e.g., the (1) to (13) paragraph embodiment described above), the

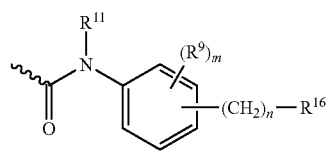

moiety is:

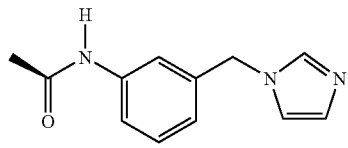

and the compound of formula 1.0 is a compound of formula 8.0B, 8.0D, 8.0F, or 8.0H.

In another embodiment of the compounds of formula 1.0, (e.g., the (1) to (13) paragraph embodiment described above), the

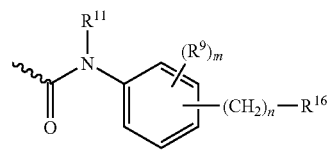

moiety is:

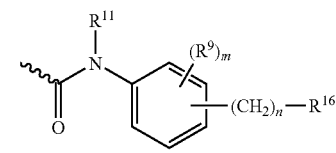

and the compound of formula 1.0 is a compound of formula 8.0A, 8.0C, 8.0E, or 8.0G.

In another embodiment of the compounds of formula 1.0, (e.g., the (1) to (13) paragraph embodiment described above), the

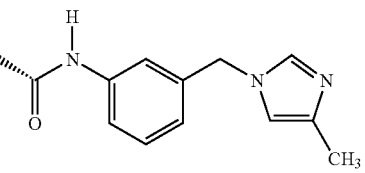

moiety is:

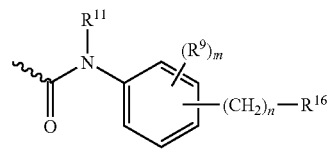

and the compound of formula 1.0 is a compound of formula 8.0A, 8.0C, 8.0E, or 8.0G.

In another embodiment of the compounds of formula 1.0, (e.g., the (1) to (13) paragraph embodiment described above), the

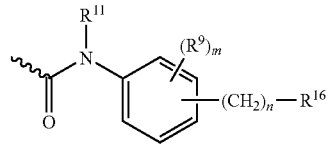

moiety is:

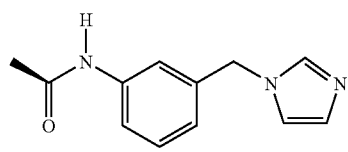

and the compound of formula 1.0 is a compound of formula 4.0A or 5.0A.

In another embodiment of the compounds of formula 1.0, (e.g., the (1) to (13) paragraph embodiment described above), the

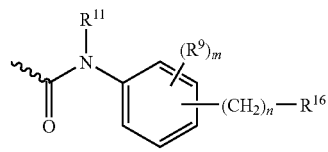

moiety is:

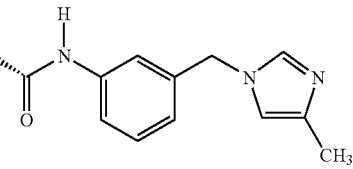

and the compound of formula 1.0 is a compound of formula 7.0A or 7.0B.

In another embodiment of the compounds of formula 1.0, (e.g., the (1) to (13) paragraph embodiment described above), the

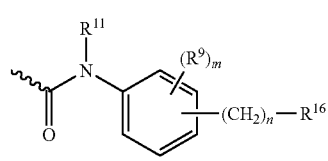

moiety is:

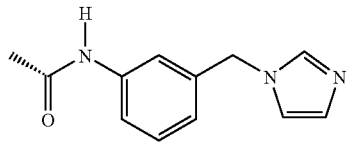

and the compound of formula 1.0 is a compound of formula 7.0.

In another embodiment of the compounds of formula 1.0, (e.g., the (1) to (13) paragraph embodiment described above), the

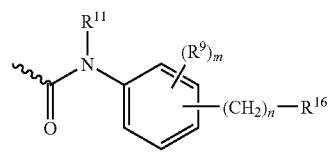

moiety is:

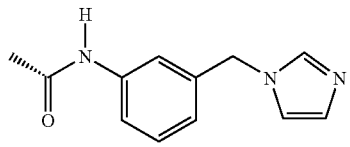

and the compound of formula 1.0 is a compound of formula 7.0C.

In another embodiment of the compounds of formula 1.0, (e.g., the (1) to (13) paragraph embodiment described above), $R^8$ is H.

In another embodiment of the compounds of formula 1.0, (e.g., the (1) to (13) paragraph embodiment described above), $R^8$ is

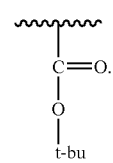

In another embodiment of the compounds of formula 1.0, (e.g., the (1) to (13) paragraph embodiment described above), $R^8$ is

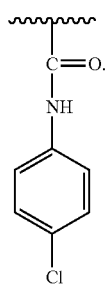

In another embodiment of the compounds of formula 1.0, (e.g., the (1) to (13) paragraph embodiment described above), $R^8$ is

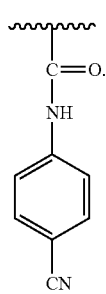

In another embodiment of the compounds of formula 1.0, (e.g., the (1) to (13) paragraph embodiment described above), $R^8$ is

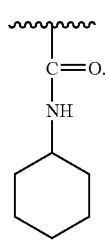

In another embodiment of the compounds of formula 1.0, (e.g., the (1) to (13) paragraph embodiment described above), $R^8$ is

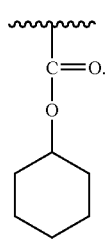

In another embodiment of the compounds of formula 1.0, (e.g., the (1) to (13) paragraph embodiment described above), $R^8$ is

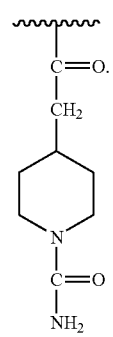

In another embodiment of the compounds of formula 1.0, (e.g., the (1) to (13) paragraph embodiment described above), $R^8$ is

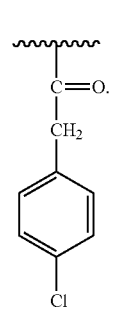

In another embodiment of the compounds of formula 1.0, (e.g., the (1) to (13) paragraph embodiment described above), $R^8$ is

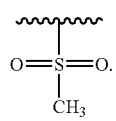

In another embodiment of the compounds of formula 1.0, (e.g., the (1) to (13) paragraph embodiment described above), $R^8$ is selected from the group consisting of:

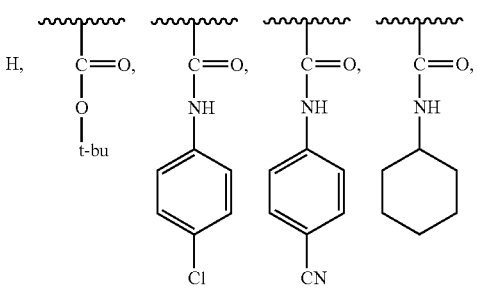

-continued

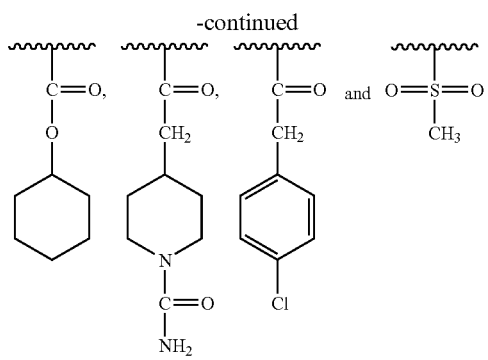

and the compound of formula 1.0 is a compound of formula 4.0.

In another embodiment of the compounds of formula 1.0, (e.g., the (1) to (13) paragraph embodiment described above), $R^8$ is selected from the group consisting of:

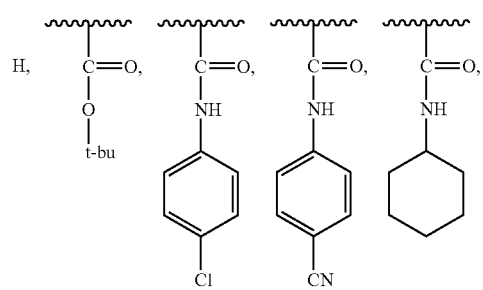

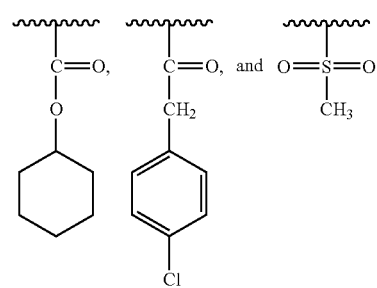

and the compound of formula 1.0 is a compound of formula 4.0.

In another embodiment of the compounds of formula 1.0, (e.g., the (1) to (13) paragraph embodiment described above), $R^8$ is selected from the group consisting of:

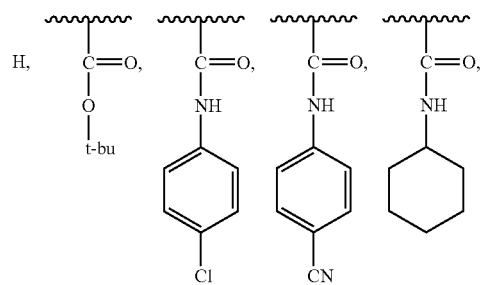

-continued

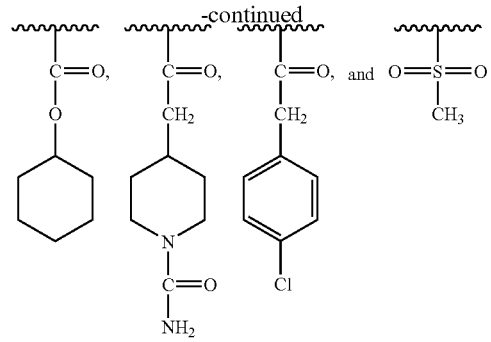

and the moiety

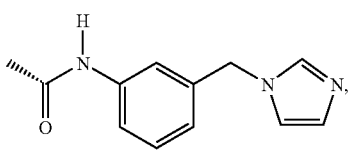

is selected from the group consisting of:

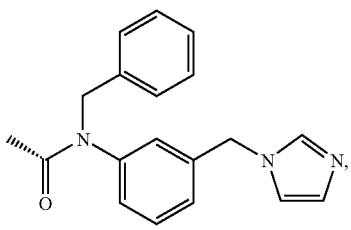

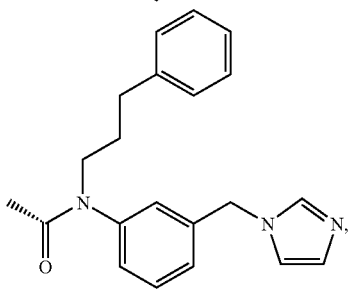

-continued
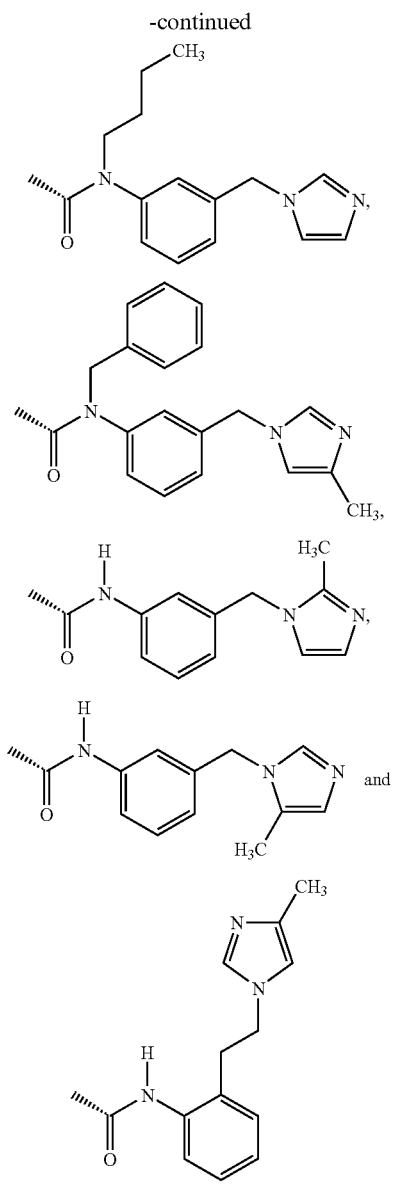
and
and the compound of formula 1.0 is a compound of formula 4.0.
In another embodiment of the compounds of formula 1.0, (e.g., the (1) to (13) paragraph embodiment described above), $R^8$ is selected from the group consisting of:
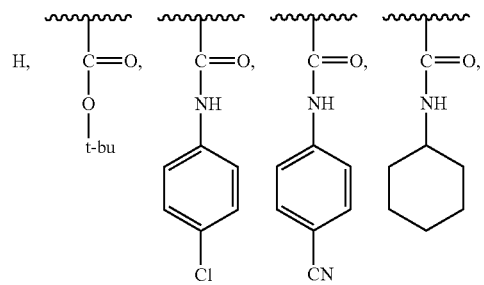
-continued
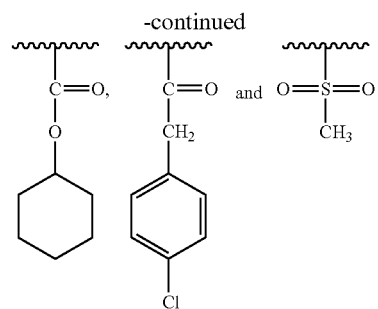
and the moiety
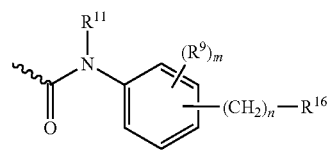
is selected from the group consisting of:
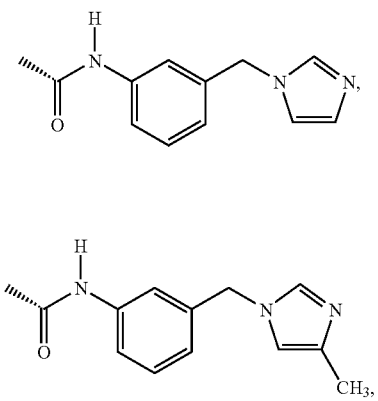
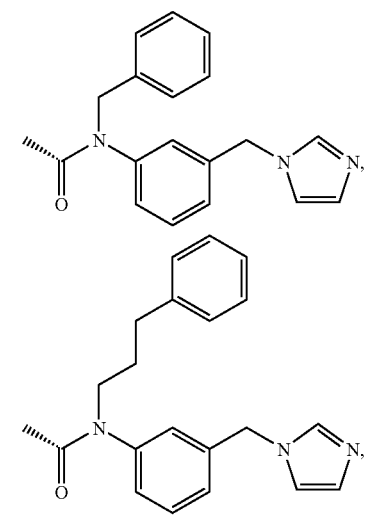

-continued
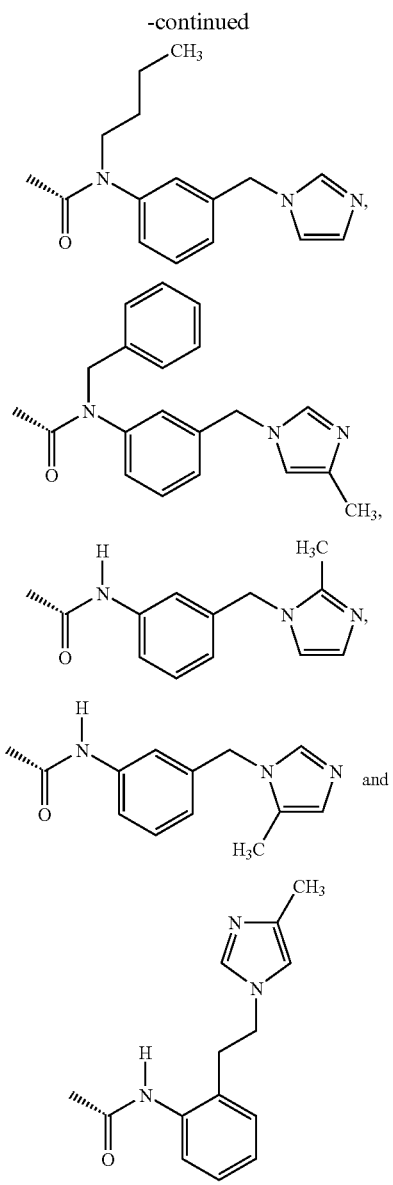
and the compound of formula 1.0 is a compound of formula 4.0.
In another embodiment of the compounds of formula 1.0, (e.g., the (1) to (13) paragraph embodiment described above), $R^8$ is selected from the group consisting of:
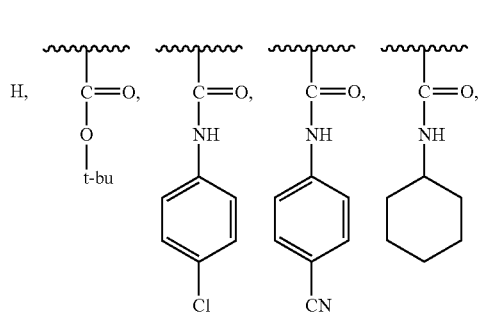
-continued
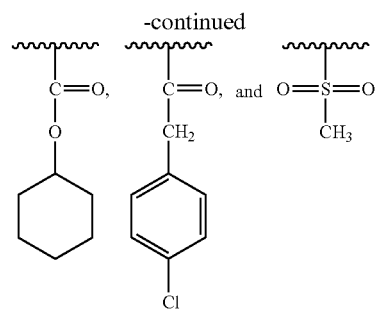
and the moiety
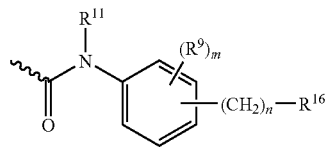
is selected from the group consisting of:
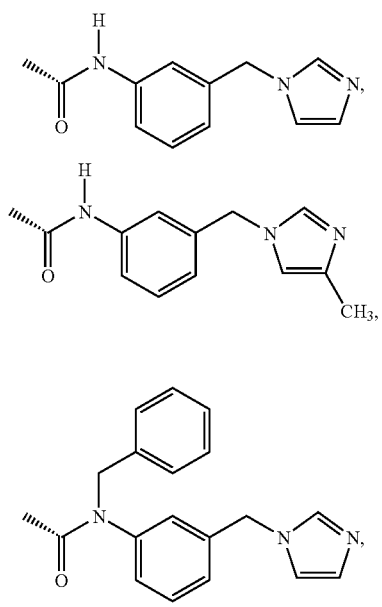
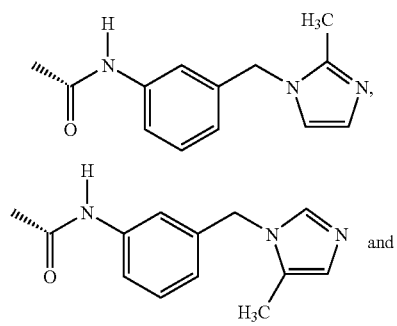

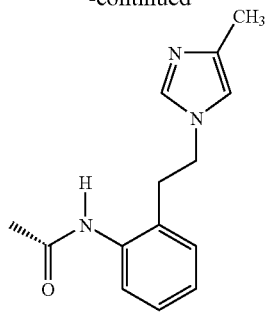

and the compound of formula 1.0 is a compound of formula 4.0.

In another embodiment of the compounds of formula 1.0, (e.g., the (1) to (13) paragraph embodiment described above), $R^8$ is selected from the group consisting of:

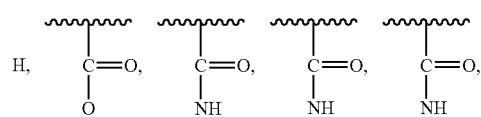

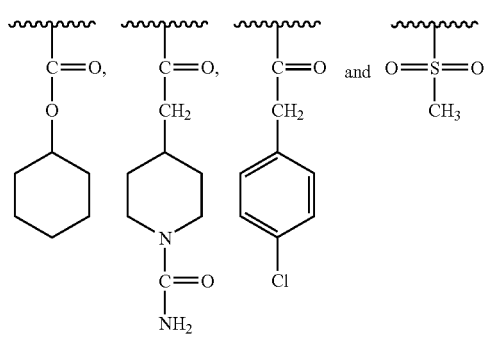

and the moiety

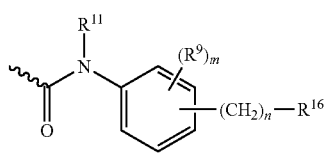

is selected from the group consisting of:

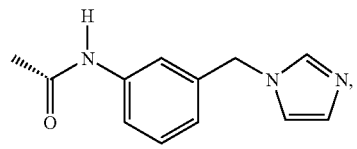

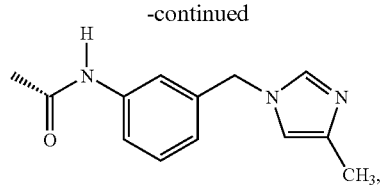

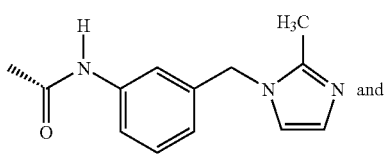

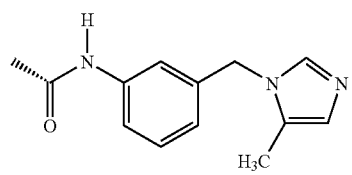

and the compound of formula 1.0 is a compound of formula 4.0.

In another embodiment of the compounds of formula 1.0, (e.g., the (1) to (13) paragraph embodiment described above), $R^8$ is selected from the group consisting of:

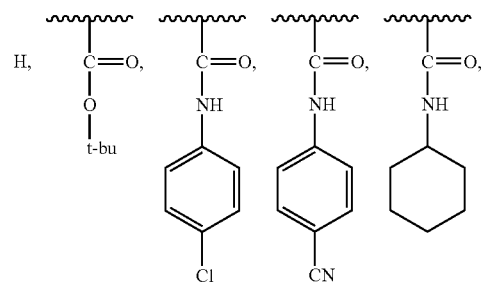

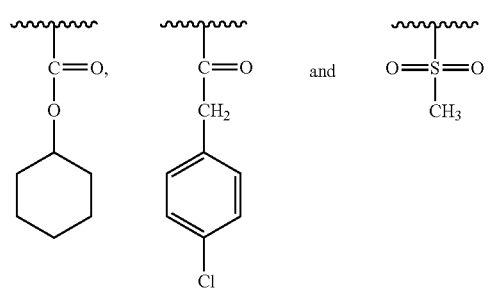

and the moiety

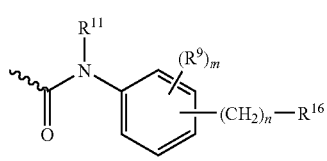

is selected from the group consisting of:

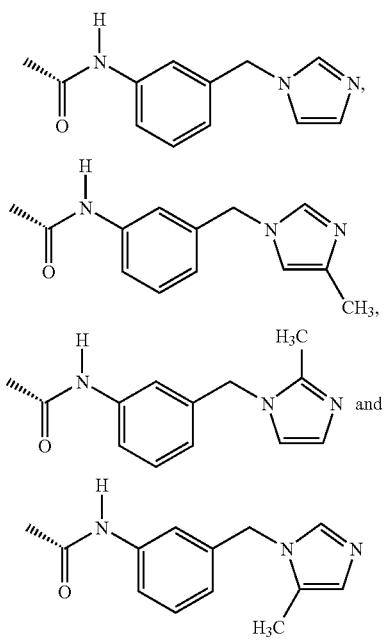

and the compound of formula 1.0 is a compound of formula 4.0.

In another embodiment of the compounds of formula 1.0, (e.g., the (1) to (13) paragraph embodiment described above), $R^8$ is selected from the group consisting of:

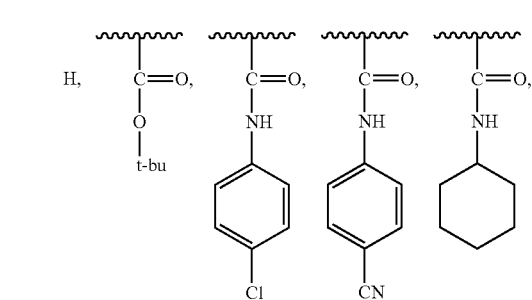

and the compound of formula 1.0 is a compound of formula 5.0.

In another embodiment of the compounds of formula 1.0, (e.g., the (1) to (13) paragraph embodiment described above), $R^8$ is selected from the group consisting of:

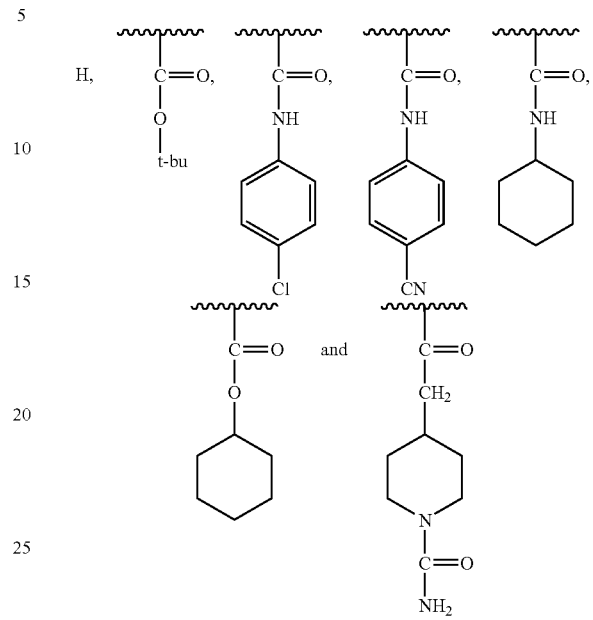

and the compound of formula 1.0 is a compound of formula 5.0.

In another embodiment of the compounds of formula 1.0, (e.g., the (1) to (13) paragraph embodiment described above), $R^8$ is selected from the group consisting of:

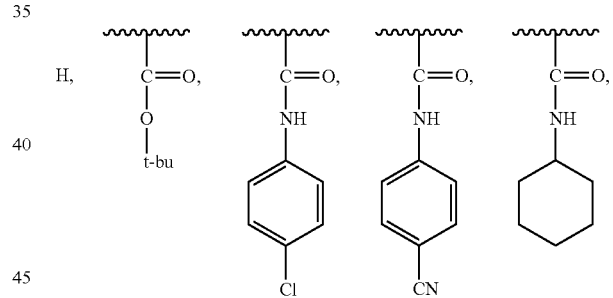

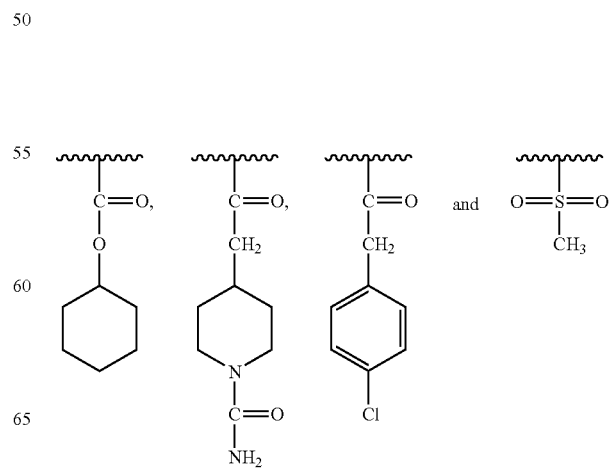

and the moiety
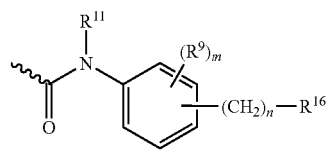
is selected from the group consisting of:
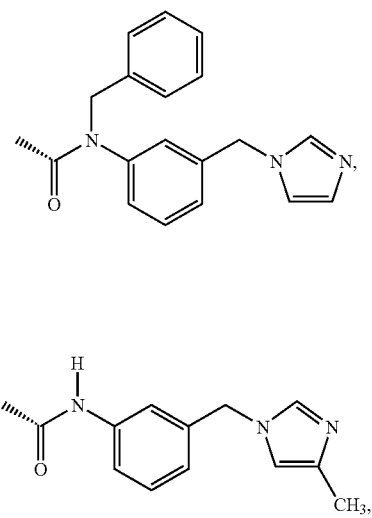
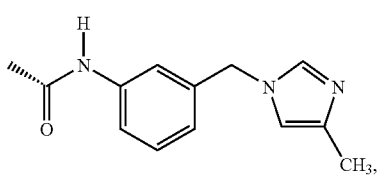
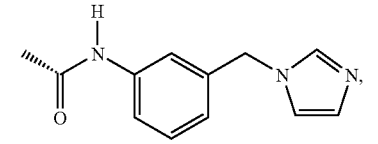
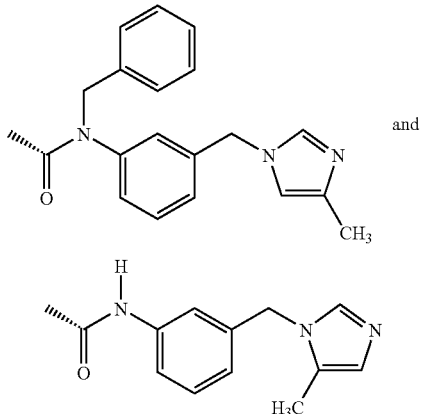
and the compound of formula 1.0 is a compound of formula 5.0.
In another embodiment of the compounds of formula 1.0, (e.g., the (1) to (13) paragraph embodiment described above), $R^8$ is selected from the group consisting of:
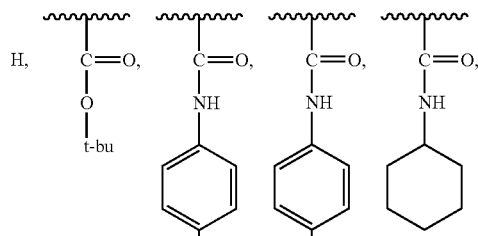
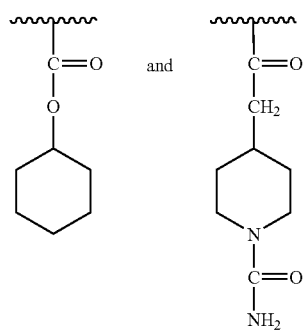
and the moiety
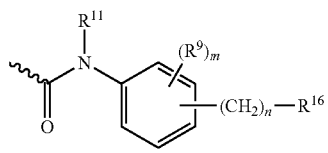
is selected from the group consisting of:
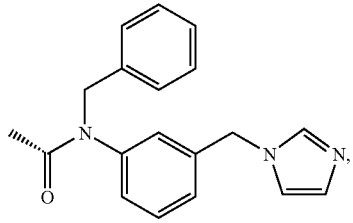
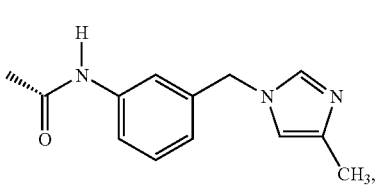

-continued

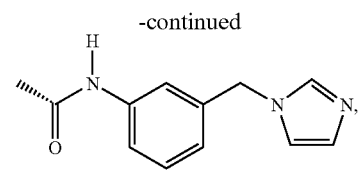

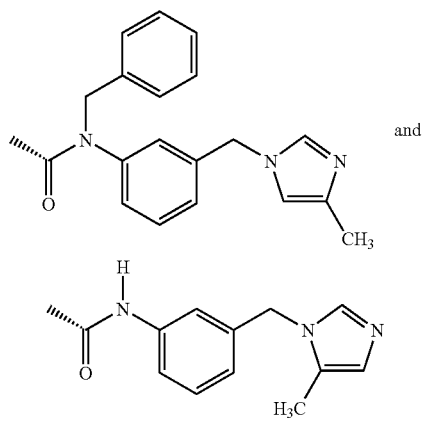

and the compound of formula 1.0 is a compound of formula 5.0.

In another embodiment of the compounds of formula 1.0, (e.g., the (1) to (13) paragraph embodiment described above), $R^8$ is selected from the group consisting of:

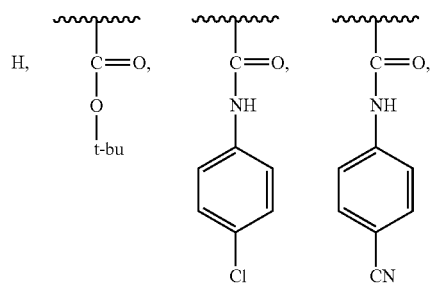

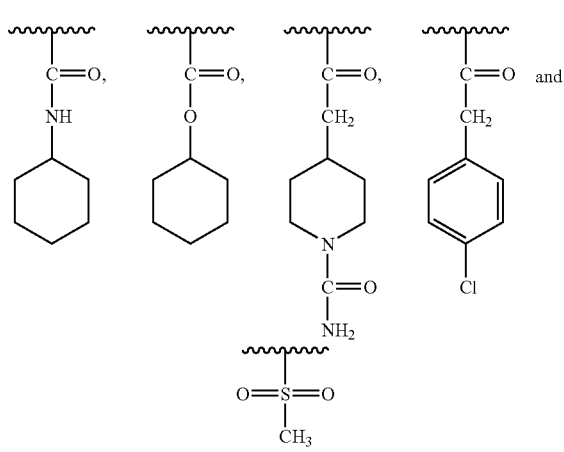

and the moiety

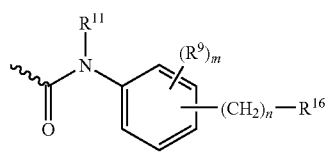

is selected from the group consisting of:

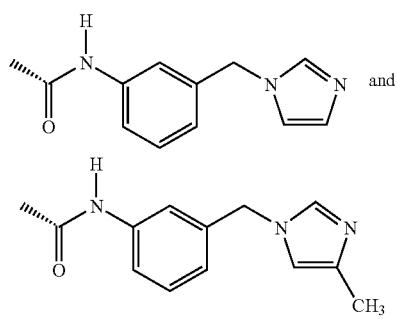

and the compound of formula 1.0 is a compound of formula 5.0.

In another embodiment of the compounds of formula 1.0, (e.g., the (1) to (13) paragraph embodiment described above), $R^8$ is selected from the group consisting of:

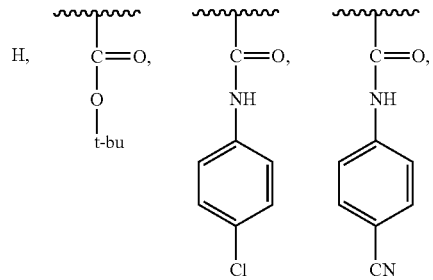

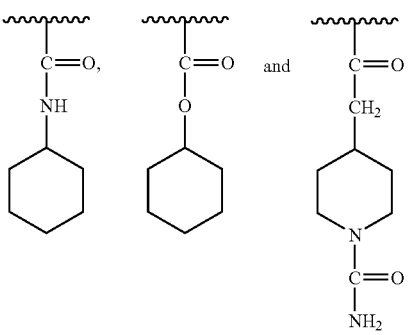

and the moiety

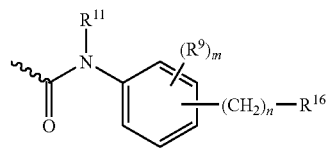

is selected from the group consisting of:

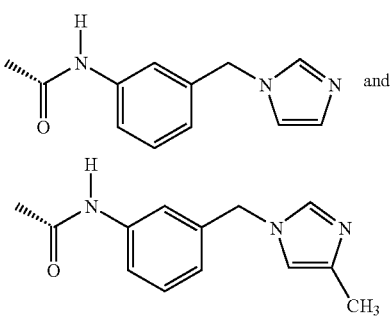

and the compound of formula 1.0 is a compound of formula 5.0.

In another embodiment of the compounds of formula 1.0, (e.g., the (1) to (13) paragraph embodiment described above), $R^8$ is

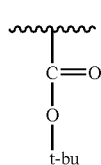

and the moiety

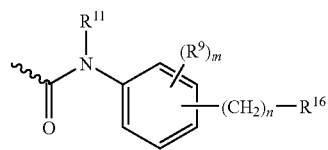

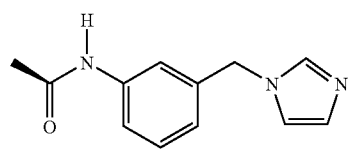

and the compound of formula 1.0 is a compound of formula 4.0A.

In another embodiment of the compounds of formula 1.0, (e.g., the (1) to (13) paragraph embodiment described above), $R^8$ is

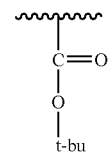

and the moiety

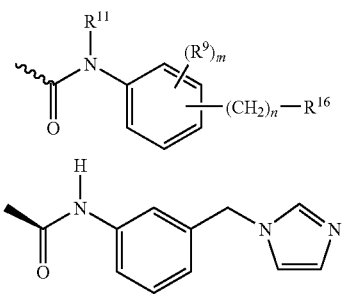

and the compound of formula 1.0 is a compound of formula 5.0A.

In another embodiment of the compounds of formula 1.0, (e.g., the (1) to (13) paragraph embodiment described above), $R^8$ is selected from the group consisting of:

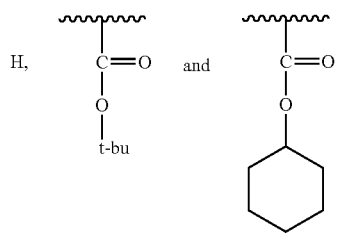

and the moiety

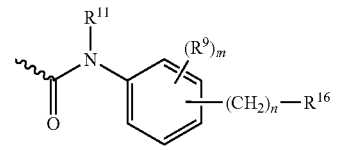

is selected from the group consisting of:

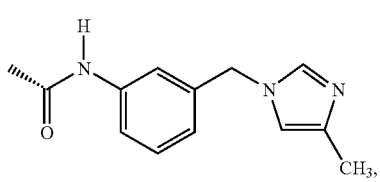

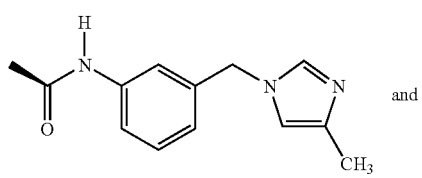 and

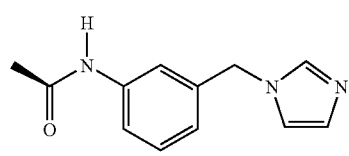

and the compound of formula 1.0 is a compound of formula 7.0A or 7.0B.

In another embodiment of the compounds of formula 1.0, (e.g., the (1) to (13) paragraph embodiment described above), $R^8$ is selected from the group consisting of:

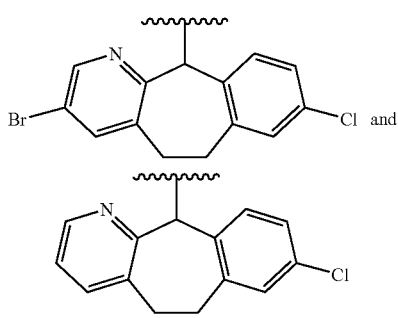

and the moiety

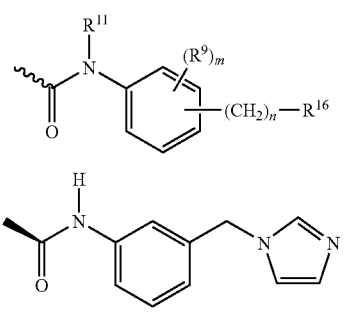

and the compound of formula 1.0 is a compound of formula 8.0B, 8.0D, 8.0F or 8.0H.

In another embodiment of the compounds of formula 1.0, (e.g., the (1) to (13) paragraph embodiment described above), $R^8$ is selected from the group consisting of:

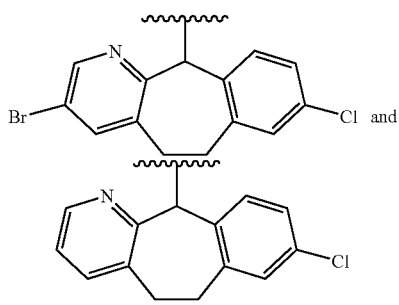

and the moiety

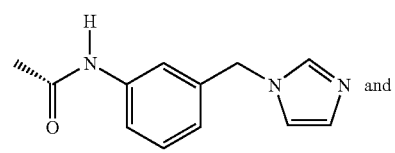

is selected from the group consisting of:

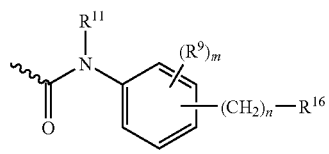

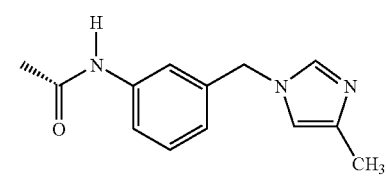

and the compound of formula 1.0 is a compound of formula 8.0A, 8.0C, 8.0E or 8.0G.

In another embodiment of the compounds of formula 1.0, (e.g., the (1) to (13) paragraph embodiment described above), $R^8$ is selected from the group consisting of:

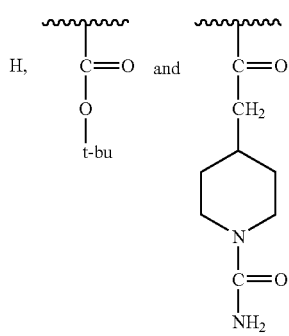

and the moiety

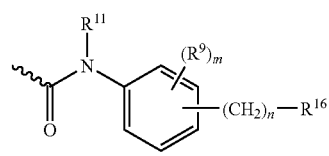

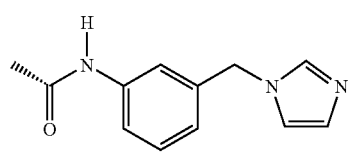

and the compound of formula 1.0 is a compound of formula 7.0.

In another embodiment of the compounds of formula 1.0, (e.g., the (1) to (13) paragraph embodiment described above), $R^8$ is selected from the group consisting of:

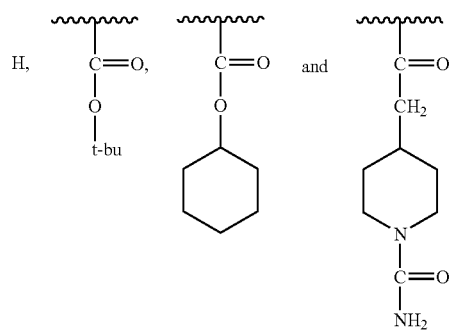

and the moiety

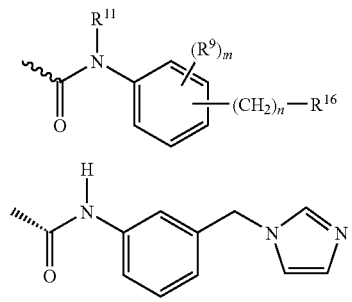

and the compound of formula 1.0 is a compound of formula 7.0.

Another embodiment of this invention is directed to compounds of the formula

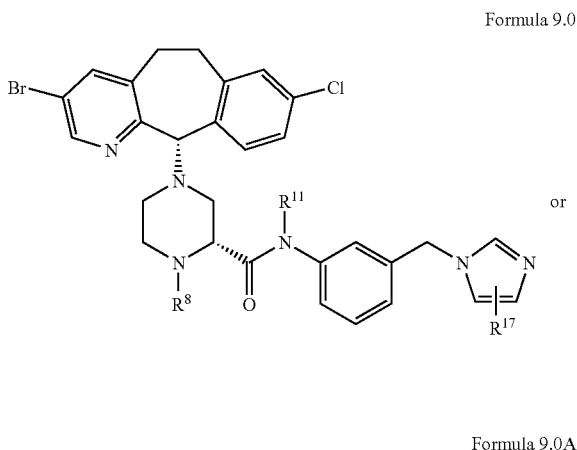

wherein:

$R^8$ is selected from the group consisting of:

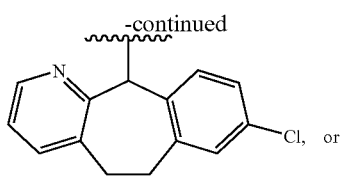

$R^8$, in yet another embodiment, is selected from the group consisting of:

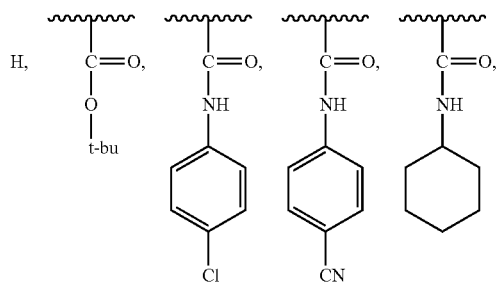

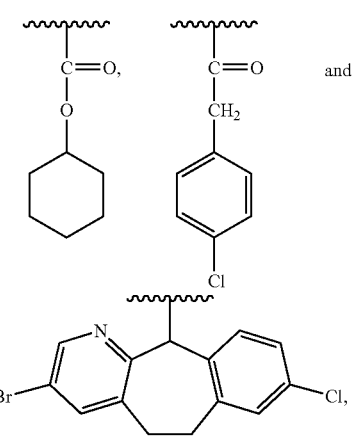

$R^8$, in yet another embodiment, is selected from the group consisting of:

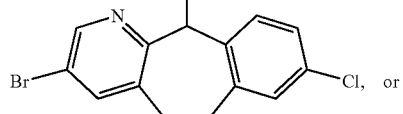

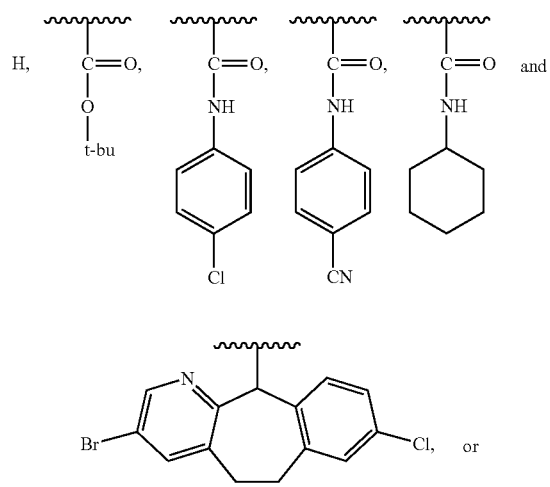

$R^8$, in yet another embodiment, is selected from the group consisting of:

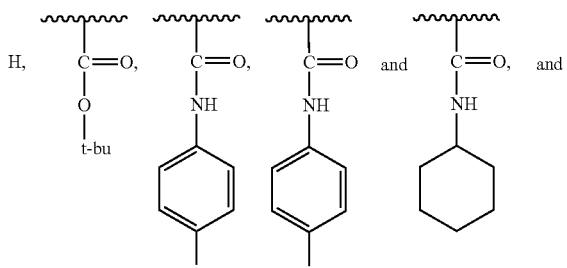

$R^{11}$ is selected from the group consisting of: H and benzyl (and preferably H), and $R^{17}$ is methyl wherein said methyl is bound to the C-4 position of the imidazolyl ring (i.e., 4-methyl).

Another embodiment of this invention is directed to compounds of the formula

Formula 9.0

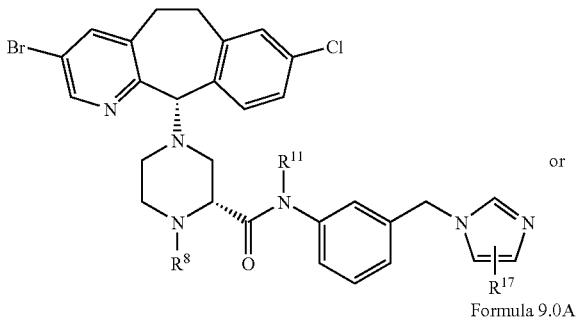

Formula 9.0A wherein:

$R^8$ is selected from the group consisting of:

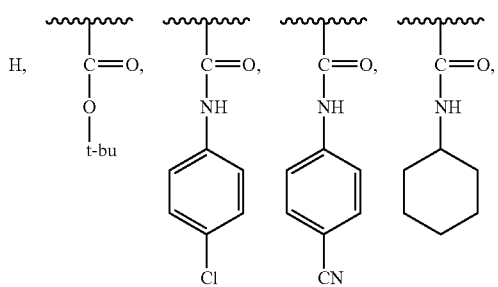

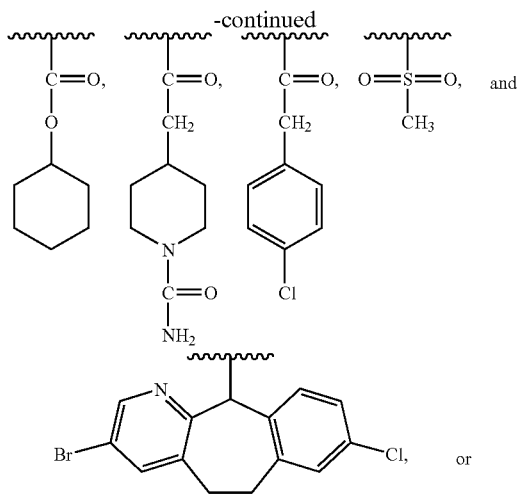

$R^8$, in yet another embodiment, is selected from the group consisting of:

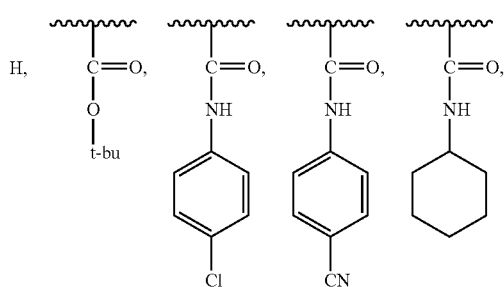

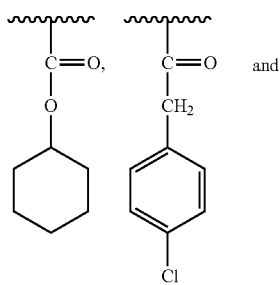

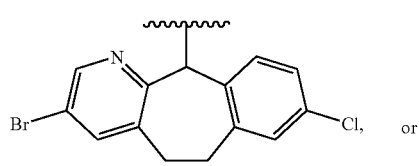

$R^8$, in yet another embodiment, is selected from the group consisting of:

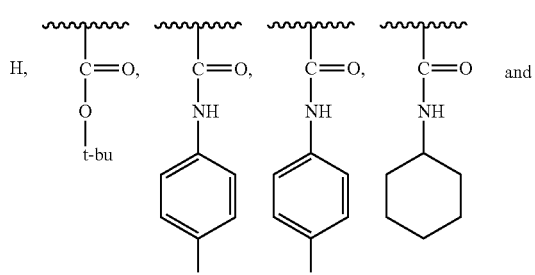

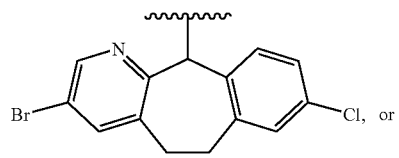

$R^8$, in yet another embodiment, is selected from the group consisting of:

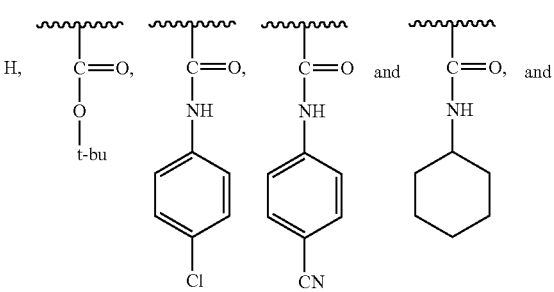

$R^{11}$ is H; and $R^{17}$ is methyl wherein said methyl is bound to the C-4 position of the imidazolyl ring (i.e., 4-methyl).

Another embodiment of this invention is directed to compounds of the formula

Formula 10.0

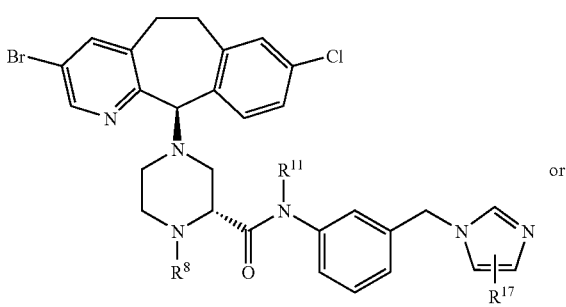

or

-continued
Formula 10.0A
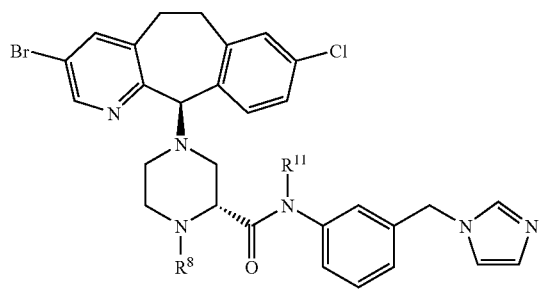
wherein:
R[8] is selected from the group consisting of:
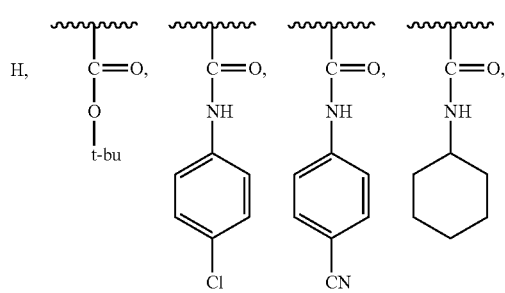
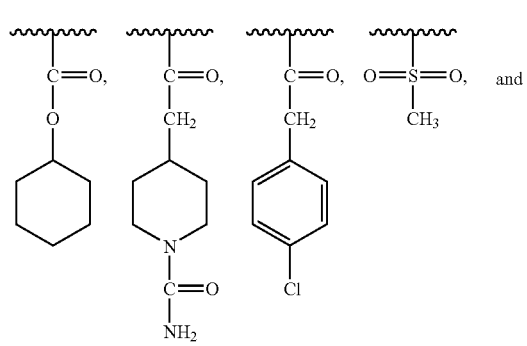
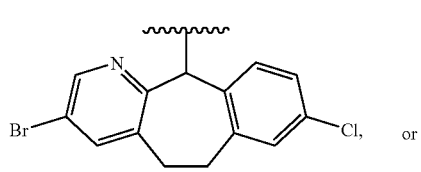
R[8], in yet another embodiment, is selected from the group consisting of:
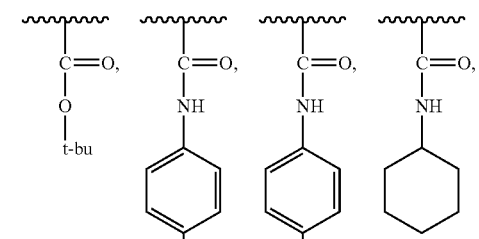
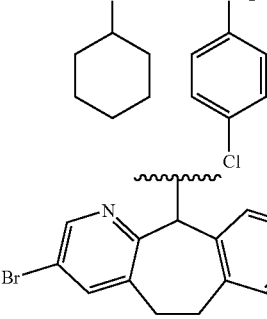
, or
R[8], in yet another embodiment, is selected from the group consisting of:
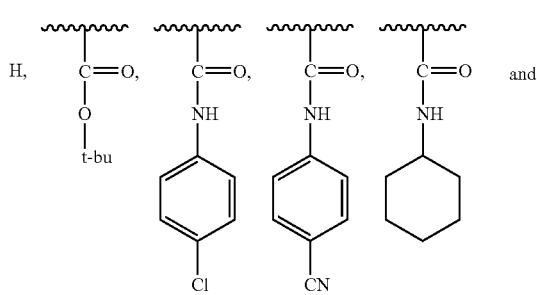
, or
R[8], in yet another embodiment, is selected from the group consisting of:
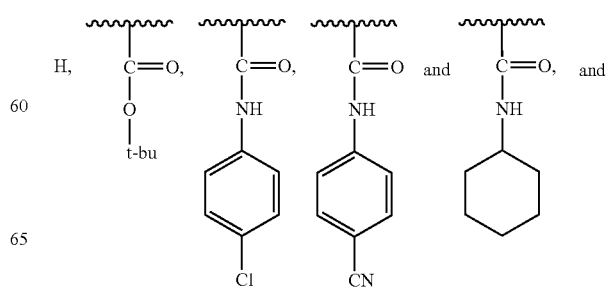
and $R^{11}$ is selected from the group consisting of: H and benzyl (and preferably H), and $R^{17}$ is methyl wherein said methyl is bound to the C-4 position of the imidazolyl ring (i.e., 4-methyl).

Another embodiment of this invention is directed to compounds of the formula

Formula 11

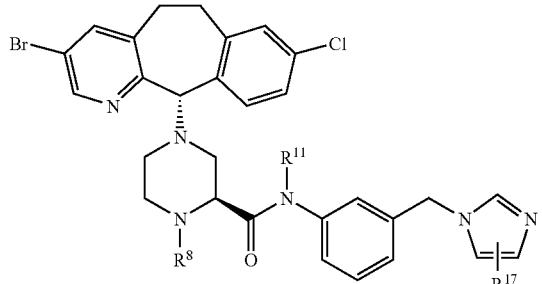

or

Formula 11.0A

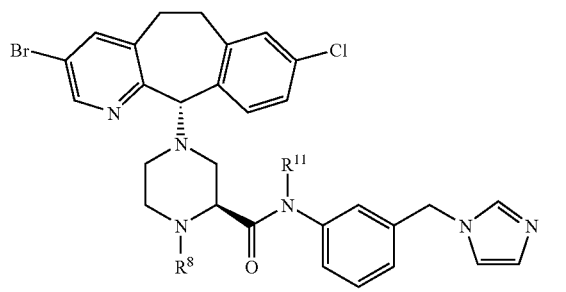

wherein:

$R^8$ is selected from the group consisting of:

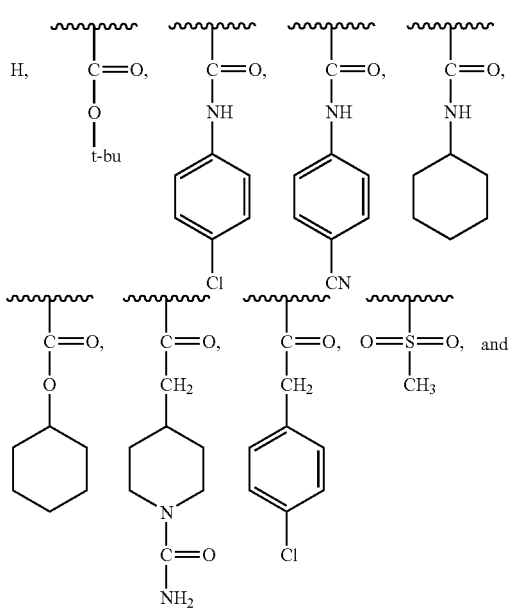

-continued

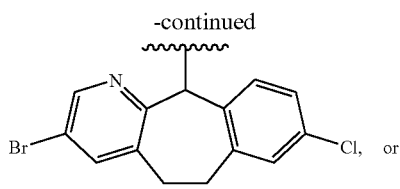

$R^8$, in yet another embodiment, is selected from the group consisting of:

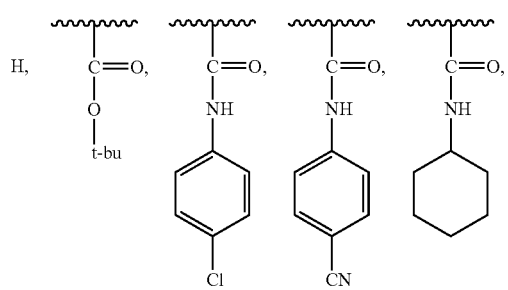

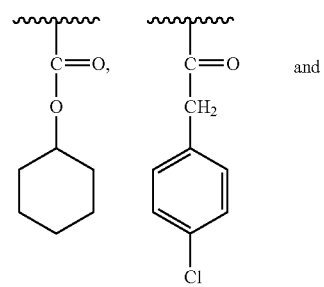

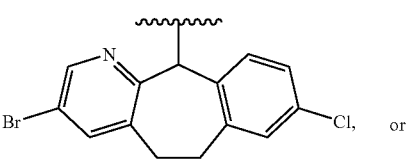

$R^8$, in yet another embodiment, is selected from the group consisting of:

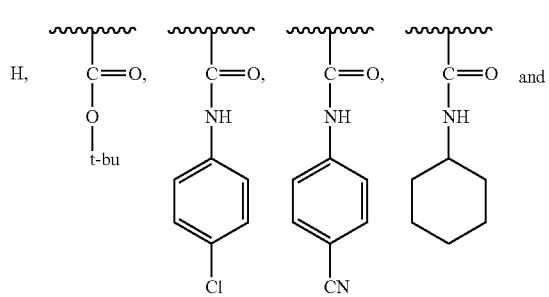

-continued

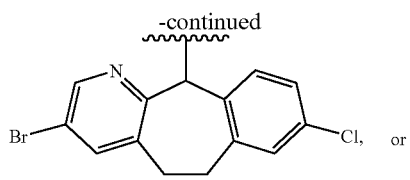

$R^8$, in yet another embodiment, is selected from the group consisting of:

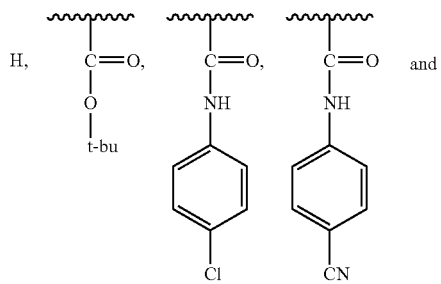

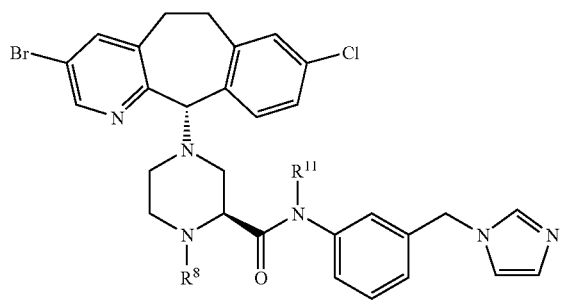

$R^{11}$ is selected from the group consisting of: H and benzyl (and preferably H), and $R^{17}$ is methyl wherein said methyl is bound to the C-4 position of the imidazolyl ring (i.e., 4-methyl).

Another embodiment of this invention is directed to compounds of the formula

Formula 11.0A

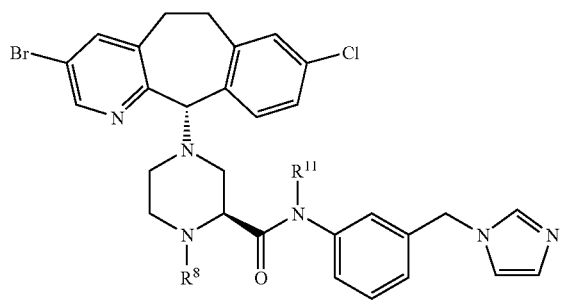

wherein:
$R^8$ is selected from the group consisting of:

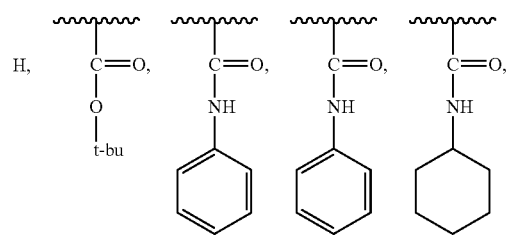

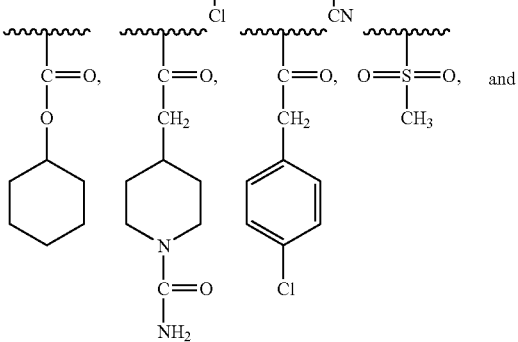

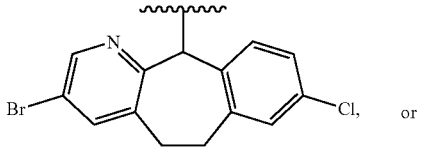

$R^8$, in yet another embodiment, is selected from the group consisting of:

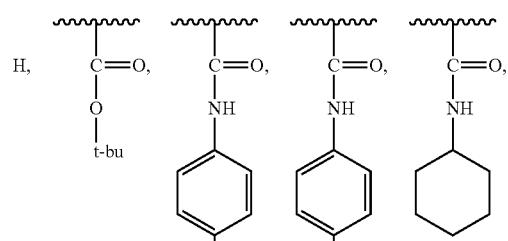

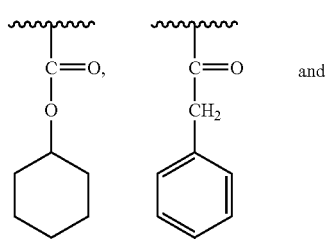

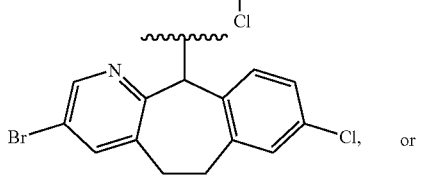

$R^8$, in yet another embodiment, is selected from the group consisting of:

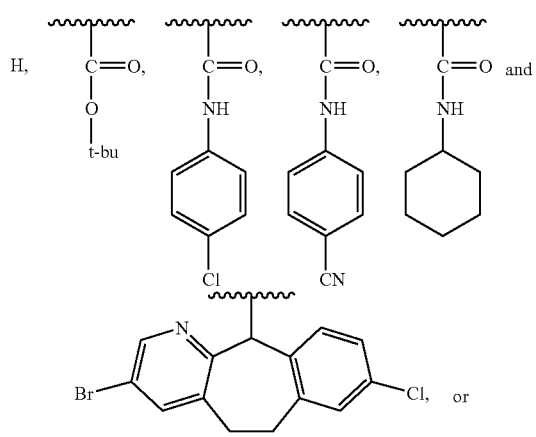

$R^8$, in yet another embodiment, is selected from the group consisting of:

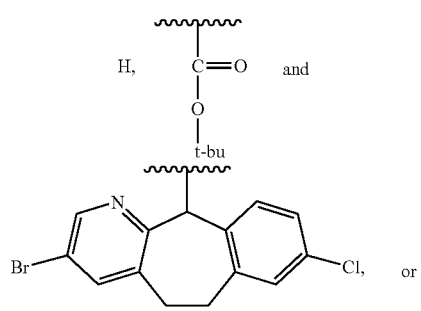

$R^8$ in yet another embodiment, is selected from the group consisting of:

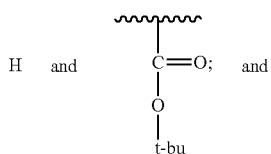

$R^{11}$ is H.

Another embodiment of this invention is directed to compounds of the formula

Formula 12.0

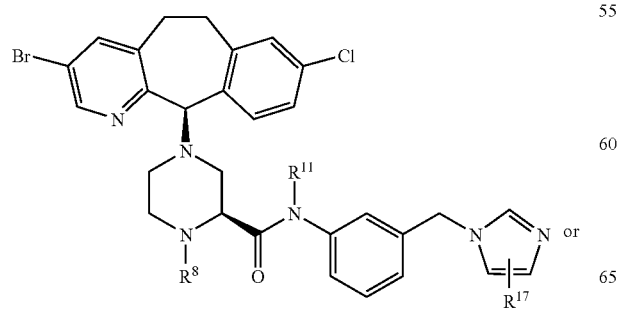

-continued

Formula 12.0A

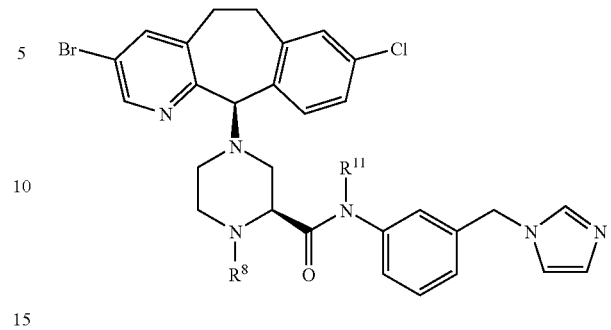

wherein:

$R^8$ is selected from the group consisting of:

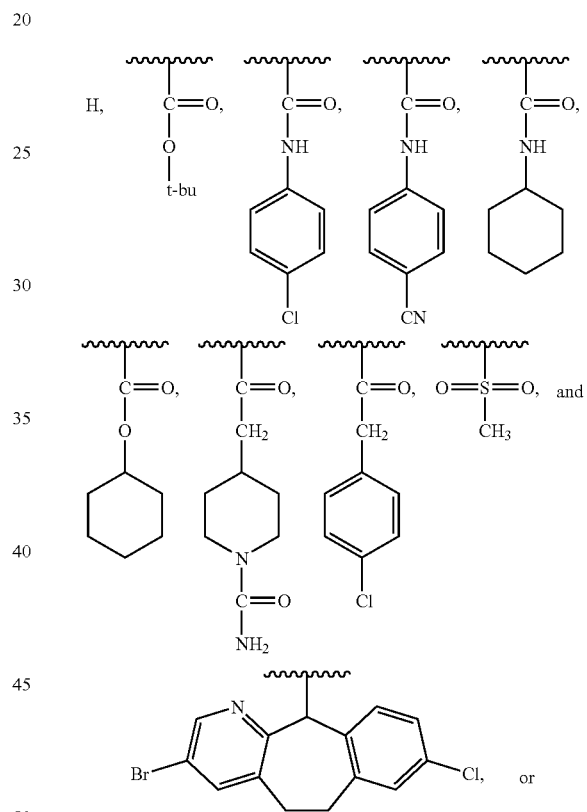

$R^8$ in yet another embodiment, is selected from the group consisting of:

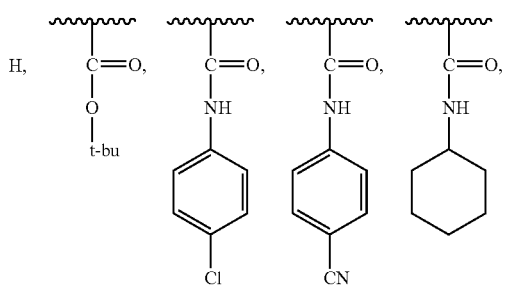

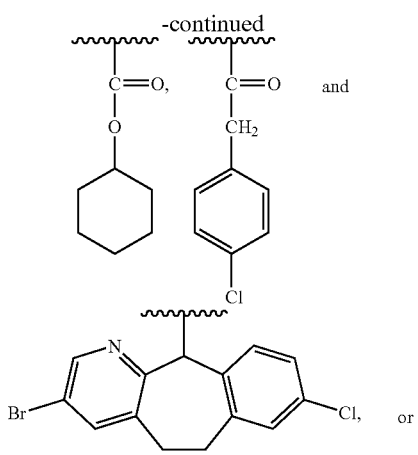

R[8], in yet another embodiment, is selected from the group consisting of:

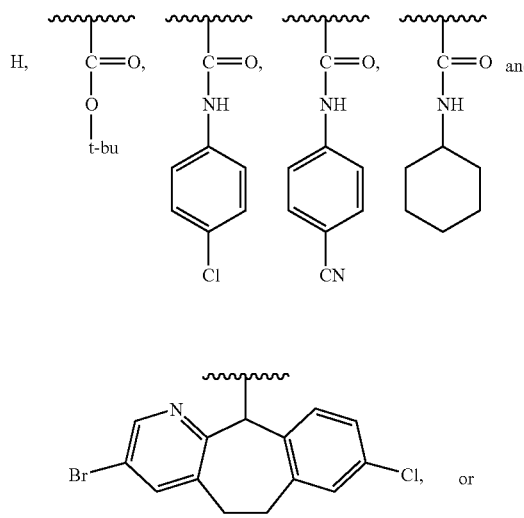

R[8], in yet another embodiment, is selected from the group consisting of:

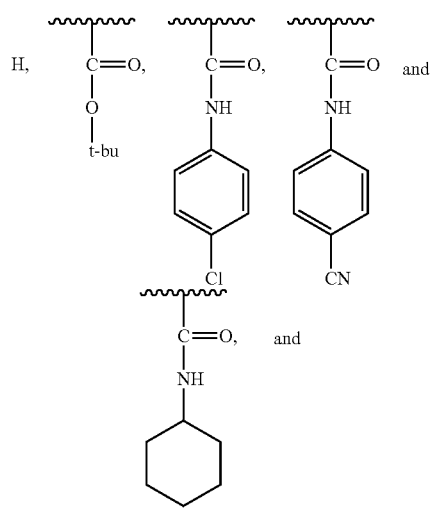

R[11] is selected from the group consisting of: H and benzyl (and preferably H); and R[17] is methyl wherein said methyl is bound to the C-4 position of the imidazolyl ring (i.e., 4-methyl).

Another embodiment of this invention is directed to compounds of the formula

Formula 12.0

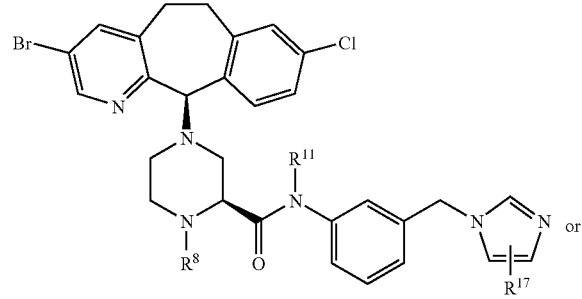

Formula 12.0A

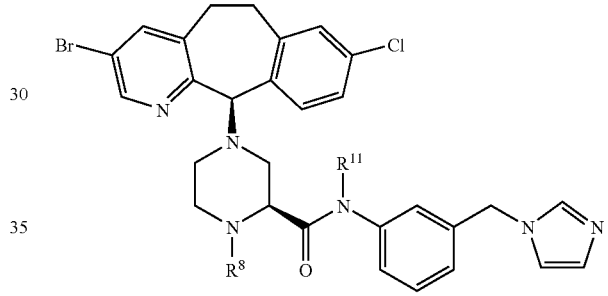

wherein:

R[8] is selected from the group consisting of:

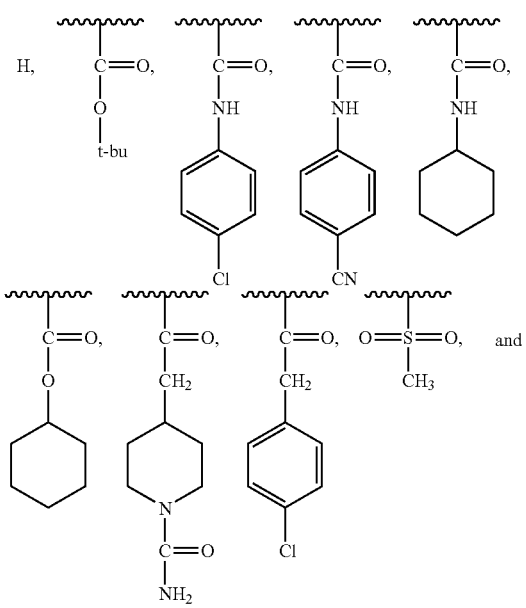

-continued

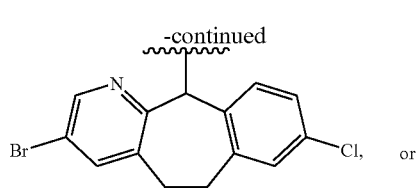

or $R^8$, in yet another embodiment, is selected from the group consisting of:

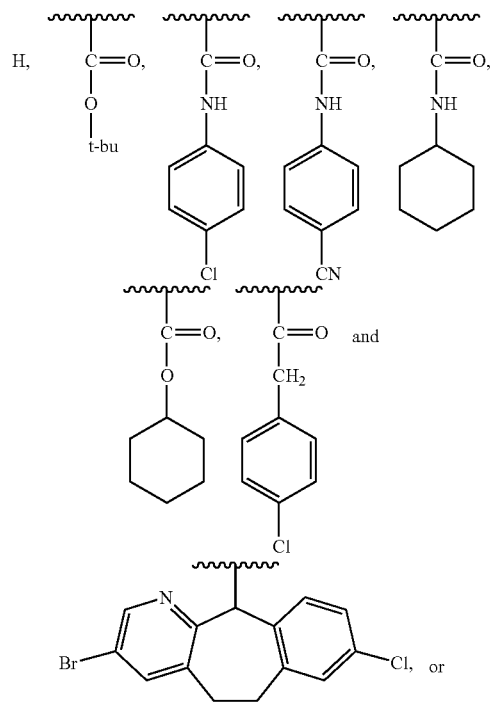

or $R^8$, in yet another embodiment, is selected from the group consisting of:

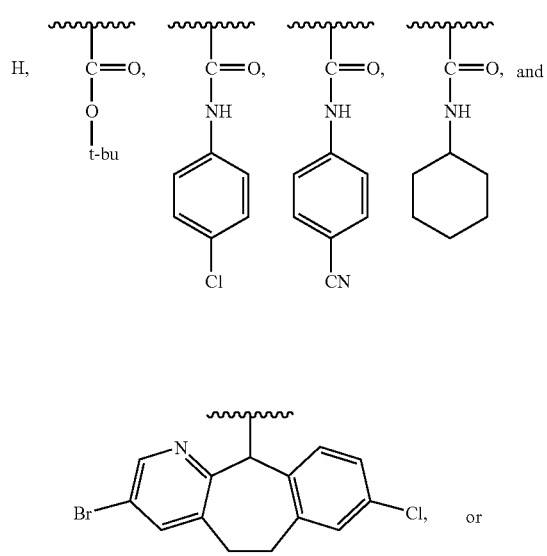

or $R^8$, in yet another embodiment, is selected from the group consisting of:

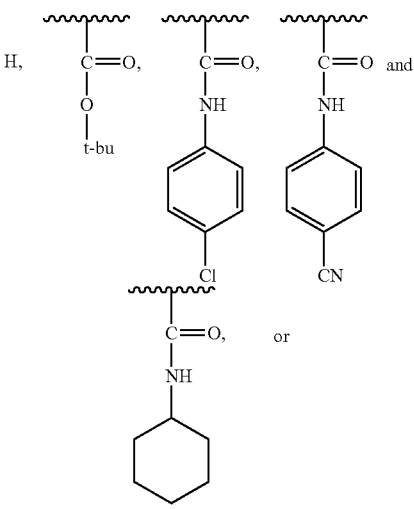

or $R^8$, in yet another embodiment, is selected from the group consisting of:

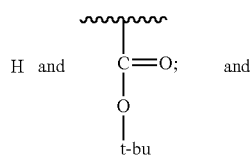

and $R^{11}$ is H; and
$R^{17}$ is methyl wherein said methyl is bound to the C-4 position of the imidazolyl ring (i.e., 4-methyl).

Another embodiment of this invention is directed to compounds of the formula

Formula 13.0

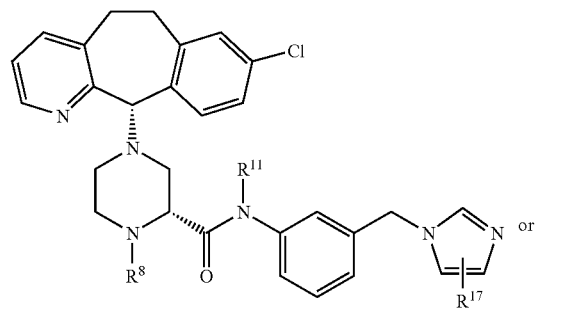

or

Formula 13.0A

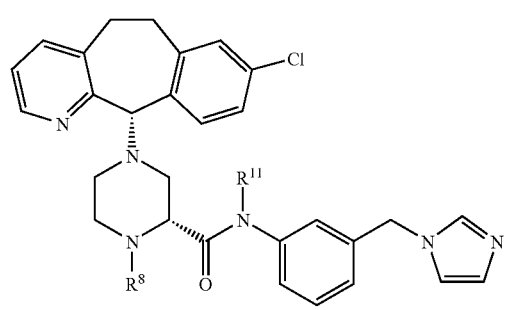

wherein:
R[8] is selected from the group consisting of:

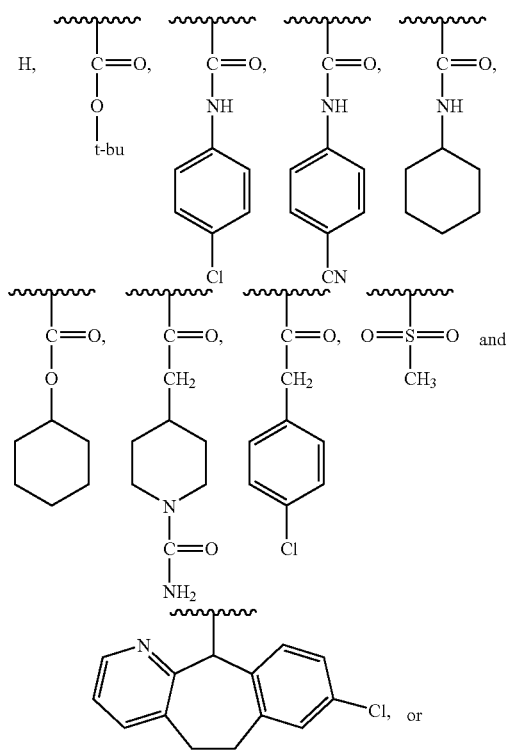

R[8], in yet another embodiment, is selected from the group consisting of:

R[11] is selected from the group consisting of: H, benzyl, n-butyl and 3-PhPr (i.e., 3-phenylpropyl); and
R[17] is selected from the group consisting of: methyl wherein said methyl is bound to the C-2, C-4 or C-5 of the imidazolyl ring (i.e., R[17] is 2-methyl, 4-methyl or 5-methyl).

Another embodiment of this invention is directed to compounds of the formula

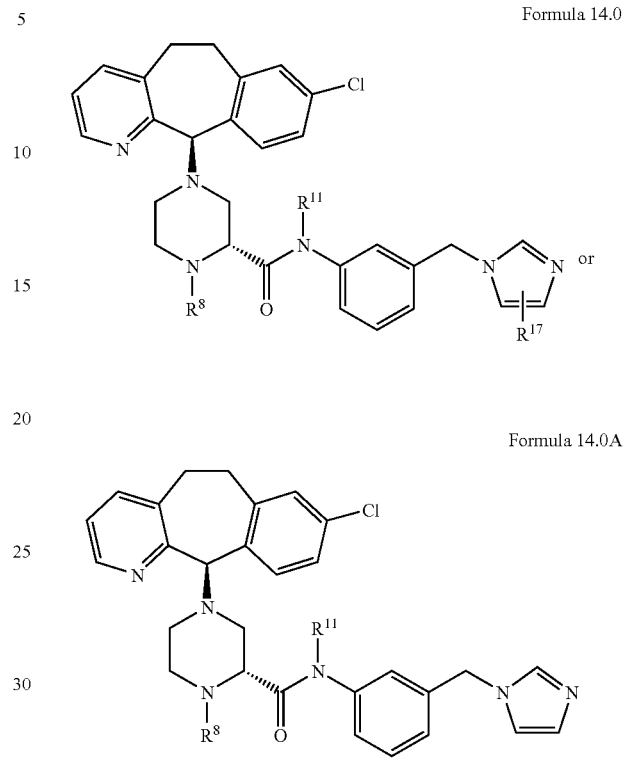

Formula 14.0

Formula 14.0A wherein:
R[8] is selected from the group consisting of:

$R^8$, in yet another embodiment, is selected from the group consisting of:

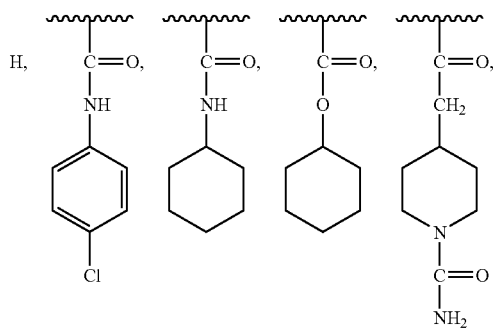

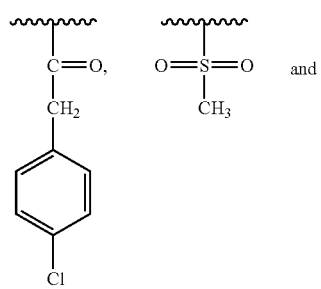

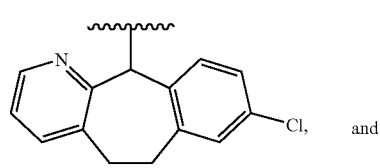 and $R^{11}$ is selected from the group consisting of: H, benzyl, n-butyl and 3-PhPr (i.e., 3-phenylpropyl); and $R^{17}$ is selected from the group consisting of: methyl wherein said methyl is bound to the C-2, C-4 or C-5 of the imidazolyl ring (i.e., $R^{17}$ is 2-methyl, 4-methyl or 5-methyl).

Another embodiment of this invention is directed to compounds of the formula

Formula 14.0

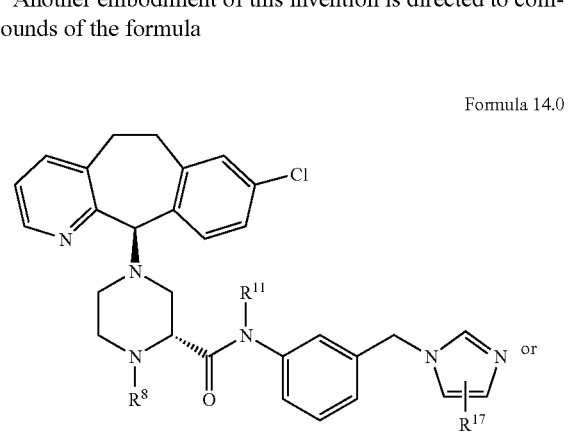

-continued

Formula 14.0A

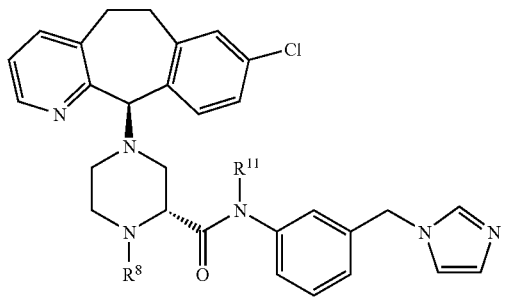

wherein:

$R^8$ is selected from the group consisting of:

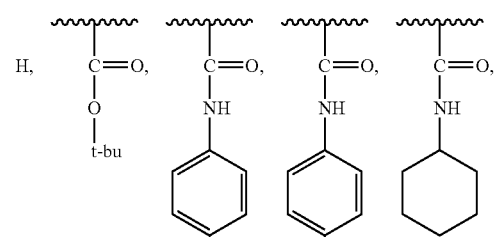

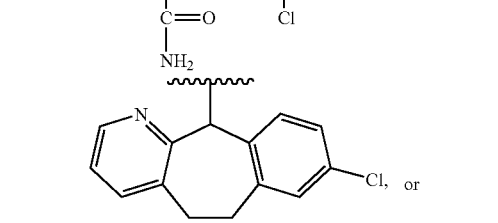 or $R^8$, in yet another embodiment, is selected from the group consisting of:

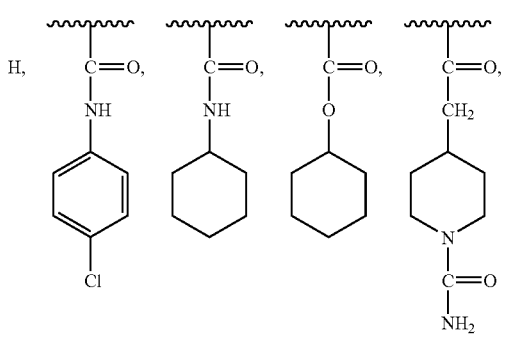

-continued

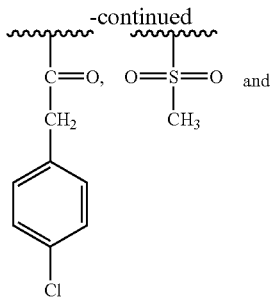

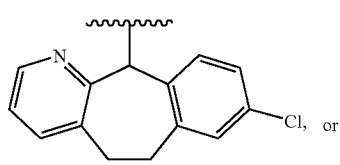

$R^8$, in yet another embodiment, is selected from the group consisting of:

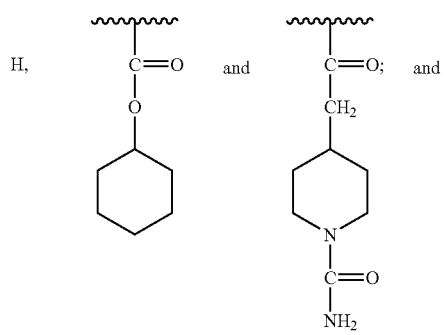

$R^{11}$ is selected from the group consisting of: H and benzyl; and $R^{17}$ is selected from the group consisting of: methyl wherein said methyl is bound to the C-2, C-4 or C-5 of the imidazolyl ring (i.e., $R^{17}$ is 2-methyl, 4-methyl or 5-methyl).

Another embodiment of this invention is directed to compounds of the formula

Formula 15.0 wherein:

$R^8$ is selected from the group consisting of:

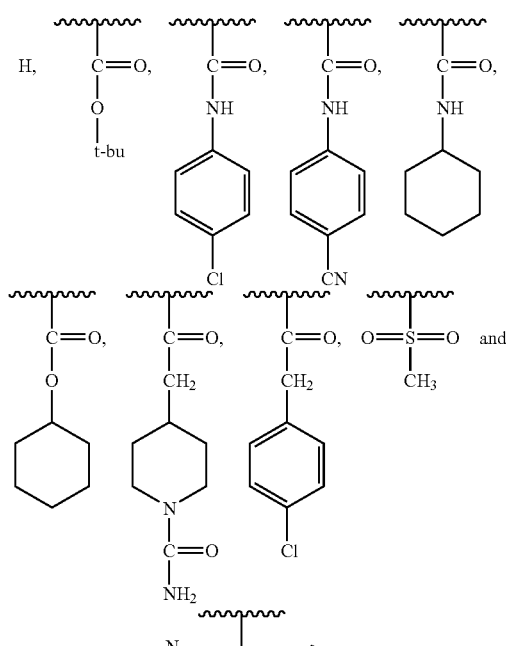

$R^8$, in yet another embodiment, is selected from the group consisting of:

H and (cyclohexyl ester group); and $R^{11}$ is H; and $R^{17}$ is methyl wherein said methyl is bound to the C-4 of the imidazolyl (i.e., $R^{17}$ is 4-methyl.

Another embodiment of this invention is directed to compounds of the formula

Formula 16.0 wherein:

R[8] is selected from the group consisting of:

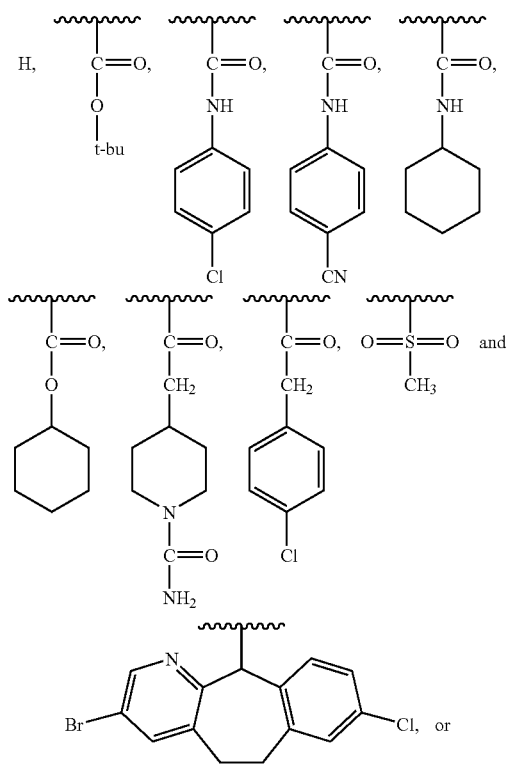

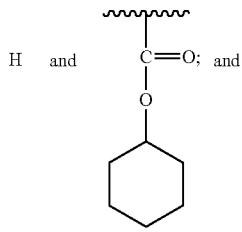

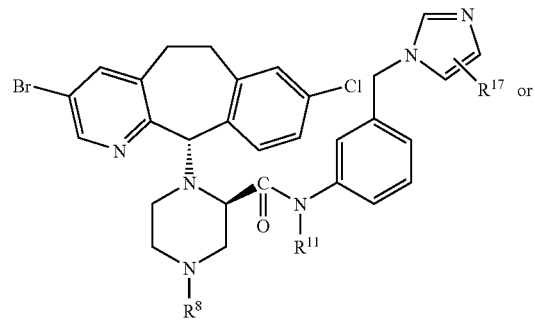

R[8], in yet another embodiment, is selected from the group consisting of:

H and <image present: C(=O)O-cyclohexyl>; and

R[11] is H; and
R[17] is methyl wherein said methyl is bound to the C-4 of the imidazolyl (i.e., R[17] is 4-methyl.

Another embodiment of this invention is directed to compounds of the formula

Formula 15.0

<image present: structure of Formula 15.0>

-continued

Formula 15.0A

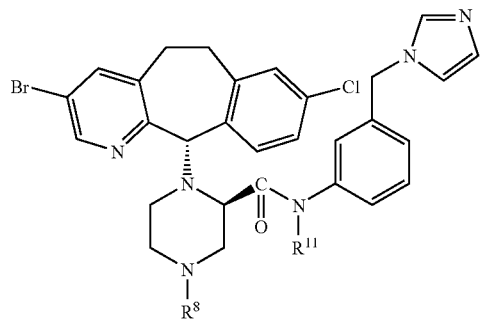

wherein:
R[8] is selected from the group consisting of:

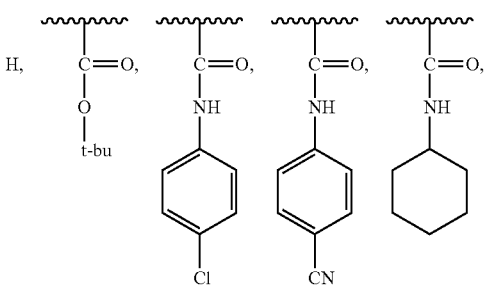

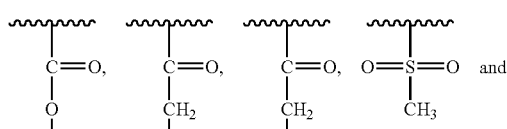

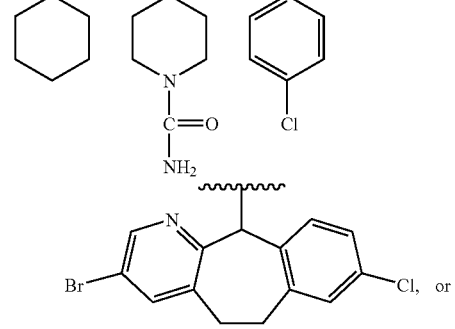

R[8], in yet another embodiment, is:

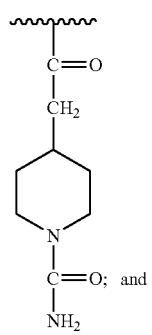

$R^{11}$ is H; and
$R^{17}$ is methyl wherein said methyl is bound to the C-4 of the imidazolyl (i.e., $R^{17}$ is 4-methyl.

Another embodiment of this invention is directed to compounds of the formula

Formula 15.0

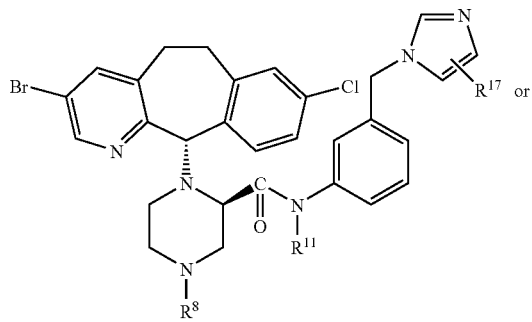

Formula 15.0A

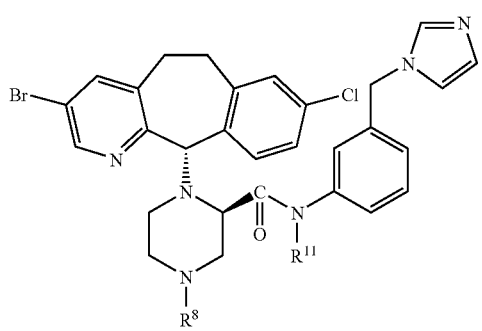

wherein:
$R^8$ is selected from the group consisting of:

H, [various substituent structures shown including t-bu ester, NH-aryl (4-Cl), NH-aryl (4-CN), NH-cyclohexyl, cyclohexyl ester, piperidinyl carbamoyl CH2, 4-chlorobenzyl CH2, and methylsulfonyl]

-continued

[pyridine-fused tricyclic with Br and Cl], or $R^8$, in yet another embodiment, is selected from the group consisting of:

H, t-bu ester, cyclohexyl ester; and $R^{11}$ is H; and
$R^{17}$ is methyl wherein said methyl is bound to the C-4 of the imidazolyl (i.e., $R^{17}$ is 4-methyl.

Another embodiment of this invention is directed to compounds of the formula

Formula 18.0

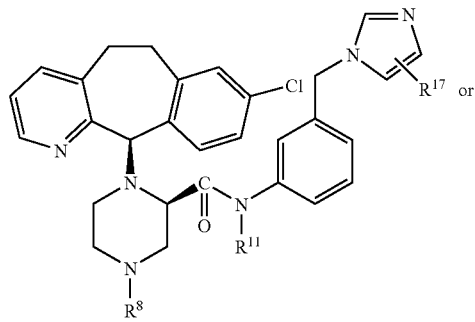

Formula 18.0A

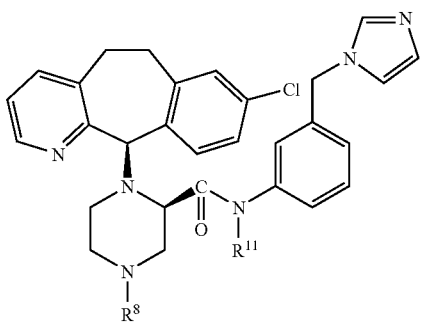

wherein:
R⁸ is selected from the group consisting of:

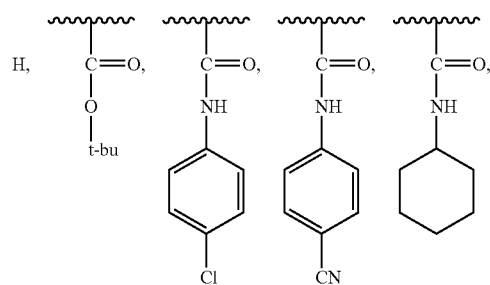

R⁸ in yet another embodiment, is selected from the group consisting of:

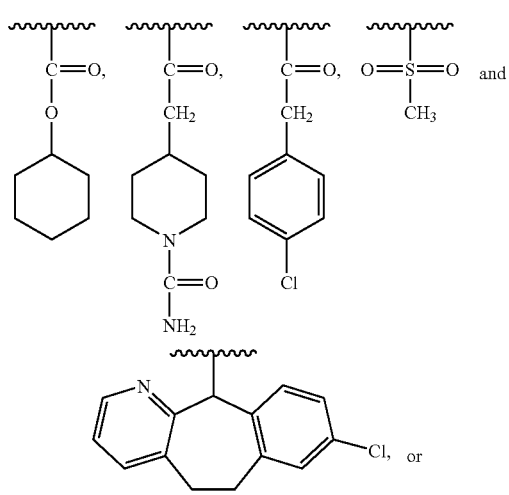

R¹¹ is H; and
R¹⁷ is methyl wherein said methyl is bound to the C-4 of the imidazolyl (i.e., R¹⁷ is 4-methyl.

Another embodiment of this invention is directed to compounds of the formula

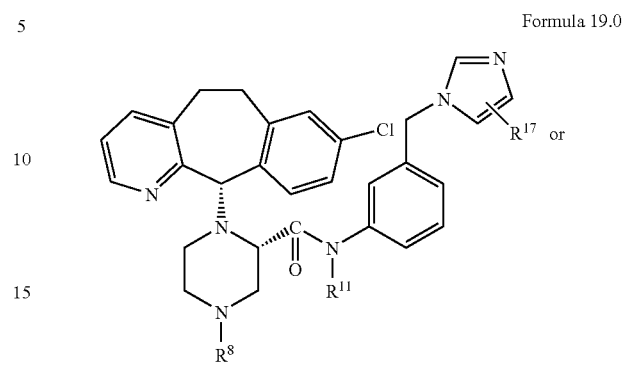
Formula 19.0

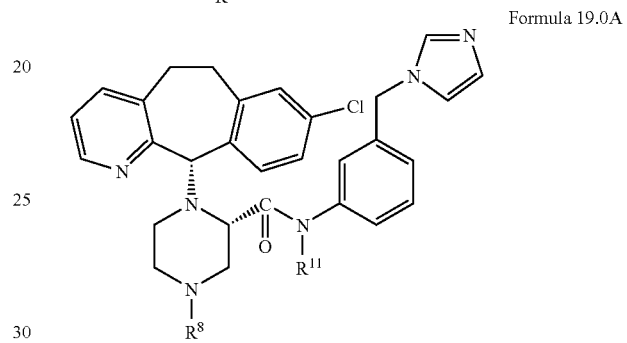
Formula 19.0A wherein:
R⁸ is selected from the group consisting of:

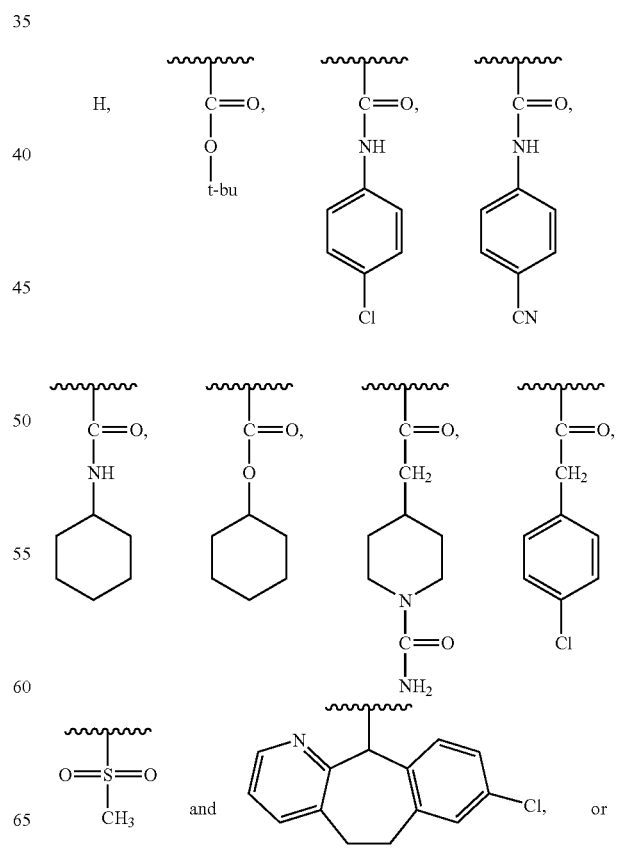

$R^8$, in yet another embodiment, is selected from the group consisting of:

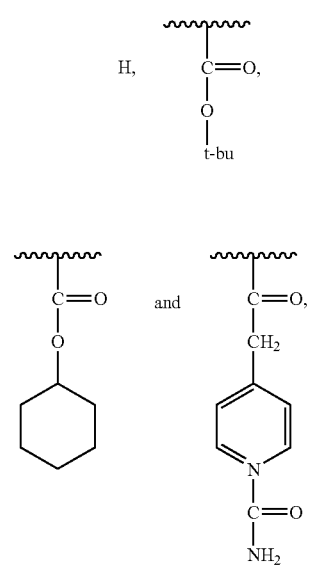

$R^8$, in yet another embodiment, is:

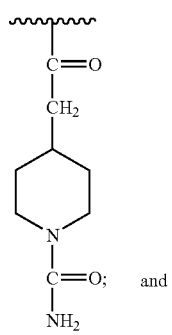

$R^{11}$ is H; and
$R^{17}$ is methyl wherein said methyl is bound to the C-4 of the imidazolyl (i.e., $R^{17}$ is 4-methyl.

Another embodiment of this invention is directed to compounds of the formula

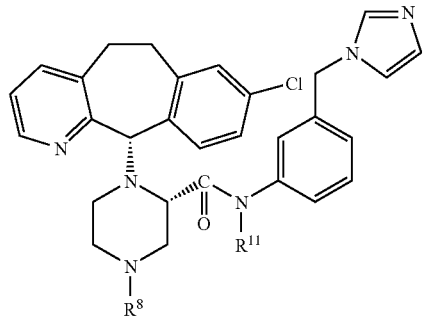

Formula 19.0A wherein:
$R^8$ is selected from the group consisting of:

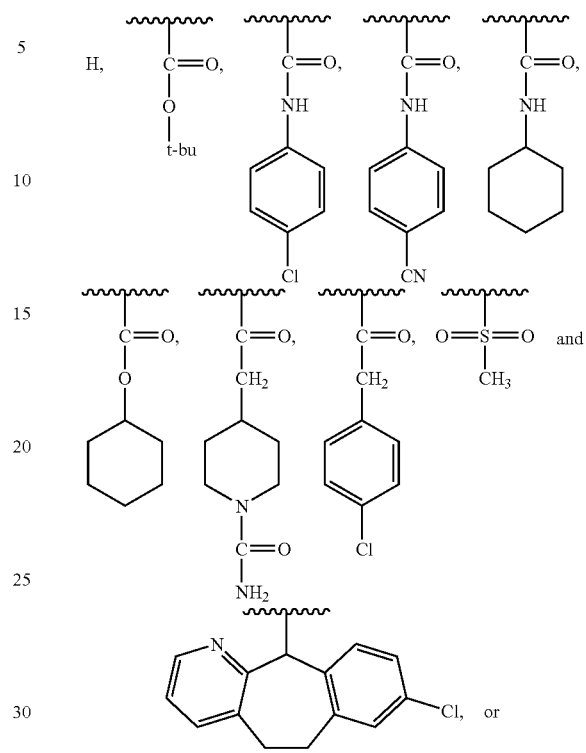

$R^8$, in yet another embodiment, is selected from the group consisting of:

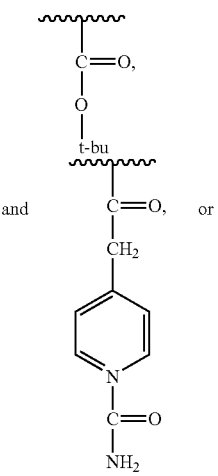

$R^8$, in yet another embodiment, is:

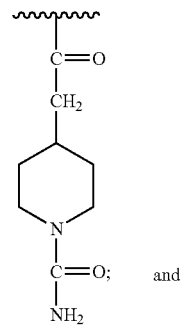

$R^{11}$ is H.

Another embodiment of this invention is directed to compounds of the formula

Formula 20.0

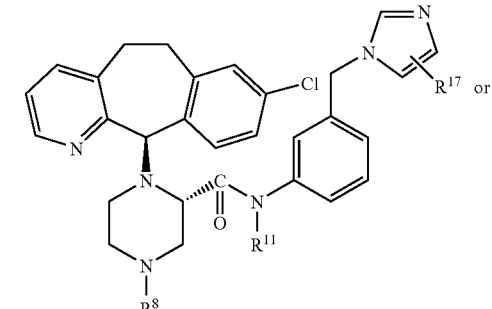

Formula 20.0A

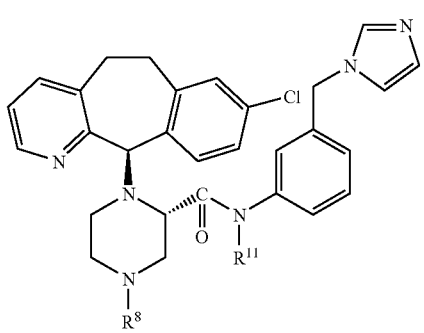

wherein:
$R^8$ is selected from the group consisting of:

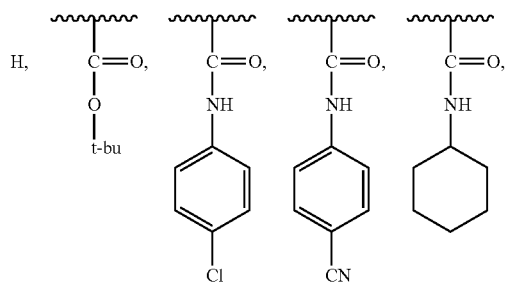

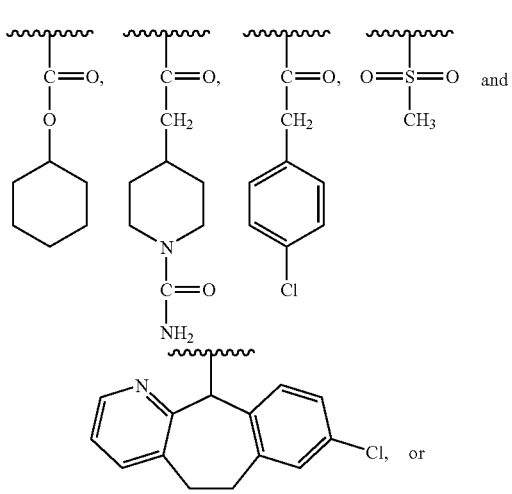

$R^8$, in yet another embodiment, is selected from the group consisting of:

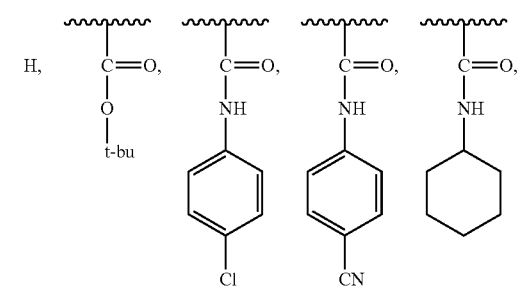

$R^{11}$ is H; and
$R^{17}$ is methyl wherein said methyl is bound to the C-4 of the imidazolyl (i.e., $R^{17}$ is 4-methyl).

Another embodiment of this invention is directed to compounds of the formula

Formula 20.0A

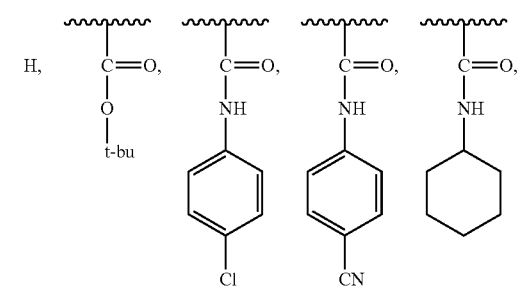

wherein:
$R^8$ is selected from the group consisting of:

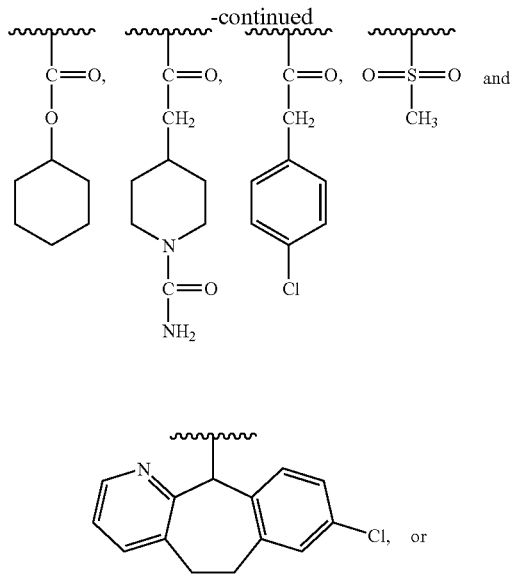

$R^8$, in yet another embodiment, is selected from the group consisting of:

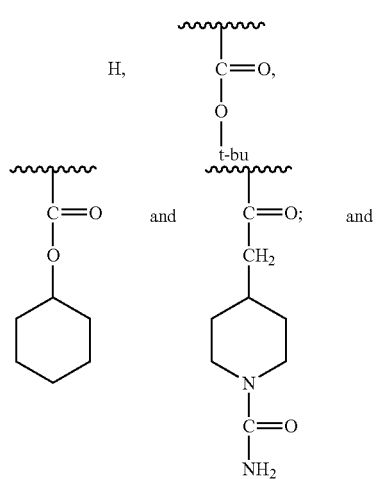

$R^{11}$ is H.

Another embodiment of this invention is directed to compounds of the formula

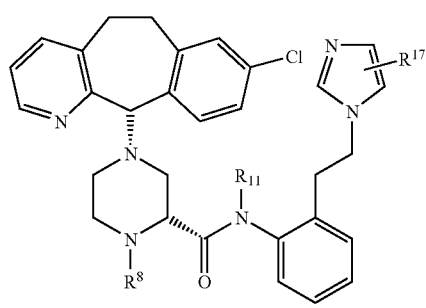

Formula 21.0 wherein:
$R^8$ is selected from the group consisting of:

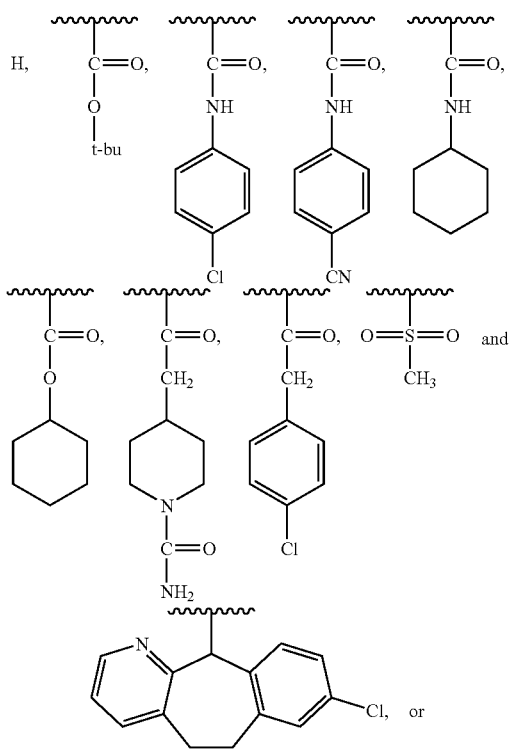

$R^8$, in yet another embodiment is

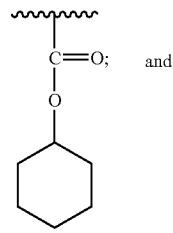

$R^{11}$ is H; and
$R^{17}$ is methyl wherein said methyl is bound to the C-4 of the imidazolyl (i.e., $R^{17}$ is 4-methyl.

The wavy line ⁓⁓ as a bond generally indicates a mixture of the possible isomers, or any one of the possible isomers. For example, the formula

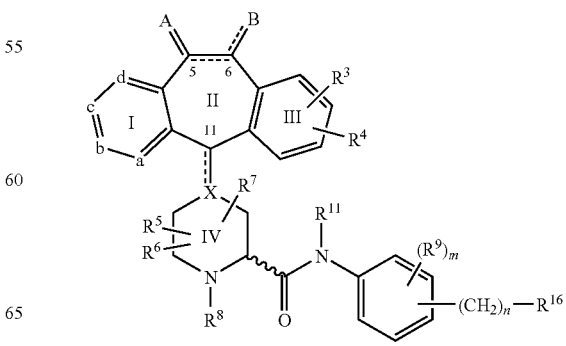

represents a mixture of the (R)- and (S)-isomers:

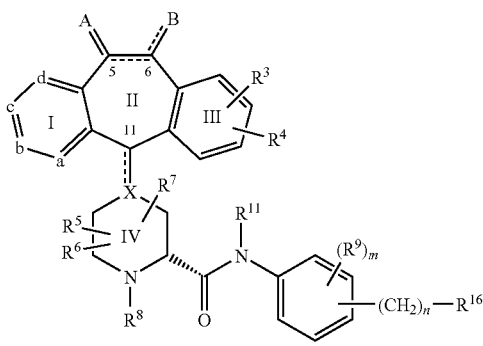

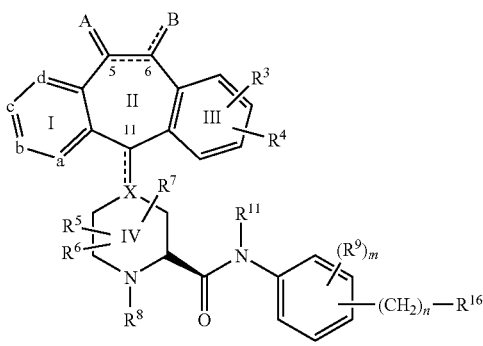

or represents either the (R)-isomer:

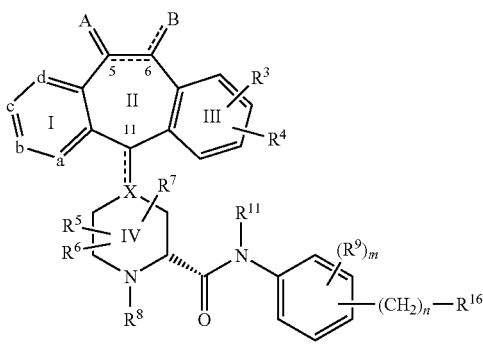

or represents the (S)-isomer:

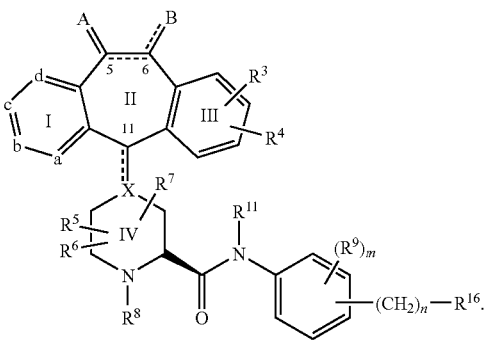

Lines drawn into the ring systems, such as, for example:

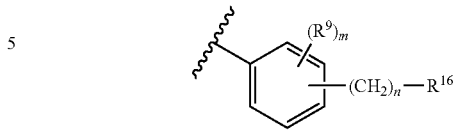

means that the indicated line (bond) may be attached to any of the substitutable ring carbon atoms (with the exception, as indicated in formula 1.0, that the amide moiety bound to Ring IV is bound at C-2 or C-3 of Ring IV).

As well known in the art, a bond drawn from a particular atom wherein no moiety is depicted at the terminal end of the bond indicates a methyl group bound through that bond to the atom, unless stated otherwise. For example:

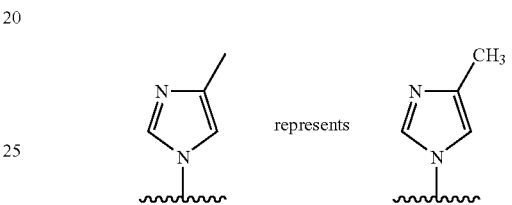

It should also be noted that any carbon or heteroatom with unsatisfied valences in the text, schemes, examples, structural formulae, and any Tables herein is assumed to have the hydrogen atom or atoms to satisfy the valences.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

This invention also includes prodrugs of the compounds of this invention. The term "prodrug," as used herein, represents compounds that are rapidly transformed in vivo to the parent compound (i.e., the compounds of formula 1.0), for example, by hydrolysis in blood. A thorough discussion is provided in T. Higuchi and V. Stella, Pro.drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

This invention also includes the compounds of this invention in isolated and purified form.

Polymorphic forms of the compounds of formula 1.0, and of the salts, solvates and prodrugs of the compounds of formula 1.0, are intended to be included in the present invention.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

The compounds of formula 1.0 form salts that are also within the scope of this invention. Reference to a compound of formula 1.0 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula 1.0 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the formula 1.0 may be formed, for example, by reacting a compound of formula 1.0 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in The Orange Book (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula 1.0, and salts, solvates and prodrugs thereof, may exist in their tautomeric form (for example, as an amide or imino ether). All such tautomeric forms are contemplated herein as part of the present invention.

The compounds of this invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount (e.g., a therapeutically effective amount) of one or more (e.g., one) compounds of this invention. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount (e.g., a therapeutically effective amount) of one or more (e.g., one) compounds of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor (i.e., cancer) growth by administering an effective amount (e.g., a therapeutically effective amount) of one or more (e.g., one) compounds of this invention to a mammal (e.g., a human) in need of such treatment. In particular, this invention provides a method for inhibiting or treating the growth of tumors expressing an activated Ras oncogene by the administration of an effective amount (e.g., a therapeutically effective amount) of the above described compounds.

The present invention also provides a method of treating proliferative diseases, especially cancers (i.e, tumors), comprising administering an effective amount (e.g., a therapeutically effective amount) of one or more (e.g., one) compounds of the invention, described herein, to a mammal (e.g., a human) in need of such treatment in combination with an effective amount of at least one anti-cancer agent (i.e., a chemotherapeutic agent) and/or radiation.

Examples of anti-cancer agents (i.e., chemotherapeutic agents) include anti-cancer agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of $\alpha V\beta 3$ integrins, (13) small molecules that are inhibitors of $\alpha V\beta 3$ integrins, (14) folate antagonists, (15) ribonucleotide reductase inhibitors, (16) anthracyclines, (17) biologics; (18) thalidomide (or related imid), and (19) Gleevec.

The present invention also provides a method of treating proliferative diseases, especially cancers (i.e., tumors), comprising administering an effective amount (e.g., a therapeutically effective amount) of one or more (e.g., one) compounds of the invention to a mammal (e.g., a human) in need of such treatment in combination with an effective amount of at least one signal transduction inhibitor.

Examples of proliferative diseases (tumors, i.e., cancers) which may be inhibited or treated include, but are not limited to: (A) lung cancer (e.g., lung adenocarcinoma and non small cell lung cancer), (B) pancreatic cancers (e.g., pancreatic carcinoma such as, for example, exocrine pancreatic carcinoma), (C) colon cancers (e.g., colorectal carcinomas, such as, for example, colon adenocarcinoma and colon adenoma), (D) myeloid leukemias (for example, acute myelogenous leukemia (AML), CML, and CMML), (E) thyroid follicular cancer, (F) myelodysplastic syndrome (MDS), (G) bladder carcinoma, (H) epidermal carcinoma, (I) melanoma, (J) breast cancer, (K) prostate cancer, (L) head and neck cancers (e.g., squamous cell cancer of the head and neck), (M) ovarian cancer, (N) brain cancers (e.g., gliomas), (O) cancers of mesenchymal origin (e.g., fibrosarcomas and rhabdomyosarcomas), (P) sarcomas, (O) tetracarcinomas, (R) nuroblastomas, (S) kidney carcinomas, (T) hepatomas, (U) non-Hodgkin's lymphoma, (V) multiple myeloma, and (W) anaplastic thyroid carcinoma.

For example, embodiments of this invention include methods of treating cancer in a patient in need of such treatment wherein said cancer is selected from the group consisting of: pancreatic cancers, lung cancers, myeloid leukemias, thyroid follicular tumors, myelodysplastic syndrome, head and neck cancers, melanomas, breast cancers, prostate cancers, ovarian cancers, bladder cancers, gliomas, epidermal cancers, colon cancers, non-Hodgkin's lymphomas, and multiple myelomas comprising administering to said patient an effective amount of a compound of this invention Also for example, embodiments of this invention include methods of treating cancer in a patient in need of such treatment wherein said cancers are selected from the group consisting of: lung cancer (e.g., non-small cell lung cancer), head and neck cancer (e.g., squamous cell cancer of the head and neck), bladder cancer, breast cancer, prostate cancer, and myeloid leukemias (e.g., CML and AML), non-Hodgkin's lymphoma and multiple myeloma.

This invention also provides a method of treating cancer in a patient in need of such treatment comprising administering a therapeutically effective amount of one or more (e.g., one) compounds of this invention and therapeutically effective amounts of at least two different antineoplastic agents selected from: (1) taxanes, (2) platinum coordinatorcompounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of $\alpha V\beta 3$ integrins, (13) small molecules that are inhibitors of $\alpha V\beta 3$ integrins, (14) folate antagonists, (15) ribonucleotide reductase inhibitors, (16) anthracyclines, (17) biologics; (18) thalidomide (or related imid), and (19) Gleevec.

This invention also provides a method of treating cancer in a patient in need of such treatment comprising administering therapeutically effective amounts of one or more (e.g., one) compounds of this invention and an antineoplastic agent selected from: (1) EGF inhibitors that are antibodies, (2) EGF inhibitors that are small molecules, (3) VEGF inhibitors that are antibodies, and (4) VEGF inhibitors that are small molecules. Radiation therapy can also be used in conjunction with the above combination therapy, i.e., the above method using a combination of compounds of the invention and antineoplastic agent can also comprise the administration of a therapeutically effect amount of radiation.

This invention also provides a method of treating leukemias (e.g., acute myeloid leukemia (AML), and chronic myeloid leukemia (CML)) in a patient in need of such treatment comprising administering therapeutically effective amounts of one or more (e.g., one) compounds of this invention and: (1) Gleevec and interferon to treat CML; (2) Gleevec and pegylated interferon to treat CML; (3) an anti-tumor nucleoside derivative (e.g., Ara-C) to treat AML; or (4) an anti-tumor nucleoside derivative (e.g., Ara-C) in combination with an anthracycline to treat AML.

This invention also provides a method of treating non-Hodgkin's lymphoma in a patient in need of such treatment comprising administering therapeutically effective amounts of one or more (e.g., one) compounds of this invention and: (1) a biologic (e.g., Rituxan); (2) a biologic (e.g., Rituxan) and an anti-tumor nucleoside derivative (e.g., Fludarabine); or (3) Genasense (antisense to BCL-2).

This invention also provides a method of treating multiple myeloma in a patient in need of such treatment comprising administering therapeutically effective amounts of one or more (e.g., one) compounds of this invention and: (1) a proteosome inhibitor (e.g., PS-341 from Millenium); or (2) Thalidomide (or related imid).

This invention also provides a method of treating cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, (12) antibodies that are inhibitors of αVβ3 integrins, (13) small molecule inhibitors of αVβ3 integrins, (14) folate antagonists, (15) ribonucleotide reductase inhibitors, (16) anthracyclines, (17) biologics, (18) Thalidomide (or related Imid), and (19) Gleevec.

This invention also provides a method of treating cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, (12) antibodies that are inhibitors of αVβ₃ integrins, (13) small molecule inhibitors of □V□3 integrins, (14) folate antagonists, (15) ribonucleotide reductase inhibitors, (16) anthracyclines, (17) biologics, and (18) Thalidomide (or related Imid).

This invention also provides a method of treating cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, (12) antibodies that are inhibitors of αVβ3 integrins, (13) small molecule inhibitors of □V□3 integrins, (14) folate antagonists, (15) ribonucleotide reductase inhibitors, (16) anthracyclines, and (17) biologics.

This invention also provides a method of treating cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, (12) antibodies that are inhibitors of αVβ3 integrins, and (13) small molecule inhibitors of αVβ3 integrins.

This invention also provides a method of treating non small cell lung cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, (12) antibodies that are inhibitors of αVβ3 integrins, and (13) small molecule inhibitors of αVβ3 integrins.

This invention also provides a method of treating non small cell lung cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) anti-tumor nucleoside derivatives, (4) topoisomerase inhibitors, and (5) vinca alkaloids.

This invention also provides a method of treating non small cell lung cancer in a patient in need of such treatment comprising administering therapeutically effective amounts of: (a) an FPT inhibitor of this invention, i.e., a compound of this invention, (b) carboplatin, and (c) paclitaxel.

This invention also provides a method of treating non small cell lung cancer in a patient in need of such treatment comprising administering therapeutically effective amounts of: (a) an FPT inhibitor of this invention, i.e., a compound of this invention, (b) cisplatin, and (c) gemcitabine.

This invention also provides a method of treating non small cell lung cancer in a patient in need of such treatment comprising administering therapeutically effective amounts of: (a) an FPT inhibitor of this invention, i.e., a compound of this invention, (b) carboplatin, and (c) gemcitabine.

This invention also provides a method of treating non small cell lung cancer in a patient in need of such treatment comprising administering therapeutically effective amounts of: (a) an FPT inhibitor of this invention, i.e., a compound of this invention, (b) Carboplatin, and (c) Docetaxel.

This invention also provides a method of treating cancer in a patient in need of such treatment comprising administering therapeutically effective amounts of: (a) an FPT inhibitor of this invention, i.e., a compound of this invention, and (b) an antineoplastic agent selected from the group consisting of: (1) EGF inhibitors that are antibodies, (2) EGF inhibitors that are small molecules, (3) VEGF inhibitors that are antibodies, (4) VEGF kinase inhibitors that are small molecules.

This invention also provides a method of treating squamous cell cancer of the head and neck, in a patient in need of such treatment comprising administering therapeutically effective amounts of: (a) an FPT inhibitor of this invention, i.e., a compound of this invention, and (b) one or more antineoplastic agents selected from the group consisting of: (1) taxanes, and (2) platinum coordinator compounds.

This invention also provides a method of treating squamous cell cancer of the head and neck, in a patient in need of such treatment comprising administering therapeutically effective amounts of: (a) an FPT inhibitor of this invention, i.e., a compound of this invention, and (b) at least two different antineoplastic agents selected from the group consisting of: (1) taxanes, (2) platinum coordinator compounds, and (3) anti-tumor nucleoside derivatives (e.g., 5-Fluorouracil).

This invention also provides a method of treating CML in a patient in need of such treatment comprising administering therapeutically effective amounts of: (a) an FPT inhibitor of this invention, i.e., a compound of this invention, (b) Gleevec, and (c) interferon (e.g., Intron-A).

This invention also provides a method of treating CML in a patient in need of such treatment comprising administering therapeutically effective amounts of: (a) an FPT inhibitor of this invention, i.e., a compound of this invention, (b) Gleevec; and (c) pegylated interferon (e.g., Peg.Intron, and Pegasys).

This invention also provides a method of treating CML in a patient in need of such treatment comprising administering therapeutically effective amounts of: (a) an FPT inhibitor of this invention, i.e., a compound of this invention and (b) Gleevec.

This invention also provides a method of treating CMML in a patient in need of such treatment comprising administering therapeutically effective amounts of an FPT inhibitor of this invention i.e., a compound of this invention.

This invention also provides a method of treating AML in a patient in need of such treatment comprising administering therapeutically effective amounts of: (a) an FPT inhibitor of this invention, i.e., a compound of this invention, (b) an anti-tumor nucleoside derivative (e.g., Cytarabine (i.e., Ara-C)).

This invention also provides a method of treating AML in a patient in need of such treatment comprising administering therapeutically effective amounts of: (a) an FPT inhibitor of this invention, i.e., a compound of this invention, (b) an anti-tumor nucleoside derivative (e.g., Cytarabine (i.e., Ara-C)), and (c) an anthracycline.

This invention also provides a method of treating non-Hodgkin's lymphoma in a patient in need of such treatment comprising administering therapeutically effective amounts of: (a) an FPT inhibitor of this invention, i.e., a compound of this invention, and (b) Rituximab (Rituxan).

This invention also provides a method of treating non-Hodgkin's lymphoma in a patient in need of such treatment comprising administering therapeutically effective amounts of: (a) an FPT inhibitor of this invention, i.e., a compound of this invention, (b) Rituximab (Rituxan), and (c) an anti-tumor nucleoside derivative (e.g., Fludarabine (i.e., F-ara-A).

This invention also provides a method of treating non-Hodgkin's lymphoma in a patient in need of such treatment comprising administering therapeutically effective amounts of: (a) an FPT inhibitor of this invention, i.e., a compound of this invention, (b) Genasense (antisense to BCL-2).

This invention also provides a method of treating multiple myeloma in a patient in need of such treatment comprising administering therapeutically effective amounts of: (a) an FPT inhibitor of this invention, i.e., a compound of this invention, and (b) a proteosome inhibitor (e.g., PS-341 (Millenium)).

This invention also provides a method of treating multiple myeloma in a patient in need of such treatment comprising administering therapeutically effective amounts of: (a) an FPT inhibitor of this invention, i.e., a compound of this invention, and (b) Thalidomide or related imid.

This invention also provides a method of treating multiple myeloma in a patient in need of such treatment comprising administering therapeutically effective amounts of: (a) an FPT inhibitor of this invention, i.e., a compound of this invention, and (b) Thalidomide.

This invention is also directed to the methods of treating cancer described herein, particularly those described above, wherein in addition to the administration of the FPT inhibitor and antineoplastic agents radiation therapy is also administered prior to, during, or after the treatment cycle.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form with said inhibition or treatment being accomplished by the administration of an effective amount (e.g. a therapeutically effective amount) of one or more (e.g., one) compounds of the invention to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, Ick, and fyn), may be inhibited or treated by the tricyclic compounds described herein.

The compounds of this invention useful in the methods of this invention inhibit or treat the abnormal growth of cells. Without wishing to be bound by theory, it is believed that these compounds may function through the inhibition of G-protein function, such as Ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

The method of treating proliferative diseases (cancers, i.e., tumors), according to this invention, includes a method for treating (inhibiting) the abnormal growth of cells, including transformed cells, in a patient in need of such treatment, by administering, concurrently or sequentially, an effective amount of a compound of this invention and an effective amount of a chemotherapeutic agent and/or radiation.

In embodiments, the methods of the present invention include methods for treating or inhibiting tumor growth in a patient in need of such treatment by administering, concurrently or sequentially, (1) an effective amount of a compound of this invention and (2) an effective amount of at least one antineoplastic agent, microtubule affecting agent and/or radiation therapy. For example, one embodiment of these methods is directed to a method of treating cancers selected from the group consisting of: lung cancer, prostate cancer and myeloid leukemias.

The methods of treating proliferative diseases, according to this invention, also include a method for treating (inhibiting) proliferative diseases, both benign and malignant, wherein ras proteins are aberrantly activated as a result of oncogenic mutation in other genes—i.e., the ras gene itself is not activated by mutation to an oncogenic form. This method comprises administering, concurrently or sequentially, an effective amount of a compound of this invention and an effective amount of an antineoplastic agent and/or radiation therapy to a patient in need of such treatment. Examples of such proliferative diseases which may be treated include: the benign proliferative disorder neurofibromatosis, or tumors in which ras is activated due to mutation or overexpression of tyrosine kinase oncogenes (e.g., neu, src, abl, lck, lyn, fyn).

For radiation therapy, γ-radiation is preferred.

The methods of treating proliferative diseases (cancers, i.e., tumors), according to this invention, also include a method for treating (inhibiting) the abnormal growth of cells, including transformed cells, in a patient in need of such treatment, by administering, concurrently or sequentially, an effective amount of a compound of this invention and an effective amount of at least one signal transduction inhibitor.

Typical signal transduction inhibitors include but are not limited to: (i) Bcr/abl kinase inhibitors such as, for example, STI 571 (Gleevec), (ii) Epidermal growth factor (EGF) receptor inhibitor such as, for example, Kinase inhibitors (Iressai OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin® (trastuzumab).

Embodiments of the methods of treatment of this invention are directed to the use of a combination of drugs (compounds) for the treatment of cancer, i.e., this invention is directed to a combination therapy for the treatment of cancer. Those skilled in the art will appreciate that the drugs are generally administered individually as a pharmaceutical composition. The use of a pharmaceutical composition comprising more than one drug is within the scope of this invention.

The antineoplastic agents are usually administered in the dosage forms that are readily available to the skilled clinician, and are generally administered in their normally prescribed amounts (as for example, the amounts described in the Physician's Desk Reference, 56$^{th}$ Edition, 2002 (published by Medical Economics company, Inc. Montvale, N.J. 07645-1742, and in the Physician's Desk Reference, 57$^{th}$ Edition, 2003 (published by Thompson PDR, Montvale, N.J. 07645-1742, the disclosures of which are incorporated herein by reference thereto)), or the amounts described in the manufacture's literature for the use of the agent).

For example, the FPT inhibitor of this invention, i.e., a compound of this invention; can be administered orally (e.g., as a capsule), and the antineoplastic agents can be administered intravenously, usually as an IV solution. The use of a pharmaceutical composition comprising more than one drug is within the scope of this invention.

The FPT inhibitor (i.e., compound of this invention) and the antineoplastic agents are administered in therapeutically effective dosages to obtain clinically acceptable results, e.g., reduction or elimination of symptoms or of the tumor. Thus, the FPT inhibitor and antineoplastic agents can be administered concurrently or consecutively in a treatment protocol. The administration of the antineoplastic agents can be made according to treatment protocols already known in the art.

The FPT inhibitor (i.e., compound of this invention) and antineoplastic agents are administered in a treatment protocol that usually lasts one to seven weeks, and is repeated typically from 6 to 12 times. Generally the treatment protocol lasts one to four weeks. Treatment protocols of one to three weeks may also be used. A treatment protocol of one to two weeks may also be used. During this treatment protocol or cycle the FPT inhibitor is administered daily while the antineoplastic agents are administered one or more times a week. Generally, the FPT inhibitor can be administered daily (i.e., once per day), and in one embodiment twice per day, and the antineoplastic agent is administered once a week or once every three weeks. For example, the taxanes (e.g., Paclitaxel (e.g., Taxol®) or Docetaxel (e.g., Taxotere®) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the FPT inhibitor (i.e., compound of this invention) can be administered discontinuously rather than continuously during the treatment cycle. Thus, for example, during the treatment cycle the FPT inhibitor can be administered daily for a week and then discontinued for a week, with this administration repeating during the treatment cycle. Or the FPT inhibitor can be administered daily for two weeks and discontinued for a week, with this administration repeating during the treatment cycle. Thus, the FPT inhibitor can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the FPT inhibitor is not dosed does not have to equal the number of days (or weeks) wherein the FPT inhibitor is dosed. Usually, if a discontinuous dosing protocol is used, the number of days or weeks that the FPT inhibitor is dosed is at least equal or greater than the number of days or weeks that the FPT inhibitor is not dosed.

The antineoplastic agent could be given by bolus or continuous infusion. The antineoplastic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

The FPT inhibitor (i.e., compound of this invention) can be administered orally, preferably as a solid dosage form, and in one embodiment as a capsule, and while the total therapeutically effective daily dose can be administered in one to four, or one to two divided doses per day, generally, the therapeutically effective dose is given once or twice a day, and in one embodiment twice a day. The FPT inhibitor can be administered in an amount of about 50 to about 400 mg once per day, and can be administered in an amount of about 50 to about 300 mg once per day. The FPT inhibitor is generally administered in an amount of about 50 to about 350 mg twice a day, usually 50 mg to about 200 mg twice a day, and in one embodiment about 75 mg to about 125 mg administered twice a day, and in another embodiment about 100 mg administered twice a day.

If the patient is responding, or is stable, after completion of the therapy cycle, the therapy cycle can be repeated according to the judgment of the skilled clinician. Upon completion of the therapy cycles, the patient can be continued on the FPT inhibitor (i.e., compound of this invention) at the same dose that was administered in the treatment protocol, or, if the dose was less than 200 mg twice a day, the dose can be raised to 200 mg twice a day. This maintenance dose can be continued until the patient progresses or can no longer tolerate the dose (in which case the dose can be reduced and the patient can be continued on the reduced dose).

The antineoplastic agents used with the FPT inhibitor (i.e., compound of this invention) are administered in their normally prescribed dosages during the treatment cycle (i.e., the antineoplastic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (f) about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25 mg/m$^2$/day every 3 to 4 weeks; (l) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (o) about 1 to about 350 mg/m$^2$ for topoisomerase inhibitors; (p) about 1 to about 50 mg/m for vinca alkaloids; (q) for the folate antagonist Methotrexate (MTX) 20-60 mg/m$^2$ by oral, IV or IM every 3 to 4 weeks, the intermediate dose regimen is 80-250 mg/m$^2$ IV over 60 minutes every 3 to 4 weeks, and the high dose regimen is 250-1000 mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); and (z) for the biologic Rituximab (Rituxan) (antibody used for non-Hodgkin's lymphoma) 200-400 mg/m$^2$ IV weekly over 4-8 weeks for 6 months.

Gleevec can be used orally in an amount of about 200 to about 800 mg/day.

Thalidomide (and related imids) can be used orally in amounts of about 200 to about 800 mg/day, and can be contiuously dosed or used until releapse or toxicity. See for example Mitsiades et al., "Apoptotic signaling induced by immunomodulatory thalidomide analoqs in human multiple myeloma cells; therapeutic implications", Blood, 99(12):4525-30, Jun. 15, 2002, the disclosure of which is incorporated herein by reference thereto.

For example, Paclitaxel (e.g., Taxol® can be administered once per week in an amount of about 50 to about 100 mg/m$^2$ and in another example about 60 to about 80 mg/m$^2$. In another example Paclitaxel (e.g., Taxol® can be administered once every three weeks in an amount of about 150 to about 250 mg/m$^2$ and in another example about 175 to about 225 mg/m$^2$.

In another example, Docetaxel (e.g., Taxotere®) can be administered once per week in an amount of about 10 to about 45 mg/m$^2$. In another example Docetaxel (e.g., Taxotere®) can be administered once every three weeks in an amount of about 50 to about 100 mg/m$^2$.

In another example Cisplatin can be administered once per week in an amount of about 20 to about 40 mg/m$^2$. In another example Cisplatin can be administered once every three weeks in an amount of about 60 to about 100 mg/m$^2$.

In another example Carboplatin can be administered once per week in an amount to provide an AUC of about 2 to about 3. In another example Carboplatin can be administered once every three weeks in an amount to provide an AUC of about 5 to about 8.

Thus, in one example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once per week in an amount of about 50 to about 100 mg/m$^2$, and in another example about 60 to about 80 mg/m$^2$, and (3) Carboplatin is administered once per week in an amount to provide an AUC of about 2 to about 3.

In another example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and yet in another example about 100 mg administered twice a day, (2) Paclitaxel (e.g., Taxol® is administered once per week in an amount of about 50 to about 100 mg/m$^2$, and in another example about 60 to about 80 mg/m$^2$, and (3) Cisplatin is administered once per week in an amount of about 20 to about 40 mg/m$^2$.

In another example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m$^2$, and (3) Carboplatin is administered once per week in an amount to provide an AUC of about 2 to about 3.

In another example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m$^2$, and (3) Cisplatin is administered once per week in an amount of about 20 to about 40 mg/m$^2$.

Thus, in one example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once every three weeks in an amount of about 150 to about 250 mg/m$^2$, and in another example about 175 to about 225 mg/m$^2$, and in yet another example 175 mg/m², and (3) Carboplatin is administered once every three weeks in an amount to provide an AUC of about 5 to about 8, and in another example 6.

In another example of treating non small cell lung cancer: (1) the FPT inhibitor (i.e., compound of this invention) is administered in an amount of 100 mg administered twice a day, (2) Paclitaxel (e.g., Taxol® is administered once every three weeks in an amount of 175 mg/m², and (3) Carboplatin is administered once every three weeks in an amount to provide an AUC of 6.

In another example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once every three weeks in an amount of about 150 to about 250 mg/m², and in another example about 175 to about 225 mg/m², and (3) Cisplatin is administered once every three weeks in an amount of about 60 to about 100 mg/m².

In another example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 50 to about 100 mg/m², and (3) Carboplatin is administered once every three weeks in an amount to provide an AUC of about 5 to about 8.

In another example (e.g., treating non small cell lung cancer): (1) the FPT inhibitor (i.e., compound of this invention) is administered in an amount of about 50 mg to about 200 mg twice a day, in another example about 75 mg to about 125 mg administered twice a day, and in yet another example about 100 mg administered twice a day, (2) Docetaxel (e.g., Taxotere® is administered once every three weeks in an amount of about 50 to about 100 mg/m², and (3) Cisplatin is administered once every three weeks in an amount of about 60 to about 100 mg/m².

In another example for treating non small cell lung cancer using the FPT inhibitor (i.e., compound of this invention), Docetaxel and Carboplatin: (1) the FPT inhibitor is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 75 mg/m², and (3) Carboplatin is administered once every three weeks in an amount to provide an AUC of about 6.

In another example of the the above examples the Docetaxel (e.g., Taxotere®) and Cisplatin, the Docetaxel (e.g., Taxotere®) and Carboplatin, the Paclitaxel (e.g., Taxol®) and Carboplatin, or the Paclitaxel (e.g., Taxol®) and Cisplatin are administered on the same day.

In another example (e.g., CML): (1) the FPT inhibitor (i.e., compound of this invention) is administered in an amount of about 100 mg to about 200 mg administered twice a day, (2) Gleevec is administered in an amount of about 400 to about 800 mg/day orally, and (3) interferon (Intron-A) is administered in an amount of about 5 to about 20 million IU three times per week.

In another example (e.g., CML): (1) the FPT inhibitor (i.e., compound of this invention) is administered in an amount of about 100 mg to about 200 mg administered twice a day, (2) Gleevec is administered in an amount of about 400 to about 800 mg/day orally, and (3) pegylated interferon (Peg-Intron or Pegasys) is administered in an amount of about 3 to about 6 micrograms/kg/day.

In another example (e.g., non-Hodgkin's lymphoma): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, and (2) Genasense (antisense to BCL-2) is administered as a continuous IV infusion at a dose of about 2 to about 5 mg/kg/day (e.g., 3 mg/kg/day) for 5 to 7 days every 3 to 4 weeks.

In another example (e.g., multiple myeloma): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, and (2) the proteosome inhibitor (e.g., PS-341—Millenium) is administered in an amount of about 1-5 mg/m² twice weekly for two consecutive weeks with a one week rest period.

In another example (e.g., multiple myeloma): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, and (2) the Thalidomide (or related imid) is administered orally in an amount of about 200 to about 800 mg/day, with dosing being continuous until relapse or toxicity.

In another example of the above examples the Taxotere and cisplatin, the Taxotere and carboplatin, the Taxol and carboplatin, or the Taxol and cisplatin are administered on the same day.

Antineoplastic agents that can be used in combination with the FPT inhibitor (i.e., compound of this invention) are: (1) taxanes such as paclitaxel (TAXOL®) and/or docetaxel (Taxotere®), (2) platinum coordinator compounds, such as, for example, carboplatin, cisplatin and oxaliplatin, (3) EGF inhibitors that are antibodies, such as: HER2 antibodies (such as, for example trastuzumab (Herceptin®), Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGbA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), CI 1033 (Pfizer Global Research and Development), trastuzmabmaytansinoid conjugate (Genentech, Inc.), mitumomab (Imclone Systems and Merck KGaA) and Melvax II (Imclone Systems and Merck KgaA), (4) EGF inhibitors that are small molecules, such as, Tarceva™ (OSI-774, OSI Pharmaceuticals, Inc.), and Iressa (ZD 1839, Astra Zeneca), (5) VEGF inhibitors that are antibodies such as: bevacizumab (Genentech, Inc.), and IMC-1C11 (ImClone Systems), DC 101 (a KDR VEGF Receptor 2 from ImClone Systems), (6) VEGF kinase inhibitors that are small molecules such as SU 5416 (from Sugen, Inc), SU 6688 (from Sugen, Inc.), Bay 43-9006 (a dual VEGF and bRAF inhibitor from Bayer Pharmaceuticals and Onyx Pharmaceuticals), (7) estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.), (8) anti-tumor nucleoside derivatives such as 5-fluorouracil, gemcitabine or capecitabine, (9)

epothilones such as BMS-247550 (Bristol-Myers Squibb), and EP0906 (Novartis Pharmaceuticals), (10) topoisomerase inhibitors such as topotecan (Glaxo SmithKline), and Camptosar (Pharmacia), (11) vinca alkaloids, such as, navelbine (Anvar and Fabre, France), vincristine and vinblastine, and (12) antibodies that are inhibitors of αVβ3 integrins, such as, LM-609 (see, Clinical Cancer Research, Vol. 6, page 3056-3061, August 2000, the disclosure of which is incorporated herein by reference thereto).

In one embodiment the antineoplastic agents are selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688. In another embodiment the antineoplastic agents are selected from the group consisting of: paclitaxel, docetaxel, carboplatin, cisplatin, navelbine, gemcitabine, and Herceptin.

In general when more than one antineoplastic agent is used in the methods of this invention, the antineoplastic agents are administered on the same day either concurrently or consecutively in their standard dosage form. For example, the antineoplastic agents are usually administered intravenously, preferably by an IV drip using IV solutions well known in the art (e.g., isotonic saline (0.9% NaCl) or dextrose solution (e.g., 5% dextrose)).

When two or more antineoplastic agents are used, the antineoplastic agents are generally administered on the same day; however, those skilled in the art will appreciate that the antineoplastic agents can be administered on different days and in different weeks. The skilled clinician can administer the antineoplastic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

Thus, one embodiment of this invention is directed to a method of treating cancer comprising administering to a patient in need of such treatment therapeutically effective amounts of the FPT inhibitor (i.e., compound of this invention), a taxane, and a platinum coordination compound.

Another embodiment of this invention is directed to a method of treating cancer comprising administering to a patient in need of such treatment therapeutically effective amounts of the FPT inhibitor (i.e., compound of this invention), a taxane, and a platinum coordination compound, wherein said FPT inhibitor is administered every day, said taxane is administered once per week per cycle, and said platinum coordinator compound is administered once per week per cycle. In another embodiment the treatment is for one to four weeks per cycle.

Another embodiment of this invention is directed to a method of treating cancer comprising administering to a patient in need of such treatment therapeutically effective amounts of the FPT inhibitor (i.e., compound of this invention), a taxane, and a platinum coordination compound, wherein said FPT inhibitor is administered every day, said taxane is administered once every three weeks per cycle, and said platinum coordinator compound is administered once every three weeks per cycle. In another embodiment the treatment is for one to three weeks per cycle.

Another embodiment of this invention is directed to a method of treating cancer comprising administering to a patient in need of such treatment therapeutically effective amounts of the FPT inhibitor (i.e., compound of this invention), paclitaxel, and carboplatin. In another embodiment, said FPT inhibitor is administered every day, said paclitaxel is administered once per week per cycle, and said carboplatin is administered once per week per cycle. In another embodiment the treatment is for one to four weeks per cycle.

Another embodiment of this invention is directed to a method of treating cancer comprising administering to a patient in need of such treatment therapeutically effective amounts of the FPT inhibitor (i.e., compound of this invention), paclitaxel, and carboplatin. In another embodiment, said FPT inhibitor is administered every day, said paclitaxel is administered once every three weeks per cycle, and said carboplatin is administered once every three weeks per cycle. In another embodiment the treatment is for one to three weeks per cycle.

Another embodiment of this invention is directed to a method for treating non small cell lung cancer in a patient in need of such treatment comprising administering daily a therapeutically effective amount of the FPT inhibitor (i.e., compound of this invention), administering a therapeutically effective amount of carboplatin once a week per cycle, and administering a therapeutically effective amount of paclitaxel once a week per cycle, wherein the treatment is given for one to four weeks per cycle. In another embodiment said FPT inhibitor is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering daily a therapeutically effective amount of the FPT inhibitor (i.e., compound of this invention), administering a therapeutically effective amount of carboplatin once every three weeks per cycle, and administering a therapeutically effective amount of paclitaxel once every three weeks per cycle, wherein the treatment is given for one to three weeks. In another embodiment said FPT inhibitor is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering about 50 to about 200 mg of the FPT inhibitor (i.e., compound of this invention) twice a day, administering carboplatin once per week per cycle in an amount to provide an AUC of about 2 to about 8 (and in another embodiment about 2 to about 3), and administering once per week per cycle about 60 to about 300 mg/m$^2$ (and in another embodiment about 50 to 100 mg/m$^2$, and in yet another embodiment about 60 to about 80 mg/m$^2$) of paclitaxel, wherein the treatment is given for one to four weeks per cycle. In another embodiment said FPT inhibitor is administered in amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

In another embodiment, this invention is directed to a method for treating non small cell lung cancer in a patient in need of such treatment comprising administering about 50 to about 200 mg of the FPT inhibitor (i.e., compound of this invention) twice a day, administering carboplatin once every three weeks per cycle in an amount to provide an AUC of about 2 to about 8 (in another embodiment about 5 to about 8, and in another embodiment 6), and administering once every three weeks per cycle about 150 to about 250 mg/m$^2$ (and in another embodiment about 175 to about 225 mg/m$^2$, and in another embodiment 175 mg/m$^2$) of paclitaxel, wherein the treatment is given for one to three weeks. In another embodiment said FPT inhibitor is administered in an amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

Other embodiments of this invention are directed to methods of treating cancer as described in the above embodiments except that in place of paclitaxel and carboplatin the taxanes and platinum coordinator compounds used together in the methods are: (1) docetaxel (Taxotere®) and cisplatin; (2) paclitaxel and cisplatin; and (3) docetaxel and carboplatin. In another embodiment of the methods of this invention cisplatin is used in amounts of about 30 to about 100 mg/m$^2$. In the another embodiment of the methods of this invention docetaxel is used in amounts of about 30 to about 100 mg/m$^2$.

In another embodiment this invention is directed to a method of treating cancer comprising administering to a patient in need of such treatment therapeutically effective amounts of the FPT inhibitor (i.e., compound of this invention), a taxane, and an EGF inhibitor that is an antibody. In another embodiment the taxane used is paclitaxel, and the EGF inhibitor is a HER2 antibody (in one embodiment Herceptin) or Cetuximab, and in another embodiment Herceptin is used. The length of treatment, and the amounts and administration of the FPT inhibitor and the taxane are as described in the embodiments above. The EGF inhibitor that is an antibody is administered once a week per cycle, and in another embodiment is administered on the same day as the taxane, and in another embodiment is administered consecutively with the taxane. For example, Herceptin is administered in a loading dose of about 3 to about 5 mg/m$^2$ (in another embodiment about 4 mg/m$^2$), and then is administered in a maintenance dose of about 2 mg/m$^2$ once per week per cycle for the remainder of the treatment cycle (usually the cycle is 1 to 4 weeks). In one embodiment the cancer treated is breast cancer.

In another embodiment this invention is directed to a method of treating cancer comprising administering to a patient in need of such treatment therapeutically effective amounts of: (1) the FPT inhibitor (i.e., compound of this invention), (2) a taxane, and (3) an antineoplastic agent selected from the group consisting of: (a) an EGF inhibitor that is a small molecule, (b) a VEGF inhibitor that is an antibody, and (c) a VEGF kinase inhibitor that is a small molecule. In another embodiment, the taxane paclitaxel or docetaxel is used. In another embodiment the antineoplastic agent is selected from the group consisting of: tarceva, Iressa, bevacizumab, SU5416, SU6688 and BAY 43-9006. The length of treatment, and the amounts and administration of the FPT inhibitor and the taxane are as described in the embodiments above. The VEGF kinase inhibitor that is an antibody is usually given once per week per cycle. The EGF and VEGF inhibitors that are small molecules are usually given daily per cycle. In another embodiment, the VEGF inhibitor that is an antibody is given on the same day as the taxane, and in another embodiment is administered concurrently with the taxane. In another embodiment, when the EGF inhibitor that is a small molecule or the VEGF inhibitor that is a small molecule is administered on the same day as the taxane, the administration is concurrently with the taxane. The EGF or VEGF kinase inhibitor is generally administered in an amount of about 10 to about 500 mg/m$^2$.

In another embodiment this invention is directed to a method of treating cancer comprising administering to a patient in need of such treatment therapeutically effective amounts of the FPT inhibitor (i.e., compound of this invention), an anti-tumor nucleoside derivative, and a platinum coordination compound.

Another embodiment of this invention is directed to a method of treating cancer comprising administering to a patient in need of such treatment therapeutically effective amounts of the FPT inhibitor (i.e., compound of this invention), an anti-tumor nucleoside derivative, and a platinum coordination compound, wherein said FPT inhibitor is administered every day, said anti-tumor nucleoside derivative is administered once per week per cycle, and said platinum coordinator compound is administered once per week per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of the FPT inhibitor (i.e., compound of this invention), an anti-tumor nucleoside derivative, and a platinum coordination compound, wherein said FPT inhibitor is administered every day, said an anti-tumor nucleoside derivative is administered once per week per cycle, and said platinum coordinator compound is administered once every three weeks per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of the FPT inhibitor (i.e., compound of this invention), gemcitabine, and cisplatin. In another embodiment, said FPT inhibitor is administered every day, said gemcitabine is administered once per week per cycle, and said cisplatin is administered once per week per cycle. In one embodiment the treatment is for one to seven weeks per cycle.

Another embodiment of this invention is directed to a method of treating cancer comprising administering to a patient in need of such treatment therapeutically effective amounts of the FPT inhibitor (i.e., compound of this invention), gemcitabine, and cisplatin. In another embodiment, said FPT inhibitor is administered every day, said gemcitabine is administered once per week per cycle, and said cisplatin is administered once every three weeks per cycle. In another embodiment the treatment is for one to seven weeks.

Another embodiment of this invention is directed to a method of treating cancer comprising administering to a patient in need of such treatment therapeutically effective amounts of the FPT inhibitor (i.e., compound of this invention), gemcitabine, and carboplatin. In another embodiment said FPT inhibitor is administered every day, said gemcitabine is administered once per week per cycle, and said carboplatin is administered once per week per cycle. In another embodiment the treatment is for one to seven weeks per cycle.

Another embodiment of this invention is directed to a method of treating cancer comprising administering to a patient in need of such treatment therapeutically effective amounts of the FPT inhibitor (i.e., compound of this invention), gemcitabine, and carboplatin. In another embodiment said FPT inhibitor is administered every day, said gemcitabine is administered once per week per cycle, and said carboplatin is administered once every three weeks per cycle. In another embodiment the treatment is for one to seven weeks per cycle.

In the above embodiments using gemcitabine, the FPT inhibitor (i.e., compound of this invention) and the platinum coordinator compound are administered as described above for the embodiments using taxanes. Gemcitabine is administered in an amount of about 500 to about 1250 mg/m$^2$. In one embodiment the gemcitabine is administered on the same day as the platinum coordinator compound, and in another embodiment consecutively with the platinum coordinator compound, and in another embodiment the gemcitabine is administered after the platinum coordinator compound.

Another embodiment of this invention is directed to a method of treating cancer in a patient in need of such treatment comprising administering to said patient the FPT inhibitor (i.e., compound of this invention) and an antineoplastic agent selected from: (1) EGF inhibitors that are antibodies, (2) EGF inhibitors that are small molecules, (3) VEGF inhibitors that are antibodies, and (4) VEGF kinase inhibitors that are small molecules all as described above. The treatment is for one to seven weeks per cycle, and generally for one to four weeks per cycle. The FPT inhibitor is administered in the same manner as described above for the other embodiments of this invention. The small molecule antineoplastic agents are usually administered daily, and the antibody antineoplastic agents are usually administered once per week per cycle. In one embodiment the antineoplastic agents are selected from the group consisting of: Herceptin, Cetuximab, Tarceva, Iressa, bevacizumab, IMC-1C11, SU5416, SU6688 and BAY 43-9006.

In the embodiments of this invention wherein a platinum coordinator compound is used as well as at least one other antineoplastic agent, and these drugs are administered consecutively, the platinum coordinator compound is generally administered after the other antineoplastic agents have been administered.

Other embodiments of this invention include the administration of a therapeutically effective amount of radiation to the patient in addition to the administration of the FPT inhibitor (i.e., compound of this invention) and antineoplastic agents in the embodiments described above. Radiation is administered according to techniques and protocols well know to those skilled in the art.

Another embodiment of this invention is directed to a pharmaceutical composition comprising at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising the FPT inhibitor (i.e., compound of this invention) and at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising the FPT inhibitor (i.e., compound of this invention) and at least one antineoplastic agent and a pharmaceutically acceptable carrier for intravenous administration. Preferably the pharmaceutically acceptable carrier is an isotonic saline solution (0.9% NaCl) or a dextrose solution (e.g., 5% dextrose).

Those skilled in the art will appreciate that the compounds (drugs) used in the methods of this invention are available to the skilled clinician in pharmaceutical compositions (dosage forms) from the manufacturer and are used in those compositions. So, the recitation of the compound or class of compounds in the above described methods can be replaced with a recitation of a pharmaceutical composition comprising the particular compound or class of compounds. For example, the embodiment directed to a method of treating cancer comprising administering to a patient in need of such treatment therapeutically effective amounts of the FPT inhibitor (i.e., compound of this invention), a taxane, and a platinum coordination compound, includes within its scope a method of treating cancer comprising administering to a patient in need of such treatment therapeutically effective amounts of a pharmaceutical composition comprising the FPT inhibitor, a pharmaceutical composition comprising a taxane, and a pharmaceutical composition comprising a platinum coordination compound.

The actual dosage employed may be varied depending upon the requirements of the patient and the severity of the condition being treated. Determination of the proper dosage for a particular situation is within the skill of the art.

The amount and frequency of administration of the FPT inhibitor (i.e., compound of this invention) and the antineoplastic agents will be regulated according to the judgment of the attending clinician (physician) considering such factors as age, condition and size of the patient as well as severity of the cancer being treated.

The antineoplastic agent can be administered according to therapeutic protocols well known in the art. It will be apparent to those skilled in the art that the administration of the antineoplastic agent can be varied depending on the cancer being treated and the known effects of the antineoplastic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of antineoplastic agent will depend upon the diagnosis of the attending physicians and their judgement of the condition of the patient and the appropriate treatment protocol.

The determination of the order of administration, and the number of repetitions of administration of the antineoplastic agent during a treatment protocol, is well within the knowledge of the skilled physician after evaluation of the cancer being treated and the condition of the patient.

Thus, in accordance with experience and knowledge, the practicing physician can modify each protocol for the administration of an antineoplastic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Other embodiments of this invention are directed to the use of a combination of at least one (e.g., one) compound of formula 1.0 and drugs for the treatment of breast cancer, i.e., this invention is directed to a combination therapy for the treatment of breast cancer. Those skilled in the art will appreciate that the compounds of formula 1.0 and drugs are generally administered as individual pharmaceutical compositions. The use of a pharmaceutical composition comprising more than one drug is within the scope of this invention.

Thus, another embodiment of this invention is directed to a method of treating (or preventing) breast cancer (i.e., postmenopausal and premenopausal breast cancer, e.g., hormone-dependent breast cancer) in a patient in need of such treatment comprising administering to said patient a therapeutically effective amount of at least one (e.g., one) compound of formula 1.0 and a therapeutically effective amount of at least one antihormonal agent selected from the group consisting of: (a) aromatase inhibitors, (b) antiestrogens, and (c) LHRH analogues; and said treatment optionally including the administration of at least one chemotherapeutic agent.

The compound of formula 1.0 is preferably administered orally, and in one embodiment is administered in capsule form.

Examples of aromatase inhibitors include but are not limited to: Anastrozole (e.g., Arimidex), Letrozole (e.g., Femara), Exemestane (Aromasin), Fadrozole and Formestane (e.g., Lentaron).

Examples of antiestrogens include but are not limited to: Tamoxifen (e.g., Nolvadex), Fulvestrant (e.g., Faslodex), Raloxifene (e.g., Evista), and Acolbifene.

Examples of LHRH analogues include but are not limited to: Goserelin (e.g., Zoladex) and Leuprolide (e.g., Leuprolide Acetate, such as Lupron or Lupron Depot).

Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

Preferably, when more than one antihormonal agent is used, each agent is selected from a different category of agent. For example, one agent is an aromatase inhibitor (e.g., Anastrozole, Letrozole, or Exemestane) and one agent is an antiestrogen (e.g., Tamoxifen or Fulvestrant).

Another embodiment of this invention is directed to a method of treating or preventing breast cancer in a patient in need of such treatment wherein said treatment comprises administering a therapeutically effective amount of at least one (e.g., one) compound of formula 1.0 and at least one antihormonal agent selected from the group consisting of: (a) aromatase inhibitors, (b) antiestrogens, and (c) LHRH analogues; and administering an effective amount of at least one chemotherapeutic agent.

Another embodiment of this invention is directed to a method of treating or preventing breast cancer in a patient in need of such treatment wherein said treatment comprises administering a therapeutically effective amount of at least one compound of formula 1.0 (e.g., one) and at least one antihormonal agent selected from the group consisting of: (a) aromatase inhibitors, (b) antiestrogens, and (c) LHRH analogues.

Another embodiment of this invention is directed to a method of treating or preventing breast cancer in a patient in need of such treatment wherein said treatment comprises administering a therapeutically effective amount of at least one compound of formula 1.0 (e.g., one) and at least one antihormonal agent selected from the group consisting of: (a) aromatase inhibitors, and (b) antiestrogens.

Another embodiment of this invention is directed to a method of treating or preventing breast cancer in a patient in need of such treatment wherein said treatment comprises administering a therapeutically effective amount of at least one compound of formula 1.0 (e.g., one), at least one antihormonal agent selected from the group consisting of: (a) aromatase inhibitors and (b) antiestrogens; and at least one chemotherapeutic agent.

Another embodiment of this invention is directed to a method of treating or preventing breast cancer in a patient in need of such treatment wherein said treatment comprises administering a therapeutically effective amount of at least one compound of formula 1.0 (e.g., one) and at least one aromatase inhibitor.

Another embodiment of this invention is directed to a method of treating or preventing breast cancer in a patient in need of such treatment wherein said treatment comprises administering a therapeutically effective amount of at least one compound of formula 1.0 (e.g., one), at least one aromatase inhibitor, and at least one chemotherapeutic agent.

Another embodiment of this invention is directed to a method of treating or preventing breast cancer in a patient in need of such treatment wherein said treatment comprises administering a therapeutically effective amount of: (1) at least one compound of formula 1.0 (e.g., one); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide; and administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one compound of formula formula 1.0 (e.g., one); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one compound of formula formula 1.0 (e.g., one); and (2) at least one antihormonal agent selected from the group consisting of: (a) aromatase inhibitors that are selected from the group consisting of Anastrozole, Letrozole, Exemestane, Fadrozole and Formestane, and (b) antiestrogens that are selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of: (1) at least one compound of formula 1.0 (e.g., one); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene; and administering an effective amount of at least one chemotherapeutic agents are selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one compound of formula 1.0 (e.g., one); and (2) at least one aromatase inhibitor selected from the group consisting of Anastrozole, Letrozole, Exemestane, Fadrozole and Formestane.

Another embodiment of this invention is directed to a method of treating or preventing breast cancer in a patient in need of such treatment wherein said treatment comprises administering a therapeutically effective amount of: (1) at least one compound of formula 1.0 (e.g., one); (2) at least one aromatase inhibitor that is selected from the group consisting of Anastrozole, Letrozole, Exemestane, Fadrozole and Formestane; and (3) administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one compound of formula 1.0 (e.g., one); (2) at least one aromatase inhibitor; and (3) at least one LHRH analogue.

Another embodiment of this invention is directed to a method of treating or preventing breast cancer in a patient in need of such treatment wherein said treatment comprises administering a therapeutically effective amount of:(1) at least one compound of formula 1.0 (e.g., one); (2) at least one antiestrogen; and (3) at least one LHRH analogue.

Another embodiment of this invention is directed to a method of treating or preventing breast cancer in a patient in need of such treatment wherein said treatment comprises administering a therapeutically effective amount of: (1) at least one compound of formula 1.0 (e.g., one); (2) at least one aromatase inhibitor that is selected from the group consisting of Anastrozole, Letrozole, Exemestane, Fadrozole and Formestane; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one compound of formula 1.0 (e.g., one); (2) at least one antiestrogen that is selected from the group consisting of: Tamoxifen, Fulvestrant, Raloxifene, and Acolbifene; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of at least one compound of formula 1.0 (e.g., one) and Anastrozole.

Another embodiment of this invention is directed to a method of treating or preventing breast cancer in a patient in need of such treatment wherein said treatment comprises administering a therapeutically effective amount of at least one compound of formula 1.0 (e.g., one) and Letrazole.

Another embodiment of this invention is directed to a method of treating or preventing breast cancer in a patient in need of such treatment wherein said treatment comprises administering a therapeutically effective amount of at least one compound of formula 1.0 (e.g., one) and Exemestane.

Another embodiment of this invention is directed to a method of treating or preventing breast cancer in a patient in need of such treatment wherein said treatment comprises administering a therapeutically effective amount of at least one compound of formula 1.0 (e.g., one) and and Fadrozole.

Another embodiment of this invention is directed to a method of treating or preventing breast cancer in a patient in need of such treatment wherein said treatment comprises administering a therapeutically effective amount of at least one compound of formula 1.0 (e.g., one) and Formestane.

Another embodiment of this invention is directed to a method of treating or preventing breast cancer in a patient in need of such treatment wherein said treatment comprises administering a therapeutically effective amount of at least one compound of formula 1.0 (e.g., one) and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one) Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one) and Raloxifene.

Another embodiment of this invention is directed to a method of treating or preventing breast cancer in a patient in need of such treatment wherein said treatment comprises administering a therapeutically effective amount of at least one compound of formula 1.0 (e.g., one) and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one) and Goserelin.

Another embodiment of this invention is directed to a method of treating or preventing breast cancer in a patient in need of such treatment wherein said treatment comprises administering a therapeutically effective amount of at least one compound of formula 1.0 (e.g., one) and and Leuprolide.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Formestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Formestane, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Formestane, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Formestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Raloxifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Goserelin, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Leuprolein, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Formestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Formestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Formestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Goserelin, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Goserelin, and Raloxifene.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide, and Raloxifene.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Anastrozole.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Letrozole.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Exemestane.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Fadrozole.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Formestane.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Anastrozole.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Letrozole.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Exemestane.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Fadrozole.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Formestane.

Another embodiment of this invention is directed to the treatment or prevention of breast cancer in a patient in need of such treatment, said treatment comprising the administration of a therapeutically effective amount of at least one compound of formula 1.0 (e.g., one) and Anastrozole.

Another embodiment of this invention is directed to the treatment or prevention of breast cancer in a patient in need of such treatment, said treatment comprising the administration of a therapeutically effective amount of at least one compound of formula 1.0 (e.g., one) and Letrozole.

Another embodiment of this invention is directed to the treatment or prevention of breast cancer in a patient in need of such treatment, said treatment comprising the administration of a therapeutically effective amount of at least one compound of formula 1.0 (e.g., one) and Exemestane.

Another embodiment of this invention is directed to the treatment or prevention of breast cancer in a patient in need of such treatment, said treatment comprising the administration of a therapeutically effective amount of at least one compound of formula 1.0 (e.g., one) and Tamoxifen.

Another embodiment of this invention is directed to the treatment or prevention of breast cancer in a patient in need of such treatment, said treatment comprising the administration of a therapeutically effective amount of at least one compound of formula 1.0 (e.g., one) and Fulvestrant.

Another embodiment of this invention is directed to the treatment or prevention of breast cancer in a patient in need of such treatment, said treatment comprising the administration of a therapeutically effective amount of at least one compound of formula 1.0 (e.g., one), Anastrozole, and Fulvestrant.

Another embodiment of this invention is directed to the treatment or prevention of breast cancer in a patient in need of such treatment, said treatment comprising the administration of a therapeutically effective amount of at least one compound of formula 1.0 (e.g., one), Letrozole, and Fulvestrant.

Another embodiment of this invention is directed to the treatment or prevention of breast cancer in a patient in need of such treatment, said treatment comprising the administration of a therapeutically effective amount of at least one compound of formula 1.0 (e.g., one), Exemestane, and Fulvestrant.

Another embodiment of this invention is directed to the treatment or prevention of breast cancer in a patient in need of such treatment, said treatment comprising the administration of a therapeutically effective amount of at least one compound of formula 1.0 (e.g., one), Anastrozole, and Tamoxifen.

Another embodiment of this invention is directed to the treatment or prevention of breast cancer in a patient in need of such treatment, said treatment comprising the administration of a therapeutically effective amount of at least one compound of formula 1.0 (e.g., one), Letrozole, and Tamoxifen.

Another embodiment of this invention is directed to the treatment or prevention of breast cancer in a patient in need of such treatment, said treatment comprising the administration of a therapeutically effective amount of at least one compound of formula 1.0 (e.g., one), Exemestane, and Tamoxifen.

Other embodiments of this invention are directed to any of the above described embodiments for the treatment of Breast Cancer wherein the chemotherapeutic agent is Trastuzumab.

Other embodiments of this invention are directed to any of the above described embodiments for the treatment of Breast Cancer wherein the method is directed to a method of treating breast cancer.

The compound of formula 1.0, antihormonal agents and chemotherapeutic agents can be administered concurrently or sequentially.

The antihormonal agents and optional chemotherapeutic agents are administered according to their protocols, dosage amounts, and dosage forms that are well know to those skilled in the art (e.g., the Physician's Desk Reference or published literature). For example, for Tamoxifen, Fulvestrant, Raloxifene, Anastrozole, Letrozole, Exemestane, Leuprolide and Goserelin, see the Physician's Desk Reference, $57^{th}$ Edition, 2003, published by Thomas PDR at Montvale, N.J. 07645-1742, the disclosure of which is incorporated herein by reference thereto.

In general, in the embodiments directed to the methods of treating Breast Cancer: (1) the compound of formula 1.0 can be administered daily (e.g., once per day, and in one embodiment twice a day), (2) the aromatase inhibitors can be administered in accordance with the known protocol for the aromatase inhibitor used (e.g., once per day), (3) the antiestrogens can be administered in accordance with the known protocol for the antiestrogen used (e.g., from once a day to once a month), (4) the LHRH analogue can be administered in accordance with the known protocol for the LHRH analogue used (e.g., once a month to once every three months), and (5) the chemotherapeutic agent can be administered in accordance with the known protocol for the chemotherapeutic agent used (e.g., from once a day to once a week).

Radiation therapy, if administered, is generally administered according to known protocols before administration of the compound of formula 1.0, antihormonal agents and optional chemotherapeutic agents.

Treatment according to the methods of treating Breast Cancer is continuous (i.e., a continuous dosing schedule is followed). The treatment is continued until there is a complete response, or until the skilled clinician determines that the patient is not benefiting from the treatment (for example, when there is disease progression).

The continuous treatment protocol for Breast Cancere can be changed to a discontinuous treatment schedule if, in the judgment of the skilled clinician, the patient would benefit from a discontinuous treatment schedule with one or more of the administered drugs. For example, the compound of formula 1.0 can be given using a discontinous treatment schedule while the remaining drugs used in the treatment are given as described herein. An example of a discontinuous treatment protocol for the compound of formula 1.0 is a repeating cycle of three weeks with the compound of formula 1.0 followed by one week without the compound of formula 1.0.

After a complete response is achieved with the Breast Cancer treatment, maintenance therapy with the compound of formula 1.0 can be continued using the dosing described in the methods of this invention. Maintenance therapy can also include administration of the antihormonal agents using the dosing described in the methods of this invention. Maintenance therapy can just be with the antihormonal agents. For example, after a complete response is achieved, an aromatase inhibitor (e.g., Anastrozole, Letrozole or Exemestane) can be continued for up to five years. Or, for example, an antiestrogen, e.g., Tamoxifen, may be used for up to five years after a complete response is achieved. Or, for example, an antiestrogen (e.g., Tamoxifen) can be used for up to five years after a complete response is achieved followed by the use of an aromatase inhibitor (e.g., Anastrozole, Letrozole or Exemestane) for up to five years.

In the embodiments directed to the treatment of Breast Cancer described above, the compound of formula 1.0 is administered continuously in a total daily dose of about 100 mg to about 600 mg. Usually this amount is administered in divided doses, and in one embodiment this amount is administered twice a day. In one embodiment the compound of formula 1.0 is dosed twice a day in an amount of about 50 mg to about 300 mg per dose. In another embodiment the compound of formula 1.0 is dosed twice a day in an amount of about 100 mg to about 200 mg per dose. Examples include the compound of formula 1.0 being dosed twice a day at 100 mg per dose. Examples also include the compound of formula 1.0 being dosed twice a day at 200 mg per dose.

Anastrozole is administered p.o. and is dosed once a day in amounts of about 0.5 to about 10 mg per dose, and in one embodiment in an amount of about 1.0 mg per dose.

Letrozole is administered p.o. and is dosed once a day in amounts of about 1.0 to about 10 mg per dose, and in one embodiment in an amount of about 2.5 mg per dose.

Exemestane is administered p.o. and is dosed once a day in amounts of about 10 to about 50 mg per dose, and in one embodiment in an amount of about 25 mg per dose.

Fadrozole is administered p.o. and is dosed twice a day in amounts of about 0.5 to about 10 mg per dose, and in one embodiment in an amount of about 2.0 mg per dose.

Formestane is administered i.m. and is dosed once every two weeks in amounts of about 100 to about 500 mg per dose, and in one embodiment in an amount of about 250 mg per dose.

Tamoxifen is administered p.o. and is dosed once a day in amounts of about 10 to about 100 mg per dose, and in one embodiment in an amount of about 20 mg per dose.

Fulvestrant is administered i.m. and is dosed once a month in amounts of about 100 to about 1000 mg per dose, and in one embodiment in an amount of about 250 mg per dose.

Raloxifene is administered p.o. and is dosed once a day in amounts of about 10 to about 120 mg per dose, and in one embodiment in an amount of about 60 mg per dose.

Acolbifene is administered p.o. and is dosed once a day in amounts of about 5 to about 20 mg per dose, and in one embodiment in an amount of about 20 mg per dose.

Goserelin is administered s.c. and is dosed once a month, or once every three months, in amounts of about 2 to about 20 mg per dose, and in one embodiment in an amount of about 3.6 mg per dose when administered once a month, and in another embodiment in an amount of about 10.8 mg per dose when administered once every three months.

Leuprolide is administered s.c. and is dosed once a month, or once every three months, in amounts of about 2 to about 20 mg per dose, and in one embodiment in an amount of about 3.75 mg per dose when administered once a month, and in another embodiment in an amount of about 11.25 mg per dose when administered once every three months.

Trastuzumab is administered by i.v. and is dosed once a week in amounts of about 2 to about 20 mpk per dose, and in one embodiment in an amount of about 2 mpk per dose. Trastuzumab is generally initially administered in a loading dose that is generally twice the dose of the weekly dose. Thus, for example, a 4 mpk loading dose is administered and then dosing is 2 mpk per dose per week.

Gefitinib is administered p.o. and is dosed once a day in amounts of about 100 to about 1000 mg per dose, and in one embodiment in an amount of about 250 mg per dose.

Erlotinib is administered p.o. and is dosed once a day in amounts of about 100 to about 500 mg per dose, and in one embodiment in an amount of about 150 mg per dose.

Bevacizumab is administered i.v. and is dosed once every two weeks in amounts of about 2.5 to about 15 mg per kilogram of body weight per dose, and in one embodiment in an amount of about 10 mg per kilogram per dose.

Cetuximab is administered i.v. and is dosed once a week in amounts of about 200 to about 500 mg per meter squared dose, and in one embodiment in an amount of about 250 mg per meter squared per dose.

Bortezomib is administered i.v. and is dosed twice a week for 2 weeks followed by a 10 day rest period (21 day treatment cycle) for a maximum of 8 treatment cycles in amounts of about 1.0 to about 2.5 mg per meter squared per dose, and in one embodiment in an amount of about 1.3 mg per meter squared per dose.

Thus in one embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Anastrozole p.o. in an amount of about 0.5 to about 10 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 100 to 200 mg per dose, wherein each dose is administered twice a day, and (2) Anastrozole in an amount of about 1.0 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Letrozole p.o. in an amount of about 1.0 to about 10 mg per dose wherein each dose is given once a day.

In another embodiment of this invention breast cancer is treated (or prevented) in a patient in need of such treatment wherein said treatment comprises administering to said patient: (1) the compound of formula 1.0 in an amount of about 100 to 200 mg per dose, wherein each dose is administered twice a day, and (2) Letrozole p.o. in an amount of about 2.5 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Exemestane p.o. in an amount of about 10 to about 50 mg per dose wherein each dose is given once a day.

In another embodiment of this invention breast cancer is treated (or prevented) in a patient in need of such treatment wherein said treatment comprises administering to said patient: (1) the compound of formula 1.0 in an amount of about 100 to 200 mg per dose, wherein each dose is administered twice a day, and (2) Exemestane in an amount of about 25 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 orally in an amount of about 100 to 200 mg per dose, wherein each dose is administered twice a day, and (2) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, and (2) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, and (2) Tamoxifen p.o. in an amount of about 20 mg per dose wherein each dose is given once a day.

In other embodiments of the invention breast cancer is treated in a patient in need of such treatment wherein said treatment comprises the administration of the compound of formula 1.0, one of the aromatase inhibitors (e.g., Anastrozole, Letrozole, or Exemestane, and in one embodiment Anastrozole), and one of the antiestrogens (e.g., Fulvestrant or Tamoxifen), wherein the compound of formula 1.0, aromatase inhibitor and antiestrogen are administered in the dosages described above.

Thus, for example in another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 p.o in an amount of about 100 to 200 mg per dose, wherein each dose is administered twice a day, (2) Anastrozole p.o. in an amount of about 1.0 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Letrozole p.o in an amount of about 1.0 to about 10 mg per dose wherein each dose is given once a day, and (3) Fulvestrant in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Letrozole p.o. in an amount of about 2.5 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Exemestane p.o. in an amount of about 10 to about 50 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Exemestane p.o. in an amount of about 25 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Tamoxifen p.o.in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Anastrozole p.o. in an amount of about 1.0 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Letrozole p.o. in an amount of about 1.0 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Letrozole p.o. in an amount of about 2.5 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Exemestane p.o. in an amount of about 10 to about 50 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Exemestane p.o. in an amount of about 25 mg per dose wherein each dose is given once a day, and (3) Tamoxifen p.o. in an amount of about 20 mg per dose wherein each dose is given once a day.

Those skilled in the art will appreciate that when other combinations of antihormonal agents are used, the individual antihormonal agent is used in the amounts specified above for that individual antihormonal agent.

Other embodiments of the treatment of Breast Cancer are directed to the methods of treating Breast Cancer described above wherein the compound of formula 1.0 is dosed twice a day in an amount of about 100 mg per dose.

Other embodiments of the treatment of Breast Cancer are directed to the methods of treating Breast Cancer described above wherein the compound of formula 1.0 is dosed twice a day in an amount of about 200 mg per dose.

Other embodiments of the treatment of Breast Cancer are directed to the methods of treating Breast Cancer described above wherein a chemotherapeutic agent is administered in addition to the compound of formula 1.0 and antihormonal agent (or antihormonal agents). In these embodiments the dosage ranges of the compound of formula 1.0 and antihormonal agents are as those described above in the combination therapies, or those described above for the individual compound of formula 1.0 and antihormonal agents, and the dosages of the chemotherapeutic agents are those described above for the individual chemotherapeutic agent. The dosages for the chemotherapeutic agents are well known in the art.

Other embodiments of this invention are directed to pharmaceutical compositions comprising the compound of formula 1.0 and at least one antihormonal agent and a pharmaceutically acceptable carrier.

Other embodiments of this invention are directed to pharmaceutical compositions comprising the compound of formula 1.0, at least one antihormonal agent, at least one chemotherapeutic agent, and a pharmaceutically acceptable carrier.

Other embodiments of this invention are directed to pharmaceutical compositions comprising the compound of formula 1.0, at least one chemotherapeutic agent, and a pharmaceutically acceptable carrier.

Other embodiments of this invention are directed to anyone of the pharmaceutical composition embodiments described above wherein the compound of formula 1.0 is selected from the group consisting of compounds: (1.3), (1.4), (2.1), (3.1), (4.1), (4.2), (4.3), (4.4), (5.1), (6.1), (7.1), (8.1), (9.1), (10.1), (11.2), (11.3), (12.1), (12.2), (13.2), (13.3), (14.1), (14.2), (14.3), (15.1), (15.2), (16.1), (17.1), (18.1), (19.1), (20.)1, (20.2), (20.3), (20.4), (21.1), (22.1), (24.1), (25.1), (26.1), (27.1), (28.1), (29.1), (30.1), (31.1), (31.2), (32.1), (32.2), (33.1), (33.2), (34.1), (34.2), (35.1), (36.1), (37.1), (38.1), (39.1), (40.1), (40.2), (41.1), (42.1), (43.1), (44.1), (45.1), (46.1), and (47.1).

Other embodiments of this invention are directed to anyone of the pharmaceutical composition embodiments described above wherein the compound of formula 1.0 is selected from the group consisting of compounds: (1.3), (1.4), (4.2), (4.3), (5.1), (6.1), (12.1), (12.2), (13.2), (13.3), (14.2), (15.1), (15.2), (16.1), (21.1), (22.1), (26.1), (27.1), (28.1), (29.1), (30.1), (31.1), (31.2), (32.1), (32.2), (45.1) and (47.1).

Other embodiments of this invention are directed to anyone of the pharmaceutical composition embodiments described above wherein the compound of formula 1.0 is selected from the group consisting of compounds: (1.3), (1.4), (5.1), (6.1), (15.1), (15.2), (21.1), (22.1), (26.1), (28.1), (29.1), (30.1), (31.1), and (32.1).

Other embodiments of this invention are directed to anyone of the pharmaceutical composition embodiments described above wherein the compound of formula 1.0 is selected from the group consisting of compounds: (1.3), (1.4), (15.1), (15.2), (21.1), (22.1), (26.1), (28.1), (29.1), (30.1), (31.1), and (32.1).

Other embodiments of this invention are directed to anyone of the pharmaceutical composition embodiments described above wherein the compound of formula 1.0 is (1.3).

Other embodiments of this invention are directed to anyone of the pharmaceutical composition embodiments described above wherein the compound of formula 1.0 is (1.4).

Other embodiments of this invention are directed to anyone of the pharmaceutical composition embodiments described above wherein the compound of formula 1.0 is (15.1).

Other embodiments of this invention are directed to anyone of the pharmaceutical composition embodiments described above wherein the compound of formula 1.0 is (15.2).

Other embodiments of this invention are directed to anyone of the pharmaceutical composition embodiments described above wherein the compound of formula 1.0 is (21.1).

Other embodiments of this invention are directed to anyone of the pharmaceutical composition embodiments described above wherein the compound of formula 1.0 is (22.1).

Other embodiments of this invention are directed to anyone of the pharmaceutical composition embodiments described above wherein the compound of formula 1.0 is (26.1).

Other embodiments of this invention are directed to anyone of the pharmaceutical composition embodiments described above wherein the compound of formula 1.0 is (28.1).

Other embodiments of this invention are directed to anyone of the pharmaceutical composition embodiments described above wherein the compound of formula 1.0 is (29.1).

Other embodiments of this invention are directed to anyone of the pharmaceutical composition embodiments described above wherein the compound of formula 1.0 is (30.1).

Other embodiments of this invention are directed to anyone of the pharmaceutical composition embodiments described above wherein the compound of formula 1.0 is (31.1).

Other embodiments of this invention are directed to anyone of the pharmaceutical composition embodiments described above wherein the compound of formula 1.0 is (32.1).

Other embodiments of this invention are directed to anyone of the method of treating embodiments described above wherein the compound of formula 1.0 is selected from the group consisting of compounds: (1.3), (1.4), (2.1), (3.1), (4.1), (4.2), (4.3), (4.4), (5.1), (6.1), (7.1), (8.1), (9.1), (10.1), (11.2), (11.3), (12.1), (12.2), (13.2), (13.3), (14.1), (14.2), (14.3), (15.1), (15.2), (16.1), (17.1), (18.1), (19.1), (20.)1, (20.2), (20.3), (20.4), (21.1), (22.1), (24.1), (25.1), (26.1), (27.1), (28.1), (29.1), (30.1), (31.1), (31.2), (32.1), (32.2), (33.1), (33.2), (34.1), (34.2), (35.1), (36.1), (37.1), (38.1), (39.1), (40.1), (40.2), (41.1), (42.1), (43.1), (44.1), (45.1), (46.1), and (47.1).

Other embodiments of this invention are directed to anyone of the method of treating embodiments described above wherein the compound of formula 1.0 is selected from the group consisting of compounds: (1.3), (1.4), (4.2), (4.3), (5.1), (6.1), (12.1), (12.2), (13.2), (13.3), (14.2), (15.1), (15.2), (16.1), (21.1), (22.1), (26.1), (27.1), (28.1), (29.1), (30.1), (31.1), (31.2), (32.1), (32.2), (45.1) and (47.1).

Other embodiments of this invention are directed to anyone of the method of treating embodiments described above wherein the compound of formula 1.0 is selected from the group consisting of compounds: (1.3), (1.4), (5.1), (6.1), (15.1), (15.2), (21.1), (22.1), (26.1), (28.1), (29.1), (30.1), (31.1), and (32.1).

Other embodiments of this invention are directed to anyone of the method of treating embodiments described above wherein the compound of formula 1.0 is selected from the group consisting of compounds: (1.3), (1.4), (15.1), (15.2), (21.1), (22.1), (26.1), (28.1), (29.1), (30.1), (31.1), and (32.1).

Other embodiments of this invention are directed to anyone of the method of treating embodiments described above wherein the compound of formula 1.0 is (1.3).

Other embodiments of this invention are directed to anyone of the method of treating embodiments described above wherein the compound of formula 1.0 is (1.4).

Other embodiments of this invention are directed to anyone of the method of treating embodiments described above wherein the compound of formula 1.0 is (15.1).

Other embodiments of this invention are directed to anyone of the method of treating embodiments described above wherein the compound of formula 1.0 is (15.2).

Other embodiments of this invention are directed to anyone of the method of treating embodiments described above wherein the compound of formula 1.0 is (21.1).

Other embodiments of this invention are directed to anyone of the method of treating embodiments described above wherein the compound of formula 1.0 is (22.1).

Other embodiments of this invention are directed to anyone of the method of treating embodiments described above wherein the compound of formula 1.0 is (26.1).

Other embodiments of this invention are directed to anyone of the method of treating embodiments described above wherein the compound of formula 1.0 is (28.1).

Other embodiments of this invention are directed to anyone of the method of treating embodiments described above wherein the compound of formula 1.0 is (29.1).

Other embodiments of this invention are directed to anyone of the method of treating embodiments described above wherein the compound of formula 1.0 is (30.1).

Other embodiments of this invention are directed to anyone of the method of treating embodiments described above wherein the compound of formula 1.0 is (31.1).

Other embodiments of this invention are directed to anyone of the method of treating embodiments described above wherein the compound of formula 1.0 is (32.1).

Those skilled in the art will recognize that the actual dosages and protocols for administration employed in the methods of this invention may be varied according to the judgment of the skilled clinician. A determination to vary the dosages and protocols for administration may be made after the skilled clinician takes into account such factors as the patient's age, condition and size, as well as the severity of the cancer being treated and the response of the patient to the treatment.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related, symptoms such as pain, and improvement in overall condition can also be used to help judge effectiveness of treatment.

Chemotherapeutic Agents

Classes of compounds that can be used as chemotherapeutic agents (antineoplastic agent/microtubule affecting agents) include but are not limited to: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), paclitaxel derivatives (e.g. taxotere), Mithramycin, Deoxycoformycin, Mitomycin-C, L-Asparaginase, Interferons (especially IFN-a), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Other chemotherapeutics include Navelbene, CPT-11, Anastrazole, Letrazole, Capecitabinbe, Reloxafine, and Droloxafine.

In one embodiment the antineoplastic agents selected from Cyclophasphamide, 5-Fluorouracil, Temozolomide, Vincristine, Cisplatin, Carboplatin, and Gemcitabine. In another embodiment, the antineoplastic agent is selected from Gemcitabine, Cisplatin and Carboplatin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742); the disclosures of which is incorporated herein by reference thereto.

Microtubule Affecting Agents

As used herein, a microtubule affecting agent (e.g., paclitaxel, a paclitaxel derivative or a paclitaxel-like compound) is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), paclitaxel derivatives (e.g., Taxotere, NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

In one embodiment the agents are compounds with paclitaxel-like activity. These include, but are not limited to paclitaxel and paclitaxel derivatives (paclitaxel-like compounds) and analogues. Paclitaxel and its derivatives (e.g. Taxol and Taxotere) are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz (1992) Trends Pharmacol. Sci. 13: 134-146, Rowinsky (1990) J. Natl. Canc. Inst. 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. For example, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) J. Molec. Biol., 89: 737-758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (cited above).

The compounds of this invention can be used according to the methods described in U.S. 2003/0185831 published Oct. 2, 2003 (see also, WO 03/047697 published Jun. 12, 2003), the disclosures of each being incorporated herein by reference thereto.

The compounds of the invention can be made following the reaction schemes below, and using procedures known in the art, for example, see U.S. Pat. No. 5,801,175 issued Sep. 1, 1998, WO 98/57960 published Dec. 23, 1998, U.S. 5,874,442 issued Feb. 23, 1999, WO 02/18368 published Mar. 7, 2002, WO 03/072549 published Sep. 4, 2003, U.S. 2004/0122018 published Jun. 24, 2004, U.S. Pat. No. 6,362,188 issued Mar. 26, 2002, U.S. Pat. No. 6,372,747 issued Apr. 16, 2002, WO 00/31064 published Jun. 2, 2000, and WO 88/03138 published May 5, 1988, the disclosures of each being incorporated herein by reference thereto.

General Procedures for Preparing the Compounds of Formula 1.0

Those skilled in the art will appreciate that in the reaction schemes below, isomers can be separated by techniques well know in the art. Such techniques can include chromatographic means, i.e., silica gel, chiral HPLC or a combination thereof.

Synthesis of compounds of Formula (1.0), wherein X is N and the

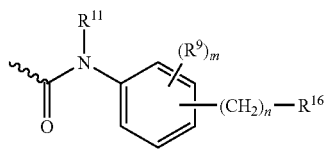

sidechain moiety (hereinafter "sidechain") is at the C-2 position of piperazine Ring IV (i.e., X is N in formula 1.0), can be done in the following manner. The synthesis of the anilino-imidazole derivative begins with the BOC protection of the amino group. Reaction with methanesulfonyl chloride gives a compound with an easily replaceable leaving group. A reaction with either a commercially obtained or synthesized sodium imidazole derivative is carried out.

Those skilled in the art will appreciate that a 2-substituted imidazole will give solely the desired 2-substituted adduct; however, reactions with a 4- or 5-substituted derivative will give a mixture of the 4- and 5-substituted derivative. These mixtures can be separated either by a trityl chloride procedure (see, for example, Tetrahedron Lett. (2002), 43, 8917-8919) or by chiral HPLC, as described in Preparative Example 2, Step B.

The BOC protecting group is then removed with acid treatment.

(See Scheme 1).

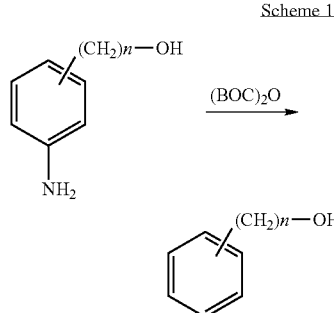

Scheme 1

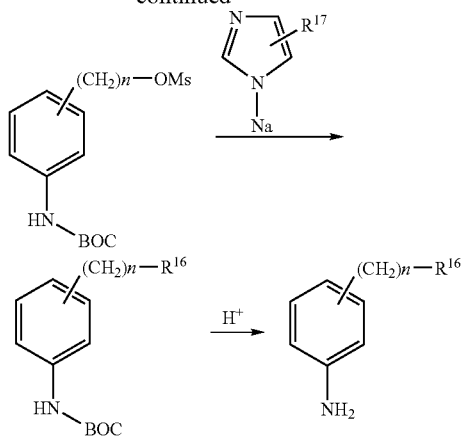

The piperazine anilino-imidazole compounds can be synthesized in the following manner. A chosen piperazinyl-2-carboxylic acid (R-isomer shown in Scheme 2) is protected as its di-BOC derivative. The appropriate anilino-imidazole derivative is then coupled to the piperazine intermediate using standard conditions (DEC, HOBT, NMM). The two BOC groups are removed with acid treatment.

Scheme 2

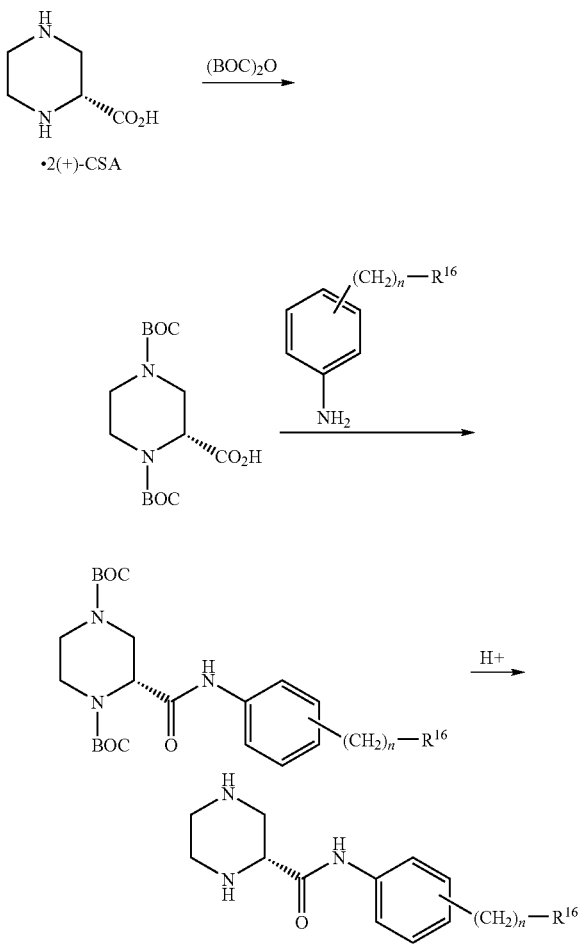

If one starts with the 2S-isomer of the piperazine carboxylic acid, then the final piperazine anilino-imidazole compound in Scheme 2 will have the opposite stereochemistry at the C-2 position.

The product from Scheme 2 can be alkylated with a chosen tricyclic chloride to give the product seen immediately below.

Scheme 3

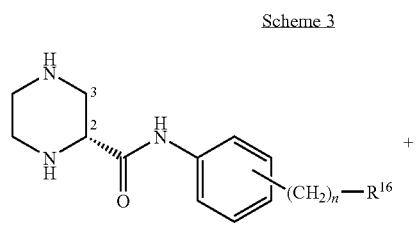

+

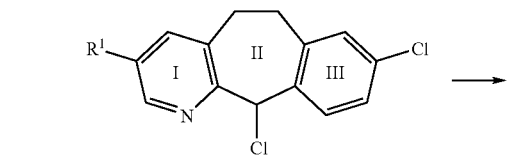

→

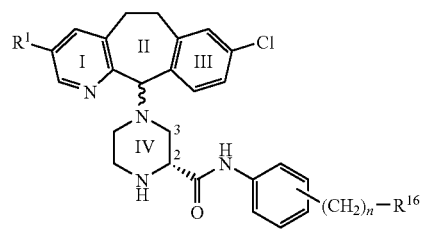

+

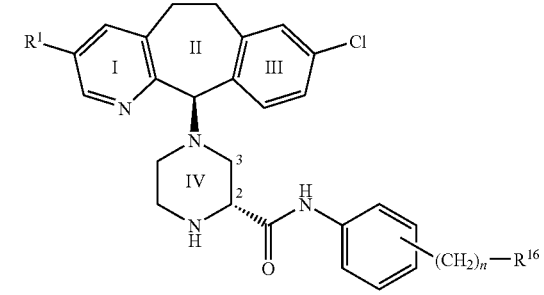

Chromatography
silica gel
and/or
chiral HPLC

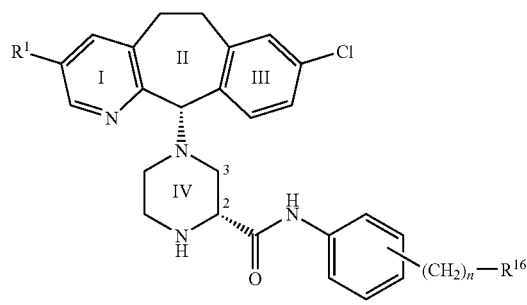

To alkylate the newly formed amide nitrogen (See Scheme 4), the racemate from Scheme 3, or preferably an individual resolved isomer, is first treated with (BOC)$_2$O. The resulting Boc protected compound is reacted with the desired alkyl- or arylalkyl chloride. The BOC group is then removed with acid treatment.

Scheme 4

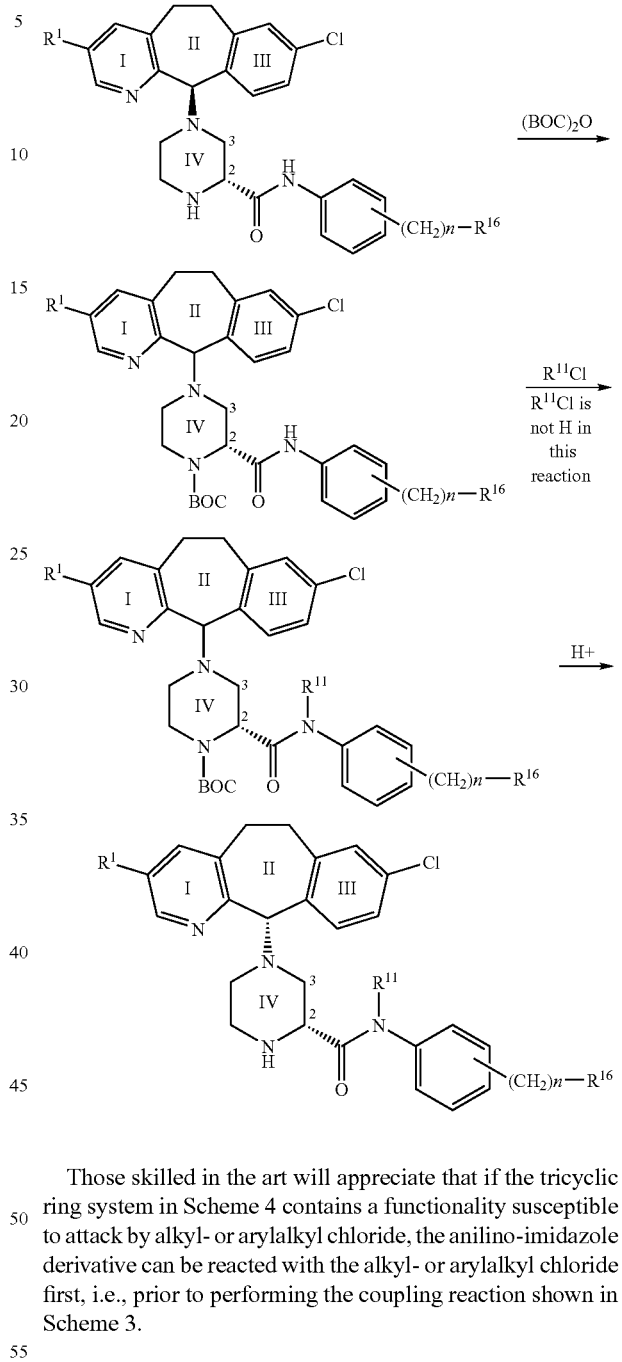

Those skilled in the art will appreciate that if the tricyclic ring system in Scheme 4 contains a functionality susceptible to attack by alkyl- or arylalkyl chloride, the anilino-imidazole derivative can be reacted with the alkyl- or arylalkyl chloride first, i.e., prior to performing the coupling reaction shown in Scheme 3.

Scheme 5

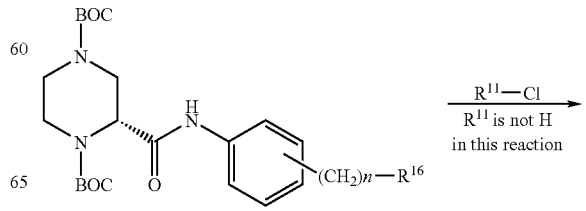

-continued

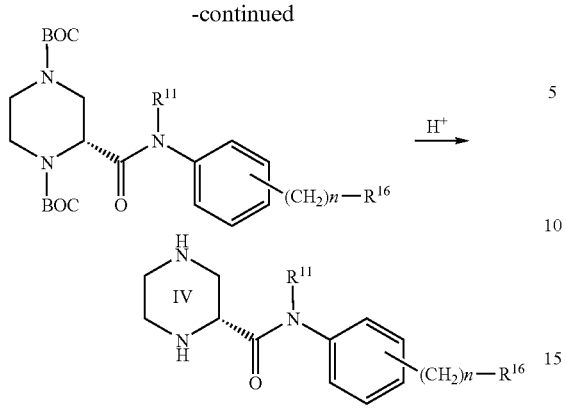

The racemate, or preferably an individual resolved isomer, of the compounds formed in Schemes 3 or 4 is treated with a carboxylic acid, acid chloride, chloroformate, isocyanate, alkylchloride, sulfonyl chloride, or carbamoyl chloride to provide the desired substituted compound (see Scheme 6).

Scheme 6

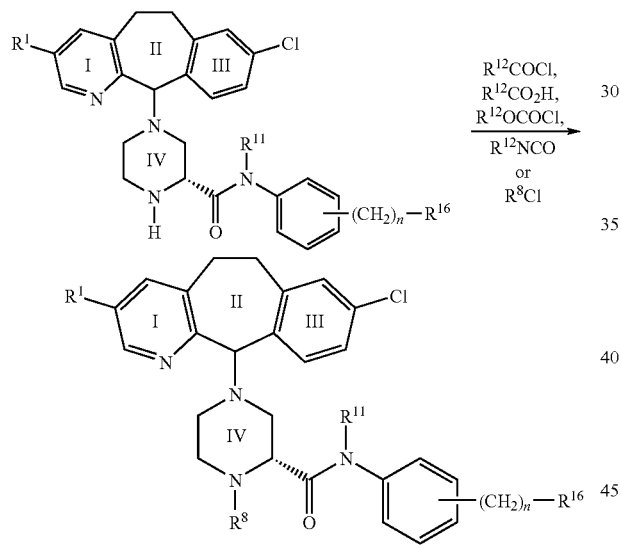

One skilled in the art can see if in Scheme 2 or Scheme 5 the other isomer of the piperazine carboxylic acid, the (2S) isomer, is used, then the subsequent compounds will have the opposite stereochemistry at C-2 position on Ring IV.

To make compounds of the Formula (1.0), wherin X=N and the

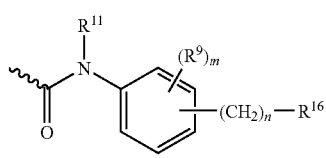

sidechain is at the C-3 position on piperazine Ring IV, the method in Scheme 7 can be employed. The unprotected anilino-imidazole piperazine compound from Scheme 5 is selectively BOCed with either a carefully controlled amount of (BOC)$_2$O or by use of BOC-ON. This intermediate can be then be alkylated with the desired tricyclic chloride.

Scheme 7

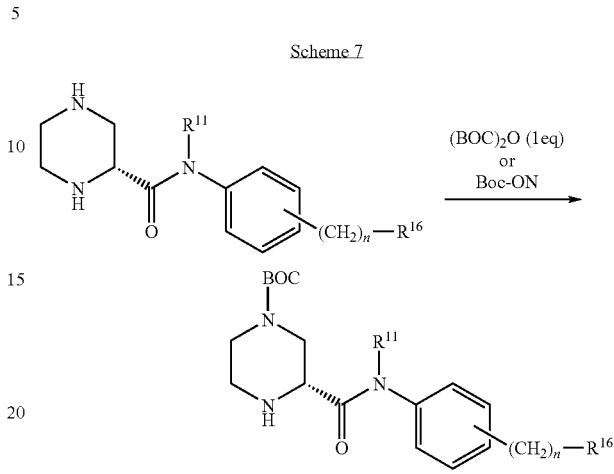

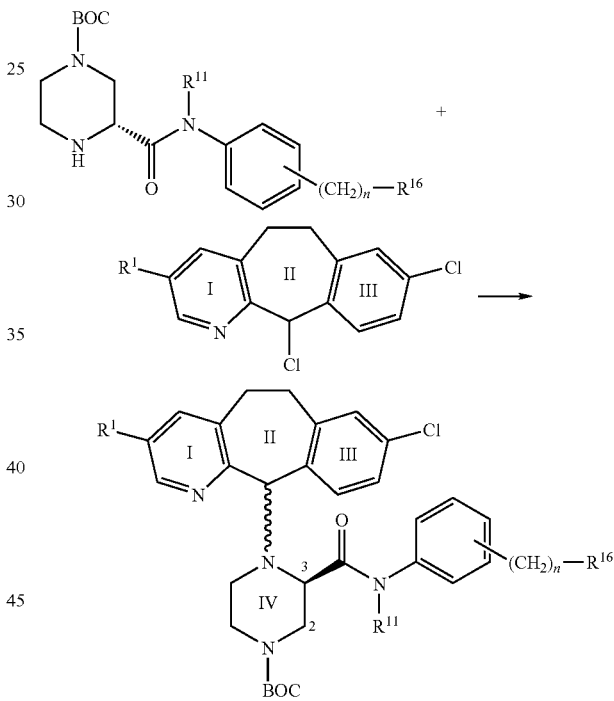

The product of Scheme 7 can then be reacted following the procedures in Schemes 4 and 6, to give the products:

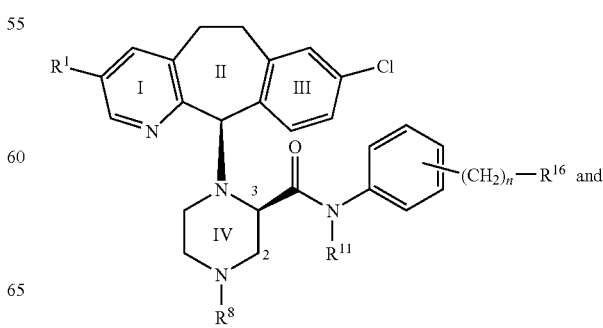

-continued

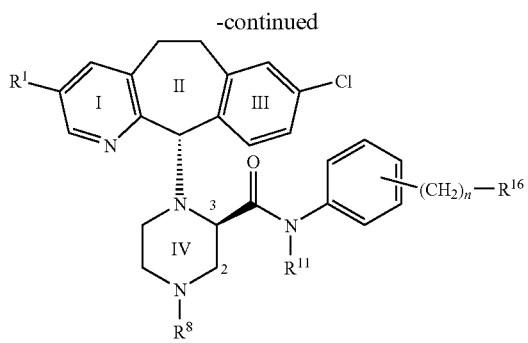

Those skilled in the art will appreciate that use of the (2S) isomer of the piperazine anilino-imidazole intermediate in Scheme 7 will provide compounds having a stereochemistry at the C-3 position of Ring IV that is opposite to that of the compounds immediately above.

Alkylating a piperazine anilino-imidazole intermediate of the type shown in Scheme 2 or Scheme 5, where both piperazinyl nitrogens are free, with an excess amount (between 2-3 equivalents) of the desired tricyclic chloride will give the doubly alkylated product shown in Scheme 8.

Scheme 8

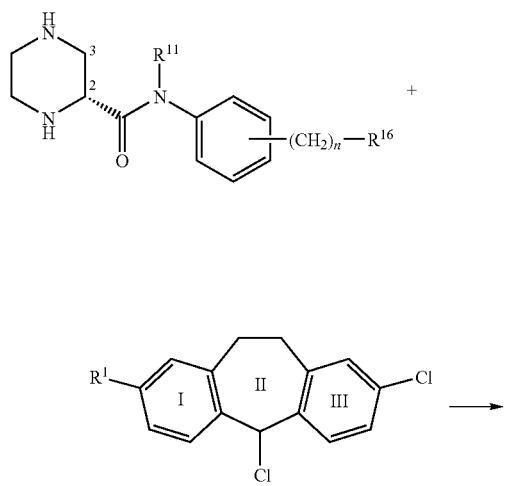

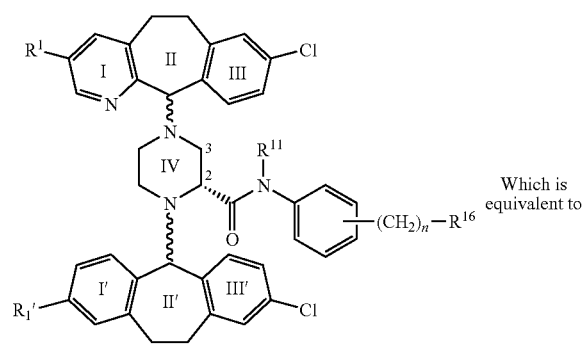

Which is equivalent to

-continued

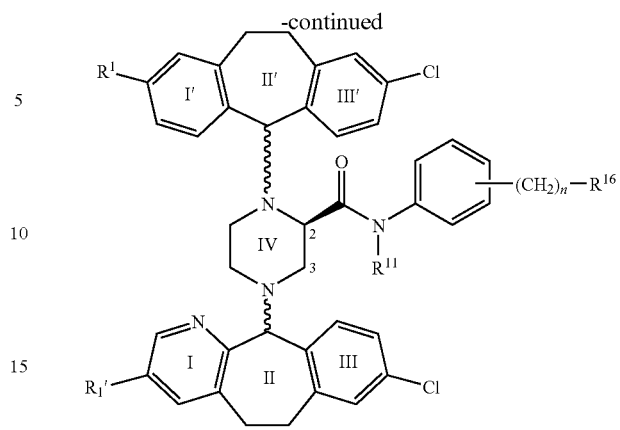

Those skilled in the art will appreciate that while the (2R) stereochemistry at C-2 on Ring IV is shown in Scheme 8, this chemistry is applicable to compounds with the (2S) stereochemistry.

Precursors of compounds of Formula (1.0) wherein X=CH and the sidechain is attached at the C-3 position on piperidine ring IV, can be prepared using chemistry disclosed in Journal of Organic Chemistry 2003, 68, 4984-4987, with the exception that instead of using an unsubstituted N-BOC 4-oxo-piperidine, the N-BOC 4-oxo-piperidine-3-carboxylic acid methyl ester is employed in the synthesis. Synthesis of that compound can be done using the procedure in Scheme 9. The 4-oxo-piperidine-3-carboxylic acid methyl ester is treated with $(BOC)_2O$. The ketone is reduced with sodium borohydride and the alcohol formed is reacted with methanesulfonyl chloride (See Scheme 9).

Scheme 9

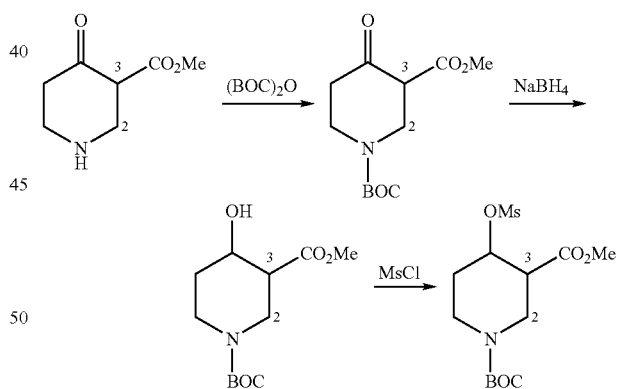

Using chemistry disclosed in WO 00/31064, published Jun. 2, 2000, following the reaction of the reduced tricyclic ketone derivative with LDA, the product of Scheme 9 is added (See Scheme 10). The racemeate, or preferably an individual resolved isomer, is put through a hydrolysis with lithium hydroxide to give the free carboxylic acid. The racemate, or preferably an individual resolved isomer, is then coupled, using standard conditions well known in the art, with a chosen anilino-imidazole derivative. Those skilled in the art will recognize that the newly formed amide nitrogen can be alkylated with an appropriate alkyl or arylalkyl chloride. Those skilled in the art will also recognize that if the tricyclic ring system contains a functionality susceptible to attack by alkylor arylalkyl chloride, the anilino-imidazole derivative can be reacted with the alkyl- or arylalkyl chloride first, prior to performing the coupling reaction (Scheme 5).

Following the procedures in Schemes 4 and 6, the final racemate, or preferably an individual resolved isomer, of Scheme 10 can then be reacted to give the products:

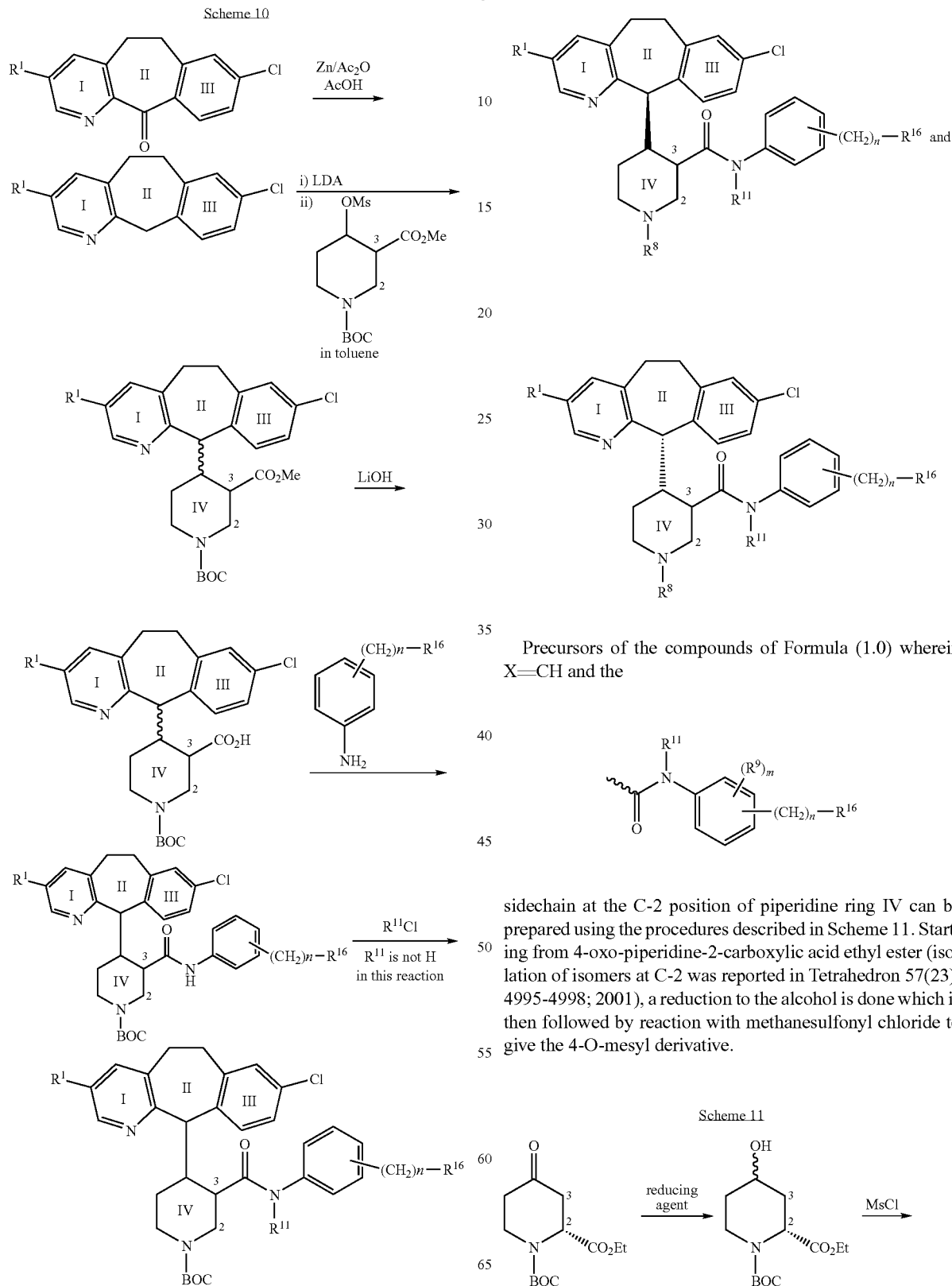

Precursors of the compounds of Formula (1.0) wherein X=CH and the sidechain at the C-2 position of piperidine ring IV can be prepared using the procedures described in Scheme 11. Starting from 4-oxo-piperidine-2-carboxylic acid ethyl ester (isolation of isomers at C-2 was reported in Tetrahedron 57(23); 4995-4998; 2001), a reduction to the alcohol is done which is then followed by reaction with methanesulfonyl chloride to give the 4-O-mesyl derivative.

-continued

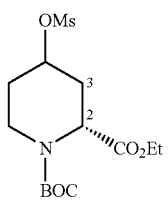

Using the product of Scheme 11 and following the procuedures in Scheme 10, and then taking the product obtained and following the procedures in Schemes 4 and Scheme 6, the compounds:

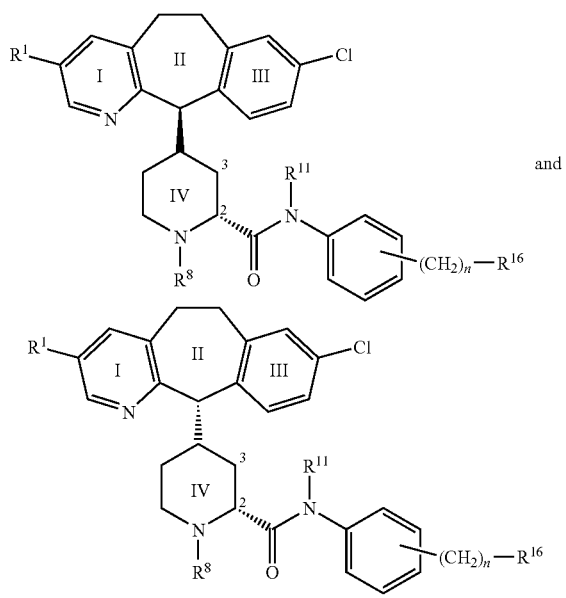

and can be obtained.

Those skilled in the art will appreciate that if the (2S) isomer of the 4-oxo-piperidine-2-carboxylic acid ethyl ester intermediate is used starting in Scheme 7, then the final products obtained would have the opposite stereochemistry at C-2 on piperidine Ring IV then that shown for the compounds immediately above.

Precursors of compounds of Formula (1.0) wherein X=C and a having the

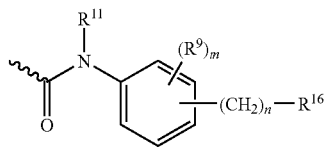

sidechain attached at the C-3 position of piperidine ring IV, can be prepared as follows (See Scheme 12). 1-Methyl-4-oxo-piperidine-3-carboxylic acid methyl ester is reduced. The primary hydroxyl group is selectively blocked using TBDMSCl. The compound formed is then treated with thionyl chloride to give the 4-chloro derivative, which is then used to make the associated Grignard intermediate. Using chemistry disclosed in the Journal of Organic Chemistry; (1990); 55(10); p3341-50, the Grignard intermediate is then reacted with the tricyclic ketone, which is then put through an acidic dehydrogenation. (Those skilled in the art will appreciate that the reaction will also generate a derivative wherein the —CH$_2$OH group is attached at the C-4 position on the piperidine Ring IV (not shown in Scheme 12), and those skilled in the art will appreciate that the early removal of this C-4 derivative from the reaction mixture is preferable). The racemate, or preferably an individual resolved isomer, is then converted, by techniques well know in the art, to the methyl carboxylate.

The N-methyl group is then removed using a procedure known in art (see, for example, WO88/03138). The N-methyl removal may, at the same time, hydrolyze the methyl ester to a carboxylic acid. If not, the product is reacted with lithium hydroxide reaction to convert it to the free carboxylic acid. The piperidine nitrogen on Ring IV is protected with a BOC group.

Scheme 12

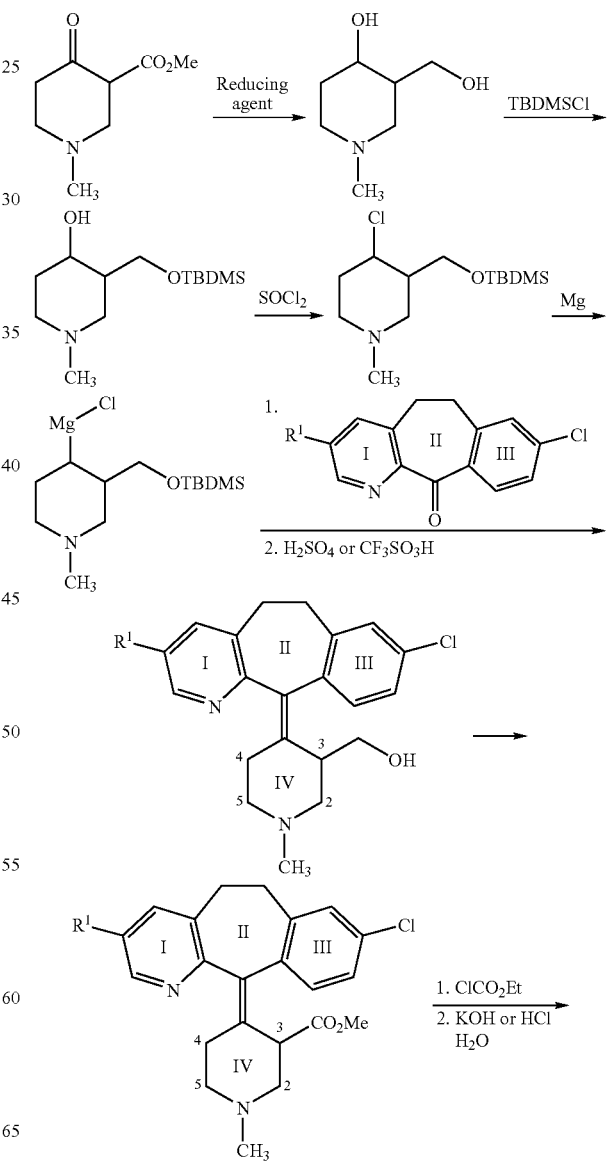

-continued

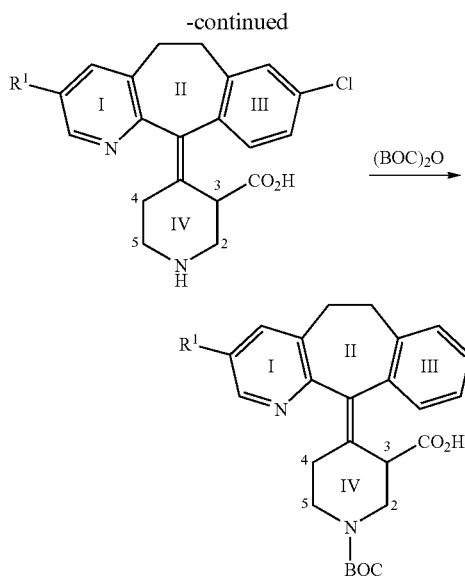

Following the procedures in Schemes 10, 4 and 6, and using the final product in Scheme 12, the compound:

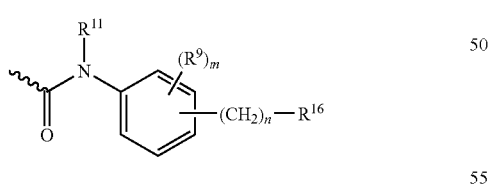

can be synthesized.

Compounds of Formula (1.0), wherein X=C and a having the

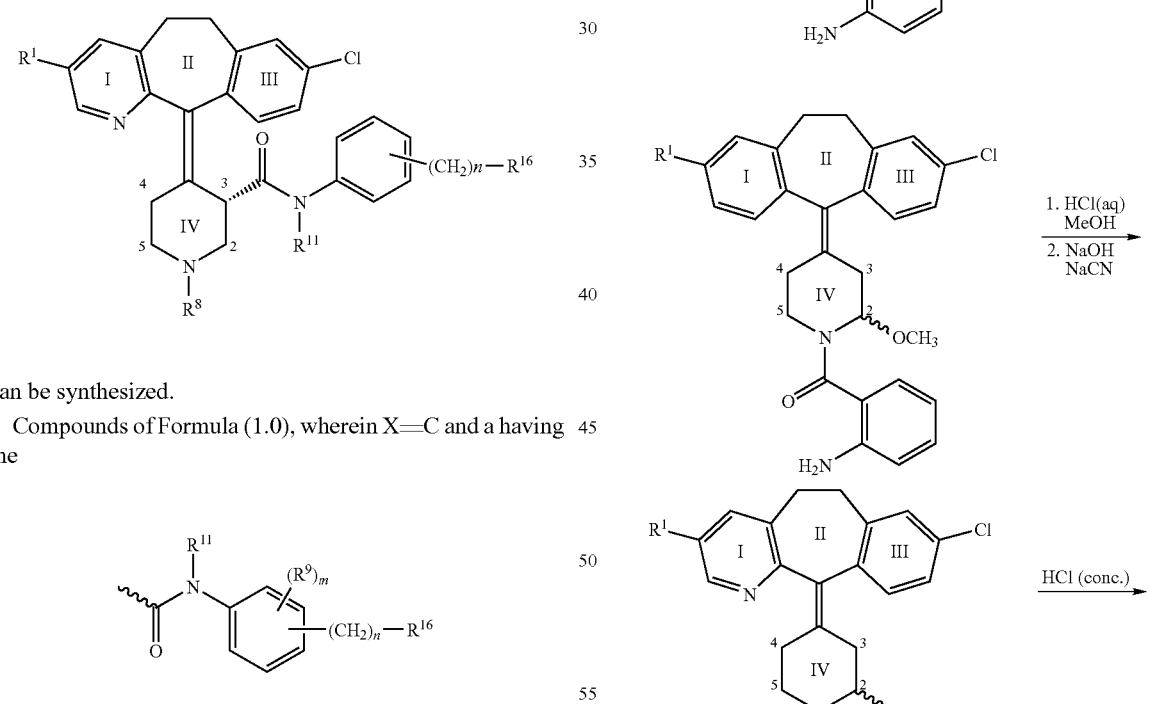

sidechain attached at the C-2 position of piperidine Ring IV, can be prepared utilizing the chemistry disclosed in U.S. Pat. No. 6,362,188 (issued Mar. 26, 2002). (Those skilled in the art will appreciate that the reaction with sodium nitrite, cuprous chloride and HCl will also generate the derivative wherein the methoxy group is attached at the C-5 position of the piperidine Ring IV (not shown in Scheme 13), and those skilled in the art will appreciate that the early removal of this derivative from the reaction mixture is preferable). The nitrogen on piperidine Ring IV is then protected with a BOC group.

Scheme 13

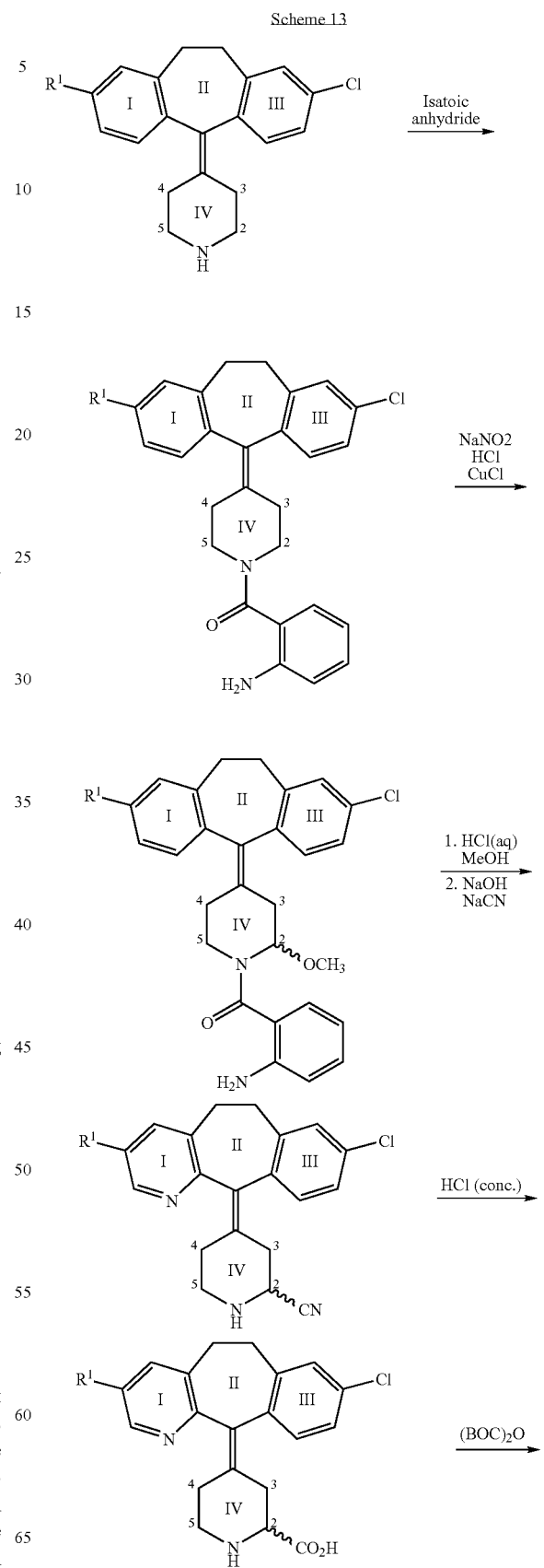

-continued

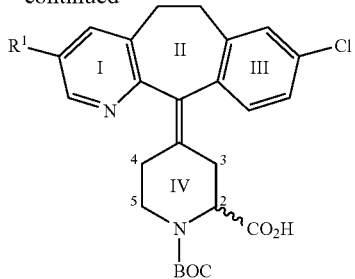

Following the procedure of Scheme 10 and using the final product shown in Scheme 13 the compounds:

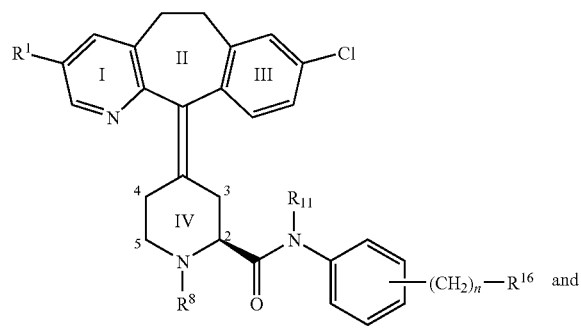

and

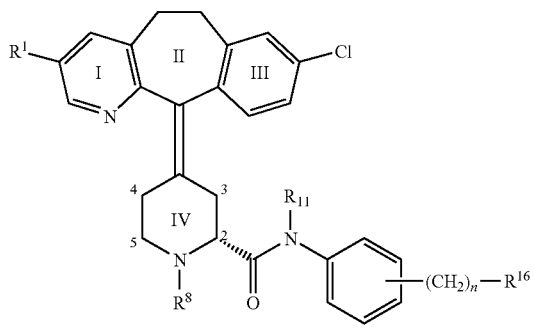

can be synthesized.

Compounds of this invention are exemplified in the following examples, which should not be construed as limiting the scope of the disclosure. Alternative mechanistic pathways and analogous structures within the scope of the invention may be apparent to those skilled in the art.

PREPARATIVE EXAMPLE 1

1-(3-aminophenyl)-1-(1H-imidazol-1-yl)methane

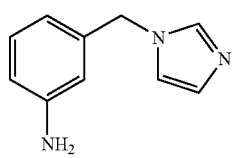

A. 1-(MESYLOXY)-1-(3-((tert-BUTOXYCARBO-NYL)AMINO)PHENYL)METHANE

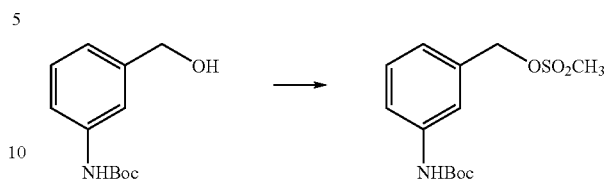

1-[3-[(tert-Butoxycarbonyl)amino]phenyl]methanol (10 g, 44.8 mmoles) (Ref.: F. J. Brown, P. R. Bernstein, L. A. Cronk, D. L. Dosset, K. C. Hebbel. T. P. Maduskuie, Jr., H. S. Shapiro, E. P. Vacek, Y. K. Lee, A. K. Willard, R. D. Krell and D. W. Snyder, *J. Med. Chem.*, 32, 1989, 807-826) and triethylamine (13 g, 17.9 mL, 138.4 mmoles) were dissolved in anhydrous THF (169 mL) and the solution was stirred and cooled to −50° C. Methanesulfonyl chloride (10.26 g, 7.02 mL, 89.6 mmoles) in anhydrous THF (85 mL) was added dropwise over a period of 20 min at −50° C. under an argon atmosphere. The mixture was stirred at −50° C. for an additional 20 min. A saturated aqueous solution of ammonium chloride (12.9 g) was added and the mixture was warmed to 25° C. The mixture was filtered and the filtrate was extracted twice with ethyl acetate. The ethyl acetate was washed with brine, water, dried (MgSO$_4$), filtered and evaporated to dryness to give the title compound (14.78 g). The material was used without further purification.

B. 1-(1H-IMIDAZOL-1-yl)-1-[3-[(tert-BUTOXY-CARBONYL)AMINO]PHENYL]-METHANE

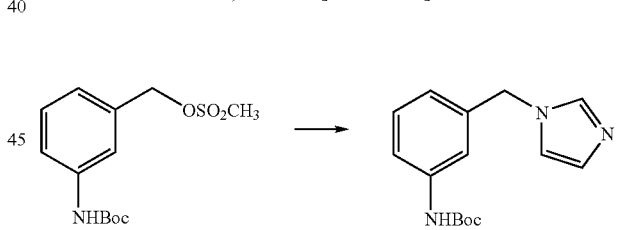

The title compound from Step A above (14.54 g, 44.8 mmoles) was dissolved in anhydrous DMF (100 mL) and sodium imidazole (6.52 g, 72.4 mmoles) was added. The mixture was heated under argon at 70° C. for 2 h. The solution was evaporated to dryness and chromatographed on silica gel using 2% (10% conc. NH$_4$OH in methanol)-dichloromethane as the eluant to give the title compound (8.92 g, 68%):

FABMS: m/z 274.2 (MH$^+$); $\delta_H$ (CDCl$_3$) 1.51 (9H, s, CH$_3$), 5.09 (2H, s, CH$_2$-Im), 6.79-6.85 (2H, d and dd, Ar—H$_4$ and Ar—H$_5$), 6.92 (1H, s, Im-H$_5$), 7.09 (1H, s, Im-H$_4$), 7.26 (1H, d, Ar—H$_6$), 7.27 (1H, s, Ar—H$_2$) and 7.60 ppm (1H, s, Im-H$_2$); $\delta_C$ (CDCl$_3$) CH$_3$: 28.4, 28.4, 28.4; CH$_2$: 50.9; CH: 117.3, 118.3, 119.4, 121.7, 129.5, 129.7, 137.4; C, 80.8, 137.1, 139.3, 146.9, 152.8.

C. 1-(1H-IMIDAZOL-1-YL)-1-(3-AMINOPHENYL)METHANE

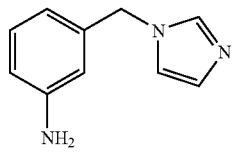

The title compound from Step B above (7.64 g, 27.95 mmoles) was dissolved in methanol (148 mL) and 10% conc. $H_2SO_4$ in dioxane (v/v) (380.8 mL) was added. The solution was stirred at 25° C. for 4 h. The solution was diluted with methanol and BioRad AG® 1-X8 (OH⁻) resin was added until the pH was basic. The resin was filtered off and washed with methanol. The combined filtrates were evaporated to dryness and the residue was chromatographed on silica gel using 2.5% (10% conc. $NH_4OH$ in methanol)-dichloromethane as the eluant to give the title compound (4.36 g, 90%): CIMS: m/z 174.25 (MH⁺); $\delta_H$ (CDCl$_3$), 3.44 (2H, bs, NH$_2$), 5.02 (2H, s, CH$_2$-Im), 6.39 (1H, s, Im-H$_5$), 6.55 (1H, d, Ar—H$_4$), 6.62 (1H, dd, Ar—H$_5$), 6.91 (1H, s, Im-H$_4$), 7.07 (1H, s, Ar—H$_2$), 7.13 (1H, m, Ar—H$_6$) and 7.54 ppm (1H, s, Im-H$_2$); $\delta_C$ (CDCl$_3$) CH$_2$: 50.8; CH: 113.4, 114.8, 117.2, 119.5, 129.8, 130.0, 137.7; C, 137.6, 147.1.

PREPARATIVE EXAMPLE 2

1-(3-AMINOPHENYL)-1-(4-METHYL-1H-IMIDAZOL-1-yl)METHANE and 1-(3-AMINOPHENYL)-1-(5-METHYL-1H-IMIDAZOL-1-yl)METHANE

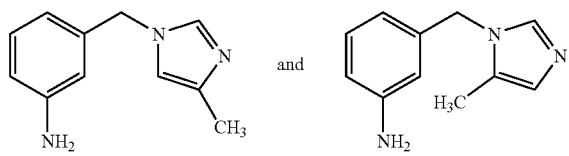

A. 1-(4/5-METHYL-1H-IMIDAZOL-1-YL)-1-[3-[(tert-BUTOXYCARBONYL)AMINO]PHENYL]METHANE

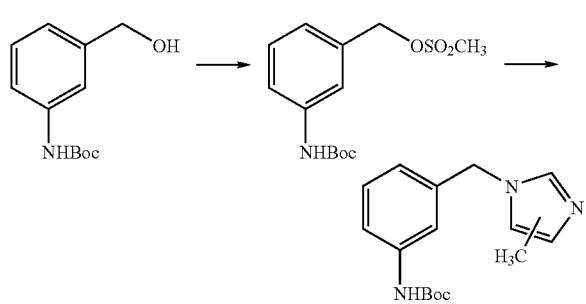

1-[3-[(tert-Butoxycarbonyl)amino]phenyl]methanol (25 g, 112 mmoles) (Ref.: F. J. Brown, P. R. Bernstein, L. A. Cronk, D. L. Dosset, K. C. Hebbel. T. P. Maduskuie, Jr., H. S. Shapiro, E. P. Vacek, Y. K. Lee, A. K. Willard, R. D. Krell, and D. W. Snyder, *J. Med. Chem.*, 32, 1989, 807-826) and triethylamine (62.4 mL, 448 mmoles) were dissolved in anhydrous dichloromethane (600 mL) and the solution was stirred and cooled to 0° C. Methanesulfonyl chloride (17.32 mL, 224 mmoles) was added dropwise over a period of 20 min at 0° C. under an argon atmosphere. The mixture was stirred at 0° C. for an additional 1 h. The mixture was poured into water and extracted with dichloromethane. The dichloromethane extract was dried (MgSO$_4$), filtered and evaporated to dryness to give the title compound which was used without further purification below.

4-Methylimidazole (10.11 g, 123.2 mmoles) was dissolved in anhydrous DMF (500 mL) and 95% sodium hydride (3.11 g, 123.2 mmoles) was added to the stirred solution under argon at 25° C. The mixture was stirred at 25° C. for 1 h. The title mesylate above dissolved in anhydrous DMF (100 mL) was added and the mixture was heated at 65° C. for 2.25 h. The solution was evaporated to dryness and the residue was chromatographed on silica gel using 1% (10% conc. NH$_4$OH in methanol)-dichloromethane as the eluant to give the title mixture of compounds (4-Methyl:5-Methyl::53%:47%) (12.14 g, 38%): FABMS: m/z 288.2 (MH⁺); $\delta_H$(CDCl$_3$) 4-Me: 2.23 (3H, s, 4-CH$_3$), 5.01 (2H, s, CH$_2$-Im), 6.61 (1H, s, Im-H$_5$) and 7.49 ppm (1H, s, Im-H$_2$) and 5-Me: 2.10 (3H, s, 5-CH$_3$), 5.04 (2H, s, CH$_2$-Im), 6.67 (1H, d, Ar—H$_4$) and 7.52 ppm (1H, s, Im-H$_2$).

B. SEPARATION of 1-(4-METHYL-1H-IMIDAZOL-1-YL)-1-[3-[(tert-BUTOXYCARBONYL)AMINO]PHENYL]METHANE and 1-(5-METHYL-1H-IMIDAZOL-1-YL)-1-[3-[(tert-BUTOXYCARBONYL)AMINO]-PHENYL]METHANE Method 1:

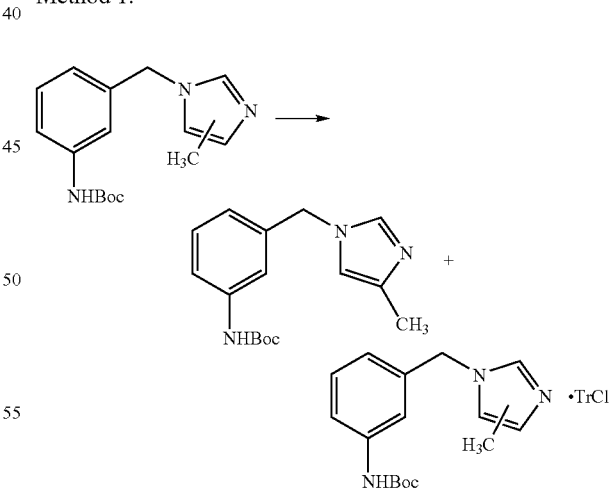

The title mixture of 4/5-methyl derivatives prepared as described in Preparative Example 2, Step A above (0.5 g) (4-Methyl:5-Methyl::57%:43%) was dissolved in anhydrous dichloromethane (6 mL) and the solution was cooled to 0° C. Trityl chloride (0.352 g, 1.3 equivalents/1 equivalent of 5-methyl compound) was added and the mixture was stirred under argon at 0° C. for 2 h. The solution was directly chromatographed on silica gel using 3.5% (10% conc. NH$_4$OH in methanol)dichloromethane as the eluant to give pure 4-methyl derivative (0.1927 g; 39%).

The silica gel was stripped with methanol to give the 4/5-methyl trityl chloride adduct which on refluxing with methanol at 80° C. for 4 h regenerated the 4/5-methyl mixture. The latter could be recycled through the trityl chloride procedure, or separated directly by chiral HPLC as described in Method 2 below.

Method 2:

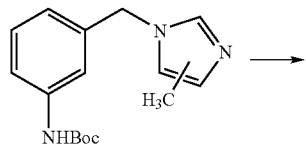

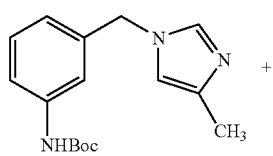

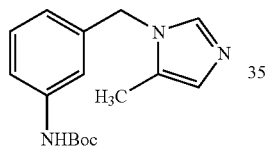

The title mixture of 4/5-methyl derivatives prepared as described in Preparative Example 2, Step A above (0.5 g) (4-Methyl:5-Methyl:: 53%:47%) (6 g) was subjected to chiral HPLC on a preparative Chiralpak® AD column using first hexane:isopropanol:diethylamine::95:5:0.2 and then hexane:isopropanol:diethylamine::92.5:7.5:0.2 after the first peak had eluted.

The first peak to elute was the 4-methyl derivative (3.104 g, 49%): FABMS: m/z 288.2 (MH$^+$), $\delta_H$ (CDCl$_3$) 1.51 (9H, s, CH$_3$), 2.21 (3H, s, 4-CH$_3$), 5.00 (2H, s, CH$_2$-Im), 6.60 (1H, s, Im-H$_5$), 6.78-7.02 (2H, dd and d, Ar—H$_5$ and Ar—H$_4$), 7.25-7.30 (2H, dd and s, Ar—H$_6$ and Ar—H$_2$) and 7.43 ppm (1H, s, Im-H$_2$); $\delta_C$ (CDCl$_3$) CH$_3$: 13.8, 28.4, 28.4, 28.4; CH$_2$: 50.7; CH: 115.8, 117.3, 118.2, 121.7, 129.6, 136.6; C, 80.8, 137.5, 138.8, 139.2, 152.7.

The second peak to elute was the 5-methyl derivative (2.72 g, 48%): FABMS: m/z 288.3 (MH$^+$); HRFABMS: m/z 288.1710 (MH$^+$), Calcd. C$_{16}$H$_{22}$N$_3$O$_2$:: m/z 288.1712; $\delta_H$ (CDCl$_3$) 1.50 (9H, s, CH$_3$), 2.09 (3H, s, 5-CH$_3$), 5.03 (2H, s, CH$_2$-Im), 6.66 (1H, d, Ar—H$_4$), 6.83 (1H, s, Im-H$_4$), 6.95 (1H, bs, NHCO), 7.16 (1H, dd, Ar—H$_2$), 7.23 (1H, dd, Ar—H$_5$), 7.28 (1H, m, Ar—H$_6$) and 7.51 ppm (1H, s, Im-H$_2$); $\delta_C$ (CDCl$_3$) CH$_3$: 9.3, 28.4, 28.4, 28.4; CH$_2$: 48.5; CH: 116.6, 118.0, 121.0, 126.9, 129.7, 137.3; C: 80.7, 127.8, 139.4, 139.4, 152.8.

C. 1-(3-AMINOPHENYL)-1-(4-METHYL-1H-IMIDAZOL-1-YL)METHANE

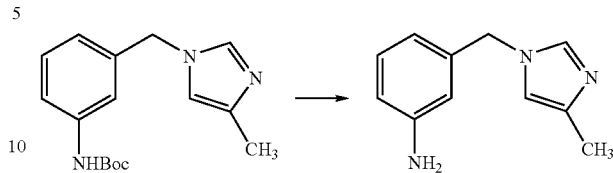

The title 4-methyl derivative from Step B above (4.61 g) was dissolved in methanol (85 mL) and 10% conc. H$_2$SO$_4$ in dioxane (v/v) (218.5 mL) was added. The solution was stirred at 25° C. for 5 h. The solution was diluted with methanol and BioRad AG® 1-X8 (OH$^-$) resin was added until the pH was basic. The resin was filtered off and washed with methanol. The combined filtrates were evaporated to dryness and the residue was chromatographed on silica gel using 2% (10% conc. NH$_4$OH in methanol)-dichloromethane as the eluant to give the title compound (2.62 g, 87%): FABMS: m/z 188.1 (MH$^+$); $\delta_H$ (CDCl$_3$) 2.00 (3H, s, 4-Me), 3.90 (2H, bs, NH$_2$), 4.92 (2H, s, CH$_2$-Im), 6.38 (1H, s, Im-H$_5$), 6.54 (1H, d, Ar—H$_4$), 6.59 (2H, s and d, Ar—H$_2$ and Ar—H$_6$), 7.11 (1H, dd, Ar—H$_5$) and 7.47 ppm (1H, s, Im-H$_2$); $\delta_C$ (CDCl$_3$) CH$_3$: 13.8; CH$_2$: 50.9; CH: 113.6, 114.8, 116.0, 117.3, 130.6, 136.6; C, 137.7, 138.5, 147.2.

D. 1-(3-AMINOPHENYL)-1-(5-METHYL-1H-IMIDAZOL-1-YL)METHANE

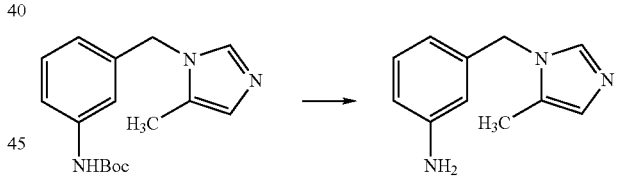

The title 5-methyl derivative from Step B above (2.81 g) was dissolved in methanol (52 mL) and 10% conc. H$_2$SO$_4$ in dioxane (v/v) (133.2 mL) was added. The solution was stirred at 25° C. for 4 h. The solution was diluted with methanol and BioRad AG® 1-X8 (OH$^-$) resin was added until the pH was basic. The resin was filtered off and washed with methanol. The combined filtrates were evaporated to dryness and the residue was chromatographed on silica gel using 2% (10% conc. NH$_4$OH in methanol)-dichloromethane as the eluant to give the title compound (1.78 g, 97%): FABMS: m/z 188.1 (MH$^+$); $\delta_H$ (CDCl$_3$) 2.10 (3H, s, 5-Me), 3.72 (2H, bs, NH$_2$), 4.96 (2H, s, CH$_2$-Im), 6.28 (1H, s, Ar—H$_2$), 6.47 (1H, d, Ar—H$_4$), 6.59 (1H, dd, Ar—H$_6$), 6.83 (1H, s, Im-H$_4$), 7.11 (1H, dd, Ar—H$_5$) and 7.51 ppm (1H, s, Im-H$_2$); $\delta_C$ (CDCl$_3$) CH$_3$: 9.3; CH$_2$: 48.4; CH: 112.7, 114.5, 116.6, 126.9, 129.9, 137.4; C, 137.5, 146.9, 147.2.

PREPARATIVE EXAMPLE 3

1-(3-AMINOPHENLY)-1-(2-METHYL-1H-IMIDAZOL-1-YL)METHANE

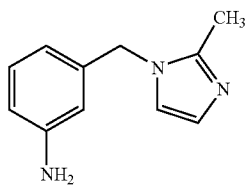

A. 1-[3-[(tert-BUTOXYCARBONYL)AMINO]PHENYL]-1-(2-METHYL-1H-IMIDAZOL-1-YL)METHANE

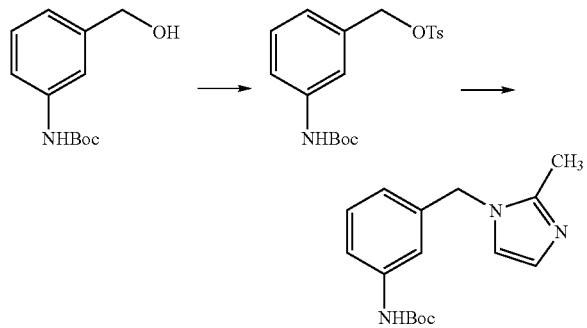

1-[3-[(tert-Butoxycarbonyl)amino]phenyl]methanol (10 g, 44.8 mmoles) (Ref.: F. J. Brown, P. R. Bernstein, L. A. Cronk, D. L. Dosset, K. C. Hebbel. T. P. Maduskuie, Jr., H. S. Shapiro, E. P. Vacek, Y. K. Lee, A. K. Willard, R. D. Krell and D. W. Snyder, *J. Med. Chem.*, 32, 1989, 807-826) (10 g, 44.8 mmoles) was dissolved in anhydrous pyridine (51 mL) and the solution was cooled to 0° C. p-Toluenesulfonyl chloride (10.25 g, 53.7 mmoles) was added and the mixture was stirred at 0° C. for 2.5 h under argon. The pyridine was azeotroped off with toluene at 51° C. and the residue was taken up in anhydrous DMF (50 mL). 2-Methylimidazole (4.05 g, 49.3 mmoles) was dissolved in anhydrous DMF (123 mL) and 95% sodium hydride (1.24 g, 49.3 mmoles) was added in portions over 20 min to the stirred solution under argon at 25° C. The mixture was stirred at 25° C. for 1.5 h. The title tosylate above in anhydrous DMF was added dropwise over 15 min and the mixture was stirred at 25° C. for 2.5 h. The solution was evaporated to dryness and the residue was chromatographed on silica gel using 0.25%.2.5% (10% conc. NH$_4$OH in methanol)-dichloromethane as the eluant to give the title compound (0.8412 g, 6.5%): FABMS: m/z 288.3 (MH$^+$); HRFABMS: m/z 526.3036 (MH$^+$), Calcd. C$_{28}$H$_{40}$N$_5$O$_5$: m/z 526.3029; $\delta_H$ (CDCl$_3$) 1.50 (9H, s, CH$_3$), 2.34 (3H, s, 2-CH$_3$), 5.02 (2H, s, CH$_2$-Im), 6.67 (1H, d, Ar—H$_4$), 6.84 (1H, s, Im-H$_5$), 6.95 (1H, s, Im-H$_4$), 7.19 (1H, s, Ar—H$_2$) and 7.28 ppm (2H, m, Ar—H$_5$ and Ar—H$_6$); $\delta_C$ (CDCl$_3$) CH$_3$: 13.0, 28.4, 28.4, 28.4; CH$_2$: 49.8; CH: 116.6, 118.0, 120.1, 121.0, 127.0, 129.7; C, 80.7, 137.2, 139.3, 145.0, 152.8.

B. 1-(3-AMINOPHENYL)-1-(2-METHYL-1H-IMIDAZOL-1-YL)METHANE

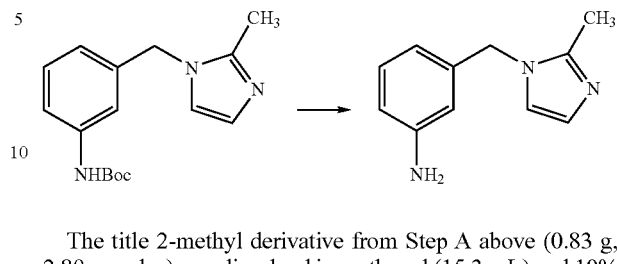

The title 2-methyl derivative from Step A above (0.83 g, 2.89 mmoles) was dissolved in methanol (15.3 mL) and 10% conc. H$_2$SO$_4$ in dioxane (v/v) (39.4 mL) was added. The solution was stirred at 25° C. for 3.5 h. The solution was diluted with methanol and BioRad AG® 1-X8 (OH$^-$) resin was added until the pH was basic. The resin was filtered off and washed with methanol. The combined filtrates were evaporated to dryness and the residue was chromatographed on silica gel using 3.25% (10% conc. NH$_4$OH in methanol)-dichloromethane as the eluant to give the title compound (0.4724 g, 87%): FABMS: m/z 188.2 (MH$^+$); HRFABMS: m/z 188.1191 (MH$^+$), Calcd.C$_{11}$H$_{14}$N$_3$: m/z 188.1188; $\delta_H$ (CDCl$_3$) 2.34 (3H, s, 2-CH$_3$), 3.83 (2H, bs, NH$_2$), 4.96 (2H, s, CH$_2$-Im), 6.28 (1H, s, Ar—H$_2$), 6.47 (1H, d, Ar—H$_6$), 6.59 (1H, d, Ar—H$_4$), 6.85 (1H, s, Im-H$_5$), 6.95 (1H, s, Im-H$_4$) and 7.11 ppm (1H, dd, Ar—H$_5$); $\delta_C$ (CDCl$_3$) CH$_3$: 13.1; CH$_2$: 49.7; CH: 112.7, 114.5, 116.6, 120.1, 126.9, 129.9; C, 137.6, 145.0, 147.1.

PREPARATIVE EXAMPLE 4

1-(2-AMINOPHENYL)-2-(4-METHYL-1H-IMIDAZOL-1-YL)ETHANE and 1-(2-AMINOPHENYL)-2-(5-METHYL-1H-IMIDAZOL-1-YL)ETHANE

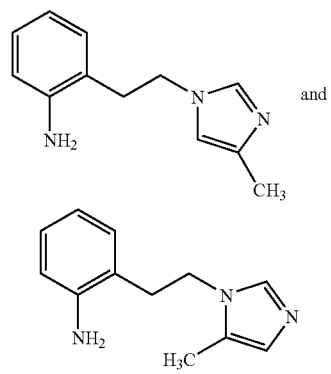

A. 2-(4/5-METHYL-1H-IMIDAZOL-1-YL)-1-[2-[(tert-BUTOXYCARBONYL)AMINO]PHENYL]ETHANE

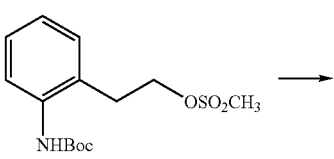

-continued

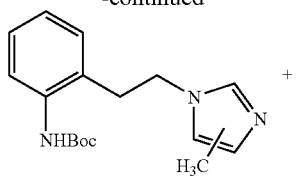

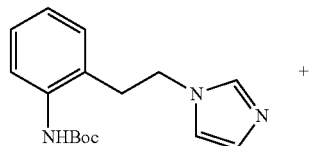

Method 1:

4-Methylimidazole (7.61 g, 92.7 mmoles) was dissolved in anhydrous DMF (230 mL) and 95% sodium hydride (2.34 g, 102 mmoles) was added to the stirred solution under argon at 25° C. The mixture was stirred at 25° C. for 30 min. 2-(Mesyloxy)-1-[2-[(tert-butoxycarbonyl)amino]phenyl]ethane (26.58 g, 84.3 mmoles) (Ref.:D. Critch and X. Hao, *J. Org. Chem.*, 62, 1997, 5982-5988) dissolved in anhydrous DMF (100 mL) was added dropwise at 25° C. over 30 min and the mixture was stirred at 25° C. for 2 h. Aqueous methanol (10 mL) was added and the solution was evaporated to dryness. The residue was chromatographed on silica gel using 5% (10% conc. NH$_4$OH in methanol)-dichloromethane as the eluant to give N-tert-butoxyindoline (16.89 g, 92%) (Ref.: I. Masatomo and K. Tsukasa, *Heterocycles*, 34(5), 1992, 1031-1038) and the title mixture of imidazole compounds (4-Methyl:5-Methyl::66%:34%) (0.866 g, 3.4%): ESMS: m/z 302.1 (MH$^+$); 4-Me: $\delta_H$ (CDCl$_3$) 1.52 (9H, s, CH$_3$), 2.23 (3H, s, 4-CH$_3$), 2.99 (2H, dd, 1-CH$_2$), 4.13 (2H, t, 2-CH$_2$), 6.11 (1H, s, NH), 6.63 (1H, s, Im-H$_5$), 7.04 (1H, t, Ar—H$_4$), 7.11 (1H, dd, Ar—H$_5$), 7.25 (1H, d, Ar—H$_3$), 7.27 (1H, s, Im-H$_2$), and 7.49 ppm (1H, d, Ar—H$_6$); $\delta_C$ (CDCl$_3$) CH$_3$: 13.6, 28.4, 28.4, 28.4; CH$_2$: 33.7, 47.4; CH: 115.3, 125.3, 125.8, 127.9, 129.9, 136.3; C, 80.6, 131.0, 135.9, 138.5, 154.0 and 5-Me: $\delta_H$ (CDCl$_3$) 1.52 (9H, s, CH$_3$), 2.13 (3H, s, 5-CH$_3$), 2.98 (2H, dd, 1-CH$_2$), 4.10 (2H, q, 2-CH$_2$), 6.11 (1H, s, NH), 6.79 (1H, s, Im-H$_4$), 7.02 (1H, dd, Ar—H$_4$), 7.11 (1H, dd, Ar—H$_5$), 7.25 (1H, d, Ar—H$_3$), 7.33 (1H, s, Im-H$_2$), and 7.49 ppm (1H, d, Ar—H$_6$); $\delta_C$ (CDCl$_3$) CH$_3$: 9.1, 28.4, 28.4, 28.4; CH$_2$: 33.5, 45.1; CH: 125.4, 126.0, 126.6, 128.1, 130.1, 136.8; C, 80.6, 131.0, 135.9, 138.5, 154.0.

Method 2:

4-Methylimidazole (6.7 g, 81.5 mmoles) and 2-(mesyloxy)-1-[2-[(tert-butoxycarbonyl)amino]phenyl]ethane (23.37 g, 74.1 mmoles) (Ref.:D. Critch and X. Hao, *J. Org. Chem.*, 62, 1997, 5982-5988) were dissolved in anhydrous toluene (250 mL) and anhydrous dichloromethane (50 mL) and the mixture was heated under an argon atmosphere at 80° C. for 30 h. and then allowed to stand at 25° C. for 41 h. The solution was evaporated to dryness and the residue was chromatographed on silica gel using dichloromethane, then 3% (conc. NH$_4$OH in methanol)-dichloromethane as the eluant to give N-tert-butoxyindoline (2.82 g, 22%) (Ref.: I. Masatomo and K. Tsukasa, *Heterocycles*, 34(5), 1992, 1031-1038) and the title mixture of imidazole compounds (4-Methyl:5-Methyl::66%:34%) (3.88 g, 34%).

B. Separation of 2-(4-METHYL-1H-IMIDAZOL-1-YL-1-[2-[(tert-BUTOXYCARBONYL)AMNO]PHENYL]EHTANE and 2-(5-METHYL-1H-IMIDAZOL-1-YL)-1-[2-[(tert-BUTOXYCARBONYL)AMINO]-PHENYL]ETHANE

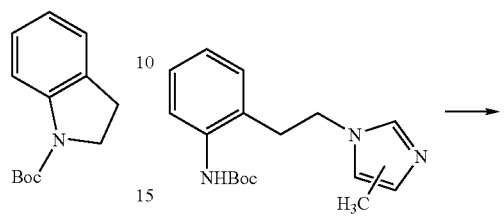

The title mixture of imidazole compounds (4-Methyl:5-Methyl::66%:34%) (6.2 g) from Step A above was dissolved in anhydrous dichloromethane (65 mL) and the solution was cooled to 0° C. Trityl chloride (2.868 g, 1.47 equivalents/1 equivalent of 5-methyl isomer) was added in portions and the mixture was stirred under argon at 0° C. for 2 h. The mixture was directly chromatographed on silica gel using first dichloromethane and then 50% ethyl acetate in acetone, followed by methanol to give 2-(4-methyl-1H-imidazol-1-yl)-1-[2-[(tert-butoxycarbonyl)amino]phenyl]ethane (2.28 g, 37%): ESMS: m/z 302.1 (MH$^+$); $\delta_H$ (CDCl$_3$) 1.52 (9H, s, CH$_3$), 2.23 (3H, s, 4-CH$_3$), 3.00 (2H, dd, 1-CH$_2$), 4.10 (2H, dd, 2-CH$_2$), 6.04 (1H, s, NH), 6.61 (1H, s, Im-H$_5$), 7.05 (1H, dd, Ar—H$_4$), 7.10 (1H, dd, Ar—H$_5$), 7.23 (1H, s, Im-H$_2$), 7.26 (1H, d, Ar—H$_3$) and 7.48 ppm (1H, d, Ar—H$_6$); $\delta_C$ (CDCl$_3$) CH$_3$: 13.6, 28.4, 28.4, 28.4; CH$_2$: 33.7, 47.4; CH: 115.3, 125.3, 125.8, 127.9, 129.9, 136.3; C, 80.6, 131.0, 135.9, 138.6, 153.9 and the mixed trityl chloride adduct (5.63 g).

C. 1-(2-AMINOPHENYL)-2-(4-METHYL-1H-IMIDAZOL-1-YL)ETHANE

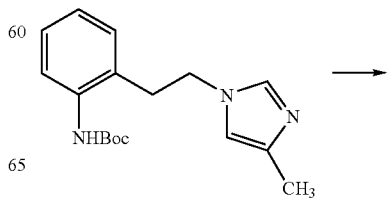

-continued

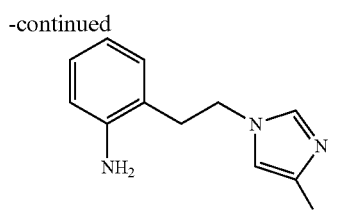

2-(4-Methyl-1H-imidazol-1-yl)-1-[2-[(tert-butoxycarbonyl)amino]-phenyl]ethane (2.555 g) from Step B above was dissolved in methanol (20 mL) and 10% conc. H₂SO₄ in dioxane (v/v) (40 mL) was added. The solution was stirred at 25° C. for 4 h. The solution was diluted with methanol and BioRad AG® 1-X8 (OH⁻) resin was added until the pH was basic. The resin was filtered off and washed with methanol. The combined filtrates were evaporated to dryness and the residue was chromatographed on silica gel using 4% (10% conc. NH₄OH in methanol)-dichloromethane as the eluant to give the title compound (1.605 g, 94%): ESMS: m/z 202.0 (MH⁺); $\delta_H$ (CDCl₃) 2.20 (3H, s, 4-CH₃), 2.90 (2H, dd, 1-CH₂), 3.33 (2H, bs, NH₂), 4.09 (2H, dd, 2-CH₂), 6.60 (1H, s, Im-H₅), 6.68 (1H, d, Ar—H₆), 6.74 (1H, dd, Ar—H₄), 6.92 (1H, d, Ar—H₃), 7.08 (1H, dd, Ar—H₅) and 7.22 ppm (1H, s, Im-H₂); $\delta_C$ (CDCl₃) CH₃: 13.8; CH₂: 33.7, 46.7; CH: 115.2, 116.3, 119.4, 128.2, 130.1, 136.3; C, 122.3, 138.7, 144.5.

PREPARATIVE EXAMPLE 5

N1,N4-DI-(tert-BUTOXYCARBONYL-(2S)-PIPERAZINECARBOXYLIC ACID

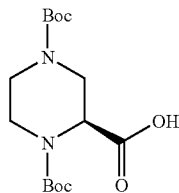

A. (2S)-PIPERAZINECARBOXYLIC ACID BIS -(+)CAMPHOR SULFONNIC ACID SALT

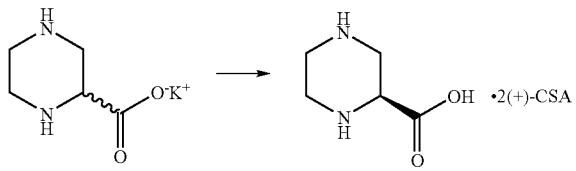

2(±)-piperazinecarboxylic acid potassium salt (287.3 g, 1.71 moles) was dissolved in deionized water (290 mL) and the mixture was heated to 70.75° C. and filtered to remove insolubles. The solution was then added to S(+).camphor sulfonic acid (1200 g, 5.17 moles) dissolved in deionized water (432 mL) at 68° C. and the mixture was allowed to cool to 25° C. After 72 h the solution containing crystals was cooled at 3° C. in a refrigerator for 3 h. The beige crystals were filtered off and dried in a vacuum oven over P₂O₅ for 17 h. to give 539.9 g of material. The material was recrystallized from deionized water (750 mL) and heated to 68° C. The hot solution was filtered and the filtrate was allowed to stand at 25° C. for 41 h. and then at 3° C. for 17 h. The crystals were filtered off and dried as above to give the title compound (125.3 g, 12%): $[\alpha]_D^{20°\ C.}$+15.1° (c=2.0, H₂O).

B. N1,N4-DI-(tert-BUTYLOXYCARBONYL)-(2S)-PIPERAZINECARBOXYLIC ACID

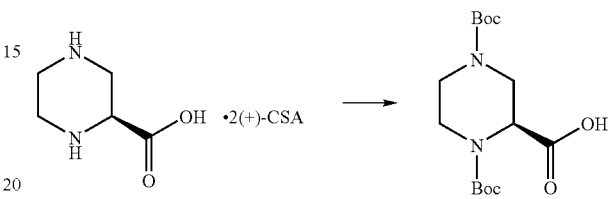

The title compound from Step A above (125.9 g, 0.2117 moles) and di-tert-butyl dicarbonate (116 g, 0.53 moles) were dissolved in deionized water (500 mL) and methanol (500 mL). 50% aqueous sodium hydroxide (27 mL) was then added dropwise to the solution until a basic pH was reached. The mixture was diluted with ice/water and extracted with ethyl acetate (2×1.5 L). The aqueous layer was acidified with solid citric acid until the pH reached 3. The mixture was then extracted with diethyl ether (3×2 L). The ether extract was dried (MgSO₄), filtered and evaporated to dryness to give the title compound (69.94 g, 100%): $\delta_H$ (CDCl₃) 1.40 ppm (18H, s, CH₃).

PREPARATIVE EXAMPLE 6

(+)-N-[3-[(1H-IMIDAZOL-1-YL)METHYL]PHENYL]-(2S)-PIPERAZINECARBOXAMIDE

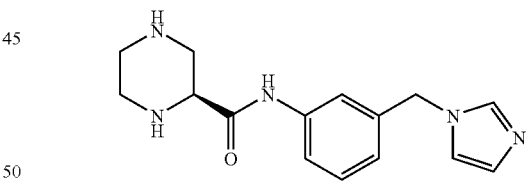

A. (−)-N1,N4-DI-(tert-BUTYLOXYCARBONYL)-N-[3-[(1H-IMIDAZOL-1-YL)METHYL]PHENYL]-(2S)-PIPERAZINECARBOXAMIDE

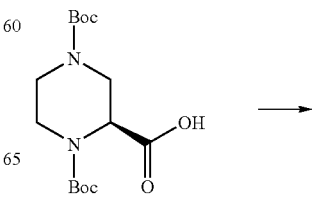

119.4, 119.5, 123.1, 129.3, 129.7, 137.0, 137.3; C, 138.3, 170.3; $[\alpha]_D^{20°\ C.}$ +2.0° (c=1.1, MeOH).

PREPARATIVE EXAMPLE 7

(+)-N-[3-[(1H-IMIDAZOL-1-YL)METHYL]PHE-NYL]-(2R)-PIPERAZINECARBOXAMIDE

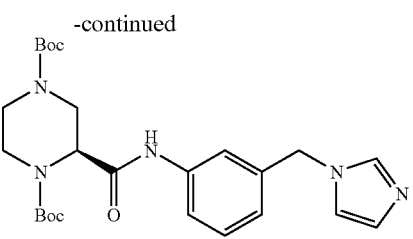

A. (+)-N1,N4-DI-(tert-BUTYLOXYCARBONYL)-N-[3-[(1H-IMIDAZOL-1-YL)METHYL]PHENYL]-(2R)-PIPERAZINECARBOXAMIDE

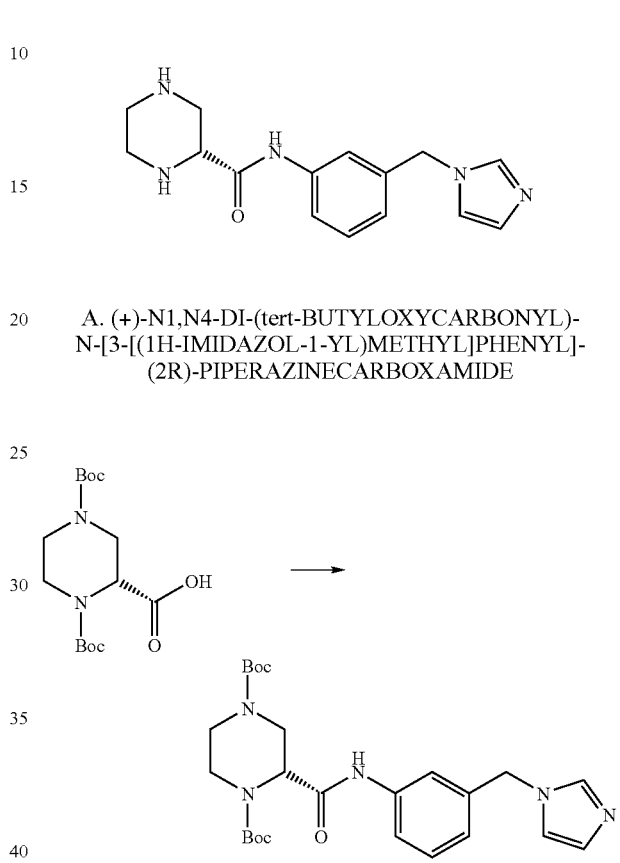

Method 1:

N1,N4-Di-(tert-butyloxycarbonyl)-(2R)-piperazinecarboxylic acid (9.32 g, 28.2 mmoles) (prepared as described in Preparative Example 2 of U.S. Pat. No. 6,362,188 issued Mar. 26, 2002, the disclosure of which is incorporated herein by reference thereto), the title compound from Preparative Example 1, Step C (2.44 g, 14.1 mmoles), 1-(3-dimethylaminopropyl)-3-ethylcarbodiimide hydrochloride (5.41 g, 28.2 mmoles), 1-hydroxybenzotriazole (3.81 g, 28.2 mmoles) and 4-methylmorpholine (2.85 g, 3.11 mL, 28.2 mmoles) were dissolved in anhydrous DMF (46 mL) and the mixture was stirred at 25° C. under argon for 329 h. The reaction was worked up as described in Preparative Example 6, Step A above and the product was chromatographed on silica gel using 5% (10% conc. NH$_4$OH in methanol)dichloromethane as the eluant to give the title compound (5.0455 g, 74%): FABMS: m/z 486 (MH$^+$); $\delta_H$(CDCl$_3$) 1.42 (9H, s, CH$_3$), 1.49 (3H, s, CH$_3$), 5.05 (2H, s, CH$_2$-Im), 6.84 (1H, d, Ar—H$_4$), 6.92 (1H, s, Im-H$_5$), 7.07 (1H, s, Im-H$_4$), 7.24 (1H, dd, Ar—H$_5$), 7.45 (2H, s and d, Ar—H$_2$ and Ar—H$_6$) and 7.68 ppm (1H, s, Im-H$_2$); $\delta_C$ (CDCl$_3$) CH$_3$: 28.4, 28.4, 28.4, 28.4, 28.4, 28.4; CH$_2$: 41.5, 43.6, 51.0, 55.3; CH: 118.8, 119.5, 119.7, 123.0, 128.8, 128.8, 136.7/137.2; C, 80.6, 81.6, 129.6, 138.7, 154.7, 154.7, 168.3; $[\alpha]_D^{20°\ C.}$ +41.4° (c=0.61, MeOH).

-continued

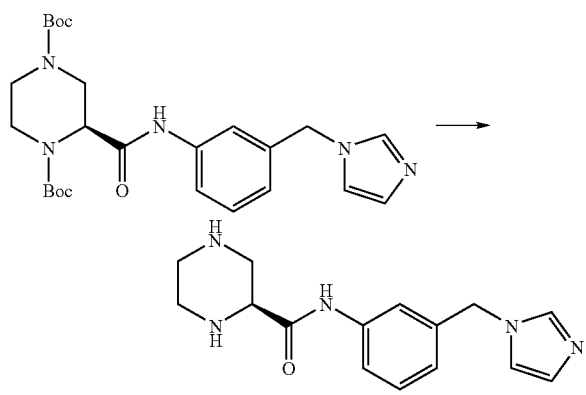

The title compound from Preparative Example 5, Step B (1 g, 3.03 mmoles), the title compound from Preparative Example 1, Step C (0.6816 g, 3.94 mmoles), 1-(3-dimethylaminopropyl)-3-ethylcarbodiimide hydrochloride (0.7543 g, 3.94 mmoles), 1-hydroxybenzotriazole (0.5317 g, 3.94 mmoles) and 4-methylmorpholine (0.398 g, 0.433 mL, 3.94 mmoles) were dissolved in anhydrous DMF (5 mL) and the mixture was stirred at 25° C. under argon for 43 h. The solution was evaporated to dryness and the residue was taken up in dichloromethane, washed with water, dried (MgSO$_4$), filtered and evaporated to dryness. The residue was chromatographed on silica gel using 3% (10% conc. NH$_4$OH in methanol)-dichloromethane as the eluant to give the title compound (1.0146 g, 69%): CIMS: m/z 486.30 (MH$^+$); $\delta_H$(CDCl$_3$) 1.41 (9H, s, CH$_3$), 1.47 (9H, s, CH$_3$), 5.04 (2H, s, CH$_2$-Im), 6.83 (1H, d, Ar—H$_4$), 6.90 (1H, s, Im-H$_5$), 7.08 (1H, s, Im-H$_4$), 7.24 (1H, dd, Ar—H$_5$), 7.27 (1H, s, Ar—H$_2$), 7.43 (1H, bd, Ar—H$_6$), 7.69 (1H, s, Im-H$_2$) and 8.92 ppm (1H, bs, NH); $\delta_C$ (CDCl$_3$) CH$_3$: 28.4, 28.4, 28.4, 28.4, 28.4, 28.4; CH$_2$: 41.6, 43.6, 51.0, 55.0; CH: 118.8, 119.6, 119.8, 123.0, 128.7, 129.6, 137.1; C, 80.5, 81.6, 130.6, 138.7, 154.7, 154.7, 168.4; $[\alpha]_D^{20°\ C.}$ −37.0° (c=0.47, MeOH).

B. (+)-N-[3-[(1H-IMIDAZOL-1-YL)METHYL]PHENYL]-(2S)-PIPERAZINECARBOXAMIDE

The title compound from Step A above (0.8147 g) was dissolved in methanol (5 mL) and 10% conc. H$_2$SO$_4$-dioxane (v/v) (20 mL) were reacted as described in Preparative Example 4, Step C and the product was chromatographed on silica gel using 10% (10% conc. NH$_4$OH in methanol)-dichloromethane as the eluant to give the title compound (0.4115 g, 93%): CIMS: m/z 486.30 (MH$^+$); $\delta_H$(CDCl$_3$) 5.07 (2H, s, CH$_2$-Im), 6.88 (1H, d, Ar—H$_4$), 6.91 (1H, s, Im-H$_5$), 7.03 (1H, s, Im-H$_4$), 7.29 (1H, dd, Ar—H$_5$), 7.48 (1H, bd, Ar—H$_6$), 7.50 (1H, s, Im-H$_2$) and 7.55 ppm (1H, s, Ar—H$_2$); $\delta_C$ (CDCl$_3$) CH$_2$: 44.3, 45.6, 48.1, 50.8; CH: 58.6, 118.5, Method 2:

N1,N4-Di-(tert-butyloxycarbonyl)-(2R)-piperazinecarboxylic acid (2.78 g, 8.42 mmoles) (prepared as described in Preparative Example 2 of U.S. Pat. No. 6,362,188 issued Mar. 26, 2002, the disclosure of which is incorporated herein by reference thereto), the title compound from Preparative Example 1, Step C (1.12 g, 6.47 mmoles), 1-(3-dimethylaminopropyl)-3-ethylcarbodiimide hydrochloride (1.61 g, 8.42 mmoles), 1-hydroxybenzotriazole (1.22 g, 8.42 mmoles) and 4-methylmorpholine (0.8502 g, 0.9241 mL, 8.42 mmoles) were dissolved in anhydrous DMF (10 mL) and the mixture was stirred at 25° C. under argon for 47 h. Additional title compound from Preparative Example 1, Step C (1.5 g, 4.54 mmoles), 1-(3-dimethylaminopropyl)-3-ethylcarbodiimide hydrochloride (0.867 g, 4.54 mmoles), 1-hydroxybenzotriazole (0.614 g, 4.54 mmoles) and 4-methylmorpholine (0.4578 g, 0.498 mL, 4.54 mmoles) were added and the reaction was allowed to proceed for a total of 239 h at 25° C. The reaction was worked up as described in Preparative Example 6, Step A above and the product was chromatographed on silica gel using 5% (10% conc. NH$_4$OH in methanol)-dichloromethane as the eluant to give the title compound (2.6642 g, 85%).

Method 3:

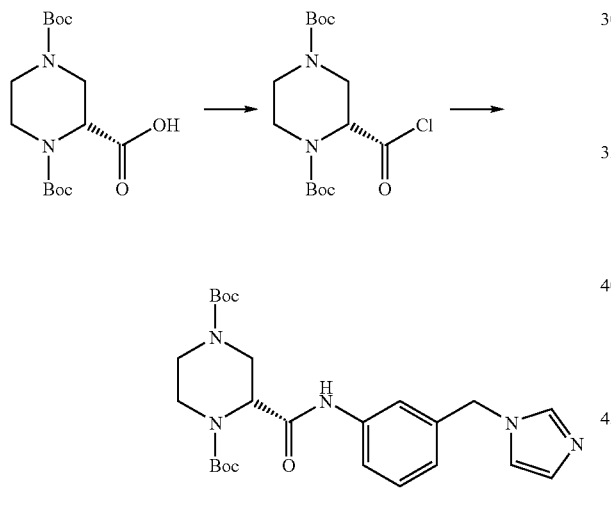

N1,N4-Di-(tert-butyloxycarbonyl)-(2R)-piperazinecarboxylic acid (0.1907 g, 0.577 mmoles) (prepared as described in Preparative Example 2 of U.S. Pat. No. 6,362,188 issued Mar. 26, 2002, the disclosure of which is incorporated herein by reference thereto), and hexachloroacetone (0.04384 mL, 0.289 mmoles) were dissolved in anhydrous dichloromethane (1.15 mL) under argon and the mixture was stirred at −78° C. Triphenylphosphine (0.1514 g, 0.578 mmoles) in anhydrous dichloromethane (0.577 mL) was added dropwise at −78° C. over 20 min. The title compound from Preparative Example 1, Step C (0.1 g, 0.577 mmoles) in anhydrous dichloromethane (0.577 mL) was added followed by triethylamine (0.0805 mL, 0.577 mmoles) in anhydrous dichloromethane (0.577 mL). The mixture was stirred at −78° C. for 1.5 h. and then directly chromatographed on silica gel using 1% (10% conc. NH$_4$OH in methanol)-dichloromethane as the eluant to give the title compound (0.113 g, 40%).

B. (+)-N-[3-[(1H-IMIDAZOL-1-YL)METHYL]PHENYL]-(2R)-PIPERAZINECARBOXAMIDE

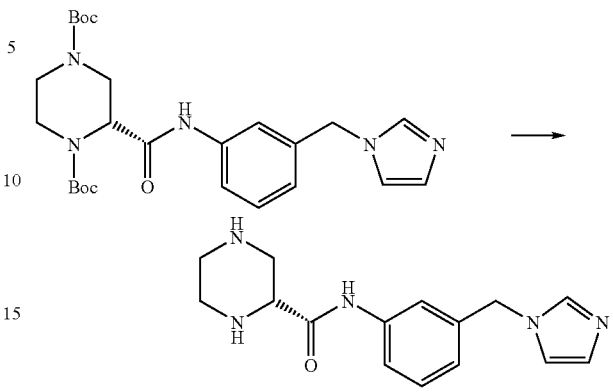

The title compound from Step A above (2.6642 g) was dissolved in methanol (16 mL) and 10% conc. H$_2$SO$_4$-dioxane (v/v) (70 mL) was added and the reaction was carried out as described in Preparative Example 4, Step C. The product was chromatographed on silica gel using 10% (10% conc. NH$_4$OH in methanol)dichloromethane as the eluant to give the title compound (1.36 g, 87%): $\delta_H$ (CDCl$_3$+drop of CD$_3$OD) 5.07 (2H, s, CH$_2$-Im), 6.87 (1H, d, Ar—H$_4$), 6.90 (1H, Im-H$_5$), 7.02 (1H, s, Im-H$_4$), 7.28 (1H, dd, Ar—H$_5$), 7.48 (1H, d, Ar—H$_6$), 7.28 (1H, s, Ar—H$_2$) and 7.54 ppm (1H, s, Im-H$_2$); $\delta_C$ (CDCl$_3$+drop of CD$_3$OD) CH$_2$: 43.6, 45.1, 47.5, 50.8; CH: 58.0, 118.5, 119.5, 119.5, 123.1, 129.2, 129.7, 137.3; C, 137.0, 138.3, 169.8; $[\alpha]_D^{20°\,C.}$ +9.2° (c=0.62, MeOH).

PREPARATIVE EXAMPLE 8

(+)-N-[3-[(4-METHYL-1H-IMIDAZOL-1-YL)METHYL]PHENYL]-(2R)-PIPERAZINECARBOXAMIDE

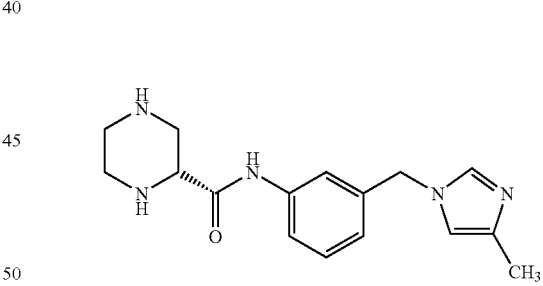

A. (+)-N1,N4-DI-(tert-BUTYLOXYCARBONYL)-N-[3-[(4-METHYL-1H-IMIDAZOL-1-YL)METHYL]PHENYL]-(2R)-PIPERAZINECARBOXAMIDE

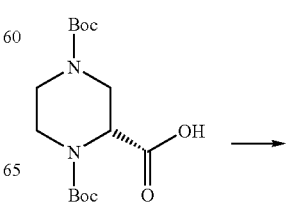

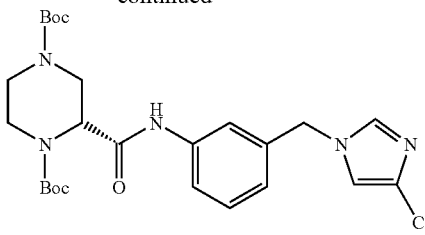

N1,N4-Di-(tert-butyloxycarbonyl)-(2R)-piperazinecarboxylic acid (5.6 g, 16.95 mmoles) (prepared as described in Preparative Example 2 of U.S. Pat. No. 6,362,188 issued Mar. 26, 2002, the disclosure of which is incorporated herein by reference thereto), the title compound from Preparative Example 2, Step C (3.175 g, 16.95 mmoles), 1-(3-dimethylaminopropyl)-3-ethylcarbodiimide hydrochloride (4.23 g, 22.0 mmoles), 1-hydroxybenzotriazole (2.979 g, 22.0 mmoles) and 4-methylmorpholine (2.42 mL, 22.0 mmoles) were dissolved in anhydrous DMF (16.6 mL) and the mixture was stirred at 25° C. under argon for 115 h. The reaction was worked up as described in Preparative Example 6, Step A above and the product was chromatographed on silica gel using 2.5.3% (10% conc. NH$_4$OH in methanol)-dichloromethane as the eluant to give the title compound (7.46 g, 88%): FABMS: m/z 500.3 (MH$^+$); $\delta_H$ (CDCl$_3$) 1.43 (9H, s, CH$_3$), 1.48 (9H, s, CH$_3$), 2.20 (3H, s, 4.CH$_3$), 4.96 (2H, s, CH$_2$-Im), 6.58 (1H, s, Im-H$_5$), 6.84 (1H, d, Ar—H$_4$), 7.23 (1H, dd, Ar—H$_5$), 7.38 (2H, s and d, Ar—H$_2$ and Ar—H$_6$) and 7.43 ppm (1H, s, Im-H$_2$); $\delta_C$ (CDCl$_3$) CH$_3$: 13.8, 28.4, 28.4, 28.4, 28.4, 28.4, 28.4; CH$_2$: 41.5, 43.2, 43.4, 50.6; CH: 55.1, 115.8, 118.6, 119.5, 122.9, 129.5, 136.5; C, 80.6, 81.6, 137.3, 138.6, 138.7, 154.7, 154.7, 168.2; $[\alpha]_D^{20°\,C}$+35.8° (c=0.49, MeOH).

B. (+)-N-[3-[(4-METHYL-1H-IMIDAZOL-1-YL)METHYL]PHENYL]-(2R)-PIPERAZINECARBOXAMIDE

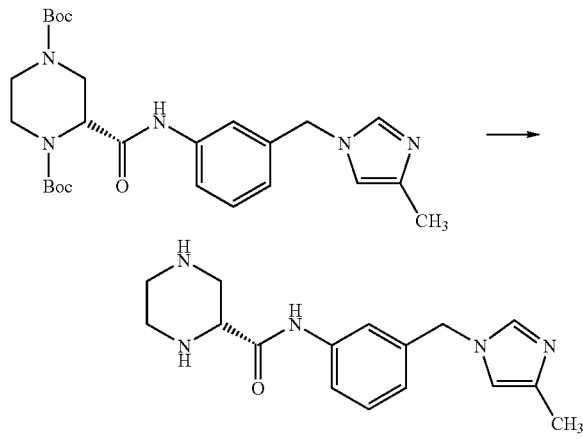

The title compound from Step A above (9.22 g) was dissolved in methanol (55 mL) and 10% conc. H$_2$SO$_4$-dioxane (v/v) (243.5 mL) was added and the reaction was carried out as described in Preparative Example 4, Step C. The product was chromatographed on silica gel using 5% (10% conc. NH$_4$OH in methanol)dichloromethane as the eluant to give the title compound (5.21 g, 97%): FABMS: m/z 300.3 (MH$^+$);

HRFABMS: m/z 500.2891 (MH$^+$), Calcd C$_{26}$H$_{38}$N$_5$O$_5$: m/z 500.2873; $\delta_H$ (CDCl$_3$) 2.20 (3H, s, 4-CH$_3$), 5.01 (2H, s, CH$_2$-Im), 6.62 (1H, s, Im-H$_5$), 6.89 (1H, d, Ar—H$_4$), 7.28 (1H, dd, Ar—H$_5$), 7.44 (1H, s, Im-H$_2$), 7.49 (1H, s, Ar—H$_2$) and 7.52 ppm (1H, d, Ar—H$_6$); $\delta_C$ (CDCl$_3$) CH$_3$: 13.8; CH$_2$: 44.8, 46.2, 48.5, 50.6; CH: 59.0, 115.8, 118.4, 119.2, 122.9, 129.5, 136.6; C, 137.5, 138.4, 138.8, 170.6; $[\alpha]_D^{20°\,C}$+13.9° (c=0.45, MeOH).

PREPARATIVE EXAMPLE 9

(+)-N-1-(CYCLOHEXYLOXYCARBONYL)-N-[3-[(4-METHYL-1H-IMIDAZOL-1-YL)METHYL]PHENYL]-(2R)-PIPERAZINECARBOXAMIDE

A. (+)-N-1-(CYCLOHEXYLOXYCARBONYL)-N-4-(tert-BUTOXYCARBONYL)-N-[3-[(4-METHYL-1H-IMIDAZOL-1-YL)METHYL]PHENYL]-(2R)-PIPERAZINECARBOXAMIDE N1-(Cyclohexyloxycarbonyl)-N-4-(tert-butoxycarbonyl)-(2R)-piperazinecarboxylic acid (0.732 g, 2.054 mmoles)) (prepared as described in Preparative Example 32 of U.S. Pat. No. 6,362,188 issued Mar. 26, 2002, the disclosure of which is incorporated herein by reference thereto), the title compound from Preparative Example 2, Step C (0.5 g; 2.67 mmoles), 1-(3-dimethylamino-propyl)-3-ethylcarbodiimide hydrochloride (0.512 g, 2.67 mmoles), 1-hydroxybenzotriazole (0.361 g, 2.67 mmoles) and 4-methylmorpholine (0.294 mL, 2.67 mmoles) were dissolved in anhydrous DMF (7 mL) and the mixture was stirred at 25° C. under argon for 66 h. The reaction was worked up as described in Preparative Example 6, Step A above and the product was chromatographed on silica gel using 2.5% (10% conc. NH$_4$OH in methanol)-dichloromethane as the eluant to give the title compound (0.9108 g, 84%): FABMS: m/z 526.4; HRFABMS: m/z 526.3034 (MH+), Calcd. $C_{28}H_{40}N_5O_5$: m/z 526.3029; $\delta_H$ (CDCl$_3$) 1.43 (9H, s, CH$_3$), 2.20 (3H, s, 4-CH$_3$), 6.60 (1H, s, Im-H$_5$), 6.87 (1H, d, Ar—H$_4$), 7.27 (1H, dd, Ar—H$_5$), 7.43 (1H, s, Im-H$_2$), 7.50 (1H, s, Ar—H$_2$), 7.51 (1H, d, Ar—H$_6$) and 8.97 ppm (1H, bs, NHCO); $\delta_C$ (CDCl$_3$) CH$_3$: 13.5, 28.4, 28.4, 28.4; CH$_2$: 23.7, 23.7, 25.4, 31.9, 31.9, 41.3, 42.5, 43.2, 50.8; CH: 55.6, 115.9, 118.7, 119.7, 123.1, 129.6, 136.4; C, 74.8, 80.6, 137.1, 138.7, 138.7, 154.7, 154.7, 168.0, $[\alpha]_D^{20\ °C}$+40.8° (c=0.51, MeOH).

B. (+)-N-1-(CYCLOHEXYLOXYCARBONYL)-N-[3-[(4-METHYL-1H-IMIDAZOLzol-1-YL)METHYL]PHENYL]-(2R)-PIPERAZINECARBOXAMIDE

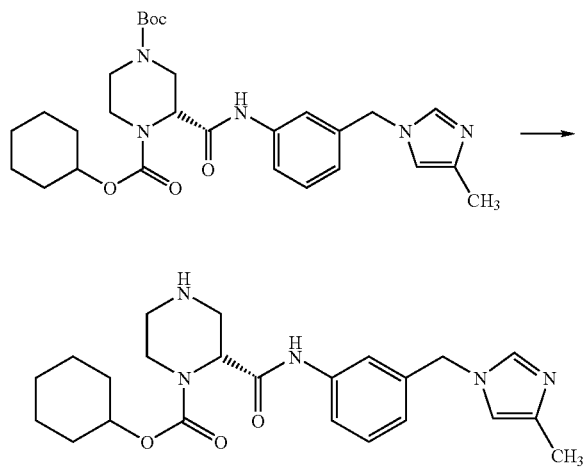

The title compound from Step A above (0.8886g) was dissolved in methanol (8.9 mL) and 10% conc. H$_2$SO$_4$-dioxane (v/v) (23 mL) was added and the reaction was carried out as described in Preparative Example 4, Step C. The product was chromatographed on silica gel using 4% (10% conc. NH$_4$OH in methanol)-dichloromethane as the eluant to give the title compound (0.6341 g, 88%): FABMS: m/z 426.1 (MH+); HRFABMS: m/z 426.2507 (MH+), Calcd. $C_{23}H_{32}N_5O_2$: m/z 426.2505; $\delta_H$(CDCl$_3$) 2.20 (3H, s, 4-CH$_3$), 4.99 (2H, s, CH$_2$-Im), 6.61 (1H, s, Im-H$_5$), 6.88 (1H, d, Ar—H$_4$), 7.28 (1H, dd, Ar—H$_5$), 7.41 (1H, d, Ar—H$_6$), 7.45 (1H, s, Im-H$_2$), 7.51 (1H, s, Ar—H$_2$ and 8.92 ppm (1H, s, NHCO); $\delta_C$ (CDCl$_3$) CH$_3$: 13.7: CH$_2$: 23.7, 23.7, 25.4, 31.9, 31.9, 42.4, 45.0, 45.8, 50.7; CH: 53.6, 115.8, 118.9, 119.6, 123.2, 129.7, 136.5; C: 74.8, 137.4, 138.4, 138.7, 169.1; $[\alpha]_D^{20\ °C}$+39.7° (c=0.49, MeOH).

PREPARATIVE EXAMPLE 10

(+)-N-[3-[(5-METHYL-1H-IMIDAZOL-1-YL)METHYL]PHENYL]-(2R)-PIPERAZINECARBOXAMIDE

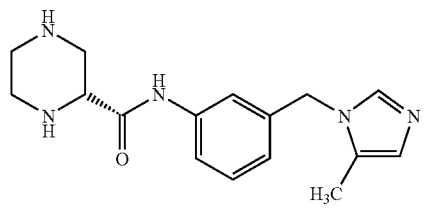

A. (+)-N1,N4-DI-(tert-BUTYLOXYCARBONYL)-N-[3-[(5-METHYL-1H-IMIDAZOL-1-YL)METHYL]PHENYL]-(2R)-PIPERAZINECARBOXAMIDE

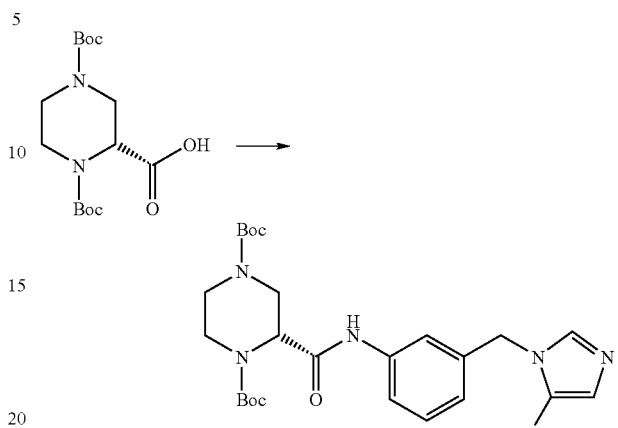

N1,N4-Di-(tert-butyloxycarbonyl)-(2R)-piperazinecarboxylic acid (1.685 g, 5.1 mmoles) (prepared as described in Preparative Example 2 of U.S. Pat. No. 6,362,188 issued Mar. 26, 2002, the disclosure of which is incorporated herein by reference thereto), the title compound from Preparative Example 2, Step D (0.955 g, 5.1 mmoles), 1-(3-dimethylaminopropyl)-3-ethylcarbodiimide hydrochloride (1.2711 g, 6.63 mmoles), 1-hydroxybenzotriazole (0.896 g, 6.63 mmoles) and 4-methylmorpholine (0.729 mL, 6.63 mmoles) were dissolved in anhydrous DMF (5 mL) and the mixture was stirred at 25° C. under argon for 330 h. The reaction was worked up as described in Preparative Example 6, Step A above and the product was chromatographed on silica gel using 2.5.3% (10% conc. NH$_4$OH in methanol)-dichloromethane as the eluant to give the title compound (1.574 g, 62%): ESMS: m/z 500.1 (MH+); $\delta_H$ (CDCl$_3$) 1.40 (9H, s, CH$_3$), 1.46 (9H, s, CH$_3$), 2.07 (3H, s, 5.CH$_3$), 4.99 (2H, s, CH$_2$-Im), 6.27 (1H, s, Ar—H$_2$), 6.44 (1H, d, Ar—H$_4$), 6.58 (1H, dd, Ar—H$_6$), 6.80 (1H, s, Im-H$_4$), 7.09 (1H, dd, Ar—H$_5$), 7.57 (1H, s, Im-H$_2$) and 7.16 ppm (1H, bs, NHCO); $\delta_C$ (CDCl$_3$) CH$_3$: 9.4, 28.4, 28.4, 28.4, 28.4, 28.4, 28.4; CH$_2$: 41.5, 42.4, 43.7, 48.6; CH: 55.3, 117.8, 119.5, 122.2, 129.7, 137.2, 139.0; C, 80.3, 81.5, 127.9, 136.9, 139.0, 154.8, 154.8, 168.5.

B. (+)-N-[3-[(5-METHYL-1H-IMIDAZOL-1-YL)METHYL]PHENYL]-(2R)-PIPERAZINECARBOXAMIDE

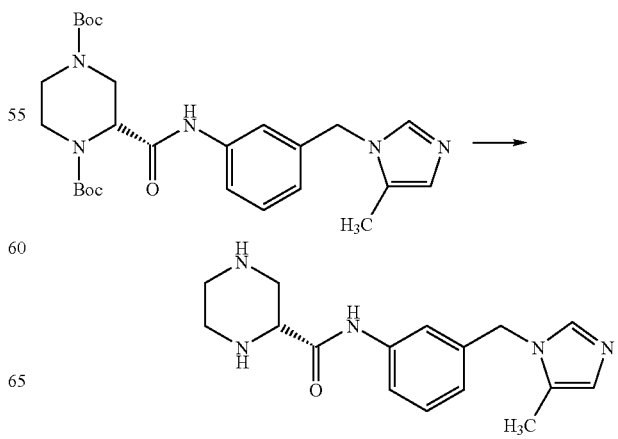

The title compound from Step A above (1.84 g) was dissolved in methanol (11 mL) and 10% conc. $H_2SO_4$-dioxane (v/v) (48.6 mL) was added and the reaction was carried out as described in Preparative Example 4, Step C. The product was chromatographed on silica gel using 3% increasing to 10% (10% conc. $NH_4OH$ in methanol)-dichloromethane as the eluant to give the title compound (0.8618 g, 94%): FABMS: m/z 300.2 ($MH^+$); HRFABMS: m/z 300.1822 ($MH^+$), Calcd $C_{16}H_{22}N_5O$: m/z 300.1824; $\delta_H$ (CDCl$_3$) 2.07 (3H, s, 5-CH$_3$), 5.02 (2H, s, CH$_2$-Im), 6.79 (1H, s, Im-H$_4$), 6.75 (1H, d, Ar—H$_4$), 7.27 (1H, dd, Ar—H$_5$), 7.36 (1H, s, Im-H$_2$), 7.49 (1H, s, Ar—H$_2$) and 7.51 ppm (1H, d, Ar—H$_6$); $\delta_C$ (CDCl$_3$) CH$_3$: 9.3; CH$_2$: 44.4, 45.8, 48.1, 48.4; CH: 58.7, 117.6/117.7, 119.1/119.2, 122.3, 127.0, 129.7, 137.3; C, 127.7, 137.2, 138.4/138.5, 170.3/170.4.

PREPARATIVE EXAMPLE 11

(+)-N-1-(CYCLOHEXLOCYCARBONYL)-N-[3-[(5-METHYL-1H-IMIDAZOL-1-YL)METHYL]PHENYL]-(2R)-PIPERAZINECARBOXAMIDE

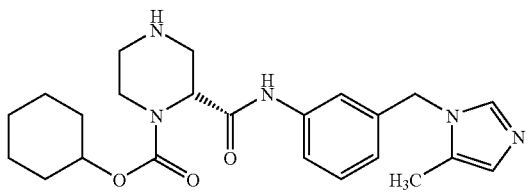

A. (+)-N-1-(CYCLOHEXLOXYCARBONYL)-N-4-(tert-BUTOXYCARBONYL)-N-[3-[(5-METHYL-1H-IMIDAZOL-1-YL)METHYL]PHENYL]-(2R)-PIPERAZINECARBOXAMIDE

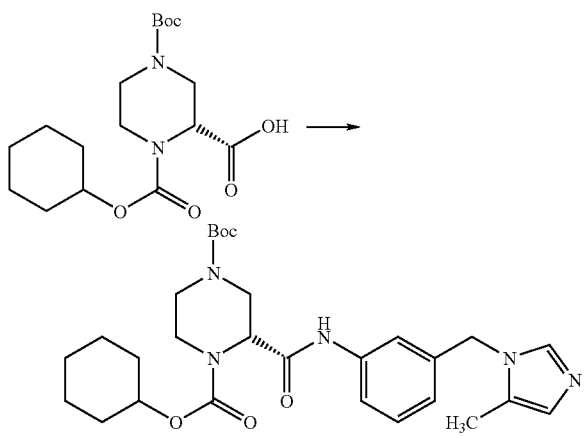

N1-(Cyclohexyloxycarbonyl)-N-4-(tert-butoxycarbonyl)-(2R)-piperazinecarboxylic acid (0.5 g, 1.4 mmoles) (prepared as described in Preparative Example 32 of U.S. Pat. No. 6,362,188 issued Mar. 26, 2002, the disclosure of which is incorporated herein by reference thereto), the title compound from Preparative Example 2, Step D (0.3415 g, 1.82 mmoles), 1-(3-dimethylaminopropyl)-3-ethylcarbodiimide hydrochloride (0.35 g, 1.82 mmoles), 1-hydroxybenzotriazole (0.246 g, 1.82 mmoles) and 4-methylmorpholine (0.2 mL, 1.82 mmoles) were dissolved in anhydrous DMF (5 mL) and the mixture was stirred at 25° C. under argon for 67 h. The reaction was worked up as described in Preparative Example 6, Step A above and the product was chromatographed on silica gel using 2.5% (10% conc. NH$_4$OH in methanol)-dichloromethane as the eluant to give the title compound (0.6701 g, 91%): FABMS: m/z 526.4 ($MH^+$); HRFABMS: m/z 526.3036 ($MH^+$), Calcd. $C_{28}H_{40}N_5O_5$: m/z 526.3029; $\delta_H$ (CDCl$_3$) 1.42 (9H, s, CH$_3$), 2.09 (3H, s, 5-CH$_3$), 5.03 (2H, s, CH$_2$-Im), 6.76 (1H, d, Ar—H$_4$), 6.82 (1H, s, Im-H$_4$), 7.27 (1H, dd, Ar—H$_5$), 7.29 (1H, s, Im-H$_2$), 7.57 (2H, s and d, Ar—H$_2$ and Ar—H$_6$) and 9.26 ppm (1H, bs, NHCO); $\delta_C$ (CDCl$_3$) CH$_3$: 9.3, 28.3, 28.3, 28.3; CH$_2$: 23.6, 23.6, 25.4, 31.9, 31.9, 41.3, 42.8, 43.5, 48.6; CH: 55.5, 117.8, 119.6, 122.2, 126.3, 129.7, 137.1; C: 74.6, 80.6, 127.9, 136.8, 139.0, 168.2; $[\alpha]_D^{20°\,C.}$+36.2° (c=0.52, MeOH).

B. (+)-N-1-(CYCLOHEXLOXYCARBONYL)-N-[3-[(5-METHYL-1H-IMIDAZOL-1-YL)METHYL]PHENYL]-(2R)-PIPERAZINECARBOXAMIDE

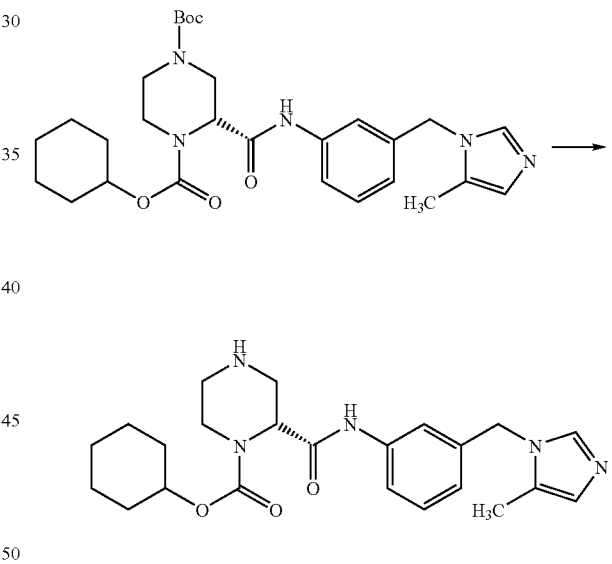

The title compound from Step A above (0.6701 g) was dissolved in methanol (6.75 mL) and 10% conc. H$_2$SO$_4$-dioxane (v/v) (17.4 mL) was added and the reaction was carried out as described in Preparative Example 4, Step C. The product was chromatographed on silica gel using 4% (10% conc. NH$_4$OH in methanol)-dichloromethane as the eluant to give the title compound (0.4546 g, 84%): FABMS: m/z 426.2 ($MH^+$); HRFABMS: m/z 426.2509 ($MH^+$), Calcd. $C_{23}H_{32}N_5O_3$: m/z 426.2505; $\delta_H$(CDCl$_3$) 2.08 (3H, s, 5-CH$_3$), 5.03 (2H, s, CH$_2$-Im), 6.74 (1H, d, Ar—H$_4$), 6.81 (1H, s, Im-H$_4$), 7.27 (1H, dd, Ar—H$_5$), 7.40 (1H, d, Im-H$_2$), 7.41 (1H, d, Ar—H$_6$), 7.49 (1H, s, Ar—H$_2$) and 8.91 ppm (1H, bs, NHCO); $\delta_C$ (CDCl$_3$) CH$_3$: 9.4; CH$_2$: 23.7, 23.7, 25.4, 31.9, 31.9, 42.4, 45.0, 45.8, 48.4; CH: 53.7, 118.1, 119.4, 122.4, 127.2, 129.7, 137.3; C: 74.8, 127.6, 137.3, 138.6, 169.1; $[\alpha]_D^{20°\,C.}$+48.4° (c=0.58, MeOH).

PREPARATIVE EXAMPLE 12

(+)-N-1-(CYCLOHEXYLOCYCARBONYL)-N-[3-[(2-METHYL-1H-IMIDAZOL-1-YL)METHYL]PHENYL]-(2R)-PIPERAZINECARBOXAMIDE

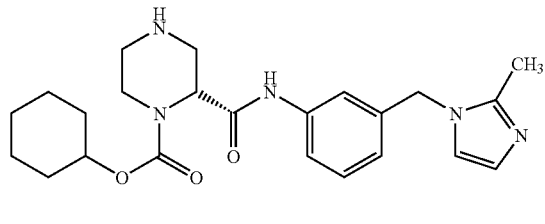

A. (+)-N-1-(CYCLOHEXYLOXYCARBONYL)-N-4-(tert-BUTOXYCARBONYL)-N-[3-[(2-METHYL-1H-IMIDAZOL-1-YL)METHYL]PHENYL]-(2R)-PIPERAZINECARBOXAMIDE

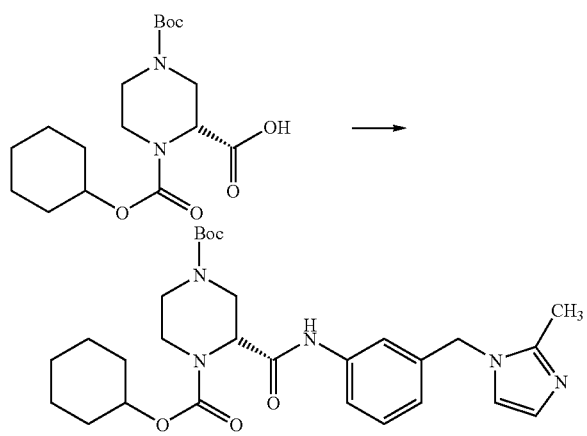

N1-(Cyclohexyloxycarbonyl)-N-4-(tert-butoxycarbonyl)-(2R)-piperazinecarboxylic acid (0.5 g, 1.4 mmoles) (prepared as described in Preparative Example 32 of U.S. Pat. No. 6,362,188 issued Mar. 26, 2002, the disclosure of which is incorporated herein by reference thereto), the title compound from Preparative Example 3, Step B (0.3415 g, 1.82 mmoles), 1-(3-dimethylaminopropyl)-3-ethylcarbodiimide hydrochloride (0.35 g, 1.82 mmoles), 1-hydroxybenzotriazole (0.246 g, 1.82 mmoles) and 4-methylmorpholine (0.2 mL, 1.82 mmoles) were dissolved in anhydrous DMF (5 mL) and the mixture was stirred at 25° C. under argon for 66 h. The reaction was worked up as described in Preparative Example 6, Step A above and the product was chromatographed on silica gel using 2.5% (10% conc. NH$_4$OH in methanol)-dichloromethane as the eluant to give the title compound (0.5877 g, 80%): FABMS: m/z 526.4 (MH$^+$); HRFABMS: m/z 526.303 (MH$^+$), Calcd. C$_{28}$H$_{40}$N$_5$O$_5$: m/z 526.3029; δ$_H$ (CDCl$_3$) 1.42 (9H, s, CH$_3$), 2.34 (3H, s, 2-CH$_3$), 5.01 (2H, s, CH$_2$-Im), 6.76 (1H, d, Ar—H$_4$), 6.84 (1H, s, Im-H$_5$), 6.93 (1H, s, Im-H$_4$), 7.27 (1H, dd, Ar—H$_5$), 7.34 (1H, bs, Ar—H$_2$), 7.53 (1H, d, Ar—H$_6$) and 9.12 ppm (1H, bs, NHCO); δ$_C$ (CDCl$_3$) CH$_3$: 12.9, 28.4, 28.4, 28.4; CH$_2$: 23.7, 23.7, 25.4, 31.9, 31.9, 41.3, 43.0, 43.6, 49.7; CH: 55.5, 74.7, 117.9, 119.5, 120.1, 122.3, 126.6, 129.7; C, 80.5, 137.0, 138.9, 144.9, 154.5, 154.5, 168.1; [α]$_D^{20°\,C.}$+36.4° (c=0.58, MeOH).

B. (+)-N-1-(CYCLOHEXYLOXYCARBONYL)-N-[3-[(2-METHYL-1H-IMIDAZOL-1-YL)METHYL]PHENYL]-(2R)- PIPERAZINECARBOXAMIDE

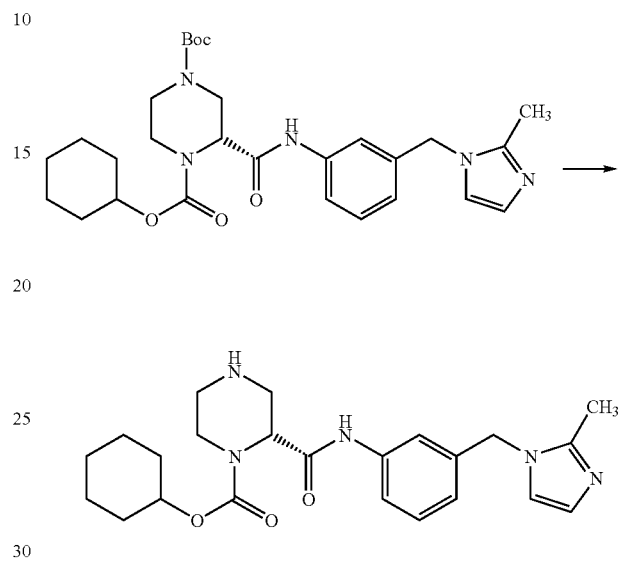

The title compound from Step A above (0.5667 g) was dissolved in methanol (5.7 mL) and 10% conc. H$_2$SO$_4$-dioxane (v/v) (14.7 mL) was added and the reaction was carried out as described in Preparative Example 4, Step C. The product was chromatographed on silica gel using 4% (10% conc. NH$_4$OH in methanol)-dichloromethane as the eluant to give the title compound (0.4129 g, 90%): FABMS: m/z 426.1 (MH$^+$); HRFABMS: m/z 426.2509 (MH$^+$), Calcd. C$_{22}$H$_{33}$N$_5$O$_3$: m/z 426.2505; δ$_H$ (CDCl$_3$) 2.34 (3H, s, 2-CH$_3$), 5.02 (2H, s, CH$_2$-Im), 6.74 (1H, d, Ar—H$_4$), 6.84 (1H, s, Im-H$_5$), 6.95 (1H, s, Im-H$_4$), 7.27 (1H, dd, Ar—H$_5$), 7.37 (1H, d, Ar—H$_6$), 7.45 (1H, s, Ar—H$_2$) and 8.80 ppm (1H, s, NHCO); δ$_C$ (CDCl$_3$) CH$_3$: 13.9; CH$_2$: 23.7, 23.7, 25.4, 31.9, 31.9, 42.5, 45.0, 45.8, 49.7; CH: 53.7, 74.8, 118.2, 119.4, 120.0, 122.5, 127.1, 129.7; C, 137.3, 138.5, 144.9, 169.1; [α]$_D^{20°\,C.}$+52.6° (c=0.54, MeOH).

PREPARATIVE EXAMPLE 13

N-(BENZYL)-N-[3-[(1H-IMIDAZOL-1-YL)METHYL]PHENYL]-(2S)- PIPERAZINECARBOXAMIDE

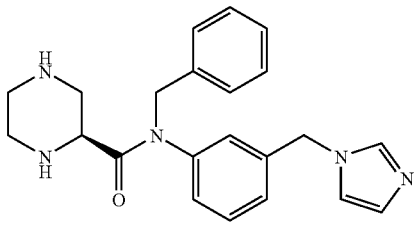

A. (+)-N1,N4-DI-(tert-BUTYLOXYCARBONYL)-N-(BENZYL)-N-[3-[(1H-IMIDAZOL-1-YL)METHYL]PHENYL9 .(2S). PIPERAZINECARBOXAMIDE

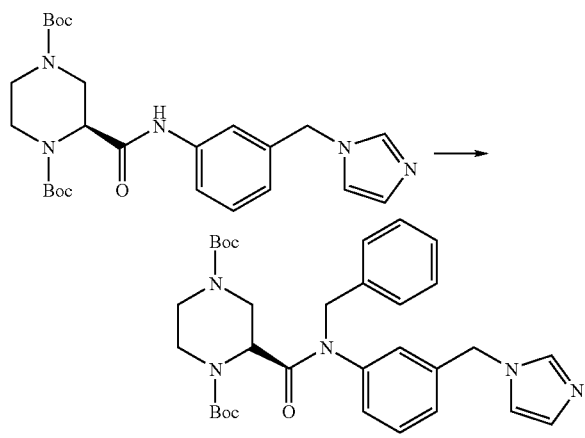

The title compound from Preparative Example 6, Step A above (0.05 g, 0.103 mmoles), KF—Al₂O₃ (0.0374 g, 0.0258 mmoles of KF) (Ref.: J. Yamawaki, T. Ando and T. Hanafusa, *Chemistry Letters,* 1981, 1143-1146) and benzyl chloride (0.0196 g, 0.0178 mL, 0.1545 mmoles) were added to anhydrous acetonitrile (3 mL) and the mixture was stirred under argon at 25° C. for 168 h. Additional benzyl chloride (0.0196 g, 0.0178 mmoles) and KF—Al₂O₃ (0.0374 g, 0.0258 mmoles of KF) were added at 188 h and then additional benzyl chloride (0.0392 g, 0.0356 mmoles) and KF—Al₂O₃ (0.0748 g, 0.0516 mmoles of KF) were again added at 212 h and the reaction was continued for a total of 354 h. The reaction mixture was filtered and the alumina was washed with acetonitrile and methanol and the combined filtrates were evaporated to dryness. The residue was chromatographed on silica gel using 1% (10% conc. NH₄OH in methanol)-dichloromethane as the eluant to give the title compound (0.0188 g, 32%): ESMS: m/z 576.1 (MH⁺); $\delta_H$ (CDCl₃) 1.42 (9H, s, CH₃), 1.47 (9H, s, CH₃), 5.08 (2H, s, CH₂-Im), 6.90, 7.08, 7.14, 7.23, 7.33 and 7.74 ppm (12H, m and s, Im-H and Ar—H); $\delta_C$ (CDCl₃) CH₃: 28.5, 28.5, 28.5, 28.5, 28.5, 28.5; CH₂: 41.4, 43.9, 50.6, 50.6, 53.6; CH: 51.9, 119.4, 119.4, 127.5, 127.5, 127.5, 127.5, 127.5, 128.5, 128.5, 128.5; C, 80.2, 80.5, 137.0, 142.0, 142.0, 155.7, 170.7; $[\alpha]_D^{20\ °C}$ +19.6° (c=0.25, MeOH).

B. N-(BENZYL)-N-[3-[(1H-IMIDAZOL-1-YL)METHYL]PHENYL]-(2S)- PIPERAZINECARBOXAMIDE

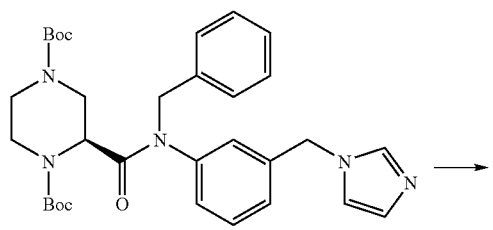

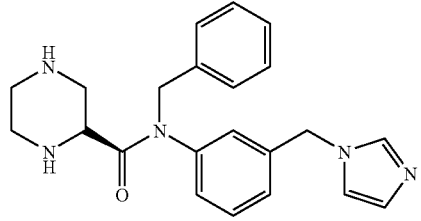

The title compound from Step A above may be deprotected as described in Preparative Example 8, step B above to give the title compound.

PREPARATIVE EXAMPLE 14

N-(BENZYL)-N-[3-[(1H-IMIDAZOL-1-YL)METHYL]PHENYL]-(2R)- PIPERAZINECARBOXAMIDE

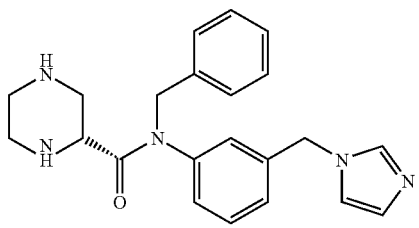

A. (−)-N1,N4-DI-(tert-BUTYLOXYCARBONYL)-N-(BENZYL)-N-[3-[(1H-IMIDAZOL-1-yl)METHYL]PHENYL]-(2R)- PIPERAZINECARBOXAMIDE

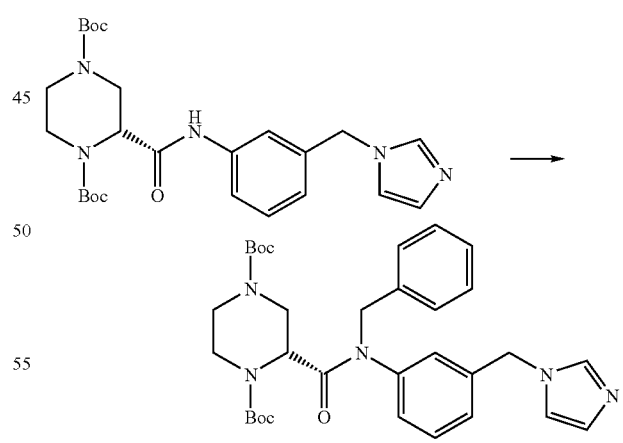

The title compound from Preparative Example 7, Step A above (5.11 g, 10.5 mmoles), KF—Al₂O₃ (15.3 g, 105 mmoles of KF) (Ref.: J. Yamawaki, T. Ando and T. Hanafusa, *Chemistry Letters,* 1981, 1143.1146) and benzyl chloride (8.0 g, 7.3 mL, 63 mmoles) were added to anhydrous acetonitrile (300 mL) and the mixture was stirred under argon at 25° C. for 141 h. Additional benzyl chloride (4.0 g, 3.65 mL, 31.5 mmoles) and KF—Al₂O₃ (7.65 g, 52.5 mmoles of KF) were added and the reaction was continued for a total of 475 h. The reaction mixture was filtered and the alumina was washed with acetonitrile and methanol and the combined filtrates were evaporated to dryness. The residue was chromatography on silica gel using 1% (10% conc. NH$_4$OH in methanol)-dichloromethane as the eluant to give the title compound (0.4379 g, 7%): ESMS: m/z 576.1 (MH$^+$); $\delta_H$ (CDCl$_3$) 1.42 (9H, s, CH$_3$), 1.47 (9H, s, CH$_3$), 5.08 (2H, s, CH$_2$-Im), 6.88, 7.08, 7.13, 7.27, 7.35 and 7.67 ppm (12H, m and s, Im-H and Ar—H); $\delta_C$ (CDCl$_3$) CH$_3$: 28.5, 28.5, 28.5, 28.5, 28.5, 28.5; CH$_2$: 41.4, 43.9, 50.5, 50.5, 53.7; CH: 51.9, 119.3, 119.3, 127.5, 127.5, 127.5, 127.5, 127.5, 128.5, 128.5, 128.5; C, 80.2, 80.2, 137.0, 142.0, 141.9, ~155.7, 170.7; $[\alpha]_D^{20\ °C.}$ −25.9° (c=0.45, MeOH).

B. N-(BENZYL)-N-[3-[(1H-IMIDAZOL-1-YL)METHYL]PHENYL]-(2R)- PIPERAZINECARBOXAMIDE

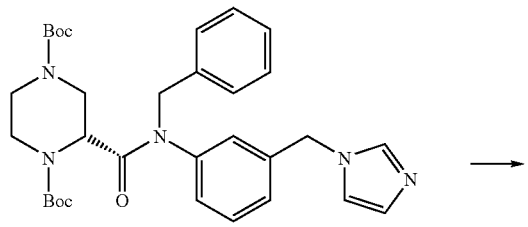

The title compound from Step A above may be deprotected as described in Preparative Example 8, step B above to give the title compound.

PREPARATIVE EXAMPLE 15

(−)-N-1-(tert-BUTYLOXYCARBONYL)-N-[3-[(4-METHYL-1H-IMIDAZOL-1-YL)METHYL]PHENYL]-(3R)- PIPERAZINECARBOXAMIDE

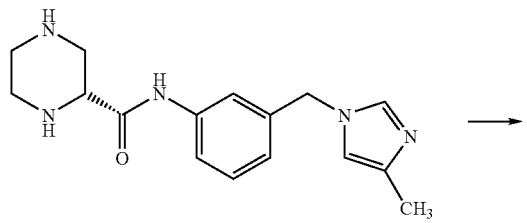

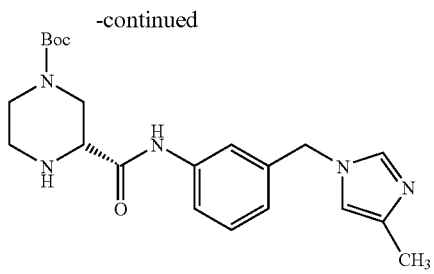

The title compound from Preparative Example 8, Step B (0.1 g, 0.334 mmoles) was dissolved in a mixture of THF (1.25 mL) and water (1.25 mL) and Boc-ON (90.5 mg, 0.367 mmoles) was added and the mixture was stirred at 25° C. for 18 h. The solution was evaporated to dryness and the residue was chromatographed on silica gel using 2.5% (10% conc. NH$_4$OH in methanol)-dichloromethane to give the title compound (0.1019 g, 76%): FABMS: m/z 400.1 (MH$^+$); $\delta_H$ (CDCl$_3$) 1.44 (9H, s, CH$_3$), 2.18 (3H, s, 4-CH$_3$), 4.06 (1H, dd, CHCO), 4.99 (2H, s, CH$_2$-Im), 6.59 (1H, s, Im-H$_5$), 6.88 (1H, d, Ar—H$_4$), 7.29 (1H, dd, Ar—H$_5$), 7.43 (1H, s, Im-H$_2$), 7.50 (1H, s, Ar—H$_2$), 7.50 (1H, d, Ar—H$_6$) and 8.94 ppm (1H, s, NHCO); $\delta_C$ (CDCl$_3$) CH$_3$: 13.8, 28.4; CH$_2$: NA, NA, 43.9, 50.6; CH: 58.6, 115.8, 118.3, 119.3, 123.1, 136.6, 137.5; C, 80.4, 129.7, 138.2, 138.9, 154.7, 169.5; $[\alpha]_D^{20\ °C.}$ −11.1° (c=0.28, MeOH).

PREPARATIVE EXAMPLE 16

(−)-N-1-(tert-BUTOXYCARBONYL)-N-[3-[(1H-IMIDAZOL-1-YL)METHYL]PHENYL]-(3R)- PIPERAZINECARBOXAMIDE

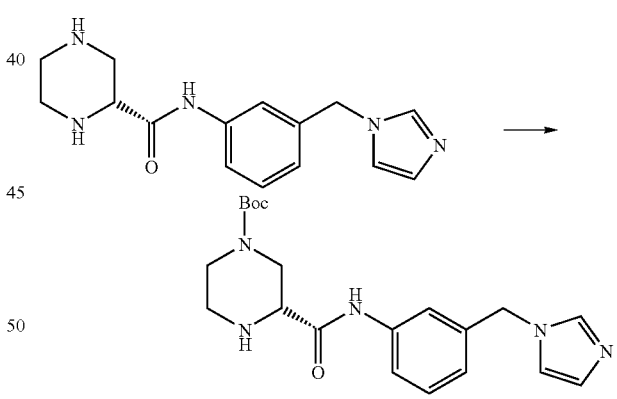

The title compound from Preparative Example 7, Step B (0.11 g, 0.385 mmoles) was dissolved in THF (2 mL) and water (0.5 mL) and di-tert-butyldicarbonate (0.0841 g, 0.385 mmoles) was added. The mixture was stirred at 25° C. for 16 h. The solution was evaporated to dryness and the product was chromatographed on silica gel using 5% (10% conc. NH$_4$OH in methanol)-dichloromethane as the eluant to give first, the title compound from Preparative Example 7, Step A (0.0251 g, 13%), followed by N1-(tert-butoxycarbonyl)-N-[3-[(1H-imidazol-1-yl)methyl]phenyl]-(3R)-piperazinecarboxamide (0.1051 g, 71%): FABMS: m/z 386.2 (MH$^+$); HRFABMS: m/z 386.2195 (MH$^+$), Calcd. C$_{20}$H$_{28}$N$_5$O$_3$ m/z 386.2192; $\delta_H$ (CDCl$_3$) 1.44 (9H, s, CH$_3$), 4.06 (1H, dd, CHCO), 5.08 (2H, s, CH$_2$-Im), 6.87 (1H, d, Ar—H$_4$), 6.91 (1H, s, Im-H$_5$), 7.08 (1H, bs, Im-H$_4$), 7.29 (1H, dd, Ar—H$_5$), 7.46 (1H, s, Ar—H$_2$), 7.50 (1H, d, Ar—H$_6$), 7.57 (1H, bs, Im-H$_2$) and 8.97 ppm (1H, s, NHCO); δ$_C$ (CDCl$_3$) CH$_3$: 28.4, 28.4, 28.4; CH$_2$: 43.9, 46.1, 50.7, 50.7; CH: 58.6, 118.4, 119.4, 119.4, 123.1, 129.7, 129.9, 137.3; C, 80.4, 137.3, 138.3, 154.7, 169.5; [α]$_D^{20°C}$ −6.9° (c=0.53, MeOH).

PREPARATIVE EXAMPLE 17

N1-(tert-BUTOXYCARBONYL)-N-[3-[(1H-IMIDAZOL-1-YL)METHYL]PHENYL]-(3R)-PIPERAZINECARBOXAMIDE

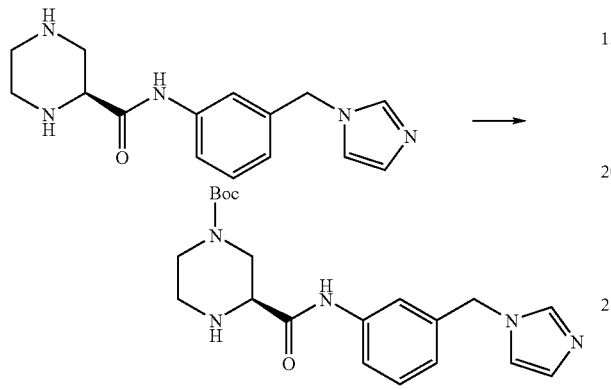

The title compound from Preparative Example 6, Step B (1.07 g, 3.75 mmoles) was dissolved in THF (19.5 mL) and water (4.9 mL) and di-tert-butyldicarbonate (0.818 g, 3.75 mmoles) was added. The mixture was stirred at 25° C. for 23 h. The solution was evaporated to dryness and the product was chromatographed on silica gel using 5% (10% conc. NH$_4$OH in methanol)-dichloromethane as the eluant to give first, N1-(tert-butoxycarbonyl)-N-[3-[(1H-imidazol-1-yl)methyl]phenyl]-(3R)-piperazinecarboxamide (0.9228 g, 64%): δ$_H$ (CDCl$_3$) 1.46 (9H, s, CH$_3$), 4.08 (1H, dd, CHCO), 5.10 (2H, s, CH$_2$-Im), 6.88 (1H, d, Ar—H$_4$), 6.91 (1H, s, Im-H$_5$), 7.08 (1H, s, Im-H$_4$), 7.32 (1H, dd, Ar—H$_5$), 7.46 (1H, s, Ar—H$_2$), 7.51 (1H, d, Ar—H$_6$) 7.54 (1H, s, Im-H$_2$) and 9.04 ppm (1H, bs, NHCO); δ$_C$ (CDCl$_3$) CH$_3$: 28.4, 28.4, 28.4; CH: 43.4, 43.9, 45.8, 50.7; CH: 58.6, 118.4, 119.4, 119.4, 123.1, 129.7, 129.8, 137.5; C, 80.4, 137.3, 138.3, 154.7, 169.4; and then the title compound from Preparative Example 6, Step A (0.3277 g, 18%), followed by unreacted starting material (0.0994 g, 9%).

In the Examples below, all isomer numbers refer to the relative order of elution of the diastereoisomers from Chiralpak® AD columns, unless otherwise stated that it refers to the order of elution from regular silica gel columns.

EXAMPLE 1

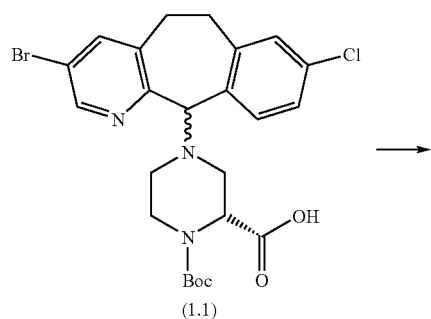
(1.1)

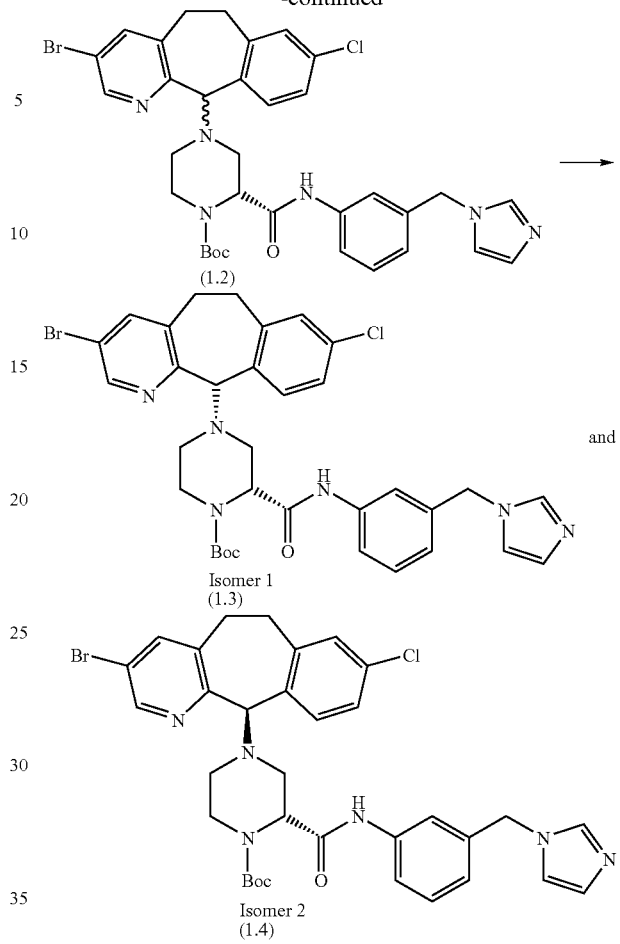

Compound (1.1) (0.250 g, 0.466 mmoles) (prepared as described in Preparative Example 6 of U.S. Pat. No. 6,362,188 issued Mar. 26, 2002, the disclosure of which is incorporated herein by reference thereto), the title compound from Preparative Example 1, Step C (0.123 g, 0.606 mmoles), 1-(3-dimethylaminopropyl)-3-ethylcarbodiimide hydrochloride (0.116 g, 0.605 mmoles), 1-hydroxybenzo-triazole (0.0818 g, 0.605 mmoles) and 4-methylmorpholine (0.0665 mL, 0.605 mmoles) were dissolved in anhydrous DMF (10 mL) and the mixture was stirred at 25° C. under argon for 69 h. The reaction was worked up as described in Preparative Example 6, Step A above and the product was chromatographed on silica gel using 1% (10% conc. NH$_4$OH in methanol)-dichloromethane as the eluant to give compound (1.2) (0.2302 g, 71%).

Compound (1.2) was subjected to chiral HPLC first on a preparative and then on a semi-preparative Chiralpak® AD column using hexane:isopropanol:diethylamine::85:15:0.2 as the eluant to give as the first eluting band compound (1.3), isomer 1 (0.0436 g): ESMS: m/z 691.2 (MH$^+$); δ H (CDCl$_3$) 1.44 (9H, s, CH$_3$), 4.30 (1H, s, CHCON), 4.68 (1H, bs, NHCO), 5.08 (3H, bs, CH$_2$-Im and H$_{11}$), 6.90.7.50 (9H, s and m, Ar—H and Im-H), 7.75 (2H, s, Ar—H$_2$ and Im-H$_2$) and 8.35 ppm (1H, s, H$_2$); δ$_C$ (CDCl$_3$) CH$_3$: 28.3, 28.3, 28.3; CH$_2$: 30.2, 30.4, 42.2, 50.8, 51.0, 52.2; CH: 56.8, 78.7, 118.3, 119.5, 119.5, 122.8, 126.1, 129.4, 129.5, 130.7, 132.5, 136.9, 141.3, 147.0; C, 81.2, 120.1, 134.1, 135.0, 137.2, 137.2, 138.8, 141.6, 155.2, 155.5, 168.8; [α]$_D^{20°C}$ +11.5° (c=0.42, MeOH), followed by compound (1.4), isomer 2 (0.1087 g):

ESMS: m/z 691.2 (MH+); $\delta_H$(CDCl$_3$) 1.46 (9H, s, CH$_3$), 4.33 (1H, s, CHCON), 4.68 (1H, bs, NHCO), 5.17 (3H, bs, CH$_2$-Im and H$_{11}$), 6.91, 7.05.7.35, 7.50.7.80 (10H, s and m, Ar—H and Im-H), 7.57 (1H, s, Im-H$_2$) and 8.68 ppm (1H, s, py-H$_2$); $\delta_C$ (CDCl$_3$) CH$_3$: 28.3, 28.3, 28.3; CH$_2$: 30.2, 30.4, 42.2, 50.5, 50.8, 52.1; CH: 55.3, 78.4, 118.2, 119.4, 119.4, 122.9, 126.2, 129.6, 129.6, 130.7, 132.4, 132.4, 141.4, 146.8; C, 81.3, 120.0, 134.2, 135.2, 137.1, 137.4, 138.7, 141.1, 155.4, 155.4, 169.0; $[\alpha]_D^{20° C.}$ +32.6° (c=0.51, MeOH).

EXAMPLE 2

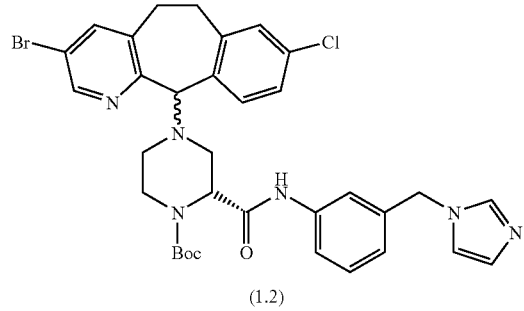

(1.2)

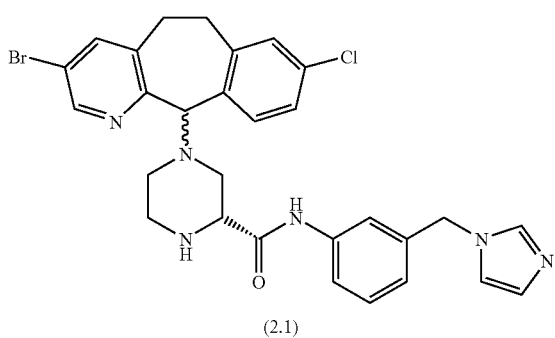

(2.1)

Compound (1.2) from Example 1 (0.2293 g, 0.331 mmoles) was dissolved in methanol (1.75 mL) and 10% conc. H$_2$SO$_4$-dioxane (v/v) (4.52 mL) was added and the reaction was stirred at 25° C. for 1 h. The reaction was worked up as described in Preparative Example 4, Step C. The product was chromatographed on silica gel using 1.5% (10% conc. NH$_4$OH in methanol).dichloromethane as the eluant to give compound (2.1) (0.1202 g, 80%): ESMS: m/z591.1 (MH+); $\delta_H$(CDCl$_3$) 4.32 (1H, s, CHCON), 5.09 (2H, s, CH$_2$-Im), 6.87 (1H, d, Ar—H$_4$), 6.92 (1H, s, Im-H$_5$), 7.05-7.15 (3H, s and d, H$_7$, Hg, H$_{10}$), 7.09 (1H, s, Im-H$_4$), 7.28 (1H, dd, Ar—H$_5$), 7.44 (1H, H$_4$), 7.46 (1H, d, Ar—H$_6$), 7.54 (1H, s, Ar—H$_2$), 7.60 (1H, s, Im-H$_2$), 8.36 (1H, s, H$_2$) and 9.08 ppm (1H, bs, NHCO); $\delta_C$ (CDCl$_3$) CH$_2$: 30.3, 30.5, 43.9, 50.7, 52.2, 53.5; CH: 58.5, 79.4, 118.1, 119.2, 119.5, 122.9, 126.2, 129.7, 129.9, 130.7, 132.4, 132.4, 141.2/141.3, 146.9; C, 120.1, 134.2, 135.2, 137.2, 137.2, 138.4, 140.8, 155.7, 170.1.

EXAMPLE 3

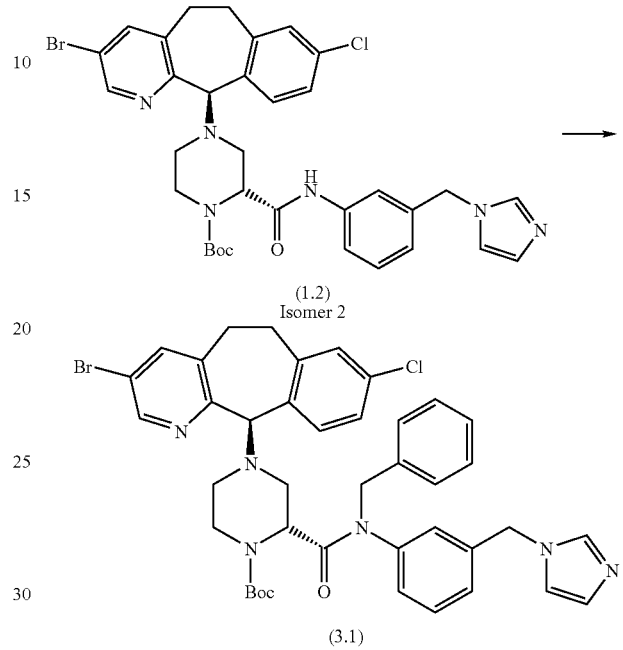

(1.2) Isomer 2

(3.1)

Compound (1.4) from Example 1 (0.045 g, 0.065 mmoles), KF—Al$_2$O$_3$ (0.0944 g, 0.65 mmoles of KF) (Ref.: J. Yamawaki, T. Ando and T. Hanafusa, *Chemistry Letters*, 1981, 1143.1146) and benzyl chloride (0.494 g, 0.0449 mL, 0.39 mmoles) were added to anhydrous acetonitrile (3 mL) and the mixture was stirred under argon at 25° C. for 113 h. The reaction mixture was filtered and the alumina was washed with methanol and the combined filtrates were evaporated to dryness. The residue was chromatographed on silica gel using 1% (10% conc. NH$_4$OH in methanol)-dichloromethane as the eluant to give compound (3.1) (0.0396 g, 78%): FABMS: m/z 781.3 (MH+); $\delta_H$ (CDCl$_3$) 1.40 (9H, s, CH$_3$), 6.70, 6.83, 7.00, 7.10, 7.16, 7.28, 7.59, 7.68, 7.80 and 8.35 ppm (17H, bs and bm, Ar—H and Im-H); $\delta_C$ (CDCl$_3$) CH$_3$: 28.4, 28.4, 28.4; CH$_2$: 30.2, 30.5, 42.1, 50.5, 50.5, 52.2/52.5, 53.5/53.8; CH: 42.9, 78.4, 119.3, 119.9, 126.3, 126.3, 126.3, 127.4, 127.4, 127.7, 128.5, 128.5, 129.3, 130.6, 130.8, 132.5, 137.4, 141.2, 146.8; C, 80.2, 119.9, 134.4, 134.9, 136.7, 137.8, 141.8, 141.8, 156.6, 156.6, 171.4; $[\alpha]_D^{20° C.}$ 0° (c=0.45, MeOH).

EXAMPLE 4

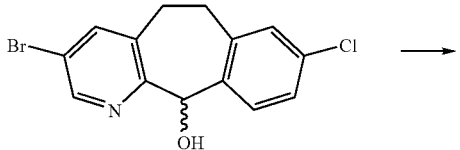

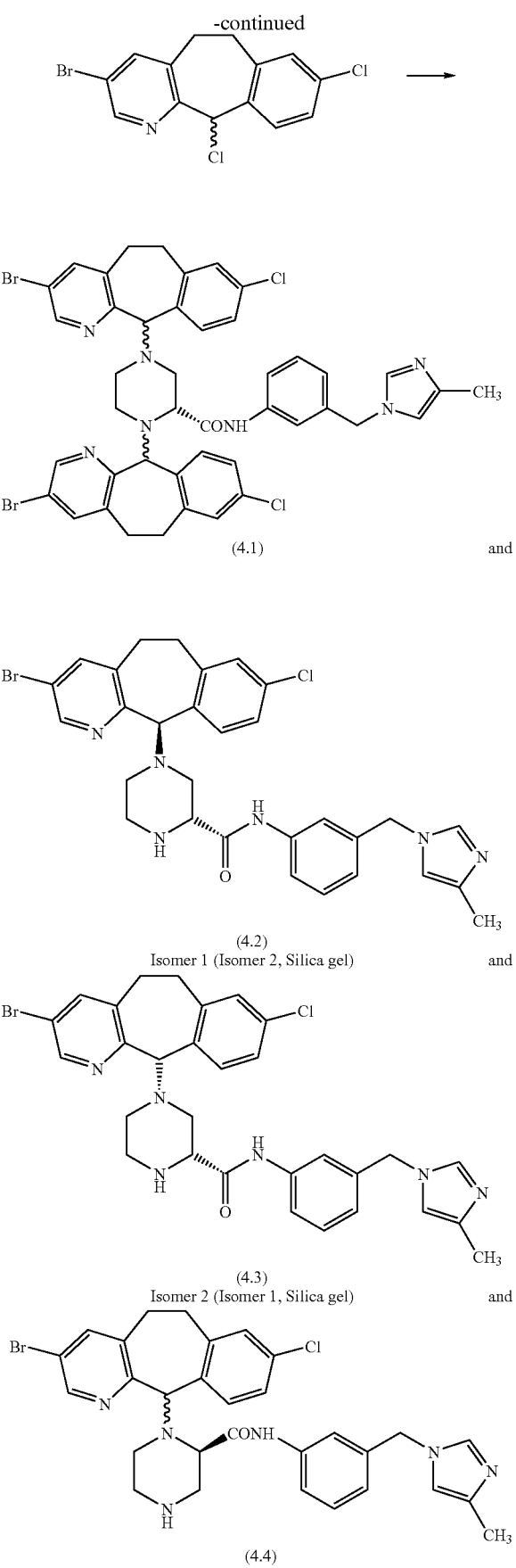

(4.1)

(4.2)
Isomer 1 (Isomer 2, Silica gel) and (4.3)
Isomer 2 (Isomer 1, Silica gel) and (4.4)

3-Bromo-8,11-dichloro-6,11-dihydro[5,6]cyclohepta[1,2-b]pyridine (2.72 g, 7.98 mmoles) (prepared from the alcohol as described in Preparative Example 40 (U.S. Pat. No. 5,719,148; Feb. 17, 1998)), the title compound from Preparative Example 8, Step B above (2.39 g, 7.98 mmoles) and triethylamine (3.33 mL, 2.395 mmoles) were dissolved in anhydrous THF (25 mL) and anhydrous dichloromethane (40 mL) and the mixture was stirred under argon at 25° C. for 19 h. The solution was evaporated to dryness and the residue was chromatographed on silica gel using 4.5% (10% conc. NH$_4$OH in methanol)-dichloromethane as the eluant to give in the order of elution the following compounds:

The first compound was rechromatographed on silica gel using 1.5% (10% conc. NH$_4$OH in methanol)-dichloromethane as the eluant to give compound (4.1) (1.3544 g, 19%): FABMS: m/z 910.2 (MH$^+$); $\delta_H$ (CDCl$_3$) 2.18/2.20/2.11/2.12 (3H, s, 4-CH$_3$), 4.32/4.34/4.35/4.38 (1H, s, CHCON), 5.04 (2H, s, CH$_2$-Im), 6.64 (1H, s, Im-H$_5$), 6.90 (1H, d Ar—H$_4$), 7.04-7.64 (12H, s and m, Ar—H and Im-H$_2$) and 8.31/8.32, 8.33/8.34, 8.35/8.36, 8.38/8.39 ppm (2H, s, H$_2$); $\delta_C$ (CDCl$_3$) CH$_2$: 13.8; CH$_2$: 30.2/30.3, 30.5/30.8, 45.5, 47.1, 48.0, 48.9, 49.7, 50.6; CH: 59.8/60.0, 72.8/73.1, 115.9, 117.5/117.6, 118.5, 122.6, 126.0/126.1/126.7, 129.5/129.6, 130.6/130.7/130.9, 134.0/134.2/135.3, 136.6, 141.2/141.4, 146.9/147.5; C, 120.1/120.2, 132.5/132.6, 133.1/133.2, 135.1/135.3, 137.0, 137.0/137.6, 138.4, 138.4, 140.1/141.6, 155.3/155.8, 169.7/169.8.

The second diastereoisomeric mixture (1.8564 g, 38%) was separated by chiral HPLC on a Chiralpak® AD column using gradient elution with hexane:isopropanol:diethylamine::60:40:0.2 to 91 min, 50:50:0.2 to 106 min and 45:55:0.2 to give in the order of elution compound (4.2), isomer 1 (isomer 2, silica gel) (0.688 g, 14%): HRFABMS: m/z 605.1432 (MH$^+$), Calcd. C$_{30}$H$_{31}$N$_6$OBrCl: 605.1431; $\delta_H$ (CDCl$_3$) 2.23 (3H, s, 4-CH$_3$), 4.34 (1H, s, CHCON), 5.02 (2H, s, CH$_2$-Im), 6.62 (1H, s, Im-H$_5$), 6.88 (1H, d, Ar—H$_4$), 7.07 (1H, dd, H$_9$), 7.13 (1H, s, H$_7$), 7.15 (1H, d, H$_{10}$), 7.30 (1H, dd, Ar—H$_5$), 7.43 (1H, s, Ar—H$_2$), 7.48 (1H, s Im-H$_2$), 7.50 (1H, d, Ar—H$_6$), 7.62 (1H, s, H$_4$), 8.37 (1H, s, H$_2$) and 9.12 ppm (1H, bs, NHCO); $\delta_C$ (CDCl$_3$) CH$_3$: 13.8; CH$_2$: 30.4, 30.5, 43.9, 50.7, 52.1, 53.5; CH: 58.5, 79.4, 115.8, 118.2, 119.1, 123.0, 126.3, 129.7, 130.7, 132.4, 136.5, 141.4, 147.0; C, 120.1, 134.2, 134.2, 135.3, 137.1, 138.4, 138.8, 140.8, 155.7, 170.0; [α]$_D^{20\,°C}$ -20.3° (c=0.42, MeOH), and compound (4.3), isomer 2, (isomer 1, silica gel) (0.735 g, 15%): HRFABMS: m/z 605.1425 (MH$^+$), Calcd. C$_{30}$H$_{31}$N$_6$OBrCl: 605.1431; $\delta_H$ (CDCl$_3$) 2.23 (3H, s, 4-CH$_3$), 4.33 (1H, s, CHCON), 5.02 (2H, s, CH$_2$-Im), 6.62 (1H, s, Im-H$_5$), 6.88 (1H, d, Ar—H$_4$), 7.07 (1H, dd, Hg), 7.16 (1H, s, H$_7$), 7.17 (1H, d, H$_{10}$), 7.29 (1H, dd, Ar—H$_5$), 7.39 (1H, s, Ar—H$_2$), 7.46 (1H, s Im-H$_2$), 7.48 (1H, d, Ar—H$_6$), 7.56 (1H, s, H$_4$), 8.34 (1H, s, H$_2$) and 8.99 ppm (1H, bs, NHCO); $\delta_C$ (CDCl$_3$) CH$_3$: 13.8; CH$_2$: 30.4, 30.5, 44.1, 50.7, 52.0, 54.1; CH: 59.0, 79.5, 115.8, 118.2, 119.2, 123.0, 126.2, 129.7, 130.6, 132.5, 136.6, 141.4, 147.1; C, 120.1, 134.2, 135.4, 136.9, 137.4, 138.3, 138.7, 141.2, 155.5, 170.1; [α]$_D^{20\,°C}$ -45.4° (c=0.42, MeOH).

The third compound was rechromatographed on silica gel using 3.5% (10% conc. NH$_4$OH in methanol)-dichloromethane as the eluant to give compound (4.4) (0.2313 g, 5%): FABMS: m/z 605.1 (MH$^+$); HRFABMS: m/z 605.1425 (MH$^+$), Calcd. C$_{30}$H$_{31}$N$_6$OBrCl: m/z 605.1431; $\delta_H$ (CDCl$_3$) 2.23/2.24 (3H, s, 4-CH$_3$), 5.03/5.06/5.07/5.14 (3H, s, CH$_2$-Im and H$_1$), 6.64/6.67 (1H, s, Im-H$_5$), 6.86/6.93 (1H, d, Ar—H$_4$), 7.07.7.69 (8H, s and m, Im-H$_2$ and Ar—H) and 8.36/8.43 ppm (1H, s, H$_2$); $\delta_C$ (CDCl$_2$) CH$_3$: 13.9; CH$_2$: 30.3, 31.4, 45.0/45.3, 45.6, 46.4/46.6, 50.7; CH: 57.4/59.0, 73.7/74.2, 115.9, 118.5/118.6, 119.3/119.4, 122.7, 126.5, 129.6/129.7, 130.0/130.2, 134.0, 136.6/136.7, 141.7/142.3, 146.8/147.3; C, 120.0/120.5, 134.2, 134.9/135.1, 137.4/137.7, 137.4/137.7, 138.7, 138.7/138.9, 140.9/141.0, 155.0/155.7, 169.0/169.3.

132.5, 136.5, 141.4, 146.8; C, 120.0, 134.3, ~134.9, 137.2, 137.2, 138.8, 138.8, 141.4, 155.5, 157.9, 169.8; $[\alpha]_D^{25°}$ $c$.+32.0° (c=0.34, MeOH).

EXAMPLE 5

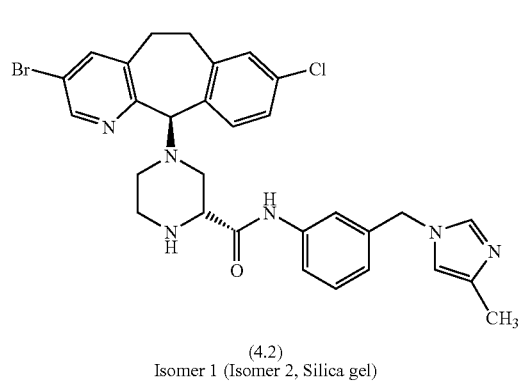

(4.2)
Isomer 1 (Isomer 2, Silica gel)

EXAMPLE 6

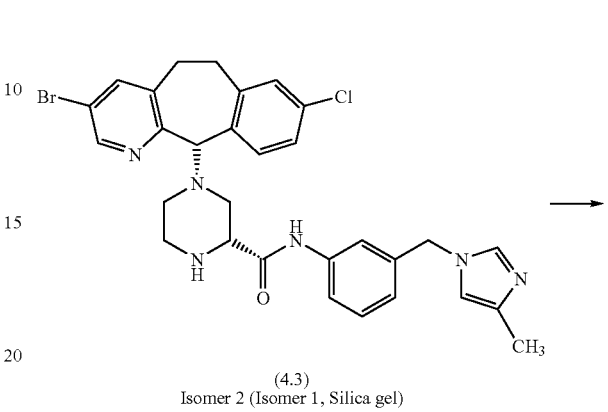

(4.3)
Isomer 2 (Isomer 1, Silica gel)

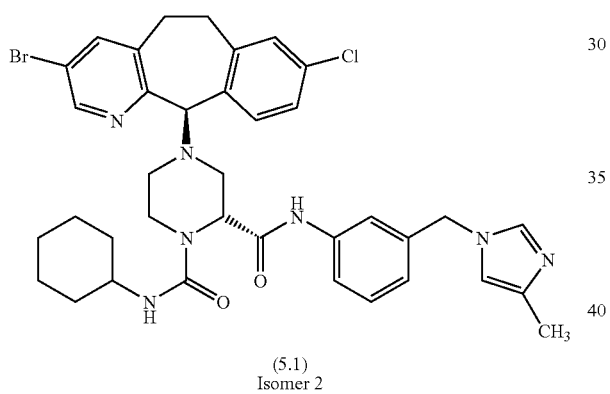

(5.1)
Isomer 2

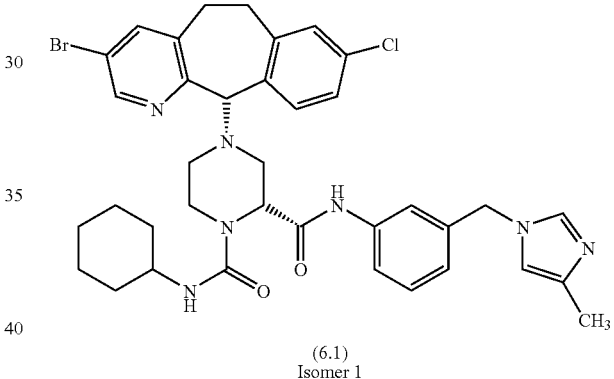

(6.1)
Isomer 1

Compound (4.2), isomer 1, (0.125 g, 0.206 mmoles) (prepared as described in Example 4 above) and cyclohexyl iso-cyanate (0.02582 g, 0.0264 mL, 0.206 mmoles) were dissolved in anhydrous dichloromethane (5 mL) and the solution was stirred under argon at 25° C. for 6.5 h. The mixture was evaporated to dryness and chromatographed on silica gel using 2.5% (10% conc. NH$_4$OH in methanol)-dichloromethane as the eluant to give compound (5.1), isomer 2 (0.1374 g, 91%): FABMS: m/z 730.2 (MH$^+$); HRFABMS: m/z 730.2266 (MH$^+$), Calcd. C$_{37}$H$_{42}$N$_7$O$_2$BrCl: m/z 730.2272; $\delta_H$ (CDCl$_3$) 2.19 (3H, s, 4-CH$_3$), 4.36 (1H, s, CHCON), 4.72 (1H, s, H$_1$), 4.96 (2H, s, CH$_2$-Im), 6.62 (1H, s, Im-H$_5$), 6.86 (1H, d, Ar—H$_4$), 7.12 (1H, dd, Ar—H$_5$), 7.08.7.17 (2H, s and m, Ar—H), 7.20.7.33 (4H, s and m, Ar—H), 7.42 (1H, s, Im-H$_2$), 8.33 (1H, s, H$_2$) and 8.94 ppm (1H, bs, NHCO); $\delta_C$ (CDCl$_3$) CH$_3$: 13.8; CH$_2$: 25.0, 25.0, 25.7, 30.2, 30.5, 33.7, 33.7, 42.2, 50.5, 50.7, 52.5; CH: 49.7, 55.5, 79.1, 115.8, 118.5, 119.5, 122.8, 126.4, 129.4, 130.7, Compound (4.3), isomer 2, (isomer 1, silica gel) (0.125 g, 0.206 mmoles) (prepared as described in Example 4 above) and cyclohexyl iso-cyanate (0.02582 g, 0.0264 mL, 0.206 mmoles) were dissolved in anhydrous dichloromethane (4 mL) and the solution was stirred under argon at 25° C. for 6.5 h. The mixture was evaporated to dryness and chromatographed on silica gel using 2.5% (10% conc. NH$_4$OH in methanol)-dichloromethane as the eluant to give compound (6.1), isomer 1 (0.1334 g, 88%): FABMS: m/z 730.2 (MH$^+$); HRFABMS: m/z 730.2258 (MH$^+$), Calcd. C$_{37}$H$_{42}$N$_7$O$_2$BrCl: m/z 730.2272; $\delta_H$ (CDCl$_3$) 2.17 (3H, s, 4-CH$_3$), 4.30 (1H, s, CHCON), 4.68 (1H, d, NHCO), 4.83 (1H, s, H$_{11}$), 4.92 (2H, s, CH$_2$-Im), 6.58 (1H, s, Im-H$_5$), 6.83 (1H, d, Ar—H$_4$), 6.87 (1H, s, H$_7$), 7.07.7.30 (5H, s and m, Ar—H$_2$, Ar—H$_5$, Ar—H$_6$, H$_9$ and H$_{10}$), 7.37 (1H, s, Im-H$_2$), 7.56 (1H, s, H$_4$), 8.36 (1H, s, H$_2$) and 8.99 ppm (1H, s, NHCO); oc (CDCl$_3$) CH$_3$: 13.8; CH$_2$: 25.0, 25.0, 25.6, 30.2, 30.5, 33.7, 33.7, 42.2, 50.7, 50.8, 52.6; CH: 49.7, 55.4, 78.7, 115.8, 118.6, 119.5, 122.7, 126.1, 129.2, 130.7, 132.6, 136.4, 141.4, 147.1; C, 120.2, 134.3, 134.9, 137.0, 137.2, 138.8, 138.8, 141.4, 155.1, 158.0, 169.7; [α]$_D^{25°\,C.}$+10.2° (c=0.26, MeOH).

EXAMPLE 7

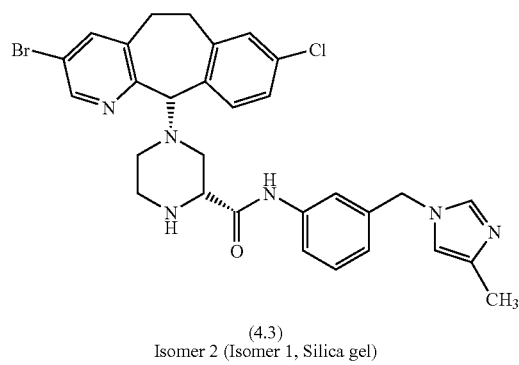

(4.3)
Isomer 2 (Isomer 1, Silica gel)

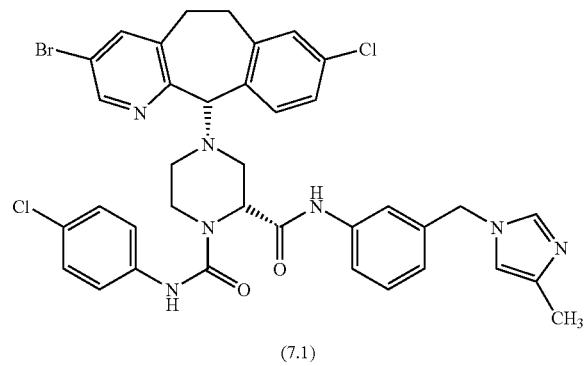

(7.1)

Compound (4.3), isomer 2 (isomer 1, silica gel) (0.2 g, 0.33 mmoles) (prepared as described in Example 4 above) and 4-chlorophenyl iso-cyanate (0.253 g, 0.33 mmoles) were dissolved in anhydrous dichloromethane (7 mL) and the solution was stirred under argon at 25° C. for 46 h. The mixture was evaporated to dryness and the residue was taken up in dichloromethane, washed with saturated NaHCO$_3$, dried (MgSO$_4$), filtered and evaporated to dryness. The residue was chromatographed on silica gel using 2% (10% conc. NH$_4$OH in methanol)-dichloromethane as the eluant to give a product that was further purified by preparative tlc on silica gel plates (250μ; 20×20 cm) using 8% (10% conc. NH$_4$OH in methanol)-dichloromethane as the eluant to give the product. The latter was rechromatographed on silica gel using 3% (10% conc. NH$_4$OH in methanol)-dichloromethane as the eluant to give compound (7.1) (0.03 g, 12%): HRFABMS: m/z 758.1417 (MH$^+$), Calcd. C$_{37}$H$_{35}$N$_7$O$_2$BrCl: m/z 758.1413; δ$_H$ (CDCl$_3$) 2.13/2.18 (3H, s, 4.CH$_3$), 4.35/4.44 (1H, s, CHCON), 4.80 (1H, s, H$_{11}$), 4.93 (2H, s, CH$_2$.Im), 6.38/6.52.6.61/6.88/6.89/ 7.02/7.08.7.42/7.48 (13H, s and m, Ar—H and Im-H), 7.58/ 7.62 (1H, s, H$_4$), 8.37 (1H, s, H$_2$) and 9.06 ppm (1H, s, NHCO); δ$_C$ (CDCl$_3$) CH$_3$: 13.8/13.9; CH$_2$: 30.5/30.7, 31.0, 39.8/42.2, 50.8/50.9, 51.1, 52.6/52.7; CH: 55.5/56.6, 78.7/ 78.8, 113.5, 114.9, 116.0, 117.4, 118.8, 119.8, 121.5, 121.5, 123.3, 127.3, 128.9, 128.9, 129.6/129.7, 130.9, 132.8/132.9, 136.3, 141.5/141.8, 147.5/147.7; C, 120.5/120.7, 128.3, 133.9/134.3, 134.5/134.7, 136.3, 137.1/137.5, 137.1/137.5, 138.1/138.2, 138.1/138.2, 141.2/141.4, 154.5/154.8, 156.1, 169.7/169.9; [α]$_D^{20°\,C.}$-27.8° (c=0.48, MeOH).

EXAMPLE 8

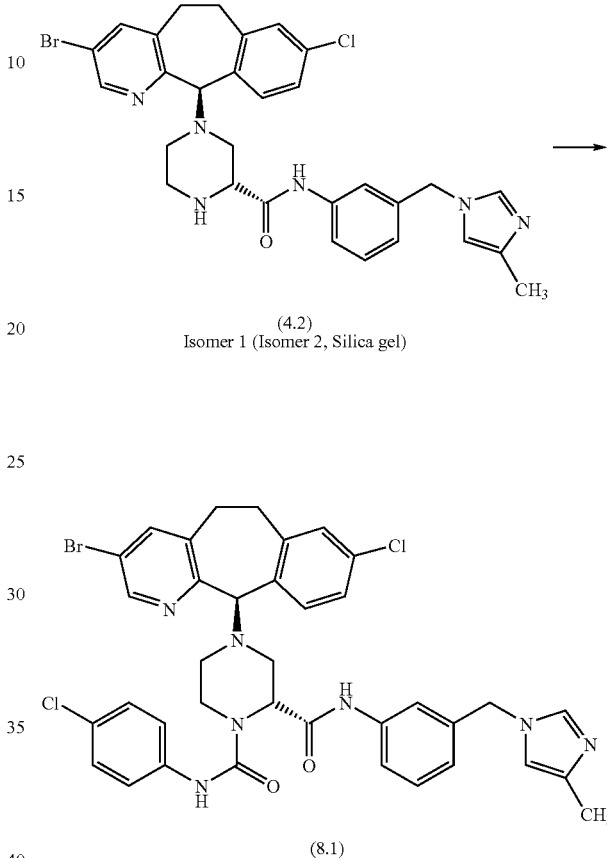

(4.2)
Isomer 1 (Isomer 2, Silica gel)

(8.1)

Compound (4.2), isomer 1, (isomer 2, silica gel) (0.2 g, 0.33 mmoles) (prepared as described in Example 4 above) and 4-chlorophenyl iso-cyanate (0.253 g, 0.33 mmoles) were dissolved in anhydrous dichloromethane (7 mL) and the solution was stirred under argon at 25° C. for 22 h. The mixture was evaporated to dryness and chromatographed on silica gel using 2% (10% conc. NH$_4$OH in methanol)-dichloromethane as the eluant to give the product that was further purified by preparative tlc on silica gel plates (250μ; 20×20 cm) using 8% (10% conc. NH$_4$OH in methanol)-dichloromethane as the eluant and the upper band was collected. The latter was subjected to chiral HPLC on a Chiralpak® AD column using hexane;isopropanol:diethylamine::85:15:0.2 as the eluant to give compound (8.1) (0.0514 g, 21%): FABMS: m/z 758.1 (MH$^+$); HRFABMS: m/z 758.1425 (MH$^+$), Calcd. C$_{37}$H$_{35}$N$_7$O$_2$BrCl: m/z 758.1413; δ$_H$ (CDCl$_3$) 2.16/2.19 (3H, s, 4-CH$_3$), 4.47/4.94 (1H, s, CHCON), 4.74 (1H, bs, H$_{11}$), 4.99 (2H, s, CH$_2$-Im), 6.39 (1H, s, Im-H$_5$), 6.56/6.62/7.93/ 7.09.7.44 (12H, s and m, Ar—H and Im-H$_2$), 7.63 (1H, s, H$_4$), 8.30 (1H, bs, NHCO) and 8.40 ppm (1H, s, H$_2$); δ$_C$ (CDCl$_3$) CH$_3$: 13.8; CH$_2$: 30.4/30.5, 30.6, 39.4, 50.7, 51.1, 52.3; CH: 55.8/56.6, 78.5, 113.5, 114.8, 115.9, 117.3, 118.9, 119.8, 121.3, 121.3, 123.5, 126.8/127.1, 128.8, 128.8, 129.7/129.9, 130.6/130.9, 132.6, 136.5, 141.6, 147.1/147.4; C, 120.3, 130.0, 133.9, 134.4/134.8, 136.6, 136.6, 137.5/137.7, 138.3, 138.3, 140.8, 153.1/154.9, 156.1, 169.5; $[\alpha]_D^{20\ °C}$ +40.3° (c=0.38, MeOH).

EXAMPLE 9

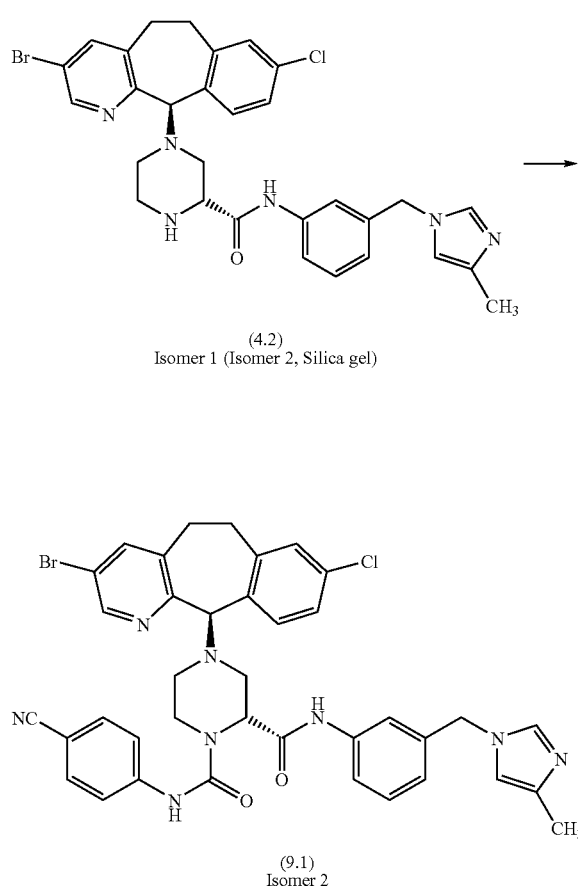

(4.2)
Isomer 1 (Isomer 2, Silica gel)

(9.1)
Isomer 2

Compound (4.2), isomer 1, (isomer 2, silica gel) (89% 11S:11% 11R) (0.11 g, 0.182 mmoles) (prepared as described in Example 4 above) and 4-cyanophenyl isocyanate (0.0279 g, 0.182 mmoles) were dissolved in anhydrous dichloromethane (5 mL) and the solution was stirred under argon at 25° C. for 6.5 h. The mixture was evaporated to dryness and chromatographed on silica gel using 2.5% (10% conc. NH$_4$OH in methanol)-dichloromethane as the eluant to give the product. The latter was subjected to chiral HPLC on a Chiralpak ® AD column using hexane:isopropanol:diethylamine::75:25:0.2 as the eluant to give the compound (9.1), isomer 2 (0.0296 g, 22%): FABMS: m/z 749.0 (MH$^+$); HRFABMS: m/z 749.1757 (MH$^+$), Calcd. C$_{38}$H$_{35}$N$_8$O$_2$BrCl: m/z 749.1755; $\delta_H$ (CDCl$_3$) 2.16/2.20 (3H, s, 4-CH$_3$), 4.49/4.93 (1H, s, CHCONH), 4.71 (1H, s, H$_{11}$), 5.01 (2H, s, CH$_2$-Im), 6.40 (1H, s, Im-H$_5$), 6.55/7.63/6.97/7.08.7.57/7.64/7.74 (13H, s and m, Ar—H and Im-H$_2$), 8.29 (1H, bs, NHCO) and 8.40 ppm (1H, s, H$_2$); $\delta_C$ (CDCl$_3$) CH$_3$: 13.6; CH$_2$: 30.4/30.5, 30.7, 32.2, 39.8, 50.8, 51.0; CH: 55.9/56.5, 78.4, 113.5/114.8, 113.5/114.8, 115.9, 119.1, 119.5, 123.8, 125.8/126.8, 129.8/129.9, 130.6/130.9, 132.9/133.1, 132.9/133.1, 132.9/133.1, 136.4/136.5, 141.6, 147.1/147.4; C, 105.3, 115.9/117.3, 119.4, 134.8/134.9, 134.8/134.9, 137.4, 137.4, 138.8, 138.8, 140.7, 143.8, 154.8, 155.7, 169.4/169.7; $[\alpha]_D^{20\ °C}$ +12.4° (c=0.4, MeOH).

EXAMPLE 10

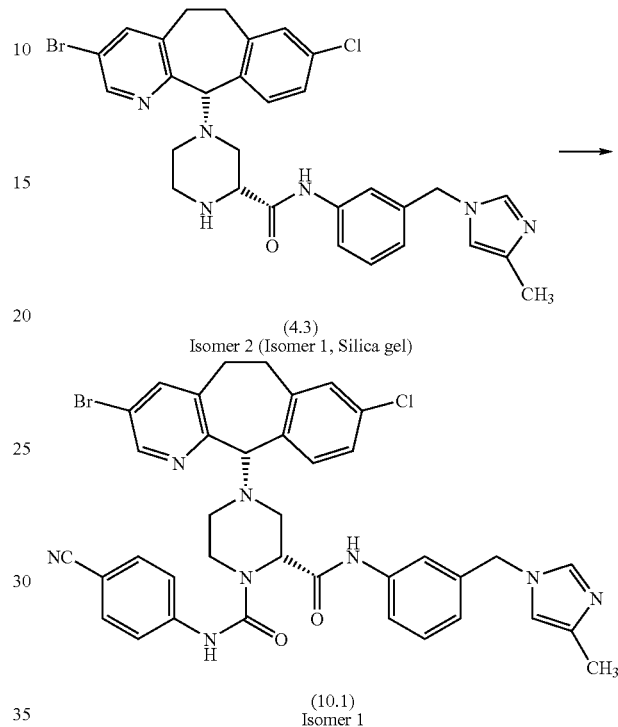

(4.3)
Isomer 2 (Isomer 1, Silica gel)

(10.1)
Isomer 1

Compound (4.3), isomer 2 (0.1 g, 0.165 mmoles) (Isomer 2) (prepared as described in Example 4 above) and 4-cyanophenyl isocyanate (0.0238 g, 0.165 mmoles) were dissolved in anhydrous dichloromethane (5 mL) and the mixture was stirred at 25° C. for 20 h. Chromatography on silica gel using 2% (10% conc. NH$_4$OH in methanol)-dichloromethane as the eluant, followed by preparative tlc on silica gel (250µ; 20×20 cm) plates using 5% (10% conc. NH$_4$OH in methanol)-dichloromethane as the eluant afforded compound (10.1), isomer 1 (0.004 g, 3.2%): ESMS: m/z 749.2 (MH$^+$).

EXAMPLE 11

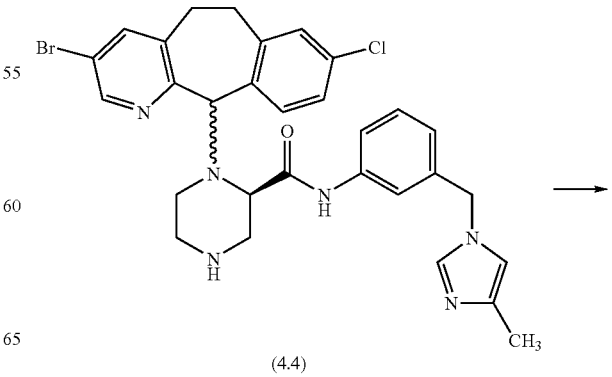

(4.4)

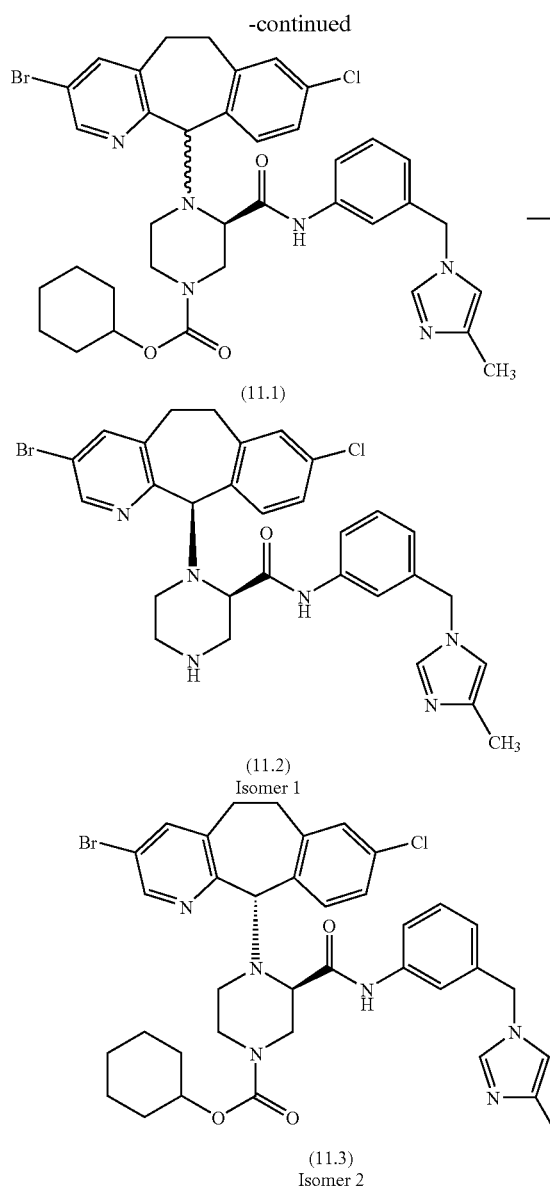

(11.1)

(11.2) Isomer 1

(11.3) Isomer 2

Compound (4.4) (0.13 g, 0.215 mmoles) (prepared as described in Example 4 above) and triethylamine (0.089 mL, 0.644 mmoles) were dissolved in anhydrous dichloromethane (4 mL) and cyclohexyl chloroformate (0.0349 g, 0.215 mmoles) in anhydrous dichloromethane (0.5 mL) was added. The mixture was stirred at 25° C. for 69 h. The solution was evaporated to dryness and chromatographed on silica gel using 2% (10% conc. NH$_4$OH in methanol)-dichloromethane as the eluant to give compound (11.1) (0.121 g, 77%): FABMS: m/z 733.1 (MH$^+$).

The racemic compound was separated by preparative HPLC on a Chiralpak® AD column using hexane:isopropanol:diethylamine::85:15:0.2 as the eluant to give in the order of elution first compound (11.2), isomer 1 (0.0215 g): FABMS: m/z 733.1 (MH$^+$); HRFABMS: m/z 731.2109 (MH$^+$) (Calcd. C$_{37}$H$_{41}$N$_6$O$_3$BrCl: m/z 731.2112); δ$_H$ (CDCl$_3$) 2.23 (3H, s, 4-CH$_3$), 4.40 (1H, dd, CHCO), 5.03 (2H, s, CH$_2$-Im), 6.63 (1H, s, Im-H$_5$), 6.86 (1H, d, Ar—H$_4'$), 7.10 (1H, d, Ar—H), 7.12 (1H, s, Ar—H$_6$), 7.19 (1H, d, Ar—H), 7.29 (1H, dd, Ar—H$_{5'}$), 7.43 (1H, s, Ar—H$_2$), 7.45 (1H, d, Ar—H$_{6'}$), 7.68 (1H, d, Ar—H$_4$), 8.42 (Ar—H$_2$) and 9.12 ppm (1H, s, NHCO); δ$_C$ (CDCl$_3$) CH$_3$: 13.9; CH$_2$: 23.6, 23.7, 25.5, 30.6, 31.2, 31.9, 31.9, 41.7, 41.7, 44.8, 50.6; CH: 58.8, 73.5, 73.6, 115.9, 118.1, 119.0, 122.7, 126.8, 129.7, 130.7, 133.0, 136.7, 141.9, 147.3; C, 120.5, 134.5, 134.9, 137.2, 137.6, 138.3, 138.5, 141.0, 154.6, 155.3, 168.3; [α]$_D^{20° C.}$+106.1° (c=0.6, MeOH) and then compound (11.3), isomer 2 (0.0284 g): FABMS: m/z 733.2 (MH$^+$); HRFABMS: m/z 731.2102 (MH$^+$) (Calcd. C$_{37}$H$_{41}$N$_6$O$_3$BrCl: m/z 731.2112); δ$_H$ (CDCl$_3$) 2.22 (3H, s, 4-CH$_3$), 4.15 (1H, dd, CHCO), 5.02 (2H, s, CH$_2$-Im), 6.63 (1H, s, Im-H$_5$), 6.86 (1H, d, Ar—H$_4'$), 7.16 (1H, d, Ar—H), 7.21 (1H, s, Ar—H$_6$), ), 7.28 (1H, dd, Ar—H$_{5'}$), 7.29 (1H, d, Ar—H), 7.39 (1H, d, Ar—H$_6$), 7.41 (1H, s, Ar—H$_2$), 7.49 (1H, d, Ar—H$_4$), 8.38 (Ar—H$_2$) and 9.04 ppm (1H, bs, NHCO); δ$_C$ (CDCl$_3$)) CH$_3$: 13.9; CH$_2$: 23.6, 23.7, 25.5, 31.0, 31.0, 31.9, 31.9, 41.9, 41.9, 45.1, 50.6; CH: 60.4, 73.8, 74.0, 115.9, 117.9, 118.9, 122.8, 126.9, 129.7, 130.3, 132.9, 136.6, 141.7, 147.6; C, 120.3, 134.2, 134.7, 136.8, 137.6, 138.5, 138.8, 141.3, 154.6, 155.3, 169.3; [α]$_D^{20° C.}$+109.9° (c=0.7, MeOH).

EXAMPLE 12

3-Bromo-8,11-dichloro-6,11-dihydro[5,6]cyclohepta[1,2-b]pyridine (0.2954 g, 0.866 mmoles) (prepared from the alcohol as described in Preparative Example 40 (U.S. Pat. No. 5,719,148; Feb. 17, 1998)), the title compound from Preparative Example 6, Step B above (0.3688 g, 1.292 mmoles) and triethylamine (0.2616 g, 0.3603 mL, 2.6 mmoles) were dissolved in anhydrous THF (3 mL) and anhydrous dichloromethane (20 mL) and the mixture was stirred under argon at 25° C. for 89 h. The solution was evaporated to dryness and the residue was taken up in dichloromethane, washed with water, dried (MgSO$_4$), filtered and evaporated to dryness. The residue was chromatographed on silica gel using 3% (10% conc. NH$_4$OH in methanol)-dichloromethane as the eluant to give in the order of elution the following compounds:

The first compound was compound (12.1) (0.0496 g, 6%): FABMS: m/z 896.3 (MH$^+$); HRFABMS: m/z 898.0887 (Calcd. C$_{43}$H$_{38}$N$_7$OBr$_2$Cl$_2$: m/z 898.0861); $\delta_C$ (CDCl$_3$) 4.32/4.37 (2H, s, H$_{11}$/H$_{11'}$), 5.18 (2H, s, CH$_2$-Im), 6.93.7.96 (17H, s and m, Ar—H and Im-H), 8.308.37 (2H, m, H$_2$ and H$_{2'}$) and 8.85/9.02 ppm (1H, bs, NHCO).

The second compound was compound (12.2) (0.2459 g, 48%): FABMS: m/z 591.2 (MH$^+$); HRFABMS: m/z 591.1265 (MH$^+$), Calcd. C$_{29}$H$_{29}$N$_6$OBrCl: m/z 591.1275; 6H (CDCl$_3$) 4.33 (1H, s, H$_{11}$), 5.07 (2H, s, CH$_2$-Im), 6.85 (2H,m, Ar—H), 6.89 (1H, s, Im-H$_5$), 7.09, 7.12, 7.25, 7.37, 7.40, 7.47, 7.55 ($\delta_H$, s and m, Ar—H), 7.57 (1H, s, Im-H$_2$), 8.31/8.36 (1H, s, H$_2$) and 9.22/9.29 ppm (1H, bs, NHCO); $\delta_C$ (CDCl$_3$) CH$_2$: 30.4/30.5, 30.6/30.7, 44.1/44.2, 50.9, 51.5/51.7, 53.5/53.7; CH: 58.2/58.5, 79.4, 118.3/118.4, 119.3/119.4/119.6, 123.0, 126.3/126.4, 126.3/126.4, 129.8, 129.8, 130.7/130.8, 132.6, 137.5, 141.5, 147.1/147.3; C, 120.2, 134.3, 135.4, 137.0/137.2, 138.5, 141.3, 141.1/141.5, 155.5/155.7, 169.4.

EXAMPLE 13

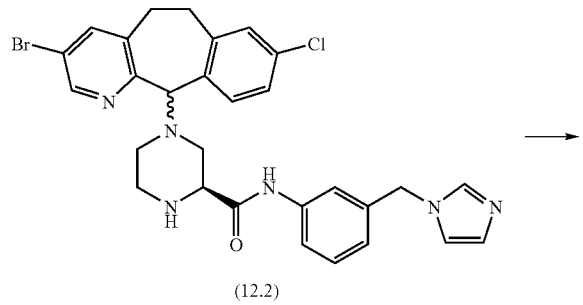

(12.2)

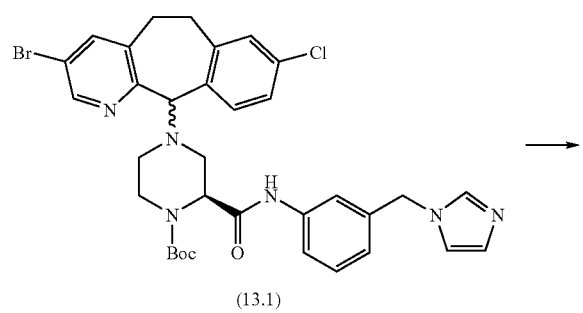

(13.1)

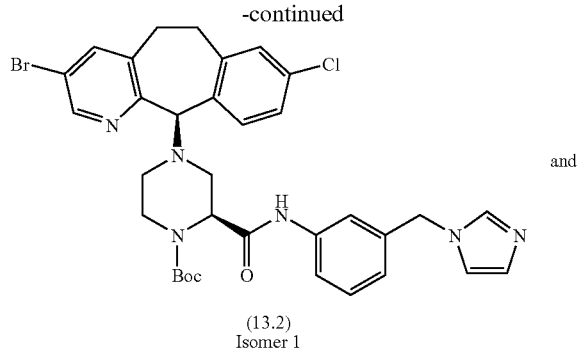

(13.2)
Isomer 1

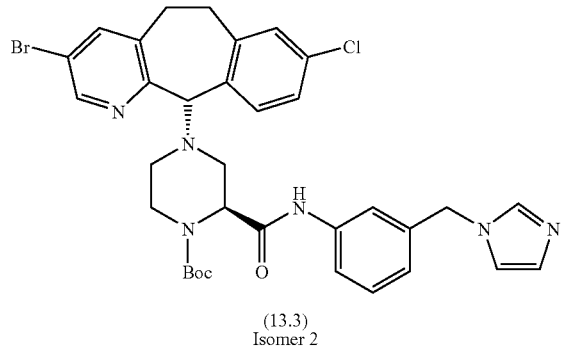

(13.3)
Isomer 2

Compound (12.2) (0.217 g, 0.367 mmoles) (prepared as described in Example 12 above), di-tert-butyldicarbonate (0.104 g, 0.477 mmoles) and sodium hydroxide (0.0147 g, 0.367 mmoles) were dissolved in THF (3 mL) and water (3 mL) and the mixture was stirred at 25° C. for 143 h. The solution was evaporated to dryness and the residue was taken up in dichloromethane and washed with water, dried (MgSO$_4$), filtered and evaporated to dryness to give compound (13.1) (0.1405 g, 55%). The latter was subjected to chiral HPLC on a Chiralpak® AD column using hexane:isopropanol:diethylamine::85:15:0.2 as the eluant to give the first eluting isomer compound (13.2), isomer 1 (0.063 g): FABMS: m/z 691.0 (MH$^+$); HRFABMS: m/z 691.1794 (MH$^+$), Calcd. C$_{34}$H$_{37}$N$_6$O$_3$BrCl: m/z 691.1799; $\delta_H$ (CDCl$_3$) 1.43 (9H, s, CH$_3$), 4.31 (1H, s, CHCON), 4.69 (1H, s H$_{11}$), 5.09 (2H, s, CH$_2$-Im), 6.83-7.4617.5717.64 (11H, s and m, Ar—H and Im-H), 87.35 (1H, s, H$_2$) and 8.54 ppm (1H, bs, NHCO); Oc (CDCl$_3$) CH$_3$: 28.4, 28.4, 28.4; CH$_2$: 30.2, 30.4, 42.3, 51.0, 51.1, 52.3; CH: 55.7, 78.6, 118.5, 119.6, 119.6, 122.9, 126.1, 128.4, 129.6, 130.7, 132.5, 137.0, 141.6, 147.0; C: 81.2, 120.1, 134.1, 135.0, 137.3, 137.3, 138.8, 141.4, 155.5, 155.5, 168.9; $[\alpha]_D^{20°\ C}$-10.5° (c=0.38, MeOH) and the second eluting isomer compound (13.3), isomer 2 (0.051 g): FABMS: m/z 691.0 (MH$^+$); HRFABMS: m/z 691.1788 (MH$^+$), Calcd. C$_{34}$H$_{37}$N$_6$O$_3$BrCl: m/z 691.1799; $\delta_H$ (CDCl$_3$) 1.45 (9H, s CH$_3$), 4.33 (1H, s, CHCON), 4.68 (1H, s, H$_{11}$), 5.09 (2H, s, CH$_2$-Im), 6.86-7.43 (10H, s and m, Ar—H and Im-H), 7.69 (1H, s, H$_4$) and 8.36 ppm (1H, s, H$_2$); °c (CDCl$_3$) CH$_3$: 28.4, 28.4, 28.4; CH$_2$: 30.2, 30.4, 42.4, 50.7, 51.0, 52.1; CH: 55.8, 78.4, 118.5, 119.5, 119.5, 123.0, 126.2, 128.5, 129.7, 130.7, 132.3, 137.0, 141.4, 146.8/146.9; C, 81.4, 120.1, 134.2, 135.2, 136.8, 137.5, 138.8, 141.1, 155.4, 155.4, 168.6; $[\alpha]_D^{20°\,C.}$ −27.3° (c=0.46, MeOH).

EXAMPLE 14

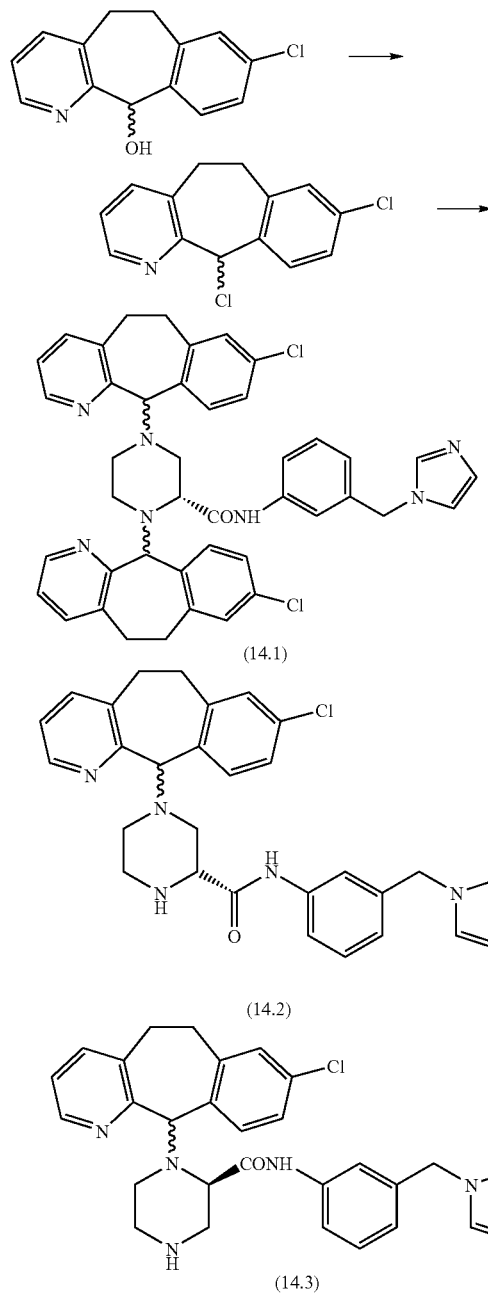

(14.1)

(14.2)

(14.3)

8,11-Dichloro-6,11-dihydro[5,6]cyclohepta[1,2-b]pyridine (0.8023 g, 3.04 mmoles) (prepared from the alcohol as described in Preparative Example 7 (U.S. Pat. No. 5,719,148; Feb. 17, 1998)), the title compound from Preparative Example 7, Step B above (1.3 g, 3.95 mmoles) and triethylamine (0.922 g, 1.27 mL, 9.11 mmoles) were dissolved in anhydrous THF (28 mL) and anhydrous dichloromethane (56 mL) and the mixture was stirred under argon at 25° C. for 90 h. The solution was evaporated to dryness and the residue was taken up in dichloromethane, washed with water, dried (MgSO₄), filtered and evaporated to dryness. The residue was chromatographed on silica gel using a gradient of 3%-5%-110% (10% conc. NH₄OH in methanol)-dichloromethane as the eluant to give in the order of elution the following compounds:

The first compound was compound (14.1) (0.2459 g, 11%): ESMS: m/z 740.2 (MH⁺); $\delta_H$ (CDCl₃) 4.38/4.43 (2H, 5, $H_{11}$/$H_{11'}$), 5.14 (2H, s, CH₂-Im), 6.89-7.72 (17H, s and m, Ar—H and Im-H), 8.29/8.32 (2H, m, H₂ and H₂') and 8.72/8.97/9.28 ppm (1H, bs, NHCO).

The second mixture (0.8594 g) was rechromatographed on silica gel using 3% (10% conc. NH₄OH in methanol)-dichloromethane as the eluant to give in the order of elution, compound (14.2) (0.7078 g, 45%): ESMS: m/z 513.1 (MH⁺); $\delta_H$ (CDCl₃) 4.37/4.39 (1H, s, $H_{11}$), 5.08/5.30 (2H, s, CH₂-Im), 6.85 (1H, d, Ar—H₄), 6.90 (1H, s, Im-H₅), 7.09 (1H, s, Im-H₄), 7.09.7.44 (8H, s and m, Ar—H), 7.56 (1H, s, Im-H₂), 8.28/8.31 (1H, m, H₂) and 9.09/9.20 ppm (1H, bs, NHCO); $\delta_C$ (CDCl₃) CH₂: 30.5/30.7, 30.8, 44.0/44.2, 50.8, 51.8/51.9, 53.7/53.9; CH: 58.5/59.0, 80.1, 118.3, 119.3, 119.4, 122.9, 122.9/123.3, 123.3, 126.0/126.1, 129.7, 130.6/130.7, 132.5, 139.2/139.3, 139.2/139.3, 146.1/146.2; C, 134.0, 135.0/136.0, 137.2, 137.2/137.5, 141.8, 141.8, 156.7, 169.9 and the compound below.

The third compound from the initial chromatography was combined with the second compound from the rechromatography above to give compound (14.3) (0.1348 g, 9%): ESMS: m/z 513.1 (MH⁺); $\delta_H$ (CDC₃) 5.05/5.11/5.17/5.20 (2H, s, CH₂-Im), 6.80.7.67 (12H, s and m, Ar—H and Im-H) and 8.30/8.38 ppm (1H, m, H₂); $\delta_C$ (CDCl₃) (major/minor diastereoisomer) CH₂: 30.8/30.0, 31.6/32.0, 44.1/43.9, 44.3/45.3, 45.4/46.3, 50.7/50.7; CH: 59.0/55.3, 74.5/73.6, 126.3/126.7, 118.7/118.7, 119.5/119.5, 119.7/119.7, 123.2/123.3, 123.3/123.3, 124.2/122.7, 129.9/129.6, 130.0/130.1, 132.7/133.7, 138.7/138.5, 139.7/141.6, 146.4, 145.5; C, 133.9/134.1, 134.8/134.9/135.0, 136.8/137.1, 137.1/137.5, 141.9/139.6, 141.9/139.6, 156.3/156.4, 169.4/168.3.

EXAMPLE 15

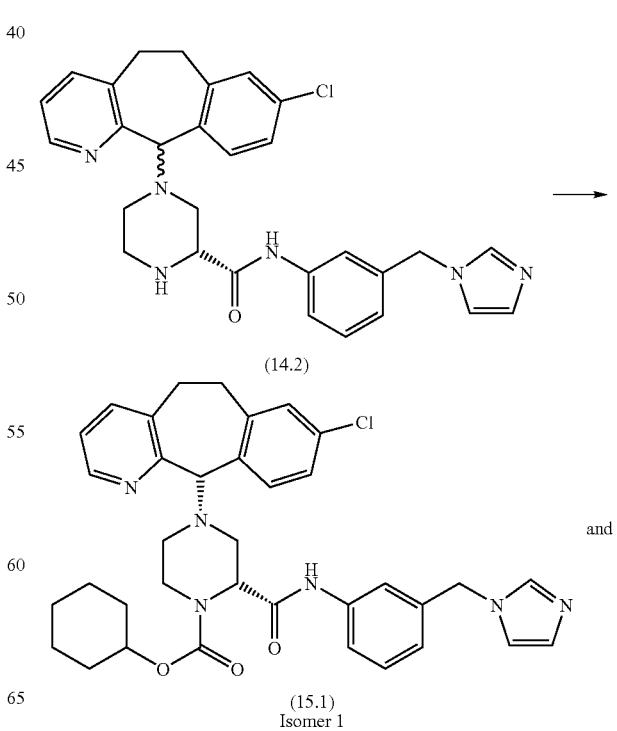

(14.2)

(15.1)
Isomer 1

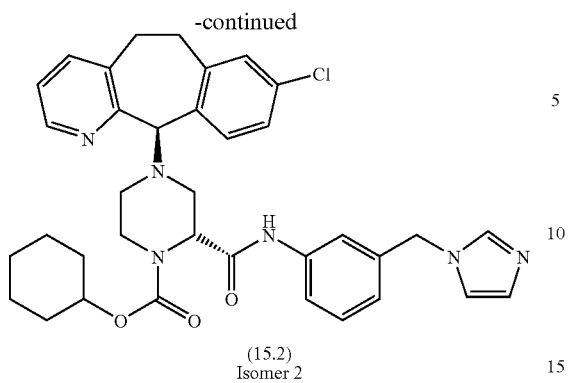

(15.2)
Isomer 2

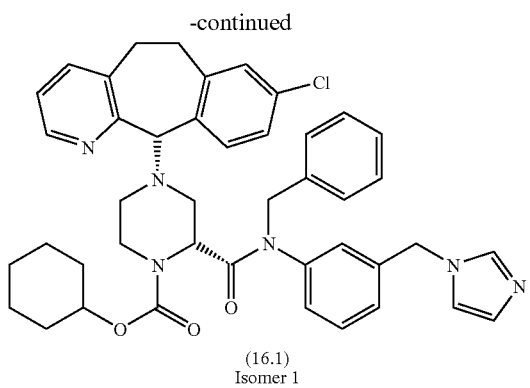

(16.1)
Isomer 1

Compound (14.2) (0.6231 g, 1.22 mmoles) (prepared as described in Example 14 above) and triethylamine (0.3687 g, 0.508 mL, 3.66 mmoles) were dissolved in anhydrous dichloromethane (5 mL). Cyclohexyl chloroformate (0.2963 g, 1.82 mmoles) in anhydrous dichloromethane (1 mL) was added and the reaction was stirred under argon at 25° C. for 23 h. The mixture was evaporated to dryness and the residue was taken up in dichloromethane, washed with saturated aqueous NaHCO$_3$, water, dried (MgSO$_4$), filtered and evaporated to dryness. The residue was chromatographed on silica gel using 2% (10% conc. NH$_4$OH in methanol)-dichloromethane as the eluant to give first compound (15.1), isomer 1 (0.3445 g, 44%): FABMS: m/z 639.4 (MH$^+$); HRFABMS: Found: m/z 639.2866 (MH$^+$), Calcd. C$_{36}$H$_{40}$N$_6$O$_3$Cl: m/z 639.2850; $\delta_H$ (CDCl$_3$) 4.35 (1H, s, H$_{11}$), 5.14 (2H, s, CH$_2$-Im), 6.90.7.52 (11H, s and m, Ar—H and Im-H$_4$, Im-H$_5$), 7.69 (1H, s, Im-H$_2$) and 8.32 ppm (1H, m, H$_2$); $\delta_C$ (CDCl$_3$) CH$_2$: 23.6, 23.6, 25.4, 30.5, 30.6, 31.8, 31.8, 42.3, 51.0, 51.1, 52.4; CH: 56.2, 74.3, 79.3, 118.4, 119.7, 119.7, 123.0, 123.3, 123.3, 125.9, 129.7, 130.7, 132.6, 139.3, 139.3, 146.1; C, 133.9, 135.3, 135.6, 138.9, 142.0, 142.0, 156.6, 156.6, 168.7; $[\alpha]_D^{20\,°C}$-12.6° (c=0.44, MeOH) and then compound (15.2), isomer 2 (0.2685 g, 35%): ESMS: m/z 639.2 (MH$^+$); HRFABMS: Found: m/z 639.2838 (MH$^+$), Calcd. C$_{36}$H$_{40}$N$_6$O$_3$Cl: m/z 639.2850; $\delta_H$ (CDCl$_3$) 4.38 (1H, s, H$_{11}$), 5.14 (2H, s, CH$_2$-Im), 6.90.7.52 (11H, s and m, Ar—H and Im-H$_4$, Im-H$_5$), 7.78 (1H, s, Im-H$_2$) and 8.30 ppm (1H, m, H$_2$); $\delta_C$ (CDCl$_3$) CH$_2$: 23.6, 23.6, 25.4, 30.4, 30.6, 31.8, 31.8, 42.3, 50.8, 51.2, 52.1; CH: 56.1, 74.5, 74.5, 118.8, 119.8, 119.8, 123.2, 123.2, 123.4, 126.1, 129.7, 130.6, 132.2, 136.6, 139.5, 145.9; C, 128.6, 134.0, 135.4, 135.8, 138.8, 146.9, 156.5, 156.5, 168.6; $[\alpha]_D^{20\,°C}$+79.7° (c=0.46, MeOH).

EXAMPLE 16

Compound (15.1) from Example 15 above, isomer 1 (0.2 g, 0.313 mmoles), KF—Al$_2$O$_3$ (0.4545 g, 3.13 mmoles of KF) (Ref.: J. Yamawaki, T. Ando and T. Hanafusa, *Chemistry Letters*, 1981, 1143-1146) and benzyl chloride (0.2376 g, 0.216 mL, 1.88 mmoles) were added to anhydrous acetonitrile (14 mL) and the mixture was stirred under argon at 25° C. for 113 h. The reaction mixture was filtered and the alumina was washed with methanol and the combined filtrates were evaporated to dryness. The residue was chromatographed on silica gel using 1% (10% conc. NH$_4$OH in methanol)-dichloromethane as the eluant to give compound (16.1), isomer 1 (0.1248 g, 55%): ESMS: m/z 729.2 (MH$^+$); HRFABMS: m/z 729.3331 (MH$^+$), Calcd. C$_{43}$H$_{46}$N$_6$O$_3$Cl: m/z 729.3320; $\delta_H$ (CDCl$_3$) 4.22 (1H, s, H$_{11}$), 4.65 (2H,s, Ar—CH$_2$-N), 4.94/4.97 (2H, s, Im-CH$_2$), 6.6.70.7.89 (17H, s and m, Ar—H and Im-H) and 8.34 ppm (1H, m, H$_2$); bc (CDCl$_3$) CH$_2$: 23.4, 23.4, 26.0, 30.6, 30.8, 31.9, 31.9, 42.4, 50.4, 50.8, 52.1, 53.7; CH: 52.9, 73.9, 79.2, 119.2, 119.2, 123.4, 123.4, 126.0, 127.5, 127.5, 127.7/127.8, 128.4/128.5, 128.5, 128.8/129.2, 129.2, 130.5, 130.8, 134.0, 139.4, 139.6, 146.2; C, 133.0, 135.2, 136.5, 141.6, 142.3, 146.9, 156.2, 156.8, 171.2; $[\alpha]_D^{20\,°C}$-65.6° (c=0.43, MeOH).

EXAMPLE 17

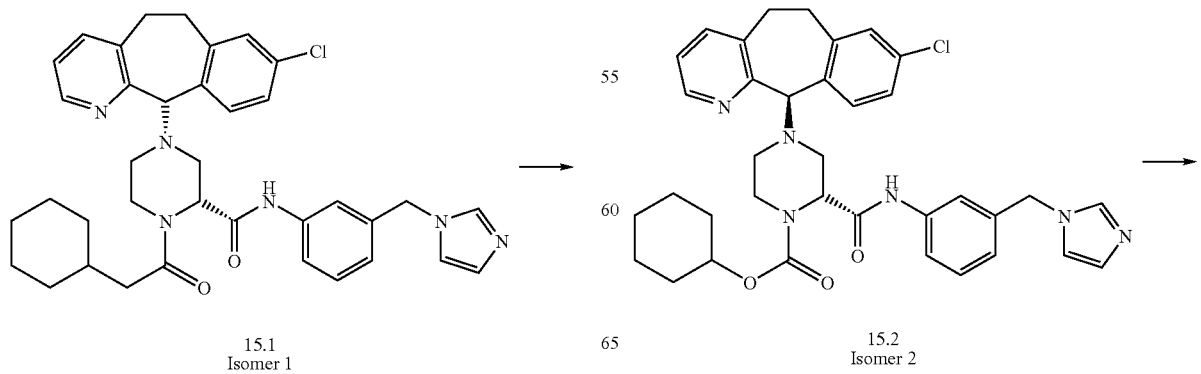

15.1
Isomer 1

15.2
Isomer 2

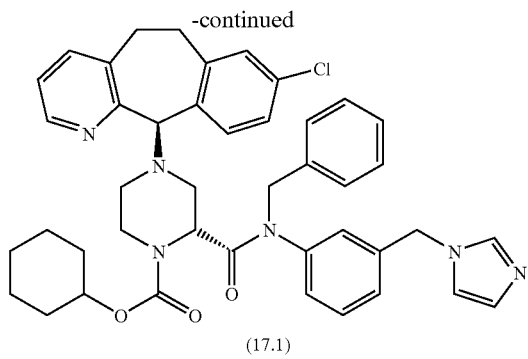

(17.1)

Compound (15.2), isomer 2, from Example 15 above (0.0706 g, 0.11 mmoles), KF—Al$_2$O$_3$ (0.1605 g, 1.1 mmoles of KF) (Ref.: J. Yamawaki, T. Ando and T. Hanafusa, *Chemistry Letters,* 1981, 1143-1146) and benzyl chloride (0.2496 g, 0.227 mL, 1.974 mmoles) were added to anhydrous acetonitrile (5 mL) and the mixture was stirred under argon at 25° C. for 113 h. The reaction mixture was filtered and the alumina was washed with methanol and the combined filtrates were evaporated to dryness. The residue was chromatographed on silica gel using 1.5% (10% conc. NH$_4$OH in methanol)-dichloromethane as the eluant to give compound (17.1) (0.0431 g, 54%): ESMS: m/z 729.3 (MH$^+$); HRFABMS: m/z 729.3331 (MH$^+$), Calcd. C$_{43}$H$_{46}$N$_6$O$_3$Cl: m/z 729.3320; $\delta_H$ (CDCl$_3$) 4.22 (1H, s, H$_{11}$), 4.60 (2H, s, Ar—CH$_2$N), 4.97 (2H, s, Im-CH$_2$), 6.70-7.82 (17H, s and m, Ar—H and Im-H) and 8.36 ppm (1H, m, H$_2$); Oc (CDCl$_3$) CH$_2$: 23.6, 23.6, 25.5, 30.3, 30.9, 31.9, 31.9, 42.5, 50.5, 50.7, 52.4, 53.6; CH: 52.8, 73.8, 79.2, 119.2, 119.2, 123.2, 123.2, 126.1, 127.3, 127.3, 127.7, 128.5, 128.5, 128.7/129.2, 130.5, 130.8, 132.1, 139.2, 139.2, 146.0; C, 132.6, 134.0, 135.8, 136.6, 137.1, 141.3, 141.5, 156.8, 158.0, 171.5; [α]$_D^{20°\,C.}$-26.8° (c=0.45, MeOH).

EXAMPLE 18

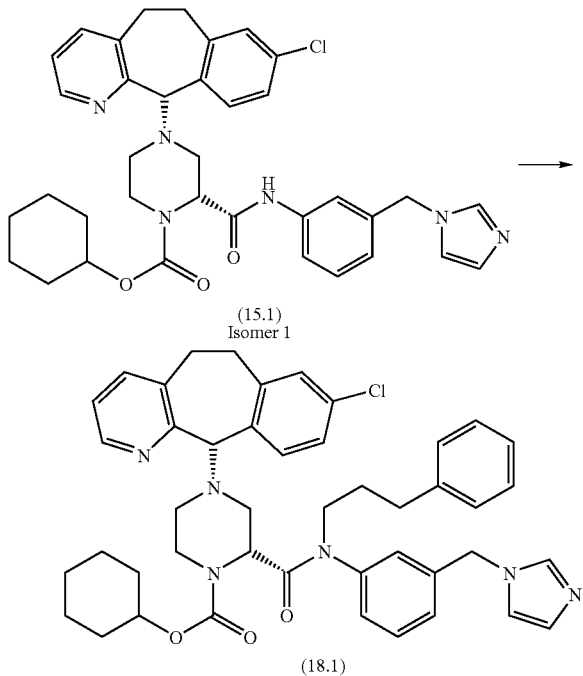

Compound (15.1), isomer 1, from Example 15 above (0.120 g, 0.188 mmoles), KF—Al$_2$O$_3$ (0.2727 g, 1.88 mmoles of KF) (Ref.: J. Yamawaki, T. Ando and T. Hanafusa, *Chemistry Letters,* 1981, 1143-1146) and 3-phenylpropyl bromide (0.2242 g, 0.171 mL, 1.128 mmoles) were added to anhydrous acetonitrile (10 mL) and the mixture was stirred under argon at 25° C. for 96 h. The reaction mixture was filtered and the alumina was washed with methanol and the combined filtrates were evaporated to dryness. The residue was chromatographed on silica gel using 1.5% (10% conc. NH$_4$OH in methanol)-dichloromethane as the eluant to give compound (18.1) (0.0326 g, 23%): FABMS: m/z 757.5 (MH$^+$); HRFABMS: m/z 757.3638 (MH$^+$), Calcd. C$_{45}$H$_{50}$N$_6$O$_3$Cl: m/z 757.3633; $\delta_H$ (CDCl$_3$) 4.22 (1H, s, H$_{11}$), 5.02 (2H, s, Im-CH$_2$), 6.85-7.90 (17H, s and m, Ar—H and Im-H) and 8.33 ppm (1H, m, H$_2$); $\delta_C$ (CDCl$_3$) CH$_2$: 23.6, 23.6, 25.5, 29.6, 30.8, 30.8, 31.9, 31.9, 33.2, 42.4, 49.9, 50.7, 52.0, 53.5; CH: 52.9, 73.8, 79.1, ~119.2, ~119.2, 123.3, 123.4, 125.9, 126.1, 127.0, 127.0, 128.4, 128.4, 128.5, 128.5, 130.4, 130.8, 130.8, 139.3, 139.3, 146.2; C, 133.1, 133.9, 135.2, 135.9, 137.5, 141.5, 142.1, 156.2, 157.0, ~171.2 [α]$_D^{20°\,C.}$-76.9° (c=0.23, MeOH).

EXAMPLE 19

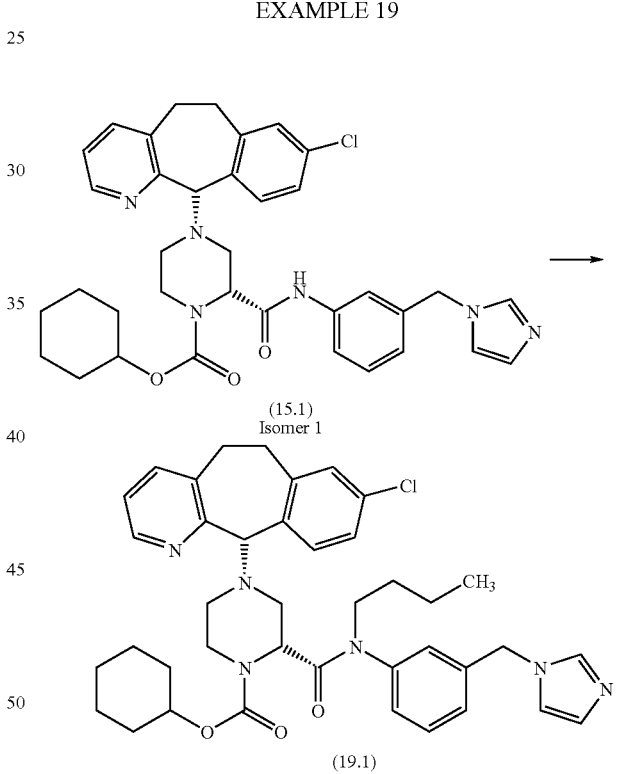

Compound (15.1), isomer 1, from Example 15 above (0.120 g, 0.188 mmoles), KF—Al$_2$O$_3$ (0.2727 g, 1.88 mmoles of KF) (Ref.: J. Yamawaki, T. Ando and T. Hanafusa, *Chemistry Letters,* 1981, 1143-1146) and n-butyl bromide (0.1543 g, 0.121 mL, 1.128 mmoles) were added to anhydrous acetonitrile (10 mL) and the mixture was stirred under argon at 25° C. for 43 h. The reaction mixture was filtered and the alumina was washed with methanol and the combined filtrates were evaporated to dryness. The residue was chromatographed on silica gel using 2% (10% conc. NH$_4$OH in methanol)-dichloromethane as the eluant to give material that was further purified by preparative tlc on silica gel plates (250μ, 20×20 cm) using 5% (10% conc. NH$_4$OH in methanol)-dichloromethane as the eluant to give compound (19.1) (0.0348 g, 27%): FABMS: m/z 695.3 (MH$^+$); HRFABMS: m/z 695.3486 (MH$^+$), Calcd. C$_{40}$H$_{48}$N$_6$O$_3$Cl: m/z 695.3476; $\delta_H$ (CDCl$_3$) 4.21 (1H, s, H$_{11}$), 5.03 (2H, s, Im-CH$_2$), 6.85-7.90 (17H, s and m, Ar—H and Im-H) and 8.32 ppm (1H, m, H$_2$); $\delta_C$ (CDCl$_3$) CH$_3$: 13.9; CH$_2$: 20.1, 23.6, 23.6, 25.5, 29.7, 30.8, 30.8, 31.9, 31.9, 42.4, 50.2, 50.6, 50.8, 52.0; CH: 52.9, 73.7, 79.2, ~119.2, ~119.2, 123.3, 123.3, 126.0, 126.9, 126.9, 130.1, 130.4, 130.7, 139.3, 139.3, 146.2; C, 133.0, 133.9, 134.9, 137.0, 142.3, 146.8, 156.2, 156.8, ~170.8; $[\alpha]_D^{20°\,C.}$ -68.0° (c=0.42, MeOH).

EXAMPLE 20

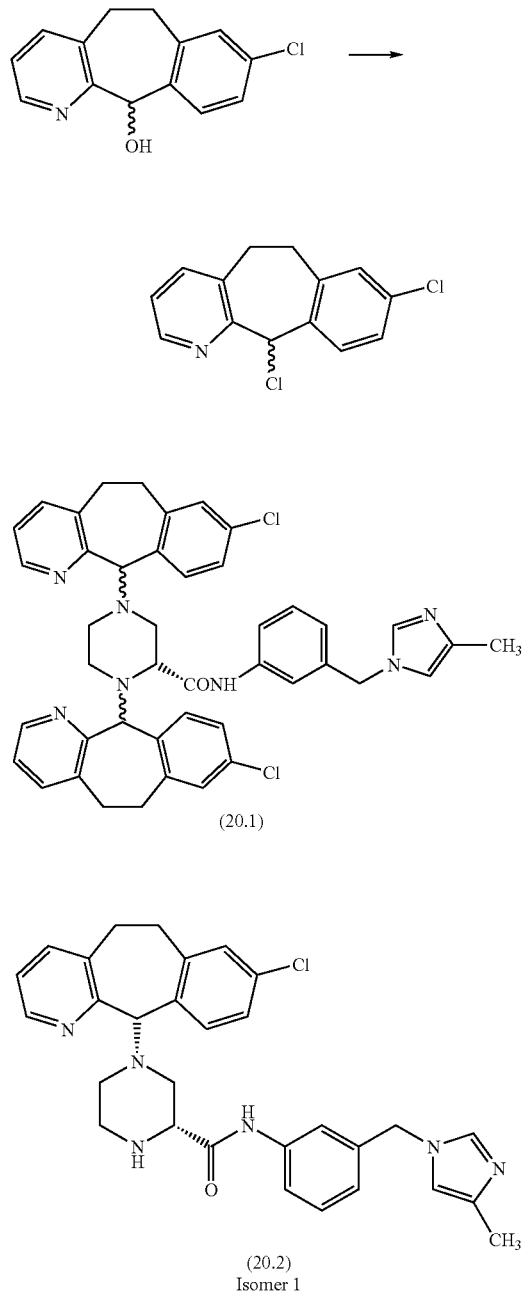

(20.1)

and (20.2)
Isomer 1

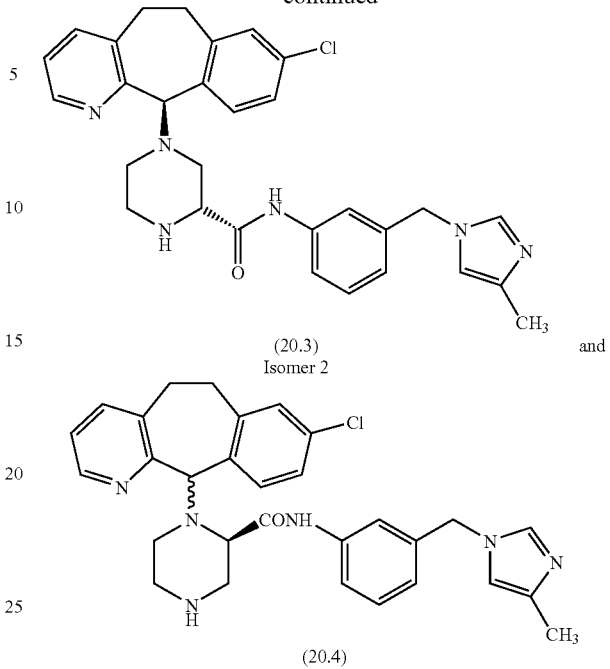

(20.3)
Isomer 2 and (20.4)

8,11-Dichloro-6,11-dihydro[5,6]cyclohepta[1,2-b]pyridine (0.5517 g, 2.09 mmoles) (prepared from the alcohol as described in Preparative Example 7 (U.S. Pat. No. 5,719,148; Feb. 17, 1998)), the title compound from Preparative Example 8, Step B above (0.938 g, 3.13 mmoles) and triethylamine (0.873 g, 0.873 mL, 6.26 mmoles) were dissolved in anhydrous THF (19.3 mL) and anhydrous dichloromethane (38.5 mL) and the mixture was stirred under argon at 25° C. for 116 h. The solution was evaporated to dryness and the residue was taken up in dichloromethane, washed with water, dried (MgSO$_4$), filtered and evaporated to dryness. The residue was chromatographed on silica gel using 2% (10% conc. NH$_4$OH in methanol)-dichloromethane as the eluant to give in the order of elution the following compounds:

The first compound was compound (20.1) (0.2613 g, 11%): HRFABMS: m/z 754.2825 (MH$^+$), Calcd. C$_{44}$H$_{42}$N$_7$OCl$_2$: m/z 754.2828; $\delta_H$ (CDCl$_3$) 4.37 (3H, s, 4.CH$_3$), 5.07 (2H, s, CH$_2$-Im), 5.28/5.32 (2H, s, H$_{11}$/H$_{11'}$), 6.66/6.90/6.93.7.68 (16H, s and m, Ar—H and Im-H), 8.27/8.31 (2H, m, H$_2$/H$_2$) and 8.77/9.33 ppm (1H, bs, NHCO); $\delta_H$ (CDCl$_3$) CH$_3$: 13.5; CH$_2$: 30.5/30.7, 31.1, 45.1/46.2, 48.9, 49.6, 50.8; CH: 59.9/60.6, 80.0/80.1, 116.1, 117.8/117.9, 118.9/119.0, 122.6/123.4, 123.1, 125.8/126.4, 129.6, 130.7/130.8, 132.5/133.3, 136.4, 139.0, 146.0/146.6; C, 133.8/134.2, 134.8/135.3, 135.1, 137.0, 138.9, 138.9, 140.9/141.9, 156.9/157.2, 169.7.

The second compound was compound (20.2), isomer 1 (0.1839 g, 11%): HRFABMS: m/z 527.2319 (MH$^+$), Calcd. C$_{30}$H$_{32}$N$_6$OCl: m/z 527.2326; $\delta_H$ (CDCl$_3$) 2.20 (3H, s, 4-CH$_3$), 4.35 (1H, s, CHCON), 4.98 (2H, s, CH$_2$-Im), 6.58 (1H, s, Im-H$_5$), 6.86 (1H, d, Ar—H$_4$), 7.04-7.12 (2H, m, H$_9$ and H$_{10}$), 7.15 (1H, s, H$_7$), 7.17 (1H, dd, H$_3$), 7.26 (1H, dd, Ar—H$_5$), 7.38 (1H, s, Im-H$_2$), 7.38 (1H, d, Ar—H$_6$), 7.44 (1H, s, Ar—H$_2$), 7.44 (1H, d, H$_4$), 8.27 (1H, d, H$_2$) and 8.99 ppm (1H, bs, NHCO); $\delta_H$ (CDCl$_3$) CH$_3$: 13.9; CH$_2$: 30.8, 30.8, 44.4, 50.8, 52.1, 54.2; CH: 59.3, 80.3, 116.0, 118.4, 119.4, 123.1, 123.4, 126.0, 129.8, 130.7, 132.6, 136.6, 139.3, 146.4; C, 134.1, 135.0, 136.0, 137.5, 138.4, 138.7, 141.8, 156.8, 170.3; $[\alpha]_D^{20°\,C.}$ -83.2° (c=0.43, MeOH).

The third compound was compound (20.3), isomer 2 (0.1726 g, 10%): HRFABMS: m/z 527.2319 (MH$^+$), Calcd. $C_{30}H_{32}N_6OCl$: m/z 527.2326; $\delta_H$ (CDCl$_3$) 2.22 (3H, s, 4-CH$_3$), 4.37 (1H, s, CHCON), 4.99 (2H, s, CH$_2$-Im), 7.62 (1H, s, Im-H$_5$), 6.88 (1H, d, Ar—H$_4$), 7.06/7.10-7.20 (3H, s and m, H$_3$, H$_9$, H$_{10}$), 7.26-7.33 (2H, s and dd, H$_7$ and Ar—H$_5$), 7.40-7.52 (4H, s and m, Im-H$_2$, Ar—H$_2$, Ar—H$_6$, H$_4$), 8.33 (1H, s, H$_2$) and 9.08 ppm (1H, bs, NHCO); $\delta_H$(CDCl$_3$) CH$_3$: 13.8; CH$_2$: 30.5, 30.8, 44.1, 50.7, 52.2, 53.5/53.7; CH: 58.8, 80.1, 115.8, 118.3, 119.2, 122.9, 123.2, 126.1, 129.7, 130.6, 132.5, 136.6, 139.0, 146.1; C, 134.0, 135.1, 135.8, 137.5, 138.5, 138.9, 141.2, 157.1, 170.2; $[\alpha]_D^{20\,°C\cdot}$+9.1° (c=0.35, MeOH).

The fourth compound was compound (20.4) (0.0492 g, 3%): HRFABMS: m/z 527.2319 (MH$^+$), Calcd. $C_{30}H_{32}N_6OCl$: 527.2326; $\delta_H$ (CDCl$_3$) (major/minor diastereoisomer) 2.23 (3H, s, 4-CH$_3$), 5.03 (2H, s, CH$_2$-Im), 5.08/5.10, 5.22 (2H, s, H$_{11}$ and CHCON), 6.63/6.67 (1H, s, Im-H$_5$), 6.86/6.93 (1H, d, Ar—H$_4$), 7.08-7.70 (9H, s and m, Im-H$_2$, Ar—H$_2$, Ar—H$_5$, Ar—H$_6$, H$_3$, H$_4$, H$_7$, H$_9$, H$_{10}$) and 8.32/8.35 ppm (1H, d, H$_2$); $\delta_H$ (CDCl$_3$) (major/minor diastereoisomer) CH$_3$: 13.9; CH$_2$: 30.8/30.2, 31.6/31.8, 44.6, 45.5/45.7, 45.9/46.0, 50.7; CH: 59.1/56.7, 74.4/74.1, 115.9, 118.6, 119.4, 122.6/122.7, 123.1/123.5, 126.3/126.4, 129.5/129.6, 129.9/130.1, 133.9/133.0, 136.6, 139.6/140.9, 146.5/145.7; C, 133.9/134.6, 135.2/134.7, 135.2/134.7, 137.4, 138.8, 138.8, 141.4/141.9, 156.8/156.1, 169.4/169.7.

EXAMPLE 21

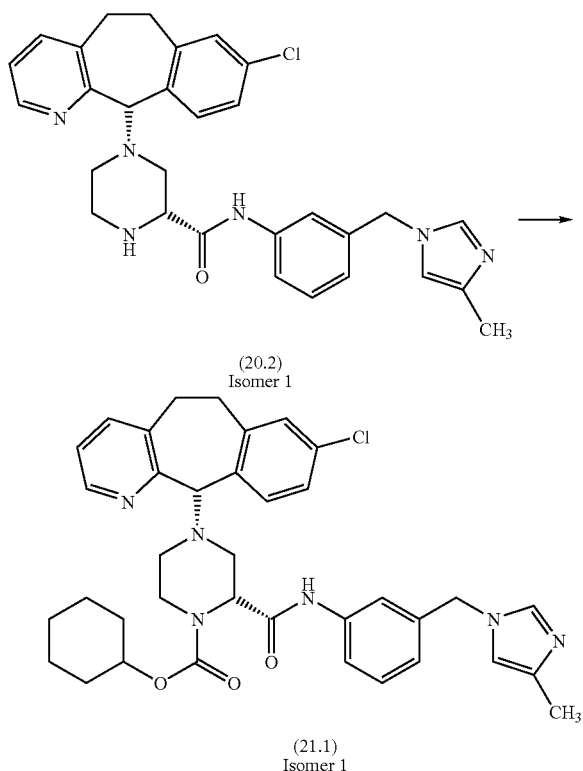

(20.2) Isomer 1

(21.1) Isomer 1

Compound 20.2, isomer 1 (0.165 g, 0.313 mmoles) (prepared as described in Example 20 above) and triethylamine (0.131 mL, 0.939 mmoles) were dissolved in anhydrous dichloromethane (5 mL). Cyclohexyl chloroformate (0.0509 g, 0.313 mmoles) in anhydrous dichloromethane (0.5 mL) was added and the reaction was stirred under argon at 25° C. for 22 h. The mixture was evaporated to dryness and the residue was taken up in dichloromethane, washed with saturated aqueous NaHCO$_3$, water, dried (MgSO$_4$), filtered and evaporated to dryness. The residue was chromatographed on silica gel using 1% (10% conc. NH$_4$OH in methanol)-dichloromethane as the eluant to give compound (21.1), isomer 1 (0.1772 g, 87%): ESMS: m/z 653.2 (MH$^+$); HRFABMS: m/z 653.3036 (MH$^+$), Calcd. $C_{37}H_{42}N_6O_3Cl$: m/z 653.3007; $\delta_H$(CDCl$_3$) 2.16 (3H, s, 4-CH$_3$), 4.35 (1H, s, CHCON), 4.73 (1H, bs, H$_{11}$), 5.04 (2H, s, CH$_2$-Im), 6.63 (1H, s, Im-H$_5$), 6.92 (1H, d, Ar—H$_4$), 6.94 (1H, s, Im-H$_2$), 7.06-7.53 (8H, s and m, Ar—H), 8.32 (1H, d, H$_2$) and 8.60 ppm (1H, bs, NHCO); $\delta_H$ (CDCl$_3$) CH$_3$: 13.2; CH$_2$: 23.6, 23.6, 25.4, 30.5, 30.6, 31.8, 31.8, 42.3, 50.9, 51.0, 52.5; CH: 56.3, 74.3, 79.4, 116.0, 118.3, 119.6, 122.9, 123.2, 125.9, 129.6, 130.7, 132.6, 136.1, 139.2, 146.2; C, 133.9, 135.2, 135.6, 137.8, 138.9, 139.2, 142.0, 156.7, 156.7, 168.7; $[\alpha]_D^{20\,°C\cdot}$-13.90 (c=0.57, MeOH).

EXAMPLE 22

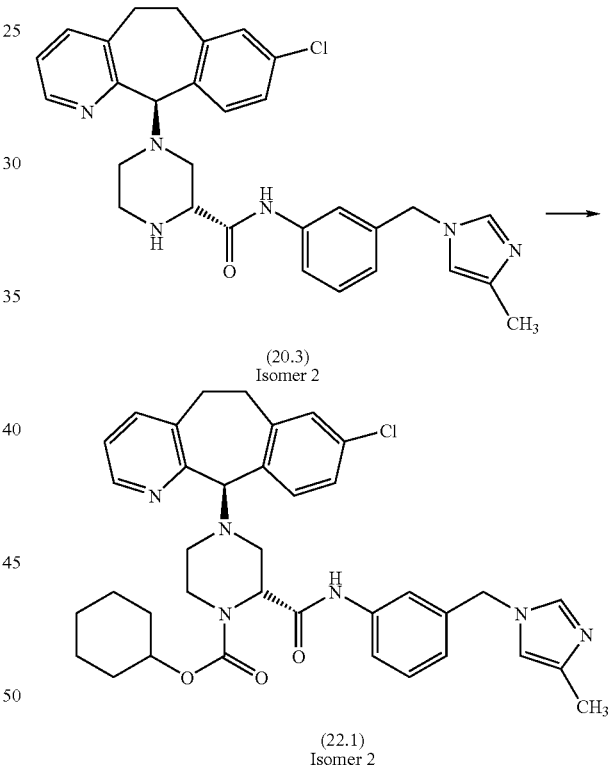

(20.3) Isomer 2

(22.1) Isomer 2

Compound (20.3), isomer 2 (0.151 g, 0.286 mmoles) (prepared as described in Example 20 above) and triethylamine (0.12 mL, 0.858 mmoles) were dissolved in anhydrous dichloromethane (5 mL). Cyclohexyl chloroformate (0.0466 g, 0.286 mmoles) in anhydrous dichloromethane (0.5 mL) was added and the reaction was stirred under argon at 25° C. for 22 h. The mixture was evaporated to dryness and the residue was taken up in dichloromethane, washed with saturated aqueous NaHCO$_3$, water, dried (MgSO$_4$), filtered and evaporated to dryness. The residue was chromatographed on silica gel using 1% (10% conc. NH$_4$OH in methanol)-dichloromethane as the eluant to give compound (22.1), isomer 2 (0.1234 g, 66%): ESMS: m/z 653.2 (MH$^+$); HRFABMS: m/z 653.3031 (MH$^+$), Calcd. C$_{37}$H$_{42}$N$_6$O$_3$Cl: m/z 653.3007; δ$_H$ (CDCl$_3$) 2.18 (3H, s, 4-CH$_3$), 4.38 (1H, s, CHCON), 4.72 (1H, bs, H$_{11}$), 5.03 (2H, s, CH$_2$-Im), 6.63 (1H, s, Im-H$_5$), 6.92 (1H, d, Ar—H$_4$), 7.09 (1H, s, Im-H$_2$), 7.04-7.43 (7H, s and m, Ar—H), 7.54 (1H, s, Ar—H$_2$) and 8.27 ppm (1H, d, H$_2$); δ$_H$ (CDCl$_3$) CH$_3$: 13.4; CH$_2$: 23.6, 23.6, 25.4, 30.4, 30.7, 31.8, 31.8, 42.3, 50.7, 50.9, 52.2; CH: ~56.0, 74.4, ~79.0, 116.0, 118.5, 119.7, 123.1, 123.3, 126.1, 129.6, 130.6, ~132.0, 136.2, 139.3, 146.0; C, 134.0, 135.2, 135.6, 138.0, 138.8, 139.3, ~141.3, 156.7, 156.7, 168.5; [α]$_D^{20°\,C}$+82.5° (c=0.4, MeOH).

EXAMPLE 23

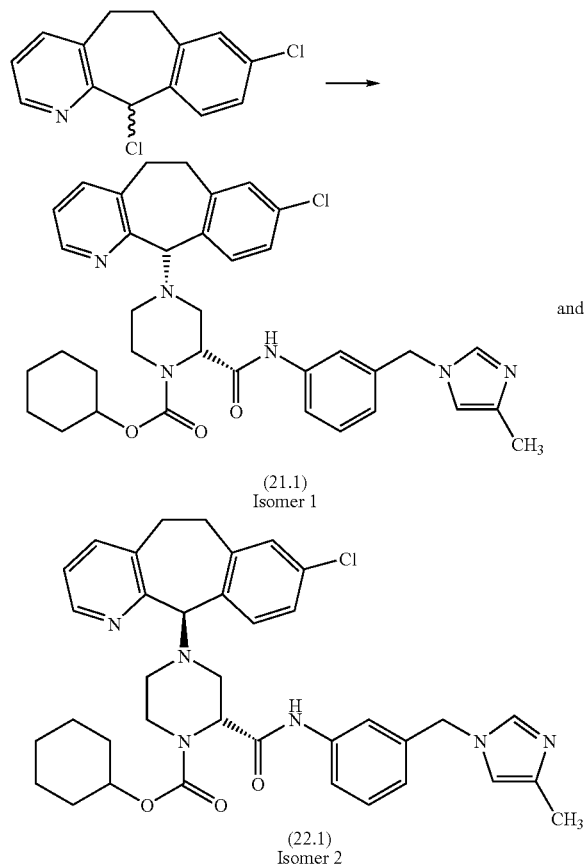

(21.1)
Isomer 1

(22.1)
Isomer 2

8,11-Dichloro-6,11-dihydro[5,6]cyclohepta[1,2-b]pyridine (1.51 g, 1.43 mmoles) (prepared from the alcohol as described in Preparative Example 7 (U.S. Pat. No. 5,719,148; Feb. 17, 1998)), the title compound from Preparative Example 9, Step B above (0.61 g, 1.43 mmoles) and triethylamine (0.599 mL, 4.3 mmoles) were dissolved in anhydrous THF (4.6 mL) and anhydrous dichloromethane (4.6 mL) and the mixture was stirred under argon at 25° C. for 19 h. Additional 8,11-Dichloro-6,11-dihydro[5,6]-cyclohepta[1,2-b]pyridine (1.51 g, 10.6 mmoles) and triethylamine (0.2 mL, 1.43 mmoles) in anhydrous THF (2 mL) were added at 19 h and again at 43 h. After a total of 48 h the solution was evaporated to dryness and the residue was taken up in dichloromethane, washed with water, dried (MgSO$_4$), filtered and evaporated to dryness. The residue was chromatographed on silica gel using 1% (10% conc. NH$_4$OH in methanol)-dichloromethane as the eluant to give in the order of elution compound (21.1), isomer 1 (0.4125 g, 44%) and then compound (22.1), isomer 2 (0.369 g, 39%).

EXAMPLE 24

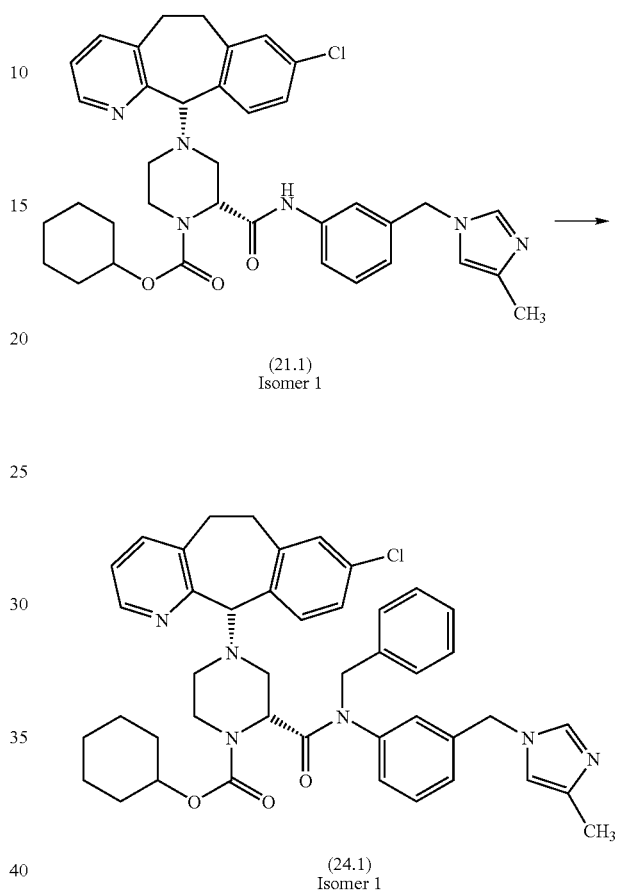

(21.1)
Isomer 1

(24.1)
Isomer 1

Compound (21.1) from Example 21 above, isomer 1 (0.0947 g, 0.145 mmoles), KF—Al$_2$O$_3$ (0.2107 g, 1.45 mmoles of KF) (Ref.: J. Yamawaki, T. Ando and T. Hanafusa, *Chemistry Letters,* 1981, 1143-1146) and benzyl chloride (0.1 mL, 0.87 mmoles) were added to anhydrous acetonitrile (6.6 mL) and the mixture was stirred under argon at 25° C. for 76 h. The reaction mixture was filtered and the alumina was washed with methanol and the combined filtrates were evaporated to dryness. The residue was chromatographed on silica gel using 2% (10% conc. NH$_4$OH in methanol)-dichloromethane as the eluant to give compound (24.1), isomer 1 (0.0425 g, 39%): ESMS: m/z 743.1 (MH$^+$); HRFABMS: m/z 743.3467 (MH$^+$), Calcd. C$_{44}$H$_{48}$N$_6$O$_3$Cl: m/z 743.3476; δ$_H$ (CDCl$_3$) 2.23 (3H, s, 4-CH$_3$), 4.11 (1H, s, CHCON), 4.68 (1H, s, H$_{11}$), 4.82 (2H, s, CH$_2$-Im), 6.35-6.47, 6.92, 7.03-7.54 (17H, s and m, Ar—H and Im-H) and 8.31 ppm (1H, m, H$_2$); δ$_C$ (CDCl$_3$) CH$_3$: 13.4; CH$_2$: 23.6, 23.6, 25.5, 30.6, 30.8, 31, 31.9, 42.4, 50.4, 50.8, 52.1, 53.7; CH: 52.9, 73.8/74.5, 79.2, 115.8, 123.3, 123.3, 126.0, 127.2, 127.6, 127.7, 128.3/128.5, 129.2, 129.2, 129.4, 129.4, 130.4, 132.9, 135.9, 139.3, 146.2; C, 133.9, 135.0, 135.9, 136.5, 137.5, 139.4, 141.4, 142.3, 156.7, 157.1, 171.3; [α]$_D^{20°\,C}$-54.8° (c=0.54, MeOH).

EXAMPLE 25

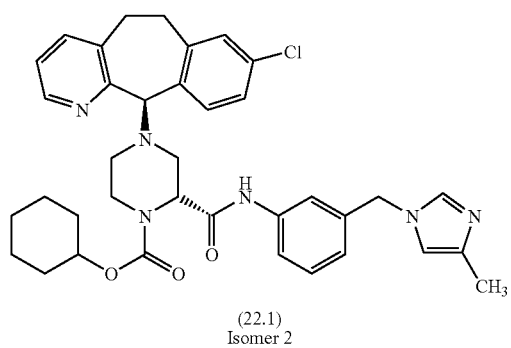

(22.1)
Isomer 2

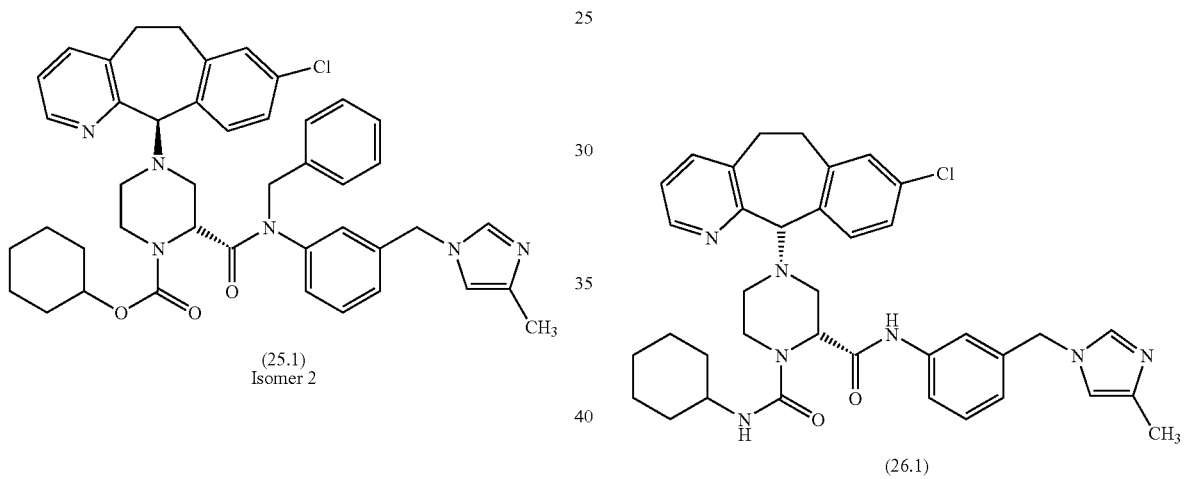

(25.1)
Isomer 2

Compound (22.1) from Example 22 above, isomer 2 (0.1058 g, 0.162 mmoles), KF—Al$_2$O$_3$ (0.2354 g, 1.62 mmoles of KF) (Ref.: J. Yamawaki, T. Ando and T. Hanafusa, *Chemistry Letters,* 1981, 1143-1146) and benzyl chloride (0.112 mL, 0.972 mmoles) were added to anhydrous acetonitrile (7.4 mL) and the mixture was stirred under argon at 25° C. for 116 h. The reaction mixture was filtered and the alumina was washed with methanol and the combined filtrates were evaporated to dryness. The residue was chromatographed on silica gel using 1% (10% conc. NH$_4$OH in methanol)-dichloromethane as the eluant to give compound (25.1), isomer 2 (0.0282 g, 23%): ESMS: m/z 743.4 (MH$^+$); HRFABMS: m/z 743.3467 (MH$^+$), Calcd. C$_{44}$H$_{48}$N$_6$O$_3$Cl: m/z 743.3476; δ$_H$ (CDCl$_3$) 2.24 (3H, s, 4-CH$_3$), 4.20 (1H, s, CHCON), 4.62 (1H, s, H$_{11}$), 4.82 (2H, s, CH$_2$-Im), 6.40/6.44 (1H, s, Im-H$_5$), 6.92 (1H, d, Ar—H$_4$), 7.02-7.60 (14H, s and m, Ar—H and Im-H$_2$) and 8.36 ppm (1H, d, H$_2$); δ$_C$ (CDCl$_3$) CH$_3$: 13.4; CH$_2$:: 23.6, 23.6, 25.5, 30.3, 30.9, 31.9, 31.9, 42.5, 50.3, 50.5, 52.4, 53.6; CH: 52.8, 73.8/74.0, 79.2, 115.6, 123.1, 123.1, 126.0, 127.1, 127.6, 127.6, 128.4, 129.1, 129.1, 129.1, 130.4, 130.7, 132.6, 136.0, 139.1, 146.0; C, 134.0, 135.3, 135.8, 136.6, 137.6, 139.1, 141.4, 141.5, 156.7, 157.9, 171.3; [α]$_D^{20°\,C.}$-24.7° (c=1.06, MeOH).

EXAMPLE 26

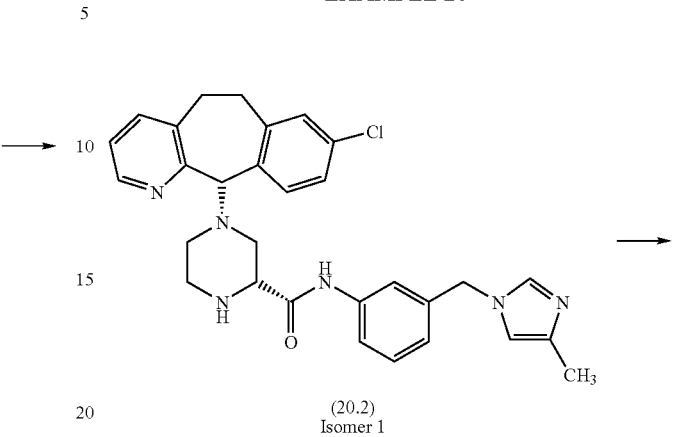

(20.2)
Isomer 1

(26.1)

Compound (20.2), isomer 1 (0.145 g, 0.275 mmoles) (prepared as described in Example 20 above) was dissolved in anhydrous dichloromethane (5 mL) and cyclohexyl isocyanate (0.035 mL, 0.275 mmoles) was added. The mixture was stirred under argon at 15° C. for 6.5 h and then directly chromatographed on silica gel using 2.5% (10% conc. NH$_4$OH in methanol)-dichloromethane as the eluant to give compound (26.1) (0.1532 g, 85%): HRFABMS: m/z 652.3156 (MH$^+$), Calcd. C$_{37}$H$_{43}$N$_5$O$_2$Cl; m/z 652.3167; δ$_H$ (CDCl$_3$) 2.16 (3H, s, 4-CH$_3$), 4.34 (1H, s, CHCON), 4.77 (1H, s, H$_{11}$), 4.93 (2H, s, CH$_2$-Im), 6.58 (1H, s, Im-H$_5$), 6.83 (1H, d, Ar—H$_4$), 6.86 (1H, s, Im-H$_2$), 7.07 (1H, dd, H$_{10}$), 7.13 (1H, dd, H$_9$), 7.14 (1H, s, H$_7$), 7.14 (1H, dd, H$_3$), 7.19 (1H, dd, Ar—H$_5$), 7.27 (1H, d, Ar—H$_6$), 7.37 (1H, s, Ar—H$_2$), 7.40 (1H, d, H$_4$), 8.29 (1H, d, H$_2$) and 8.92 ppm (1H, bs, NHCO); δc (CDCl$_3$) CH$_3$: 13.8; CH$_2$: 25.0, 25.0, 25.7, 30.6, 30.7, 33.7, 33.7, 42.2, 50.7, 50.9, 52.8; CH: 49.7, 55.5, 79.4, 115.8, 118.8, 119.8, 122.8, 123.9, 125.9, 129.3, 130.7, 132.7, 136.5, 139.2, 146.2; C, 133.9, 135.3, 136.5, 137.0, 138.7, 141.8, 156.5, 158.0, 169.9; [α]$_D^{20\,°\,C.}$ -18.7° (c=0.49, MeOH).

EXAMPLE 27

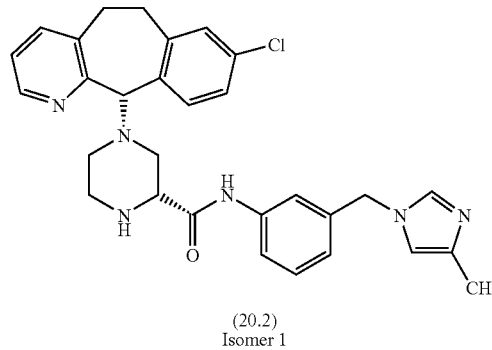

(20.2) Isomer 1

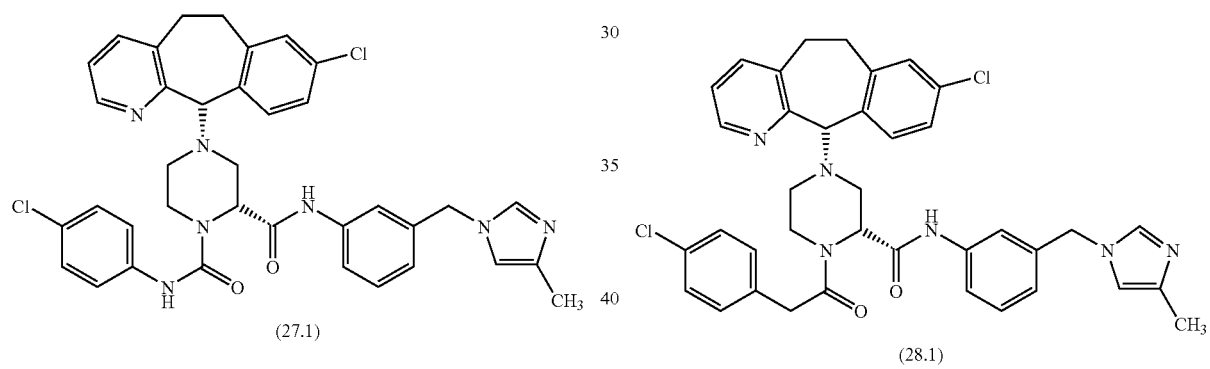

(27.1)

Compound (20.2), isomer 1 (0.1 g, 0.19 mmoles) (prepared as described in Example 20 above) was dissolved in anhydrous dichloromethane (5 mL) and 4-chlorophenyl isocyanate (0.0291 g, 0.19 mmoles) was added. The mixture was stirred under argon at 15° C. for 43 h and was then directly chromatographed on silica gel using 3% (10% conc. NH$_4$OH in methanol)-dichloromethane as the eluant to give a product that was further purified by preparative tlc on silica gel plates (250μ, 20×20 cm) using 7% (10% conc. NH$_4$OH in methanol)-dichloromethane as the eluant to compound (27.1) (0.0198 g, 14%): HRFABMS: m/z 680.2295 (MH$^+$), Calcd. C$_{37}$H$_{36}$N$_7$O$_2$Cl: m/z 680.2308; δ$_H$ (CDCl$_3$) 2.16/2.20 (3H, s, 4-CH$_3$), 4.42 (1H, s, CHCON), 4.78 (1H, s, H$_{11}$), 5.94/5.97 (2H, s, CH$_2$-Im), 6.57 (1H, d, Ar—H$_4$), 6.60 (1H, s, Im-H$_5$), 6.93 (1H, s, H$_7$), 6.91, 7.05-7.33, 7.39 (8H, s and m, Ar—H and Im-H$_2$), 7.44 (1H, s, Ar—H$_2$), 7.47 (1H, d, Ar—H$_6$), 7.74 (1H, bs, H$_4$), 8.34 (1H, d, H$_2$) and 9.03 ppm (1H, s, NHCO); δ$_C$(CDCl$_3$) CH$_3$: 13.5; CH$_2$: 30.8, 30.9, 42.0/42.2, 50.8, 51.1, 52.8; CH: 55.7, 79.5, 113.5, 114.8, 116.0, 117.4, 119.2, 120.0/120.5, 121.4, 121.4, 123.6, 123.6, 126.2/127.2, 128.8, 128.8, 129.3/129.5, 130.7/130.8, 133.0, 136.4, 139.2, 146.6;

C, 128.2, 134.2, 134.9/135.1, 134.9/135.1, 137.0, 137.6, 138.1, 141.5, 155.9, 156.2, 169.6; [α]$_D^{20\,°\,C.}$ -6.5° (c=0.5, MeOH).

EXAMPLE 28

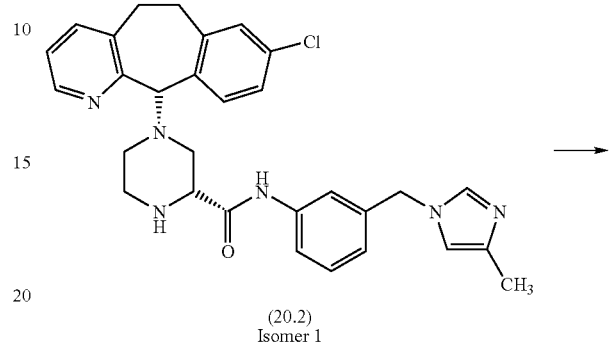

(20.2) Isomer 1

Compound (20.2), isomer 1 (0.092 g, 0.175 mmoles) (prepared as described in Example 20 above), 1-(3-dimethylaminopropyl)-3-ethylcarbodiimide hydrochloride (0.0435 g, 0.228 mmoles), 1-hydroxy-benzotriazole (0.031 g, 0.228 mmoles), 4-methylmorpholine (0.025 mL, 0.228 mmoles) and 4-chlorophenyl acetic acid (0.039 g, 0.228 mmoles) were dissolved in anhydrous DMF (5 mL) and the mixture was stirred at 25° C. under argon for 18 h. The reaction was worked up as described in Preparative Example 6, Step A above and the product was chromatographed on silica gel using 3% (10% conc. NH$_4$OH in methanol)-dichloromethane as the eluant to give compound (28.1) (0.0838 g, 71%): HRFABMS: m/z 679.2345 (MH$^+$), Calcd. C$_{38}$H$_{37}$N$_6$O$_2$Cl$_2$: m/z 679.2355; δ$_H$ (CDCl$_3$) 2.12 (1H, bs, 4-CH$_3$), 4.31 (1H, bs, CHCON), 4.98 (2H, bs, CH$_2$-Im), 5.17 (1H, bs, H$_{11}$), 6.58 (1H, bs, Im-H$_5$), 6.89 (2H, bs, Im-H$_2$ and Ar—H$_4$), 6.89, 6.95.7.45 (12H, bs and m, Ar—H), 8.30 (1H, bs, H$_2$) and 8.93 ppm (1H, bs, NHCO); ° c (CDCl$_3$) CH$_3$: 13.6; CH$_2$: 30.4, 30.7, 40.1, 44.3, 50.7, 51.1, 52.8; CH: 53.8, 79.2, 115.9, 118.0, 119.5, 122.7, 123.3, 126.0, 129.0, 129.0, 129.4, 130.2, 130.2, 130.6, 132.5, 136.9, 139.4, 146.2; C, 133.0, 134.0, 135.3, 135.5, 137.1, 138.9, 138.9, 142.1, 156.4, 168.3, 171.3; $[\alpha]_D^{20\,°C.}$ +4.4° (c=0.43, MeOH).

EXAMPLE 29

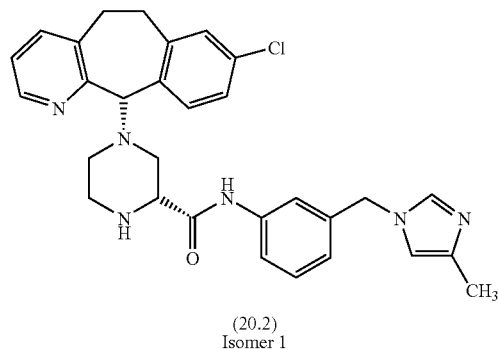

(20.2)
Isomer 1

135.2, 135.6, 137.2, 138.1, 138.1, 142.1, 156.2, 168.9; $[\alpha]_D^{20\,°C.}$ -20.3° (c=0.41, MeOH).

EXAMPLE 30

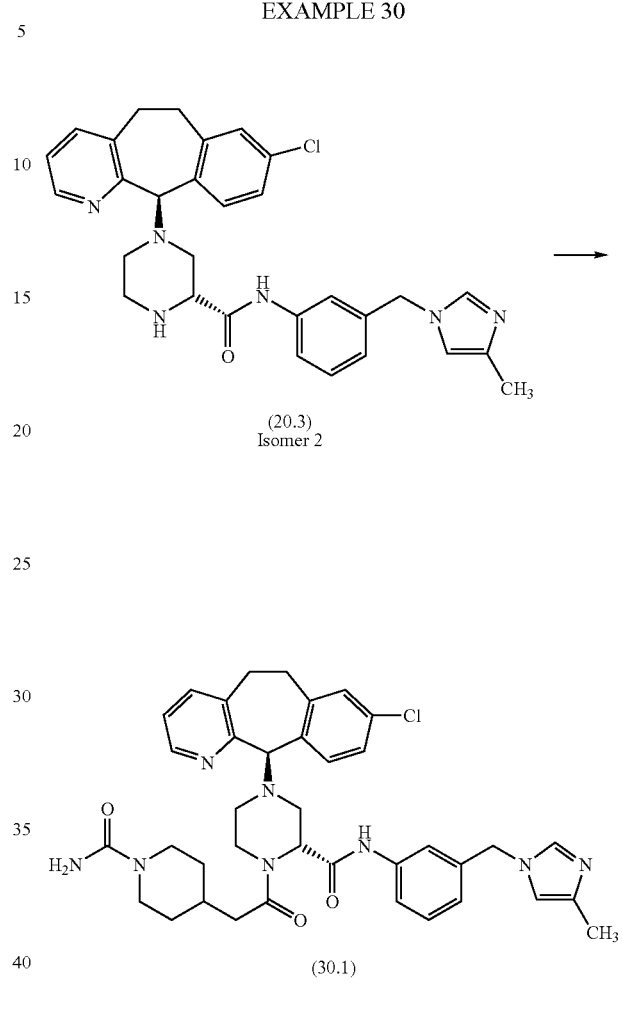

Compound (20.2), isomer 1 (0.1 g, 0.19 mmoles) (prepared as described in Example 20 above) and triethylamine (0.132 mL, 0.57 mmoles) were dissolved in anhydrous dichloromethane (5 mL). Methanesulfonyl chloride (0.0147 mL, 0.19 mmoles) was added and the mixture was stirred at 25° C. under argon for 19 h. Additional methanesulfonyl chloride (0.0147 mL, 0.19 mmoles) was added and the reaction was allowed to proceed for a total of 41 h. The solution was evaporated to dryness and the residue was chromatographed on silica gel using 3% (10% conc. NH$_4$OH in methanol)-dichloromethane as the eluant to give compound (29.1) (0.1007 g, 88%): HRFABMS: m/z 605.2098 (MH$^+$), Calcd. C$_{31}$H$_{34}$N$_6$O$_3$SCl: m/z 605.2102; $\delta_H$ (CDCl$_3$) 2.00 (3H, s, 4-CH$_3$), 2.94 (3H, s, CH$_3$SO$_2$N), 4.37 (1H, s, CHCON), 4.56 (1H, s, H$_{11}$), 5.04 (2H, dd, AB system, CH$_2$-Im), 6.57 (1H, s, Im-H$_5$), 6.79 (1H, s, Im-H$_2$), 6.79 (1H, d, Ar—H$_4$), 6.98 (1H, d, H$_{10}$), 7.09 (1H, dd, H$_9$), 7.14 (1H, d, H$_7$), 7.12-7.20 (2H, dd and dd, H$_3$, Ar—H$_2$ and Ar—H$_5$), 7.36 (1H, dd, Ar—H$_5$), 7.39 (1H, d, Ar—H$_6$), 7.80 (1H, d, H$_4$) and 8.30 ppm (1H, d, H$_2$); $\delta_C$ (CDCl$_3$) CH$_3$: 13.2, 39.1; CH$_2$: 30.5, 30.7, 42.5, 50.6, 50.8, 54.2; CH: 57.1, 79.0, 116.1, 117.3, 119.4, 122.6, 123.4, 126.0, 129.5, 130.5, 132.6, 136.2, 139.3, 146.3; C, 133.9, Compound (20.3), isomer 2 (0.15 g, 0.285 mmoles) (prepared as described in Example 20 above), 1-(3-dimethylaminopropyl)-3-ethylcarbodiimide hydrochloride (0.0709 g, 0.371 mmoles), 1-hydroxy-benzotriazole (0.05 g, 0.371 mmoles) and 4-methylmorpholine (0.814 mL, 0.741 mmoles) were dissolved in anhydrous DMF (1 mL) and 1-(carboxamido-piperidine)-4-acetic acid (0.0691 g, 0.371 mmoles) was added in anhydrous DMF (3 mL). The mixture was stirred at 25° C. for 45 h. and the reaction was then worked up as described in Preparative Example 6, Step A above. The product was chromatographed on silica gel using 6% (10% conc. NH$_4$OH in methanol)-dichloromethane as the eluant to give compound (30.1) (0.1033 g, 52%): FABMS: m/z 695.3 (MH$^+$); HRFABMS: m/z 695.3234 (MH$^+$). Calcd. C$_{38}$H$_{44}$N$_8$O$_3$Cl: m/z 695.3225 (MH$^+$); $\delta_H$ (CDCl$_3$) 2.16 (3H, s, 4-CH$_3$), 4.36 (1H, s, CHCON), 4.83 (1H, s, H$_{11}$), 4.97 (2H, s, CH$_2$-Im), 6.59 (1H, s, Im-H$_5$), 6.83 (1H, d, Ar—H$_{4'}$), 7.04-7.19 (5H, s and m, Ar—H), (7.27 (2H, dd, Ar—H$_3$ and Ar—H$_5$), 7.37 (1H, s, Im-H$_2$), 7.41 (1H, d, Ar—H$_4$), 8.25 (1H, d, Ar—H$_2$) and 8.83 ppm (1H, bs, NHCO); $\delta_C$ (CDCl$_3$) CH$_3$: 13.7; CH$_2$: 30.2, 30.8, 31.9, 32.0, 39.7, 44.1, 44.3, 44.5, 50.7, 50.9, 52.6; CH: 32.9, 53.7, 78.7, 115.9, 118.2, 119.5/119.9, 123.0, 123.4, 126.1, 129.5, 130.8, 132.4, 136.4, 139.3/

139.4, 146.0; C: 134.1, 135.6, 137.2, 137.2, 138.7, 139.1, 141.4, 156.7, 158.2, 168.7, 171.6, 172.4; $[\alpha]_D^{20°\,C}$ +74.6° (c=0.50, MeOH).

EXAMPLE 31

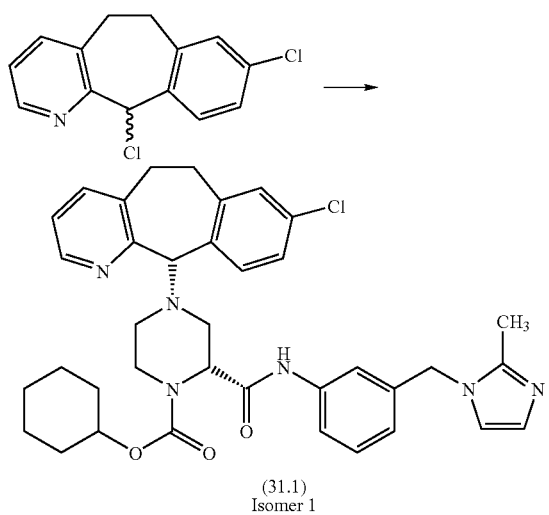

(31.1) Isomer 1

(31.2) Isomer 2

The title compound from Preparative Example 12, Step B above (0.2 g, 0.47 mmoles) and triethylamine (0.197 mL, 1.41 mmoles) were dissolved in anhydrous THF (1.5 mL) and anhydrous dichloromethane (1.5 mL). A solution of 8,11-Dichloro-6,11-dihydro[5,6]cyclohepta[1,2-b]pyridine (0.2473 g, 0.94 mmoles) (prepared from the alcohol as described in Preparative Example 7 in U.S. Pat. No. 5,719,148; Feb. 17, 1998) in anhydrous THF (2 mL) was added and the mixture was stirred under argon at 25° C. for 94 h. Additional 8,11-Dichloro-6,11-dihydro[5,6]cyclohepta[1,2-b]pyridine (0.2473 g, 0.94 mmoles) and triethylamine (0.13 mL, 0.94 mmoles) in anhydrous THF (2 mL) were added at 94 h and again at 118 h and at 142 h. After a total of 166 h the solution was evaporated to dryness and the residue was taken up in dichloromethane, washed with water, dried (MgSO$_4$), filtered and evaporated to dryness. The residue was chromatographed on silica gel using gradient elution with 1%-1.5%-7% (10% conc. NH$_4$OH in methanol)-dichloromethane as the eluant to give two fractions. Each one was rechromatographed on a Chiralpak® AD column using hexane:isopropanol:diethylamine::85:15:0.2 as the eluant to give in the order of elution first compound (31.1), isomer 1 (0.0694 g, 22%): HRFABMS: m/z 653.3010 (MH$^+$), Calcd. C$_{37}$H$_{42}$N$_6$O$_3$Cl; m/z 653.3007; $\delta_H$ (CDCl$_3$) 2.18 (3H, s, 2-CH$_3$), 4.34 (1H, s, CHCON), 4.64 (1H, bs, H$_{11}$), 5.04 (2H, dd, AB system, CH$_2$-Im), 6.60 (1H, s, Im-H$_5$), 6.83 (1H, s, Im-H$_4$), 6.89 (1H, s, H$_7$), 6.89 (1H, d, Ar—H$_4$), 7.18 (1H, s, Ar—H$_2$), 7.11-7.21 (3H, m, H$_3$, H$_9$ and H$_{10}$), 7.32 (1H, dd, Ar—H$_5$), 7.38 (1H, d, Ar—H$_6$), 7.77 (1H, d, H$_4$), 8.31 (1H, d, H$_2$) and 9.57 ppm (1H, bs, NHCO); $\delta_C$ (CDCl$_3$) CH$_3$: 12.7; CH$_2$: 23.6, 23.6, 25.4, 30.4, 30.7, 31.9, 31.9, 42.3, 49.5, 50.9, 52.8; CH: 55.9, 74.1, 79.3, 116.7, 119.0, 120.1, 121.7, 123.2, 125.9, 126.8, 129.5, 130.5, 132.5, 139.3, 146.1; C, 133.9, 135.2, 135.9, 137.1, 139.6, 142.2, 145.5, 156.7, 156.7, 168.7; $[\alpha]_D^{20°\,C}$ -116.7° (c=0.5, MeOH) and then compound (31.2), isomer 2 (0.0639 g, 21%): HRFABMS: m/z 653.2997 (MH$^+$), Calcd. C$_{37}$H$_{42}$N$_6$O$_3$Cl; m/z 653.3007; $\delta_H$ (CDCl$_3$) 2.28 (3H, s, 2-CH$_3$), 4.38 (1H, bs, CHCON), 4.67 (1H, bs, H$_{11}$), 5.03 (2H, s, CH$_2$-Im), 6.80-6.90, 7.07-7.22, 7.25-7.12 (10H, s and m, Ar—H and Im-H), 7.43 (1H, d, H$_4$) and 8.30 ppm (1H, d, H$_2$); $\delta_C$ (CDCl$_3$) CH$_3$: 13.0; CH$_2$: 23.6, 23.6, 25.4, 30.4, 30.7, 31.8, 31.8, 42.3, 49.7, 50.8, 52.2; CH: 55.9, 74.4, 79.2, 117.7, 119.3, 119.9, 122.3, 123.3, 126.1, 127.3, 129.6, 130.6, 132.3, 139.3, 146.0; C, 134.0, 135.4, 135.8, 137.3, 138.9, 144.8, 144.8, 156.7, 156.7, 168.7; $[\alpha]_D^{20°\,C}$ +77.0° (c=0.31, MeOH).

EXAMPLE 32

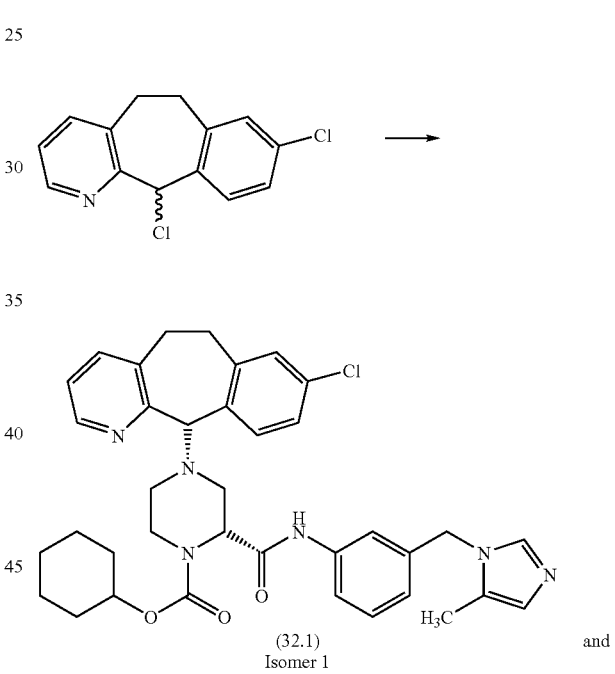

(32.1) Isomer 1 and

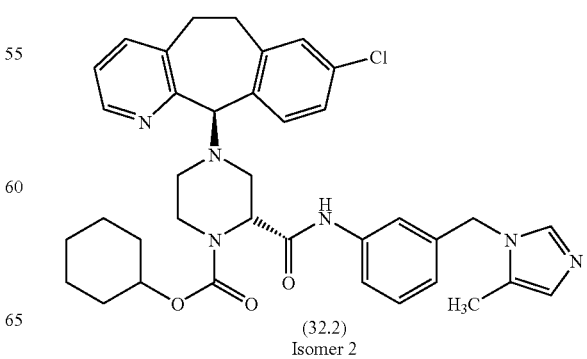

(32.2) Isomer 2

Method 1:

The title compound from Preparative Example 11, Step B above (0.2 g, 0.47 mmoles) and triethylamine (0.197 mL, 1.41 mmoles) were dissolved in anhydrous THF (1.5 mL) and anhydrous dichloromethane (1.5 mL). A solution of 8,11-Dichloro-6,11-dihydro[5,6]cyclohepta[1,2-b]pyridine (0.2473 g, 0.94 mmoles) (prepared from the alcohol as described in Preparative Example 7 in U.S. Pat. No. 5,719, 148; Feb. 17, 1998) in anhydrous THF (2 mL) was added and the mixture was stirred under argon at 25° C. for 94 h. Additional 8,11-Dichloro-6,11-dihydro[5,6]cyclohepta[1,2-b]pyridine (0.2473 g, 0.94 mmoles) and triethylamine (0.13 mL, 0.94 mmoles) in anhydrous THF (2 mL) were added at 94 h and again at 118 h and at 142 h. After a total of 166 h the solution was evaporated to dryness and the residue was taken up in dichloromethane, washed with water, dried ($MgSO_4$), filtered and evaporated to dryness. The residue was chromatographed on silica gel using gradient elution with 1%-1.5%-7% (10% conc. $NH_4OH$ in methanol)-dichloromethane as the eluant to give two fractions. Each one was rechromatographed on a Chiralpak® AD column using hexane:isopropanol:diethylamine::85:15:0.2 as the eluant to give in the order of elution first compound (32.1), isomer 1 (0.0759 g, 25%): HRFABMS: m/z 653.3010 ($MH^+$), Calcd. $C_{37}H_{42}N_6O_3Cl$; m/z 653.3007; $\delta_H$ ($CDCl_3$) 2.10 (3H, s, 5-$CH_3$), 4.32 (1H, s, CHCON), 4.71 (1H, bs, $H_{11}$), 5.04 (2H, dd, AB system, $CH_2$-Im), 6.19(1H, s, Im-$H_4$), 6.84 (1H, d, Ar—$H_4$), 6.95 (1H, s, $H_7$), 7.01 (1H, s, Im-$H_2$), 7.70-7.17 (3H, m, $H_3$, $H_9$ and $H_{10}$), 7.14 (1H, s, Ar—$H_2$), 7.32 (1H, dd, Ar—$H_5$), 7.39 (1H, d, Ar—$H_6$), 7.63 (1H, d, $H_4$), 8.30 (1H, d, $H_4$) and 9.15 ppm (1H, bs, NHCO); $\delta_C$ ($CDCl_3$) $CH_3$: 9.4; $CH_2$: 23.6, 23.6, 25.4, 30.5, 30.5, 31.8, 31.8, 42.2, 48.2, 51.1; CH: 55.9, 74.1, 79.4, 117.3, 119.3, 122.0, 123.2, 125.9, 126.8, 129.5, 130.6, 132.6, 139.1, 139.1, 146.1; C, 127.7, 133.9, 135.2, 135.6, 137.0, 139.3, 142.0, 156.8, 156.8, 168.9, $[\alpha]_D^{20\ °C}$ -21.6° C. (c=0.51, MeOH) and then compound (32.2), isomer 2 (0.068 g, 22%): HRFABMS: m/z 653.3004 ($MH^+$), Calcd. $C_{37}H_{42}N_6O_3Cl$; m/z 653.3007; $\delta_H$ ($CDCl_3$) 2.10 (3H, s, 5-$CH_3$), 4.38 (1H, s, CHCON), 4.68 (1H, bs, $H_{11}$), 5.03 (2H, s, $CH_2$-Im), 6.72 (1H, s, Im-$H_4$), 6.83 (1H, d, Ar—$H_4$), 7.01-7.14 ($\delta_H$, s and m, Ar—H and Im-$H_2$), 7.30 (1H, dd, Ar—$H_5$), 7.35 (1H, d, Ar—$H_6$), 7.54 (1H, d, $H_4$) and 8.25 ppm (1H, d, $H_2$); $\delta_C$ ($CDCl_3$) $CH_3$: 9.4; $CH_2$: 23.6, 23.6, 25.4, 30.3, 30.7, 31.8, 31.8, 42.3, 48.8, 50.8, 52.4; CH: 55.9, 74.3, 79.1, 117.5, 119.4, 122.2, 123.3, 126.0, 127.0, 129.6, 130.7, 132.3, 139.2, 139.2, 146.0; C, 127.6, 134.0, 135.5, 135.8, 137.1, 139.2, 141.4, 156.8, 156.8, 168.8; $[\alpha]_D^{20°C}$.+74.9° (c=0.5, MeOH).

Method 2:

8,11-Dichloro-6,11-dihydro[5,6]cyclohepta[1,2-b]pyridine (prepared from the alcohol as described in Preparative Example 7 in U.S. Pat. No. 5,719,148; Feb. 17, 1998), the title compound from Preparative Example 10, Step B above and triethylamine may be reacted essentially as described in Example 20 above to give compound (32.1), isomer 1 and compound (32.2), isomer 2. The latter may each be converted into the respective title compounds by reaction with cyclohexyl chloroformate and triethylamine as described in Example 15 above.

EXAMPLE 33

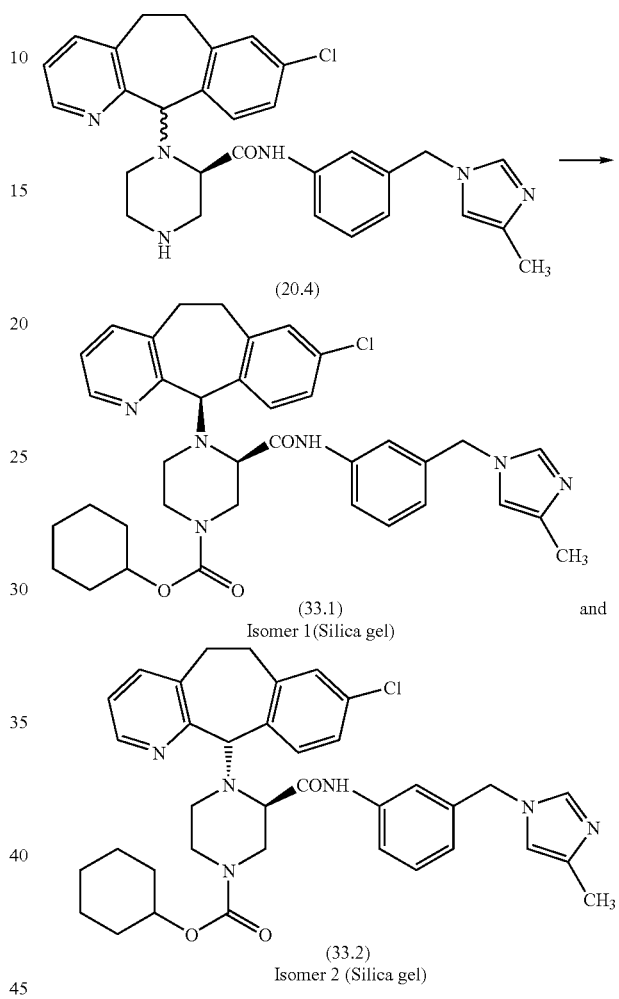

(20.4)

(33.1)
Isomer 1(Silica gel)

and (33.2)
Isomer 2 (Silica gel)

Compound (20.4) (0.2042 g, 0.388 mmoles) (prepared as described in Example 20 above) and triethylamine (0.1623 mL, 1.165 mmoles) were dissolved in anhydrous dichloromethane (6.76 mL). Cyclohexyl chloroformate (0.0636 g, 0.388 mmoles) in anhydrous dichloromethane (1.69 mL) was added and the reaction was stirred under argon at 25° C. for 3 h. The mixture was evaporated to dryness and chromatographed on silica gel using 3% (10% conc. $NH_4OH$ in methanol)-dichloromethane as the eluant to give in the order of elution first compound (33.1), isomer 1 (silica gel) (0.0582 g, 23%): HRFABMS: m/z 653.3030 ($MH^+$), Calcd. $C_{37}H_{42}N_6O_3Cl$: m/z 653.3007; $\delta_H$ ($CDCl_3$) 2.23 (3H, s, 4-$CH_3$), 4.68 (1H, m, CHCON), 5.03 (2H, s, $CH_2$-Im), 5.22 (1H, s, $H_{11}$), 6.64 (1H, s, Im-$H_5$), 6.84 (1 h, d, Ar—$H_4$), 7.09 (1H, d, $H_{10}$), 7.13 (2H, s, Im-$H_2$ and $H_7$), 7.19 (1H, d, Hg), 7.24 (1H, dd, $H_3$), 7.29 (1H, dd, Ar—$H_5$), 7.44 (1H, s, Ar—$H_2$), 7.51 (1H, d, Ar—$H_6$), 7.53 (1H, d, $H_4$), 8.37 (1H, d, $H_2$) and 9.63/9.73 ppm (1H, bs, NHCO); $\delta_C$ ($CDCl_3$) $CH_3$: 14.0; $CH_2$: 23.7, 23.8, 25.7, 30.9, 31.6, 32.1, 32.1, ~41.7, 44.8, 50.8, 50.8; CH: ~58.4, 73.5, 74.1, 116.1, 118.4, 119.1, 122.6, 123.9, 126.7, 129.7, 130.6, 133.0, 136.8, 140.2, 146.3;

C, 134.7, 135.1, 135.7, 137.7, 138.9, 138.9, 141.6, 155.8, 155.8, 168.3; $[\alpha]_D^{20°\,C.}$+88.4° (c=0.3, MeOH) and then compound (33.2), isomer 2 (silica gel) (0.1411 g, 56%): HRFABMS: m/z 653.3026 (MH$^+$), Calcd. $C_{37}H_{42}N_6O_3Cl$: m/z 653.3007; $\delta_H$ (CDCl$_3$) 2.23 (3H, s, 4-CH$_3$), 4.63 (1H, m, CHCON), 5.02 (2H, s, CH$_2$-Im), 5.25 (1H, s, H$_{11}$), 6.62 (1H, s, Im-H$_5$), 6.87 (1H, d, Ar—H$_4$), 7.12 (1H, dd, H$_3$), 7.16 (1H, d, H$_{10}$), 7.18 (1H, s, Im-H$_2$), 7.21 (1H, d, H$_9$), 7.23 (1H, s, H$_7$), 7.28 (1H, dd, Ar—H$_5$), 7.34 (1H, d, Ar—H$_6$), 7.42 (1H, s, Ar—H$_2$), 7.44 (1H, d, H$_4$), 8.33 (1H, d, H$_2$) and 9.39 ppm (1H, bs, NHCO); $\delta_C$ (CDCl$_3$) CH$_3$: 14.0; CH$_2$: 23.7, 23.8, 25.6, 31.7, 32.0, 32.0, 32.1, 41.1, 44.7, 50.7, 50.7; CH: 60.3, 73.8, 74.1, 116.0, 118.0, 119.0, 122.8, 123.6, 126.9, 129.8, 130.3, 133.1, 136.8, 139.8, 146.9; C, 134.6, 134.9, 134.9, 137.7, 138.7, 139.0, 141.8, 155.4, 155.4, 169.7; $[\alpha]_D^{20°\,C.}$+121.0° (c=0.5, MeOH).

EXAMPLE 34

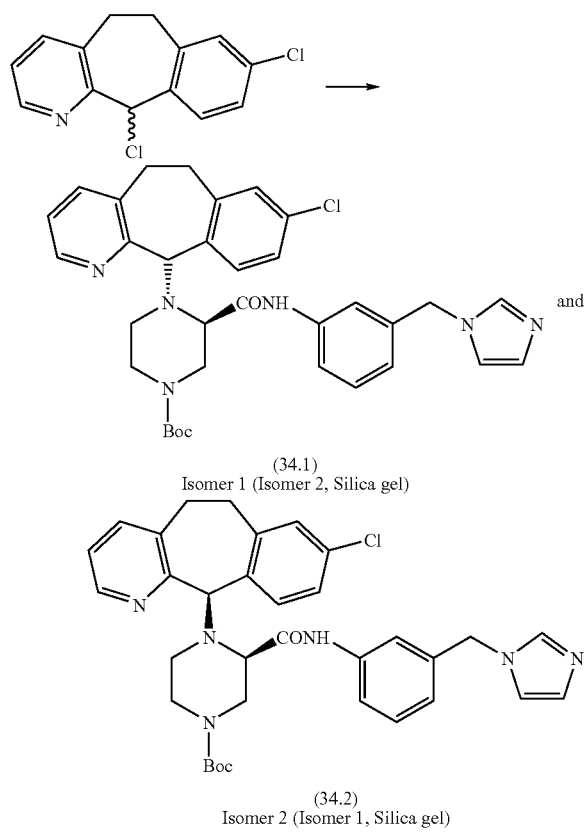

(34.1)
Isomer 1 (Isomer 2, Silica gel)

(34.2)
Isomer 2 (Isomer 1, Silica gel)

The title compound from Preparative Example 16 (1.5325 g, 3.98 mmoles) and triethylamine (1.66 mL, 11.93 mmoles) were dissolved in anhydrous dichloromethane (6.5 mL). 8,11-Dichloro-6,11-dihydro[5,6]-cyclohepta[1,2-b]pyridine (1.364 g, 5.17 mmoles), prepared from the alcohol as described in Preparative Example 7 in U.S. Pat. No. 5,719,148 (Feb. 17, 1998), dissolved in anhydrous dichloromethane (3.4 mL) was added and the mixture was stirred at 25° C. for 91 h. Additional 8,11-dichloro-6,11-dihydro[5,6]-cyclohepta[1,2-b]-pyridine (0.21 g, 0.795 mmoles) and triethylamine (0.553 mL, 3.98 mmoles) in anhydrous dichloromethane (0.76 mL) were added and the reaction was allowed to continue at 25° C. for a total of 139 h. The reaction mixture was evaporated to dryness and the residue was chromatographed on silica gel using 1.3% (10% conc. NH$_4$OH in methanol).

dichloromethane as the eluant to give compound (34.2), isomer 2, (isomer 1, silica gel) (0.5825 g., 24%): FABMS: m/z 613.3 (MH$^+$); HRFABMS: m/z 615.280 (Isotope MH$^+$), Calcd. $C_{34}H_{40}N_6O_3Cl$ m/z 615.280; $\delta_H$ (CDCl$_3$) 1.43 (9H, s, CH$_3$), 4.34 (1H, d, CHCON), 5.11 (2H, s, CH$_2$-Im), 5.22 (1H, s, H$_{11}$), 6.86 (1H, d, Ar—H$_{4'}$), 6.95 (1H, s, Im-H$_5$), 7.07-7.14 (2H, d, Ar—H$_{9,11}$), 7.17 (1H, s, Ar—H$_7$), 7.20 (1H, s, Im-H$_4$), 7.22 (1H, dd, Ar—H$_3$), 7.29 (1H, dd, Ar—H$_5$), 7.48 (1H, d, Ar—H$_{6'}$), 7.50 (1H, s, Ar—H$_{2'}$), 7.52 (1H, d, Ar—H$_4$), 7.57 (1H, s, Im-H$_2$), 8.38 (1H, d, Ar—H$_2$) and 9.59 ppm (1H, bs, NHCO); $\delta_C$ (CDCl$_3$) CH$_3$: 28.4, 28.4, 28.4; CH$_2$: 30.8, 31.4, 41.8, 44.8, 50.8, 50.8, 58.7; CH: 74.1, 118.2, 119.1, 119.5, 122.5, 123.7, 126.6, 129.7, 129.7, 130.5, 133.0, 140.0, 146.3; C, 79.9, 134.6, 135.1, 137.3, 138.8, 141.5, 155.0, 155.8, 168.5; $[\alpha]_D^{20°\,C.}$+77.6° (c=0.52, MeOH). Further elution of the column afforded compound (34.1), isomer 1, (isomer 2, silica gel) (0.2461 g., 10%): FABMS: m/z 613.3 (MH$^+$); HRFABMS: m/z 615.2850 (Isotope MH$^+$), Calcd. $C_{34}H_{40}N_6O_3Cl$ m/z 615.280; $\delta_H$ (CDCl$_3$) 1.38 (9H, s, CH$_3$), 4.14 (1H, d, CHCON), 5.09 (2H, s, CH$_2$-Im), 5.25 (1H, s, H$_1$), 6.85 (1H, d, Ar—H$_{4'}$), 6.92 (1H, s, Im-H$_5$), 7.08 (1H, s, Im-H$_4$), 7.07-7.17 (2H, d, Ar—H$_{9,10}$), 7.16 (1H, s, Ar—H$_7$), 7.21 (1H, s, Im-H$_4$), 7.21 (1H, dd, Ar—H$_3$), 7.32 (1H, d, Ar—H$_{6'}$), 7.36 (1H, s, Ar—H$_{2'}$), 7.43 (1H, d, Ar—H$_4$), 7.55 (1H, s, Im-H$_2$), 8.31 (1H, d, Ar—H$_2$) and 9.31 ppm (1H, bs, CONH); $\delta_C$ (CDCl$_3$) CH$_3$: 28.4, 28.4, 28.4; CH$_2$: 31.5, 32.1, 41.4, 44.7, 50.7, 50.7; CH: 60.3, 74.2, 118.0, 119.1, 119.5, 122.7, 123.4, 126.7, 129.7, 129.8, 130.2, 133.0, 137.5, 139.7, 146.7; C, 80.3, 134.5, 134.9, 137.3, 137.5, 138.7, 141.7, 155.0, 155.5, 169.7; $[\alpha]_D^{20°\,C.}$+106.0° (c=0.53, MeOH).

EXAMPLE 35

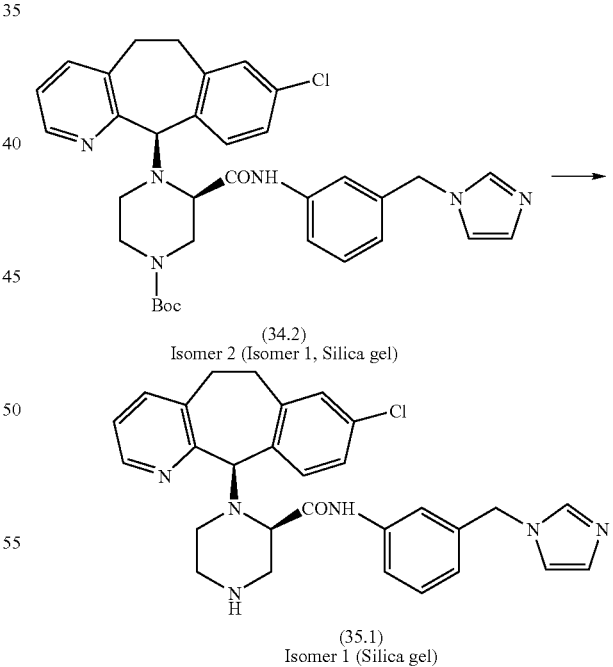

(34.2)
Isomer 2 (Isomer 1, Silica gel)

(35.1)
Isomer 1 (Silica gel)

Compound (34.2), isomer 2, (isomer 1, silica gel) (0.435 g, 0.709 mmoles) from Example 34 was dissolved in methanol (7.25 mL) and 10% conc. H$_2$SO$_4$-dioxane (v/v) (9.7 mL) was added and the reaction was stirred at 25° C. for 2.5 h. The reaction was worked up as described in Preparative Example 4, Step C, The product was chromatographed on silica gel using 3.5% (10% conc. NH$_4$OH in methanol)-dichloromethane as the eluant to give compound (35.1) (0.3227 g, 85%): FABMS: m/z 513.0 (MH$^+$); HRFABMS: m/z 513.2173 (MH$^+$), Calcd. C$_{29}$H$_{30}$N$_6$OCl m/z 513.2170; δ$_H$ (CDCl$_3$) 4.28 (1H, m, CHCON), 5.08 (1H, s, H$_{11}$), 5.17 (1H, s, CH$_2$-Im), 6.92 (1H, d, Ar—H$_{4'}$), 6.96 (1H, s, Im-H$_5$), 7.13 (3H, bs, Ar—H$_{7,9,10}$) 7.18 (1H, Im-H$_4$), 7.30 (1H, bs, 1H, Ar—H$_3$), 7.37 (1H, bs, Ar—H$_{5'}$), 7.56 (1H, d, Ar—H$_{6'}$), 7.58 (1H, s, Ar—H$_{2'}$), 7.66 (1H, D, Ar—H$_4$), 7.66 (1H, s, Im-H$_2$) and 8.36 ppm (1H d, Ar—H$_2$); δ$_C$ (CDCl$_3$) CH$_2$: 30.1, 31.9, 45.3, 45.3, 47.0, 50.8; CH: 56.6, 74.0, 118.6, 119.5, 119.5, 122.9, 123.9, 126.5, 129.8, 129.9, 130.1, 132.7, 137.5, 141.1, 145.5; C, 134.6, 135.1, 136.3, 137.6, 138.9, 142.0, 155.5, 169.3; [α]$_D^{20°\,C}$+132.5° (c=0.56, MeOH).

EXAMPLE 36

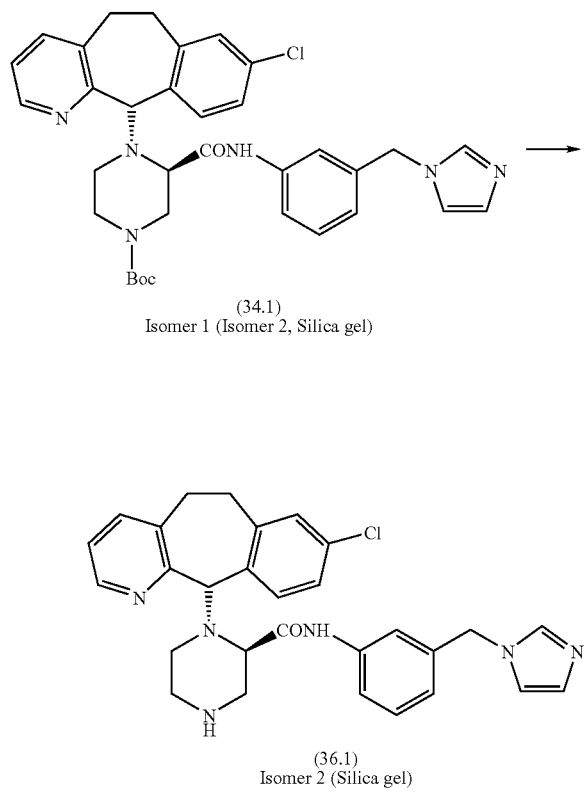

(34.1)
Isomer 1 (Isomer 2, Silica gel)

(36.1)
Isomer 2 (Silica gel)

Compound (34.1), isomer 1, (isomer 2, silica gel) (0.2396 g, 0.391 mmoles) from Example 34 was dissolved in methanol (3.2 mL) and 10% conc. H$_2$SO$_4$-dioxane (v/v) (4.25 mL) was added and the reaction was stirred at 25° C. for 2.75 h. The reaction was worked up as described in Preparative Example 4, Step C, The product was chromatographed on silica gel using 3.5% (10% conc. NH$_4$OH in methanol)-dichloromethane as the eluant to give compound (36.1) (0.1106 g, 68%): FABMS: m/z 512.9 (MH$^+$); HRFABMS: m/z 513.2173 (MH$^+$), Calcd. C$_{29}$H$_{30}$N$_6$OCl m/z 513.2170; δ$_H$ (CDCl$_3$) 4.11 (1H, m, CHCON), 5.10 (2H, s, CH$_2$-Im), 5.21 (1H, s, H$_{11}$), 6.85 (1H, d, Ar.H$_{4'}$), 6.94 (1H, s, Im-H$_5$), 7.08 (1H, s, Im-H$_4$), 7.08-7.18 (3H, M, Ar—H$_{3,9,10}$), 7.17 (1H, 1H, Ar—H$_7$), 7.29 (1H, s, Ar—H$_{5'}$), 7.29 (1H, dd, Ar—H$_5$), 7.39 (1H, d, Ar—H$_{4'}$), 7.42 (1H, d, Ar—H$_{6'}$), 7.49 (1H, d, Ar—H$_4$), 7.53 (1H, s, Ar—H$_{2'}$), 7.56 (1H, s, Im-H$_2$) and 8.32 ppm (1H, d, Ar—H$_2$); δ$_C$ (CDCl$_3$) CH$_2$: 30.8, 31.6, 44.3, 45.3, 45.7, 50.8; CH: 58.9, 74.5, 118.6, 119.5, 119.5, 122.6, 123.2, 126.3, 129.6, 129.8, 130.0, 133.8, 139.7, 146.4; C, 134.0, 134.7, 135.2, 137.1, 138.8, 141.4, 156.5,169.4; [α]$_D^{20°\,C}$-68.7° (c=0.46, MeOH).

EXAMPLE 37

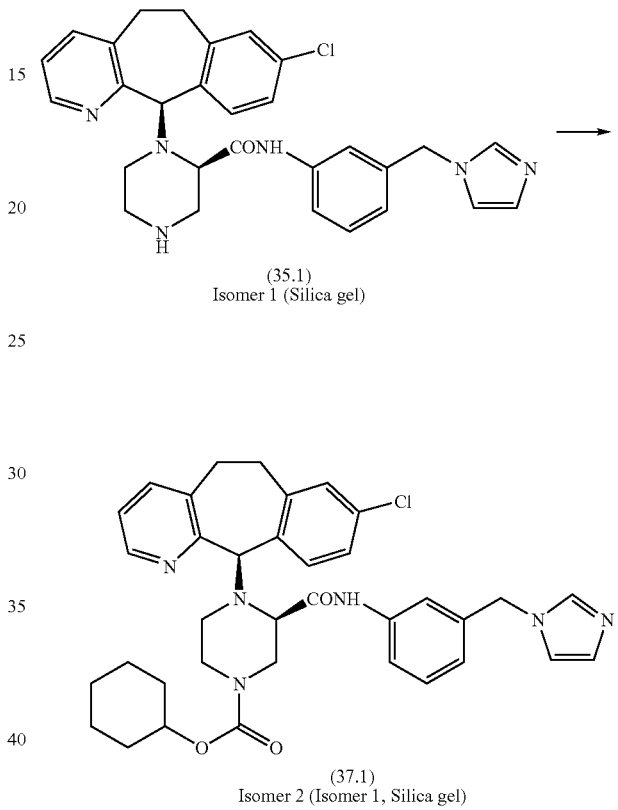

(35.1)
Isomer 1 (Silica gel)

(37.1)
Isomer 2 (Isomer 1, Silica gel)

Compound (35.1), isomer 1 (silica gel) (0.15 g, 0.292 mmoles) (prepared as described in Example 35 above) and triethylamine (0.122 mL, 0.877 mmoles) were dissolved in anhydrous dichloromethane (5 mL). Cyclohexyl chloroformate (0.0475 g, 0.292 mmoles) in anhydrous dichloromethane (0.5 mL) was added and the reaction was stirred under argon at 25° C. for 18 h. The reaction was worked up as described in Example 15 and the product was chromatographed on silica gel using 2.5% (10% conc. NH$_4$OH in methanol)-dichloromethane as the eluant to give compound (37.1) (0.1471 g, 79%): FABMS: m/z 639.0 (MH$^+$); HRFABMS: m/z 639.2839 (MH$^+$), Calcd. C$_{36}$H$_{40}$N$_6$O$_3$Cl m/z 639.2850; δ$_H$ (CDCl$_3$) 4.41 (1H, d, CHCON), 5.13 (2H, s, CH$_2$-Im), 5.22 (1H, s, H$_{11}$), 6.86 (1H, d, Ar—H$_{4'}$), 6.97 (1H, s, Im-H$_5$), 7.08-7.17 (2H, d, Ar—H$_{9,10}$), 7.15 (1H, s, Ar—H$_7$), 7.19 (1H, s, Im-H$_4$), 7.23 (1H, dd, Ar—H$_3$), 7.30 (1H, dd, Ar—H$_{5'}$), 7.51 (1H, d, Ar—H$_{6'}$), 7.51 (1H, s, Ar—H$_{2'}$), 7.53 (1H, d, Ar—H$_4$), 7.61 (1H, s, Im-H$_2$), 8.37 (1H, d, Ar—H$_2$) and 9.71 ppm (1H, bs, NHCO); δ$_C$ (CDCl$_3$) CH$_2$: 23.6, 23.7, 25.5, 30.7, 31.5, 31.9, 31.9, 42.0, 44.8, 50.8, 50.8; CH: 58.4, 73.4, 74.0, 118.2, 119.1, 119.5, 123.8, 123.8, 126.6, 129.7, 130.5, 130.5, 133.0, 137.5, 140.1, 146.2; C, 134.6, 135.0, 135.6, 137.2, 138.8, 141.5, 155.3, 155.7, 168.3; $[\alpha]_D^{25°\,C.}$+87.0° (c=0.55, MeOH).

EXAMPLE 38

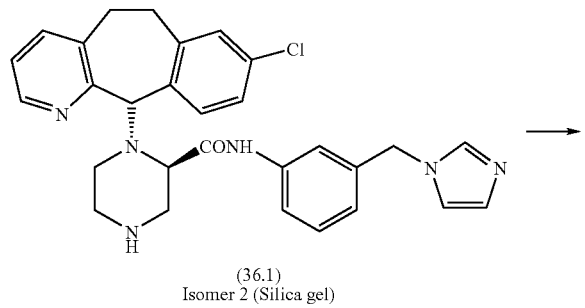

(36.1)
Isomer 2 (Silica gel)

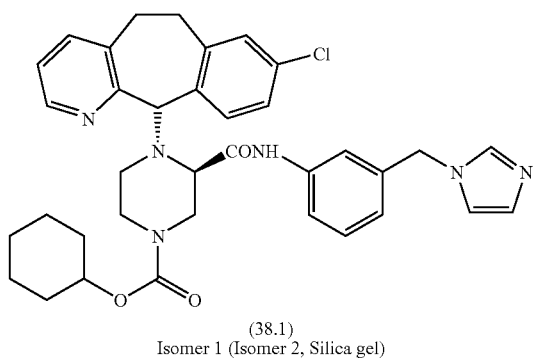

(38.1)
Isomer 1 (Isomer 2, Silica gel)

Compound (36.1), isomer 2 (silica gel) (0.068 g, 0.133 mmoles) (prepared as described in Example 36 above) and triethylamine (0.0553 mL, 0.399 mmoles) were dissolved in anhydrous dichloromethane (2.3 mL). Cyclohexyl chloroformate (0.0215 g, 0.133 mmoles) in anhydrous dichloromethane (0.068 mL) was added and the reaction was stirred under argon at 25° C. for 41 h. The reaction was worked up as described in Example 15 and the product was chromatographed on silica gel using 2.5% (10% conc. NH$_4$OH in methanol)-dichloromethane as the eluant to give compound (38.1) (0.0617 g, 73%): FABMS: m/z 639.3 (MH$^+$); HRFABMS: m/z 639.2839 (MH$^+$), Calcd. C$_{36}$H$_{40}$N$_6$O$_3$Cl m/z 639.2850; $\delta_H$ (CDCl$_3$) 4.18 (1H, dd, CHCON), 5.11 (2H, s, CH$_2$-Im), 5.25 (1H, s, H$_{11}$), 6.87 (1H, d, Ar—H$_4$·), 6.94 (1H, s, Im-H$_5$), 7.08-7.17 (2H, d, Ar—H$_{9,10}$), 7.18 (1H s, Ar—H$_7$), 7.23 (1H, s, Im-H$_4$), 7.23 (1H, dd, Ar—H$_3$), 7.29 (1H, dd, Ar—H$_5$·), 7.37 (1H, d, Ar—H$_6$·), 7.38 (1H, s, Ar—H$_2$·), 7.43 (1H, d, Ar—H$_4$), 7.57 (1H, s, Im-H$_2$), 8.33 (1H, d, Ar—H$_2$) and 9.37 ppm (1H, bs, NHCO); $\delta_C$ (CDCl$_3$) CH$_2$: 23.6, 23.7, 25.5, 31.5, 31.8, 31.8, 32.1, 41.0, 44.6, 50.8, 50.8; CH: 60.2, 73.7, 74.0, 118.0, 119.0, 119.5, 122.8, 123.5, 126.8, 129.7, 130.2, 130.2, 133.0, 137.5, 139.8, 146.7; C, 134.5, 134.8, 137.3, 137.3, 138.7, 141.7, 155.4, 155.4, 169.6; $[\alpha]_D^{25°\,C.}$-97.5° (c=0.55, MeOH).

EXAMPLE 39

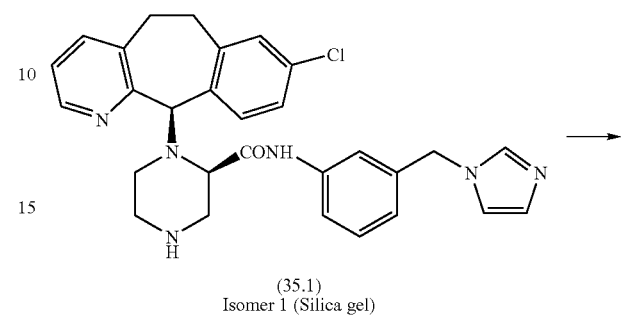

(35.1)
Isomer 1 (Silica gel)

(39.1)

Compound (35.1), isomer 1 (silica gel) (0.14 g, 0.273 mmoles) (prepared as described in Example 35 above), 1-(3-dimethylaminopropyl)-3-ethylcarbodiimide hydrochloride (0.068 g, 0.355 mmoles), 1-hydroxybenzotriazole (0.0479 g, 0.355 mmoles) and 4-methylmorpholine (0.039 mL, 0.355 mmoles) were dissolved in anhydrous DMF (3 mL) and 1-(carboxamido-piperidine)-4-acetic acid (0.0661 g, 0.355 mmoles) was added in anhydrous DMF (2 mL). The mixture was stirred at 25° C. for 41 h. Additional 1-(carboxamido-piperidine)-4-acetic acid (0.0102 g, 0.0546 mmoles) was added. The reaction was allowed to proceed for a total of 66 h. The reaction was then worked up as described in Preparative Example 6, Step A above. The product was chromatographed on silica gel using 3.5% (10% conc. NH$_4$OH in methanol)-dichloromethane as the eluant to give compound (39.1) (0.1185 g, 64%): FABMS: m/z 681.38 (MH$^+$); HRFABMS: m/z 681.3066 (MH$^+$), Calcd. C$_{37}$H$_{42}$N$_8$O$_3$ m/z 681.3068; $\delta_H$ (CDCl$_3$) 4.35 (1H, dd, CHCON), 5.14 (2H, s, CH$_2$-Im), 5.30 (1H, s, H$_{11}$), 6.95 (1H, d, Ar—H$_4$·), 6.95 (1H, s, Im-H$_5$), 7.14 (1H, s, Im-H$_4$), 7.18 (1H, s, Ar—H$_7$), 7.15-7.42 (4H, m, Ar—H), 7.47 (1H, s, Ar—H$_2$·), 7.54 (1H, d, Ar—H$_6$·), 7.68 (1H, d, Ar—H$_4$), 7.71 (1H, s, Im-H$_2$), 8.38 (1H, d, Ar—H$_2$) and 9.78/9.94 ppm (1H, s, NHCO); $\delta_C$ (CDCl$_3$) (Principal rotamer) CH$_2$: 30.7, 31.7, 32.0, 38.4, 42.0, 44.3, 44.7, 44.8, 50.7, 50.7; CH: 39.0, 58.4, 118.0, 119.0, 119.5, 123.0, 123.9, 126.7, 129.7, 130.7, 130.7, 132.8, 137.3, 137.5, 138.6, 140.2, 146.4; C, 73.5, 134.9, 135.4, 137.3, 141.4, 155.2, 158.2, 168.2, 170.9; $[\alpha]_D^{25°\ C.}$+76.1° (c=0.51, MeOH).

EXAMPLE 40

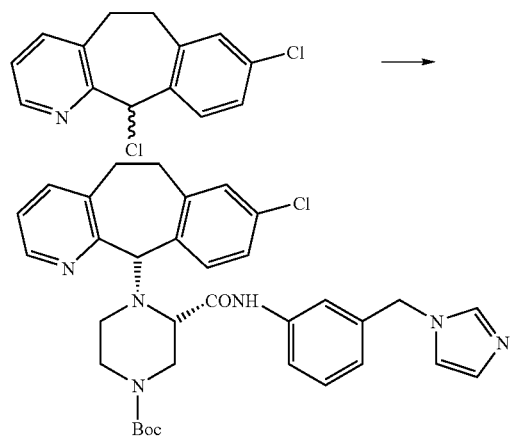

(40.1)
Isomer 1 (Silica gel)

and

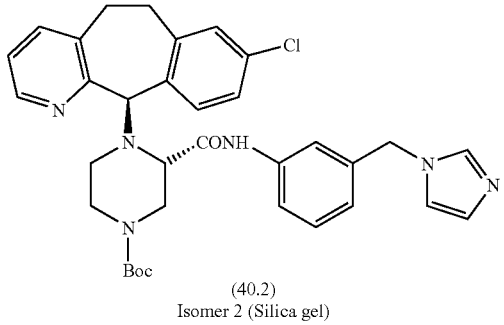

(40.2)
Isomer 2 (Silica gel)

The title compound from Preparative Example 17 (0.9228 g, 2.39 mmoles) and triethylamine (1 mL, 7.18 mmoles) were dissolved in anhydrous dichloromethane (4 mL). 8,11-Dichloro-6,11-dihydro[5,6]-cyclohepta[1,2-b]pyridine (0.822 g, 3.11 mmoles) (prepared from the alcohol as described in Preparative Example 7 in U.S. Pat. No. 5,719,148, (Feb. 17, 1998) dissolved in anhydrous dichloromethane (2.32 mL) was added and the mixture was stirred at 25° C. for 116 h. Additional 8,11-Dichloro-6,11-dihydro[5,6]-cyclohepta[1,2-b]pyridine (0.1265 g, 0.479 mmoles) and triethylamine (0.33 mL, 2.39 mmoles) in anhydrous dichloromethane (0.71 mL) were added and the reaction was allowed to continue at 25° C. for a total of 164 h. The reaction mixture was evaporated to dryness and the residue was chromatographed on silica gel using 1.3.5% (10% conc. NH$_4$OH in methanol)-dichloromethane as the eluant to give first compound (40.1), isomer 1 (silica gel) (0.3152 g., 21%): FABMS: m/z 613.3 (MH$^+$); HRFABMS: m/z 613.2695 (MH$^+$), Calcd. C$_{34}$H$_{38}$N$_6$O$_3$Cl m/z 613.2694; OH (CDCl$_3$) 1.44 (9H, s, CH$_3$), 4.34 (1H, d, CHCON), 5.12 (2H, s, CH$_2$-Im), 5.22 (1H, s, H$_{11}$), 6.86 (1H, d, Ar—H$_{4'}$), 6.95 (1H, s, Im-H$_5$), 7.07-7.13 (2H, d, Ar—H$_{9,10}$), 7.17 (1H, s, Ar—H$_7$), 7.20 (1H, s, Im-H$_4$), 7.22 (1H, dd, Ar—H$_3$), 7.31 (1H, dd, Ar—H$_{5'}$), 7.48 (1H, d, Ar—H$_{6'}$), 7.50 (1H, s, Ar—H$_{2'}$), 7.51 (1H, d, Ar—H$_4$), 7.56 (1H, s, Im-H$_2$), 8.37 (1H, d, Ar—H$_2$) and 9.57 ppm (1H, bs, NHCO); $\delta_C$ (CDCl$_3$) CH$_3$: 28.5, 28.5, 28.5; CH$_2$: 30.8, 31.4, 40.3, 41.8, 44.8, 50.8; CH: 58.7, 74.2, 118.1, 119.1, 119.6, 122.5, 123.7, 126.6, 129.7, 129.7, 130.5, 133.0, 137.6, 140.0, 146.3; C, 79.9, 134.6, 135.1, 135.5, 137.3, 138.8, 141.5, 155.0, 155.8, 168.5; $[\alpha]_D^{20°\ C.}$-77.0° (c=0.49, MeOH). The second product to elute was compound (40.2), isomer 2 (silica gel) (0.4363 g., 30%): FABMS: m/z 613.3 (MH$^+$); HRFABMS: m/z 613.2695 (MH$^+$), Calcd. C$_{34}$H$_{38}$N$_6$O$_3$Cl m/z 613.2694; $\delta_H$ (CDCl$_3$) 1.40 (9H, s, CH$_3$), 4.14 (1H, d, CHCON), 5.09 (2H, s, CH$_2$-Im), 5.27 (1H, s, H$_{11}$), 6.87 (1H, d, Ar—H$_{4'}$), 6.93 (1H, s, Im-H$_5$), 7.07-7.17 (2H, d, Ar—H$_{9,10}$), 7.18 (1H, s, Im-H$_7$), 7.22 (1H, s, Im-H$_4$), 7.22 (1H, d, Ar—H$_3$), 7.26 (1H, dd, Ar—H$_{5'}$), 7.33 (1H, d, Ar—H$_{6'}$), 7.36 (1H, s, Ar—H$_{2'}$), 7.44 (1H, d, Ar—H$_4$), 7.55 (1H, s, Im-H$_2$), 8.33 (1H, d, Ar—H$_2$) and 9.33 ppm (1H, bs, NHCO); $\delta_C$ (CDCl$_3$) CH$_3$: 28.4, 28.4, 28.4; CH$_2$: 31.5, 32.1, 40.5, 41.4, 44.7, 50.7; CH: 60.3, 74.1, 118.0, 119.1, 119.5, 122.7, 123.4, 126.7, 129.7, 129.8, 130.2, 133.0, 137.5, 139.7, 146.7; C, 80.3, 134.5, 134.9, 134.9, 137.3, 138.7, 141.7, 155.0, 155.4, 169.7; $[\alpha]_D^{25°\ C.}$-98.2° (c=0.39, MeOH).

EXAMPLE 41

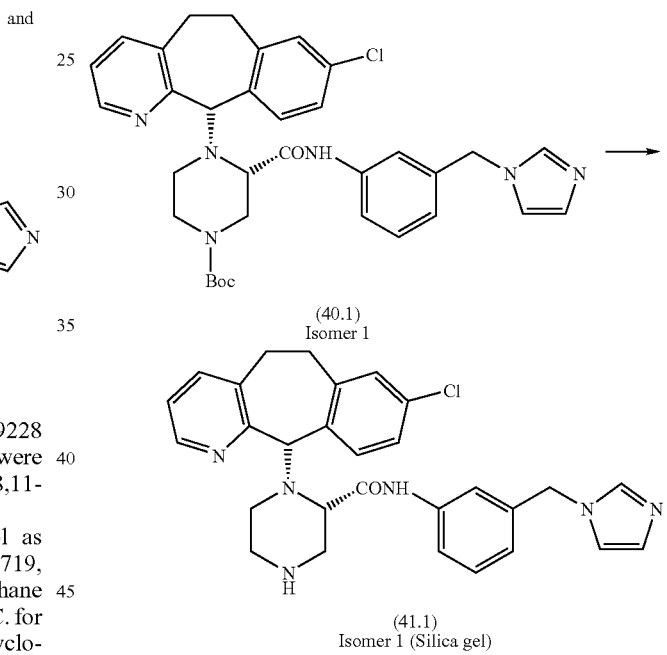

(40.1)
Isomer 1

(41.1)
Isomer 1 (Silica gel)

Compound (40.1), isomer 1 (silica gel) (0.2101 g, 0.343 mmoles) from Example 40 was dissolved in methanol (3.2 mL) and 10% conc. H$_2$SO$_4$-dioxane (v/v) (4.25 mL) was added and the reaction was stirred at 25° C. for 2.25 h. The reaction was worked up as described in Preparative Example 4, Step C, The product was chromatographed on silica gel using 3.5% (10% conc. NH$_4$OH in methanol)-dichloromethane as the eluant to give compound (41.1), isomer 1 (silica gel) (0.1502 g, 85%): FABMS: m/z 513.0 (MH$^+$); HRFABMS: m/z 513.2173 (MH$^+$), Calcd. C$_{29}$H$_{30}$N$_6$OCl m/z 513.2170; $\delta_H$ (CDCl$_3$) 4.27 (1H, m, CHCON), 5.08 (1H, s, H$_{11}$), 5.17 (2H, s, CH$_2$-Im), 6.94 (1H, d, Ar.H$_{4'}$), 6.98 (1H, s, Im-H$_5$), 7.10 (1H, d, Ar—H$_{10}$), 7.11 (1H, d, Ar—H$_9$), 7.12 (1H, s, Ar—H$_7$), 7.20 (1H, s, Im-H$_4$), 7.30 (1H, dd, Ar—H$_3$), 7.37 (1H, dd, Ar—H$_{5'}$), 7.57 (1H, d, Ar—H$_{6'}$), 7.61 (1H, s, Ar—H$_{2'}$), 7.64 (1H, s, Im-H$_2$), 7.68 (1H, d, Ar—H$_4$) and 8.37 ppm (1H, d, Ar—H$_2$); δ$_C$(CDCl$_3$) CH$_2$: 30.1, 31.9, 45.2, 45.2, 47.0, 50.8; CH: 56.4, 73.9, 118.6, 119.5, 119.5, 122.9, 123.9, 126.5, 129.8, 129.9, 130.1, 132.7, 137.6, 141.2, 145.5; C, 134.7, 135.0, 136.4, 137.6, 138.9, 142.0, 155.4, 169.2; [α]$_D^{25°\,C.}$ −183.7° (c=0.53, MeOH).

EXAMPLE 42

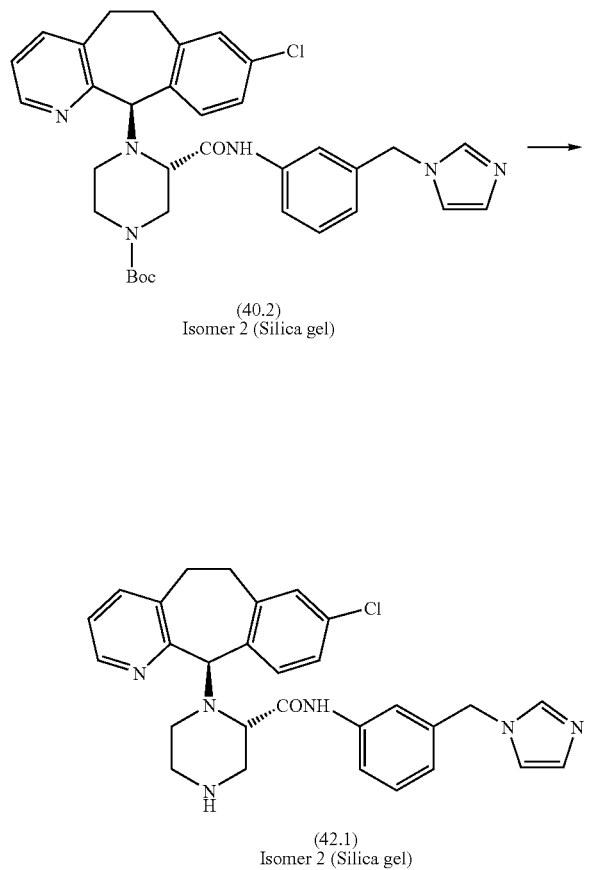

(40.2)
Isomer 2 (Silica gel)

(42.1)
Isomer 2 (Silica gel)

Compound (40.2), isomer 2 (silica gel) (0.3427 g, 0.559 mmoles) from Example 40 was dissolved in methanol (5 mL) and 10% conc. H$_2$SO$_4$-dioxane (v/v) (6.7 mL) was added and the reaction was stirred at 25° C. for 2.25 h. The reaction was worked up as described in Preparative Example 4, Step C, The product was chromatographed on silica gel using 3.5% (10% conc. NH$_4$OH in methanol)-dichloromethane as the eluant to give compound (42.1), isomer 2 (silica gel) (0.2232 g, 78%): FABMS: m/z 512.9 (MH$^+$); HRFABMS: m/z 513.2173 (MH$^+$), Calcd. C$_{29}$H$_{30}$N$_6$OCl m/z 513.2170; δ$_H$(CDCl$_3$) 4.10 (1H, m, CHCON), 5.11 (2H, s, CH$_2$-Im), 5.20 (1H, s, H$_{11}$), 6.85 (1H, d, Ar—H$_{4'}$), 6.95 (1H, s, Im-H$_5$), 7.08 (1H, s, Im-H$_4$), 7.08-7.17 (3H, d, Ar—H$_{3,9,10}$), 7.16 (1H, s, Ar—H$_7$), 7.28 (1H, dd, Ar—H$_3$), 7.39 (1H, d, Ar—H$_4$), 7.41 (1H, d, Ar—H$_{6'}$), 7.48 (1H, d, Ar—H$_4$), 7.52 (1H, s, Ar—H$_{2'}$), 7.57 (1H, s, Im-H$_2$) and 8.30 ppm (1H, d, Ar—H$_2$); δ$_C$ (CDCl$_3$) CH$_2$: 30.8, 31.6, 44.4, 45.4, 45.7, 50.8; CH: 59.0, 76.7, 118.6, 119.5, 119.5, 122.6, 123.2, 126.3, 129.7, 129.7, 130.0, 133.8, 137.6, 139.7, 146.4; C, 134.0, 134.7, 135.2, 137.1, 138.8, 141.4, 156.5, 169.5; [α]$_D^{25°\,C.}$ +64.2° (c=0.61, MeOH).

EXAMPLE 43

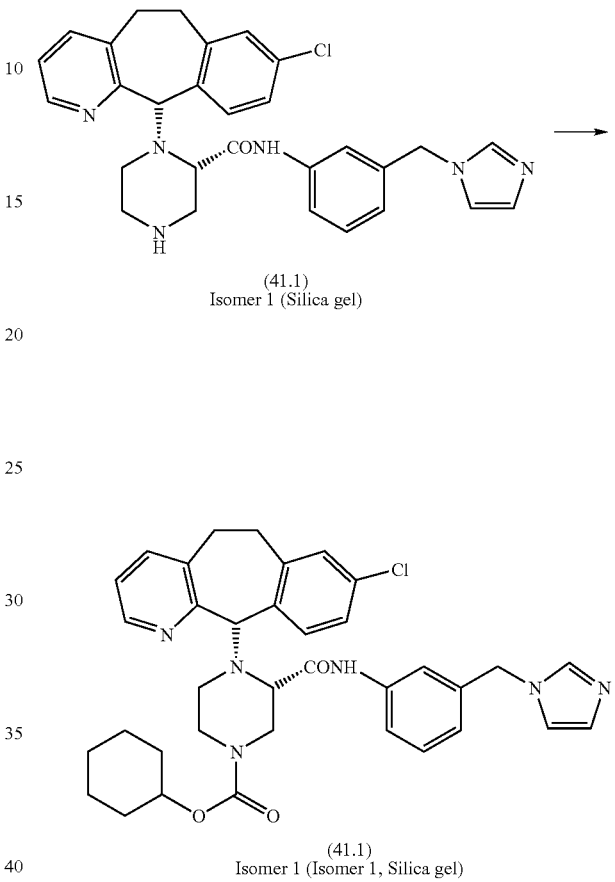

(41.1)
Isomer 1 (Silica gel)

(43.1)
Isomer 1 (Isomer 1, Silica gel)

Compound (41.1), isomer 1 (silica gel) (0.09 g, 0.175 mmoles) (prepared as described in Example 41 above) and triethylamine (0.0732 mL, 0.525 mmoles) were dissolved in anhydrous dichloromethane (3 mL). Cyclohexyl chloroformate (0.0285 g, 0.175 mmoles) in anhydrous dichloromethane (0.09 mL) was added and the reaction was stirred under argon at 25° C. for 45 h. The reaction was worked up as described in Example 15 and the product was chromatographed on silica gel using 2% (10% conc. NH$_4$OH in methanol)-dichloromethane as the eluant to give compound (43.1), isomer 1 (isomer 1, silica gel) (0.1121 g, 72%): FABMS: m/z 639.4 (MH$^+$); HRFABMS: m/z 639.2849 (MH$^+$), Calcd. C$_{36}$H$_{40}$N$_6$O$_3$Cl m/z 639.2850; δ$_H$ (CDCl$_3$) 4.40 (1H, d, CHCON), 5.11 (2H, s, CH$_2$-Im), 5.22 (1H, s, H$_{11}$), 6.85 (1H, d, Ar—H$_4$), 6.94 (1H, s Im-H$_5$), 7.08-7.12 (2H, d, Ar—H$_{9,10}$), 7.14 (1H, s, Ar—H$_7$), 7.19 (1H, s, Im-H$_4$), 7.23 (1H, dd, Ar—H$_3$), 7.30 (1H, dd, Ar—H$_{5'}$), 7.51 (1H, d, Ar—H$_{6'}$), 7.53 (1H, s, Ar—H$_{2'}$), 7.56 (1H, d, Ar—H$_4$), 8.38 (1H, d, Ar—H$_2$) and 9.68 ppm (1H, bs, NHCO); δ$_C$ (CDCl$_3$) CH$_2$: 23.6, 25.5, 26.3, 30.7, 31.5, 31.9, 31.9, ~41.0, 44.7, 50.7, 50.7; CH: ~58.3, 73.4, 74.0, 118.6, 119.1, 119.5, 123.6, 123.8, 126.6, 129.7, 130.5, 130.5, 133.0, 137.6, 140.1, 146.2: C: 134.6, 135.0, ~135.6, 137.3, 138.8, ~141.5, 155.4, 155.7, 168.3; $[\alpha]_D^{25°\ C.}$ -85.8° (c=0.51, MeOH).

EXAMPLE 44

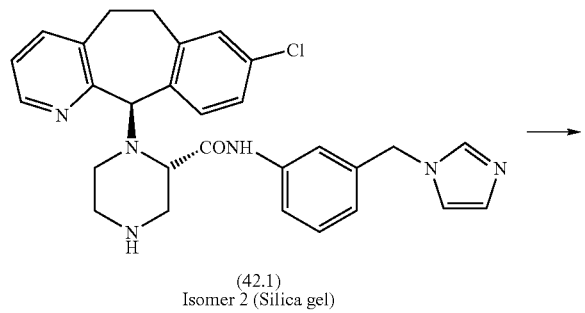

(42.1)
Isomer 2 (Silica gel)

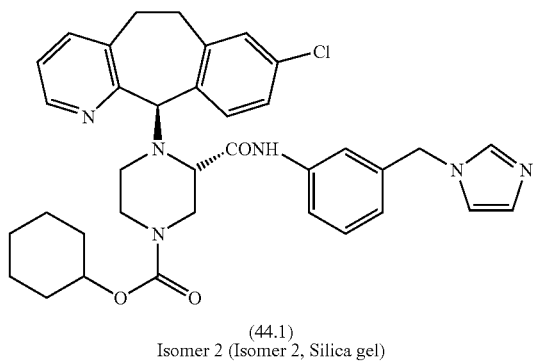

(44.1)
Isomer 2 (Isomer 2, Silica gel)

Compound (42.1), isomer 2 (silica gel) (0.1 g, 0.195 mmoles) (prepared as described in Example 42 above) and triethylamine (0.0813 mL, 0.585 mmoles) were dissolved in anhydrous dichloromethane (3.3 mL). Cyclohexyl chloroformate (0.0317 g, 0.195 mmoles) in anhydrous dichloromethane (0.1 mL) was added and the reaction was stirred under argon at 25° C. for 45 h. The reaction was worked up as described in Example 15 and the product was chromatographed on silica gel using 2% (10% conc. NH$_4$OH in methanol)-dichloromethane as the eluant to give compound (44.1), isomer 2 (isomer 2, silica gel) (0.0912 g, 73%): FABMS: m/z 639.4 (MH$^+$); HRFABMS: m/z 639.2849 (MH$^+$), Calcd. $C_{36}H_{40}N_6O_3Cl$ m/z 639.2850; $\delta_H$ (CDCl$_3$) 4.17 (1H, dd, CHCON), 5.11 (2H, s, CH$_2$-Im), 5.26 (1H, s, H$_{11}$), 6.88 (1H, d, Ar—H$_{4'}$), 6.95 (1H, s, Im-H$_5$), 7.09-7.17 (2H, d, Ar—H$_{9,10}$), 7.18 (1H, s, Ar—H$_7$), 7.23 (1H, Im-H$_4$), 7.23 (1H, dd, Ar—H$_3$), 7.30 (1H, dd, Ar—H$_{5'}$), 7.37 (1H, d, Ar—H$_{6'}$), 7.40 (1H, s, Ar—H$_{2'}$), 7.43 (1H, d, Ar—H$_4$), 7.62 (1H, s, Im-H$_2$), 8.33 (1H, d, Ar—H$_2$) and 9.73 ppm (1H, bs, NHCO); $\delta_C$ (CDCl$_3$) CH$_2$: 23.6, 23.6, 25.5, 31.5, 31.8, 31.9, 32.1, ~41.1, 44.7, 50.8, 50.8; CH: 60.2, 73.7, ~74.0, 118.0, 119.1, 119.7, 122.8, 123.5, 126.8, 129.5, 129.7, 130.2, 133.0, 137.4, 139.8, 146.7; C, 134.5, 134.9, 137.1, 137.1, 138.7, 141.7, 155.3, ~155.4, 169.6; $[\alpha]_D^{25°\ C.}$ +104.8° (c=0.50, MeOH).

EXAMPLE 45

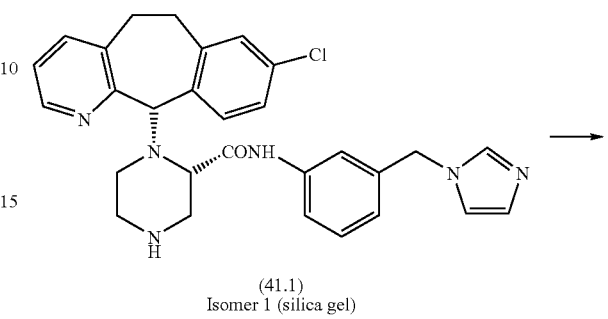

(41.1)
Isomer 1 (silica gel)

(45.1)
Isomer 1 (Isomer 1, Silica gel)

Compound (41.1), isomer 1 (silica gel) (0.0356 g, 0.069 mmoles) (prepared as described in Example 41 above), 1-(3-dimethylaminopropyl)-3-ethylcarbodiimide hydrochloride (0.0173 g, 0.09 mmoles), 1-hydroxybenzotriazole (0.0122 g, 0.09 mmoles) and 4-methylmorpholine (0.0099 mL, 0.09 mmoles) were dissolved in anhydrous DMF (1 mL) and 1-(carboxamidopiperidine)-4-acetic acid (0.0168 g, 0.09 mmoles) was added in anhydrous DMF (1 mL). The mixture was stirred at 25° C. for 166 h. The reaction was then worked up as described in Preparative Example 6, Step A above. The product was chromatographed on silica gel using 3.5% (10% conc. NH$_4$OH in methanol)-dichloromethane as the eluant to give compound (45.1), isomer 1 (isomer 1, silica gel) (0.014 g, 30%): FABMS: m/z 681.2 (MH$^+$); HRFABMS: m/z 681.3066 (MH$^+$), Calcd. $C_{37}H_{42}N_8O_3$ m/z 681.3068; $\delta_H$ (CDCl$_3$) 4.35 (1H, dd, CHCON), 5.14 (2H, s, CH$_2$-Im), 5.30 (1H, s, H$_{11}$), 6.94 (1H, d, Im-H$_5$), 6.97 (1H s, Ar—H$_{4'}$), 7.11 (1H, s, Ar—H$_7$), &.15 (1H, s, Im-H$_4$), 7.15-7.42 (4H, m, Ar—H), 7.47 (1H, s, Ar—H$_{2'}$), 7.54 (1H, d, Ar—H$_{6'}$), 7.68 (1H, d, Ar—H$_4$), 7.69 (1H, s, Im-H$_2$), 8.38 (1H, d, Ar—H$_2$) and 9.77/9.93 ppm (1H, s, NHCO); $\delta_C$ (CDCl$_3$) (Principal rotamer) CH$_2$: 30.7, 31.7, 31.9, 38.4, 38.4, 42.0, 44.3, 44.8, 44.9, 50.8, 50.8; CH: 32.6, 39.0, 58.6, 118.0, 119.0, 119.6, 123.1, 123.9, 126.8, 129.8, 130.8, 130.8, 132.9, 137.4, 137.5, 138.5, 140.2, 146.5; C, 73.5, 134.9, 135.3, 137.4, 141.4, 155.1, 158.2, 168.2, 170.8; $[\alpha]_D^{25°\ C.}$ -58.3° (c=0.17, MeOH).

EXAMPLE 46

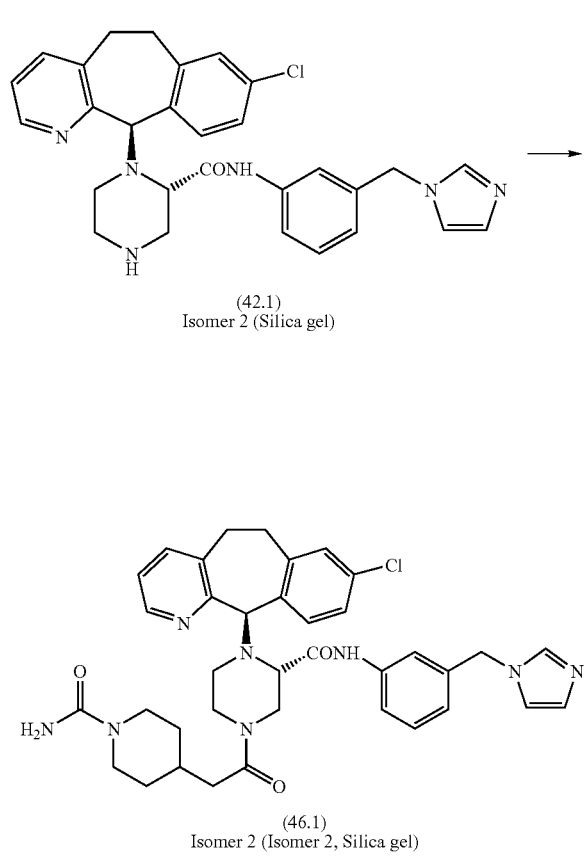

(42.1)
Isomer 2 (Silica gel)

↓

(46.1)
Isomer 2 (Isomer 2, Silica gel)

Compound (42.1), isomer 2 (silica gel) (0.0912 g, 0.178 mmoles) (prepared as described in Example 42 above), 1-(3-dimethylaminopropyl)-3-ethylcarbodiimide hydrochloride (0.0443 g, 0.231 mmoles), 1-hydroxybenzotriazole (0.0312 g, 0.231 mmoles) and 4-methylmorpholine (0.0254 mL, 0.231 mmoles) were dissolved in anhydrous DMF (2 mL) and 1-(carboxamidopiperidine)-4-acetic acid (0.0431 g, 0.231 mmoles) was added in anhydrous DMF (2 mL). The mixture was stirred at 25° C. for 166 h. The reaction was then worked up as described in Preparative Example 6, Step A above. The product was chromatographed on silica gel using 3.5% (10% conc. NH$_4$OH in methanol)-dichloromethane as the eluant to give compound (46.1), isomer 2 (isomer 2, silica gel) (0.059 g, 49%): FABMS: m/z 681.3 (MH$^+$); HRFABMS: m/z 681.3066 (MH$^+$), Calcd. C$_{37}$H$_{42}$N$_8$O$_3$ m/z 681.3068; $\delta_H$ (CDCl$_3$) 4.30 (1H, d, CHCON), 5.12 (2H, d, CH$_2$-Im), 5.28/ 5.30 (1H, s, H$_{11}$), 6.92 (1H, s, Im-H$_5$), 6.94 (1H, d, Ar—H$_{4'}$), 7.10 (1H, s, Ar—H$_7$), 7.14-7.32 (6H, m, Ar—H and Im-H$_4$), 7.36 (1H, s, Ar—H$_{2'}$), 7.41 (1H, d, Ar—H$_{6'}$), 7.60 (1H, s, Im-H$_2$), 8.33 (1H, d, Ar—H$_2$) and 9.30 ppm (1H, s NHCO); $\delta_C$ (CDCl$_3$) (Principal rotamer) CH$_2$: 31.2, 31.9, 32.0, 37.3, 40.4, 44.3, 44.5, 44.6, 50.7, 50.7; CH: 32.6, 38.9, 59.7, 117.7, 118.8, ~119.6, 123.2, 123.7, 127.0, 129.8, 130.4, 130.4, 132.6, 137.5, 137.5, 138.3, 140.2, 146.8; C, 73.3, 134.7, 134.8, 137.5, 141.3, 155.0, 158.2, 169.1, 171.0; $[\alpha]_D^{25°\ C.}$ +80.0° (c=0.23, MeOH).

EXAMPLE 47

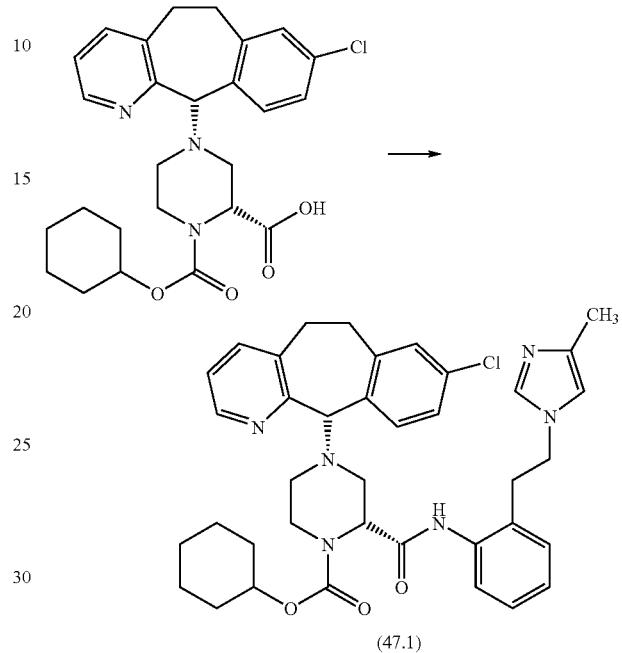

↓

(47.1)

4-(8-Chloro-6,11-dihydro-5H-benzo[5,6]cyclohepta[1,2-b]pyridin-11 (S)-yl)-N-2(R)-piperazinecarboxylic acid (0.402 g, 0.175 mmoles) (prepared as described in U.S. Pat. No. 6,362,188 B1 (Mar. 26, 2002), Preparative Example 32), 1-(2-aminophenyl)-2-(4-methyl-1H-imidazol-1-yl)ethane (0.2508 g, 0.263 mmoles) (prepared as described in Preparative Example 4, Step C above), 1-(3-dimethylaminopropyl)-3-ethylcarbodiimide hydrochloride (0.2388 g, 0.263 mmoles), 1-hydroxybenzotriazole (0.1684 g, 0.263 mmoles) and 4-methylmorpholine (0.1252 g, 0.1361 mL, 0.263 mmoles) were dissolved in anhydrous DMF (3 mL) and the mixture was stirred at 25° C. under argon for 668 h. The reaction was worked up as described in Preparative Example 6, Step A above and the product was chromatographed on silica gel using 2% (10% conc. NH$_4$OH in methanol)-dichloromethane as the eluant to give a product that was further purified on preparative tlc plates (250μ, 20×20 cm) using 4% (10% conc. NH$_4$OH in methanol)-dichloromethane as the eluant to give compound (47.1) (0.1026 g, 19%): FABMS: m/z 667.2 (MH$^+$); HRMS: m/z 667.3162, Calcd. C$_{38}$H$_{44}$N$_6$O$_3$Cl: 667.3163; $\delta_H$ (CDCl$_3$) 3.99 (2H, m, CH$_2$-Im), 4.72 (1H,bs, H$_{11}$), 7.05-7.42 (11H, s and m, Ar—H and Im-H) and 8.32 ppm (1H, d, H$_2$); $\delta_C$ (CDCl$_3$) CH$_3$: 13.7; CH$_2$: 23.7, 23.7, 25.5, 30.6, 30.9, 32.0, 32.0, 34.0, 42.3, 51.3, 53.6, 54.0; CH: 51.9, 74.7, 80.0, 115.5, 123.4, 126.0, 126.1, 126.7, 128.2, 130.2, 130.2, 131.0, 136.4, 139.3, 146.3; C, 134.3, 134.3, 135.3, 135.5, 141.9, 156.9, 156.9, 169.3; $[\alpha]_D^{20°\ C.}$ -30.0° (c=0.51, MeOH).

Assays

FPT activity was determined by measuring the transfer of [$^3$H] farnesyl from [$^3$H] farnesyl pyrophosphate to a biotinylated peptide derived from the C-terminus of H-ras (biotin- CVLS). The reaction mixture contains: 50 mM Tris pH7.7, 5 mM MgCl$_2$, 5 µM Zn$^{++}$, 5 mM DTT, 0.1% Triton-X, 0.05 µM peptide, 0.03 nM purified human farnesyl protein transferase, 0.180 µM [$^3$H] farnesyl pyrophosphate, plus the indicated concentration of tricyclic compound or vehicle control in a total volume of 100 µl. The reaction was incubated in a Vortemp shaking incubator at 37° C., 45 RPM for 60 minutes and stopped with 150 µl of 0.25 M EDTA containing 0.5% BSA and 1.3 mg/ml Streptavidin SPA beads. Radioactivity was measured in a Wallach 1450 Microbeta liquid scintillation counter. Percent inhibition was calculated relative to the vehicle control.

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of farnesyl transferase inhibitor as the top layer. After the top layer is solidified, plates can be incubated for 10-16 days at 37° C. under 5% CO$_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the IC$_{50}$'s can be determined.

Compounds (1.3), (1.4), (2.1), (3.1), (4.1), (4.2), (4.3), (4.4), (5.1), (6.1), (7.1), (8.1), (9.1), (10.1), (11.2), (11.3), (12.1), (12.2), (13.2), (13.3), (14.2), (14.3), (15.1), (15.2), (16.1), (17.1), (18.1), (19.1), (20.1), (20.2), (20.3), (20.4), (21.1), (22.1), (24.1), (25.1), (26.1), (27.1), (28.1), (29.1), (30.1), (31.1), (31.2), (32.1), (32.2), (33.1), (33.2), (34.1), (34.2), (35.1), (36.1), (37.1), (38.1), (39.1), (40.1), (40.2), (41.1), (42.1), (43.1), (44.1), (45.1), (46.1), and (47.1) had an FPT IC$_{50}$ within the range of about <0.05 nM to about >200 nM (e.g., about <0.05 nm to about 180 nM).

Compounds (1.3), (1.4), (4.2), (4.3), (5.1), (6.1), (12.1), (12.2), (13.2), (13.3), (14.2), (14.3), (15.1), (15.2), (16.1), (21.1), (22.1), (26.1), (27.1), (28.1), (29.1), (30.1), (31.1), (31.2), (32.1), (32.2), (45.1) and (47.1) had an FPT IC$_{50}$ within the range of about <0.05 nM to about 8.9 nM.

Compounds (1.3), (1.4), (5.1), (6.1), (15.1), (15.2), (21.1), (22.1), (26.1), (28.1), (29.1), (30.1), (31.1), and (32.1) had an FPT IC$_{50}$ within the range of about <0.05 nM to about 2.7 nM.

Compounds (1.3), (1.4), (15.1), (15.2), (21.1), (22.1), (26.1), (28.1), (29.1), (30.1), (31.1), and (32.1) had an FPT IC$_{50}$ within the range of about <0.05 nM to about 1.2 nM.

Compound (31.1) had an FPT IC$_{50}$ of about 0.31 nM.

Compounds (1.3), (1.4), (4.1), (4.2), (4.3), (5.1), (6.1), (12.1), (12.2), (13.2), (13.3), (14.1), (14.2), (14.3), (15.1), (15.2), (16.1), (17.1), (19.1), (20.1), (20.2), (20.3), (21.1), (22.1), (24.1), (25.1), (28.1), (30.1), (31.1), (31.2), (32.1), (32.2), (34.1), (37.1), (38.1), (39.1), (40.1), (40.2), (43.1), (44.1), (45.1), and (46.1) had a Soft Agar IC$_{50}$ within the range of about <0.3 nm to about >500 nM.

Compounds (1.3), (1.4), (4.2), (4.3), (5.1), (6.1), (13.2), (14.1), (14.2), (14.3), (15.1), (15.2), (16.1), (21.1), (22.1), (28.1), (30.1), (31.1), (31.2), (32.1), (32.2), (40.1), (40.2), and (45.1) had a Soft Agar IC$_{50}$ within the range of about <0.3 nM to about >50 nM.

Compounds (1.3), (1.4), (5.1), (6.1), (15.1), (21.1), (22.1), (28.1), (30.1), (31.1), (31.2), (32.1), (32.2), (40.1), (40.2) and (45.1) had a Soft Agar IC$_{50}$ within the range of about <0.3 nM to about <5.0 nM.

Compounds (15.1), (28.1), (30.1), (31.1), and (32.1) had a Soft Agar IC$_{50}$ within the range of about <0.3 nM to about 1.0 nM.

Compound (31.1) had a Soft Agar IC$_{50}$ of about <0.5 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., which is incorporated by reference herein.

Liquid form preparations include solutions, suspensions and emulsions. As an example, water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations, which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of Formula 1.0:

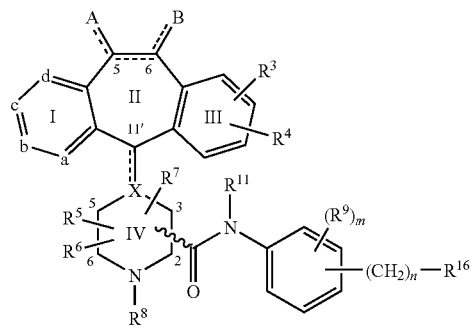

and the pharmaceutically acceptable salts thereof, wherein: the moiety

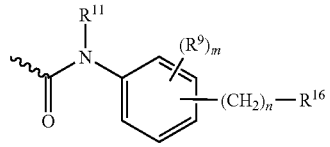

is bound to the 2- or 3-position of Ring IV (wherein the $R^5$, $R^6$, and/or $R^7$ substituents are bound to the remaining 2-, 3-, 5-, and 6-positions of Ring IV), and wherein the moiety

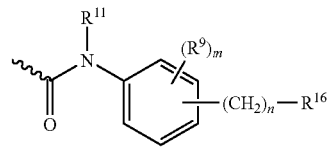

(1) is selected from the group of:

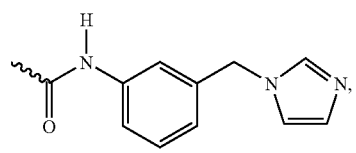

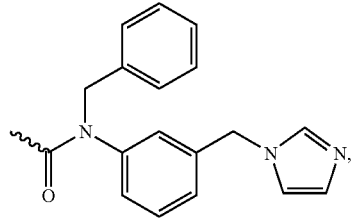

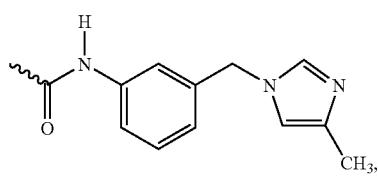

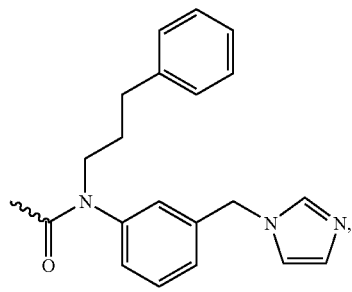

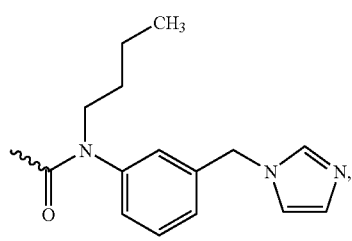

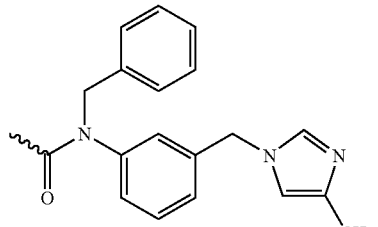

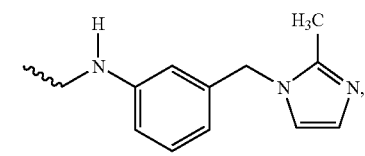

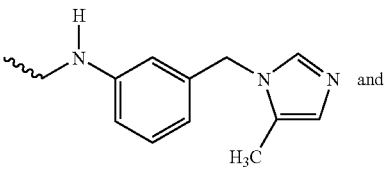

and

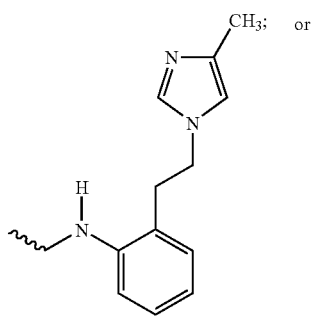

(2) is selected from the group consisting of:

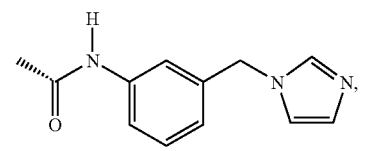

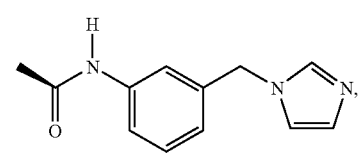

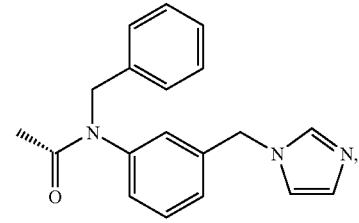

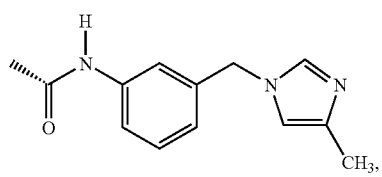

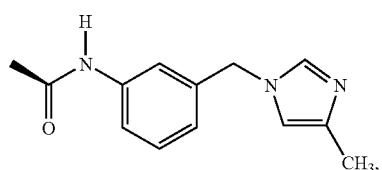

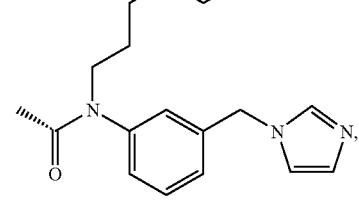

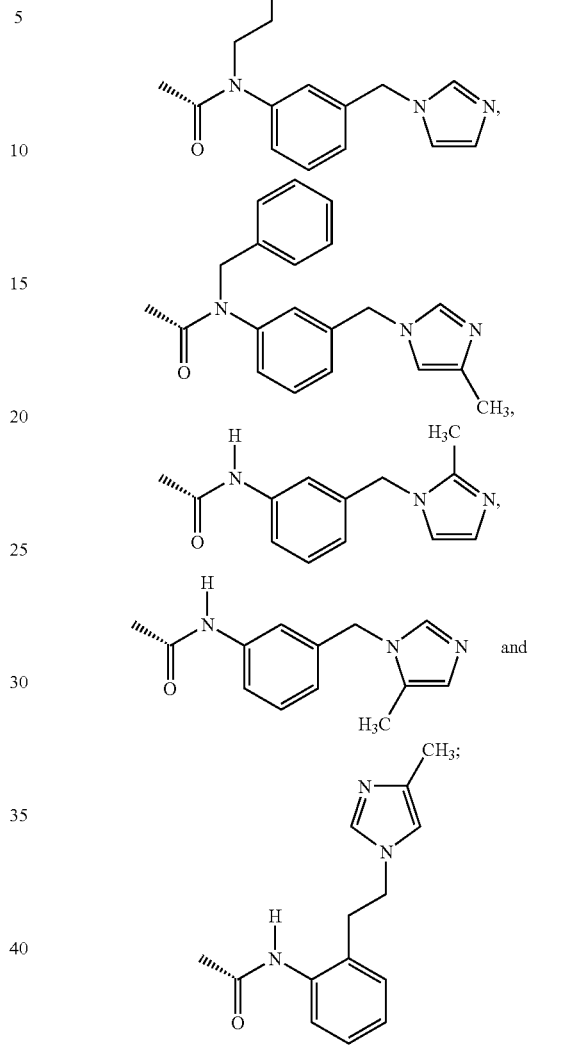

a is N, and b, c and d are $CR^1$;

each $R^1$ is independently selected from the group consisting of: H, halo, —$CF_3$, —$OR^{20}$, —$COR^{20}$, —$SR^{20}$, —$S(O)_tR^{21}$ (wherein t is 0, 1 or 2), —$N(R^{20})(R^{21})$, —$NO_2$, —$OC(O)R^{20}$, —$CO_2R^{20}$, —$OCO_2R^{21}$, —CN, —$NR^{20}COOR^{21}$, —$SR^{20}C(O)OR^{21}$, —$SR^{21}N(R^{75})_2$ (provided that $R^{21}$ in —$SR^{21}N(R^{75})_2$ is not —$CH_2$—), alkynyl, alkenyl and alkyl, wherein said alkyl or alkenyl group is optionally substituted with one or more substitutents selected from the group consisting of: halo, —$OR^{20}$ or —$CO_2R^{20}$, and wherein each $R^{75}$ is independently selected from H or —$C(O)OR^{21}$;

$R^3$ and $R^4$ are each independently selected from the group consisting of H and halo;

$R^5$, $R^6$, and $R^7$ are each H;

t is 0, 1 or 2;

each dotted line represents an optional bond;

X represents N and the optional bond to carbon atom 11 is absent;

the optional bond between carbon atoms 5 and 6 is absent, and the optional bond from carbon atom 5 to A is present, and the optional bond form carbon atom 6 to B is present, and A and B are each independently selected from the group consisting of: =O, =NOR$^{20}$, —O—(CH$_2$)$_p$—O—, the pair H and H, the pair —OR$^{21}$ and —OR$^{21}$, the pair H and halo, the pair halo and halo, the pair alkyl and H, the pair alkyl and alkyl, the pair —H and —OC(O)R$^{20}$, the pair H and —OR$^{20}$, and the pair aryl and H;

p is 2, 3 or 4;

R$^8$ is selected from the group consisting of:

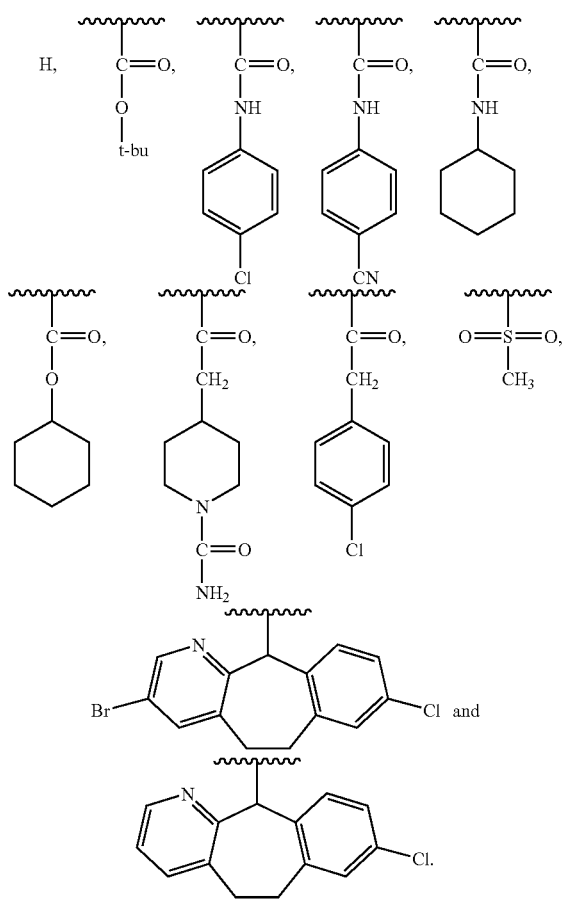

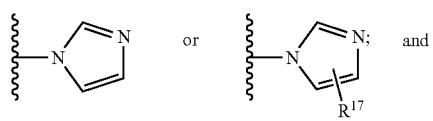

R$^{11}$ is selected from the group consisting of: H, benyl, 3-phenylpropyl and n-butyl;

R$^{16}$ is

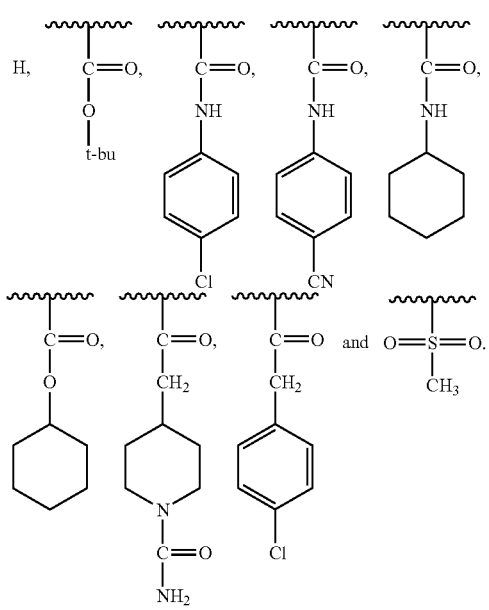

R$^{17}$ is methyl;

R$^{20}$ represents H, alkyl aryl, or aralkyl;

R$^{21}$ represents H, alkyl, aryl, or aralkyl; and n is 1 or 2.

2. The compound of claim 1 wherein R$^1$ is selected from the group consisting of H and halo.

3. The compound of claim 1 wherein R$^1$ is selected from the group consisting of H and Br.

4. The compound of claim 1 wherein R$^1$ is H.

5. The compound of claim 1 wherein a is N, and c is CR$^1$ wherein R$^1$ is halo, and the remaining b and d groups are CR$^1$ wherein R$^1$ is H.

6. The compound of claim 1 wherein a is N, and c is CR$^1$ wherein R$^1$ is Br, and the remaining b and d groups are CR$^1$ wherein R$^1$ is H.

7. The compound of claim 1 wherein the optional bond between C-5 and C-6 is absent, and the optional bond from C-5 to A and the optional bond from C-6 to B are present, and A represents H$_2$, and B represents H$_2$.

8. The compound of claim 1 wherein R$^3$ and R$^4$ are independently selected from the group consisting of: H and halo wherein at least one of R$^3$ and R$^4$ is halo.

9. The compound of claim 1 wherein R$^3$ and R$^4$ are independently selected from the group consisting of: H, Br, and Cl.

10. The compound of claim 1 wherein R$^3$ and R$^4$ are independently selected from the group consisting of: H, Br and Cl wherein at least one of R$^3$ and R$^4$ is other than H.

11. The compound of claim 1 wherein R$^8$ is selected from the group consisting of:

12. The compound of claim 1 wherein R$^{12}$ is selected from the group consisting of: C$_1$ to C$_6$ alkyl, cyclohexyl, piperidinyl substituted on the nitrogen with —C(O)NH$_2$, halophenyl and cyanophenyl.

13. The compound of claim 1 wherein:
(1) each R$^1$ is independently selected from the group consisting of: H or Br, and
(2) R$^3$ and R$^4$ are independently selected from the group consisting of: H, Br, and Cl.

14. The compound of claim 1 wherein:
(1) (i) R$^1$ is H, or (ii) one of b, c, and d is CR$^1$ wherein R$^1$ is halo and the remaining b, c, and d groups are CR$^1$ wherein R$^1$ is H,
(2) A represents H$_2$ and B represents H$_2$, and
(3) R$^3$ and R$^4$ are independently selected from the group consisting of: H, Br and Cl wherein at least one of R$^3$ and R$^4$ is other than H.

15. The compound of claim 14 wherein:

(1) (i) R¹ is H, or (ii) one of b, c, and d is CR¹ wherein R¹ is Br and the remaining b, c, and d groups are CR¹ wherein R¹ is H.

16. The compound of claim 14 wherein R⁸ is selected from the group consisting of:

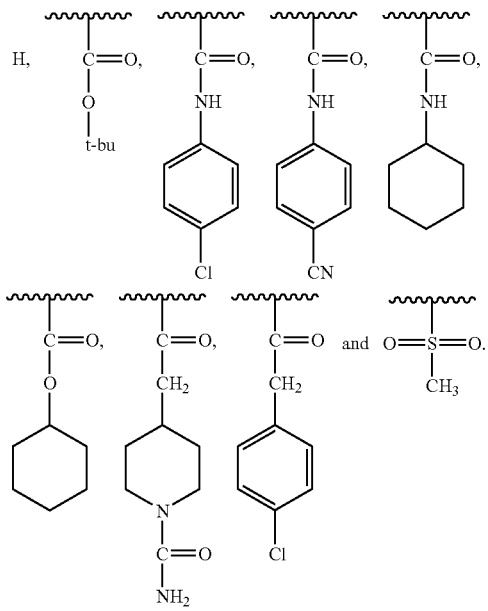

17. The compound of claim 1 wherein the

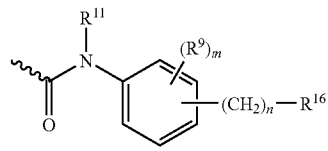

moiety is selected from the group consisting of:

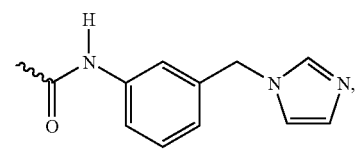

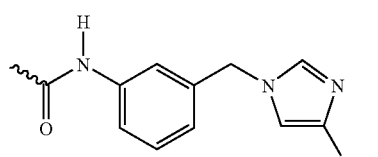

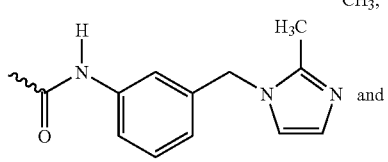

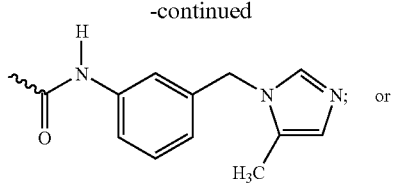

wherein the

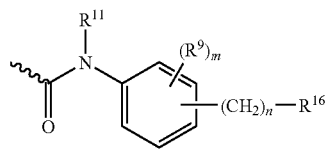

moiety is selected from the group consisting of:

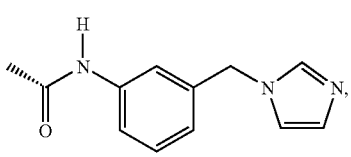

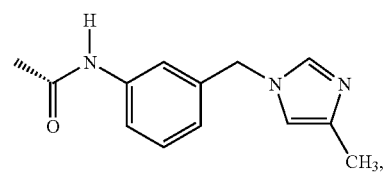

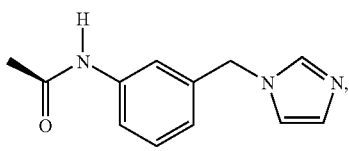

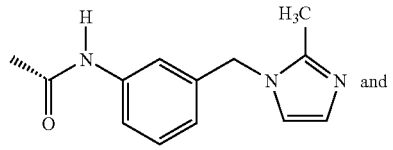

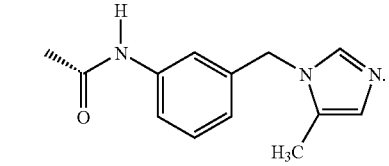

18. The compound of claim 1 wherein the

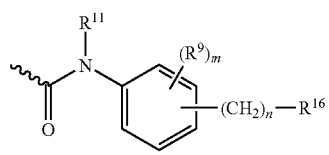

moiety is selected from the group consisting of:
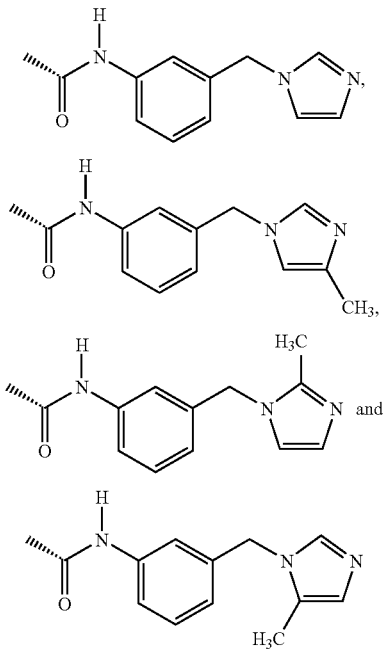
and
19. The compound of claim 1 wherein the
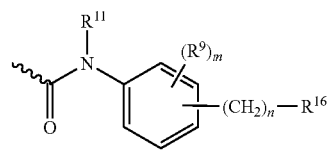
moiety is selected from the group consisting of:
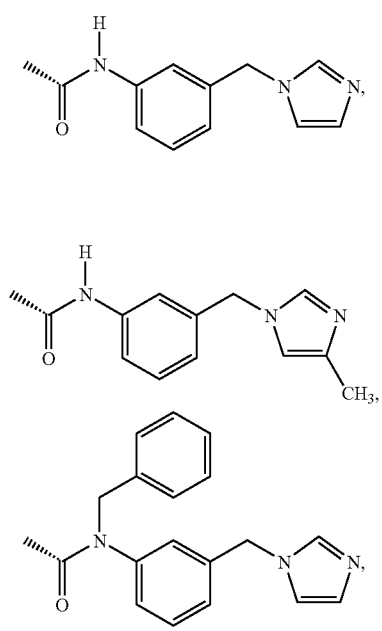
-continued
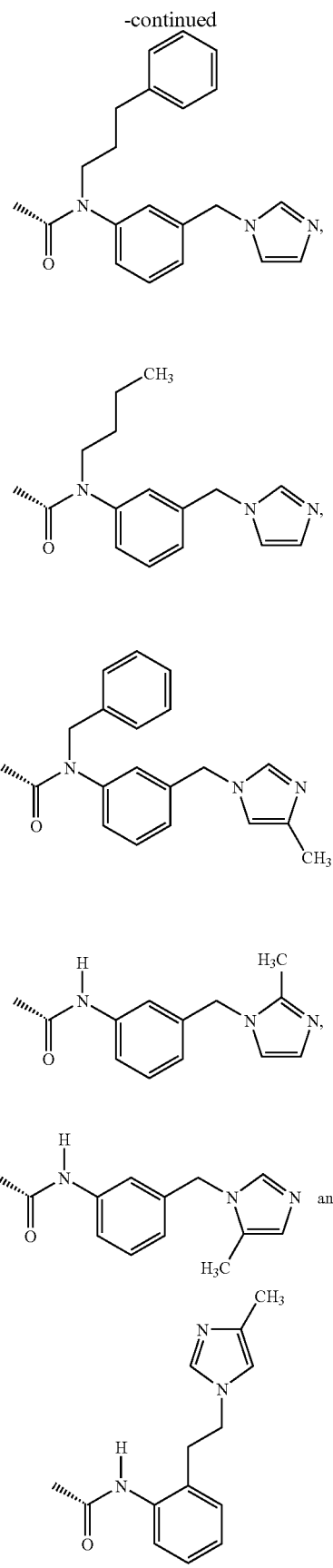

and the compound of formula 1.0 is a compound of formula 4.0:
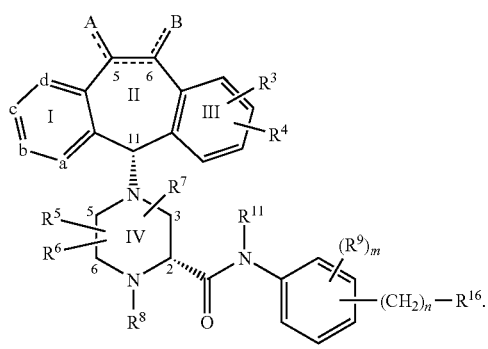
(4.0)
20. The compound of claim 1 wherein the
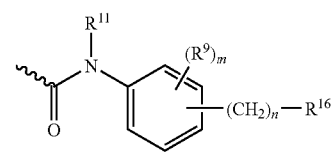
moiety is selected from the group consisting of:
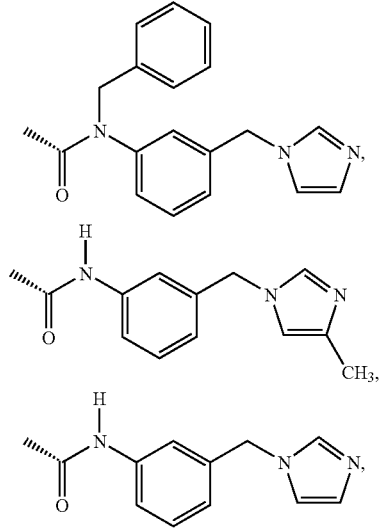
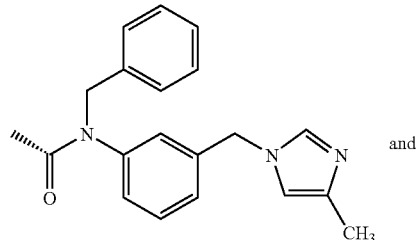
and
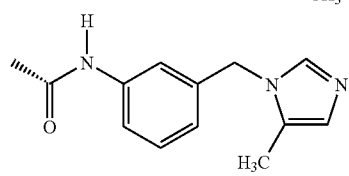
and the compound of formula 1.0 is a compound of formula 5.0:
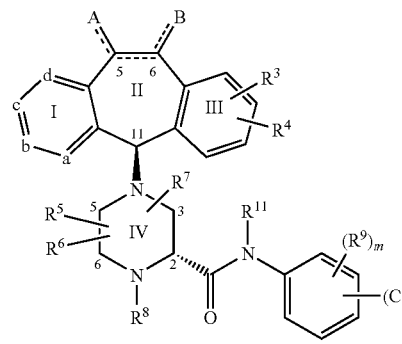
(5.0)
21. The compound of claim 1 wherein:
(1) the
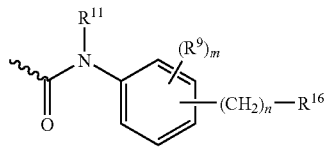
moiety is
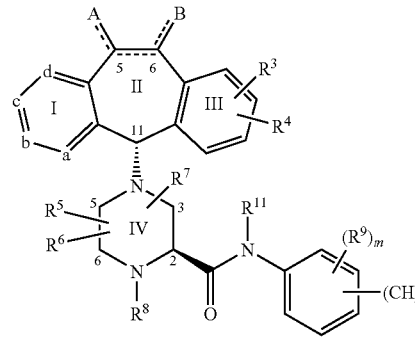
and the compound of formula 1.0 is a compound of formula 4.0A:
(4.0A)
; or (2) the
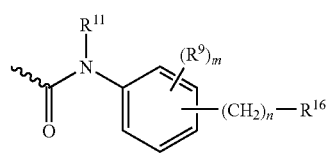
moiety is
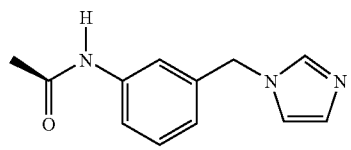
and the compound of formula 1.0 is a compound of formula 5.0A:
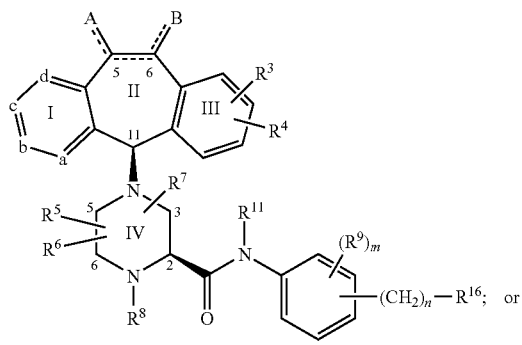
(3) the
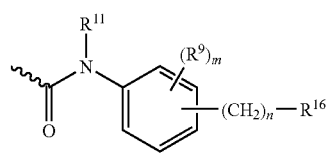
moiety is
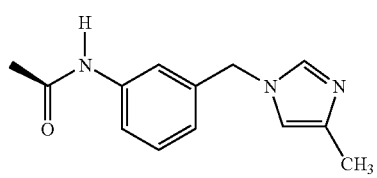
and the compound of formula 1.0 is a compound of formula 7.0A:
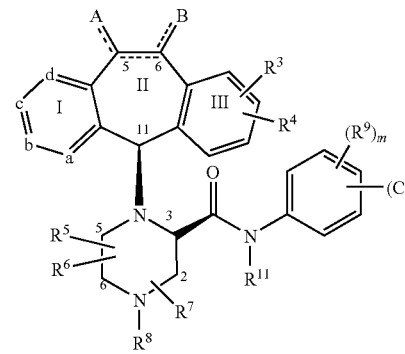
(4) the
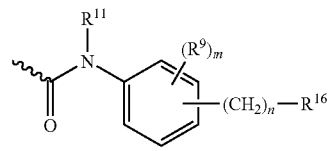
moiety is
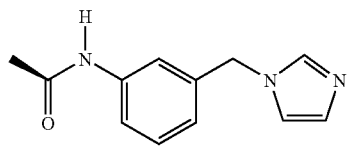
and the compound of formula 1.0 is a compound of formula 7.0A
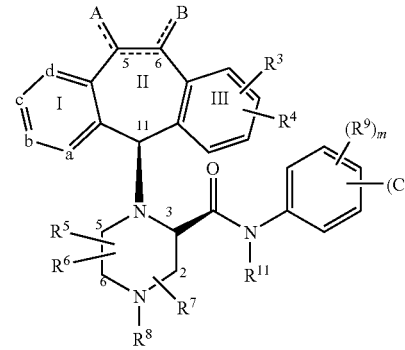

(5) the
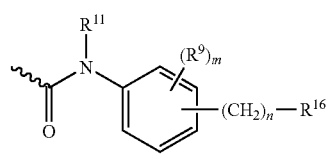
moiety is
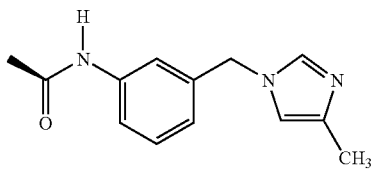
and the compound of formula 1.0 is a compound of formula 7.0B:
(7.0B)
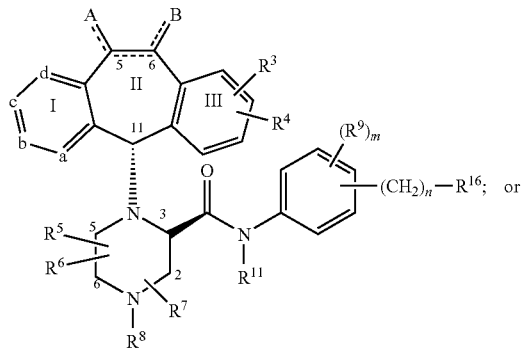
(6) the
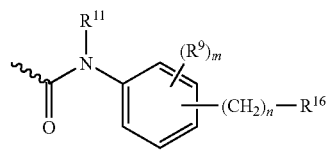
moiety is
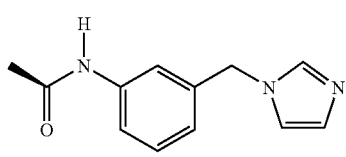
and the compound of formula 1.0 is a compound of formula 7.0B:
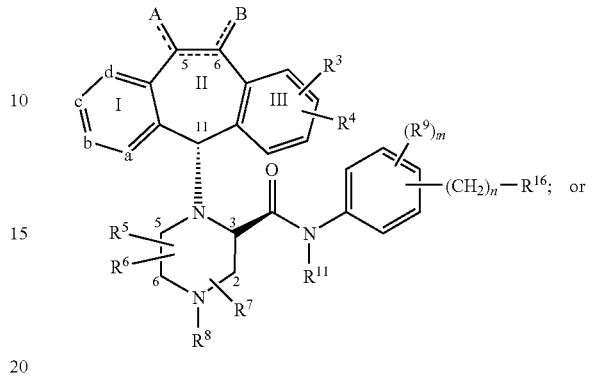
(7) the
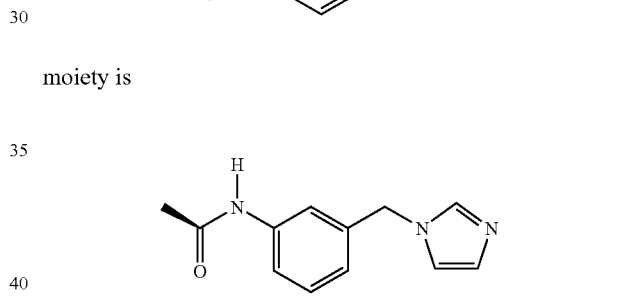
moiety is
and the compound of formula 1.0 is a compound selected from the group consisting of formulas 8.0B, 8.0D, 8.0F, and 8.0H:
(8.0B)
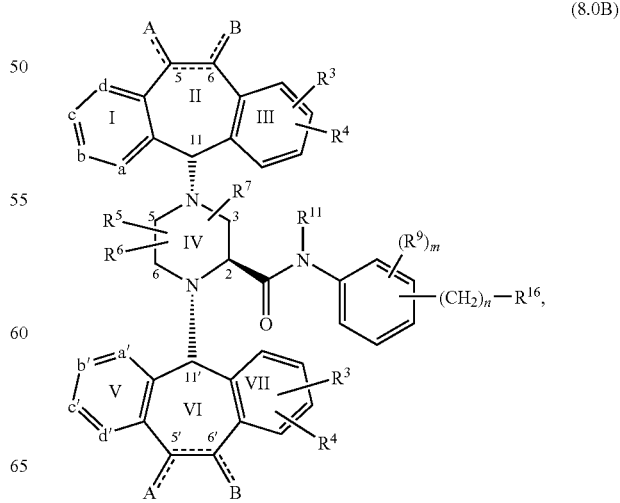

-continued
(8.0D)
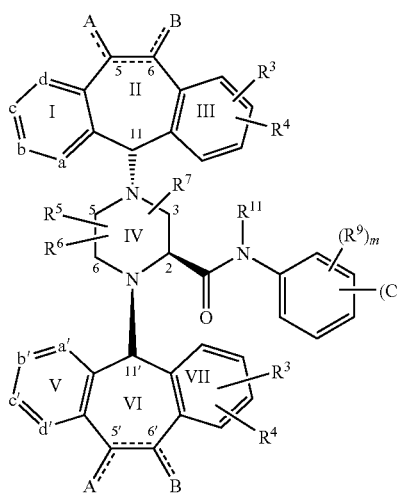
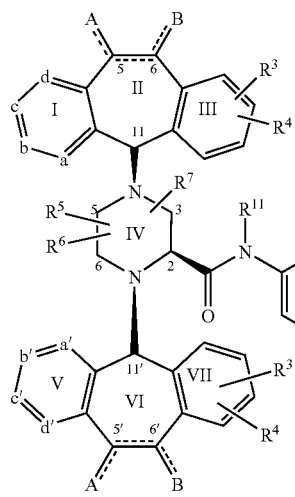
wherein the moiety
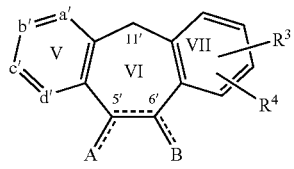
in (8.0B), (8.0D) and (8.0F) is
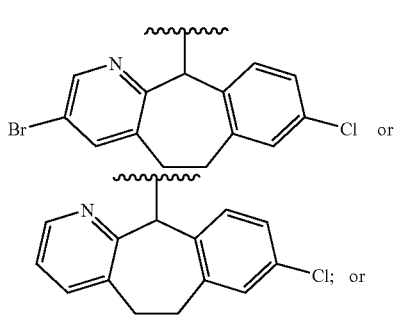
(8) the
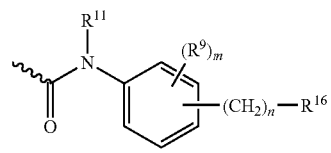
moiety is
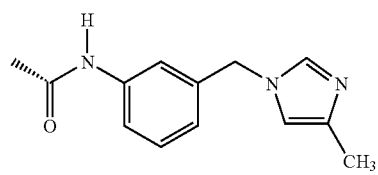
and the compound of formula 1.0 is a compound selected from the group consisting of formulas 8.0A, 8.0C, 8.0E, and 8.0G:
(8.0A)
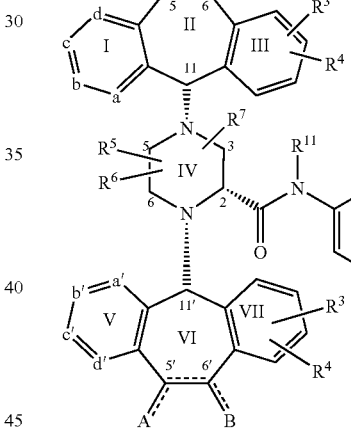
(8.0C)
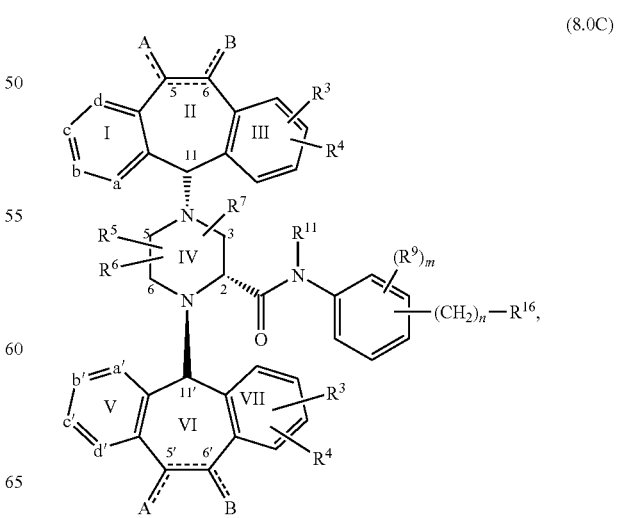

-continued
(8.0E)
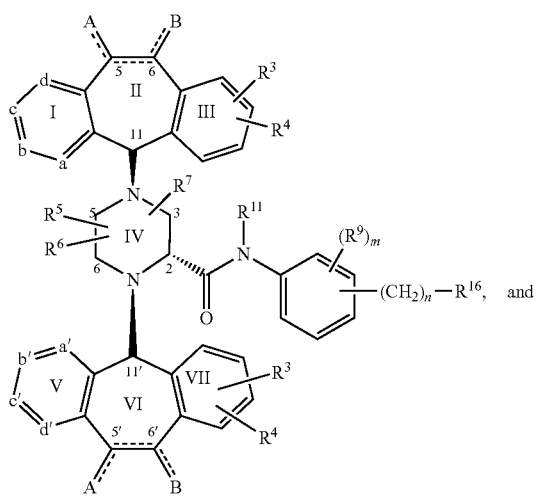
(8.0G)
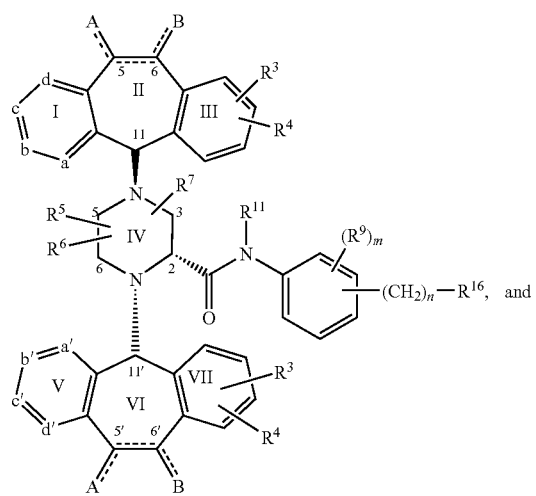
wherein the moiety
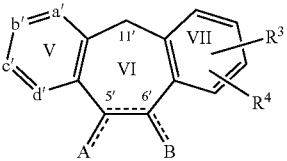
in (8.0A), (8.0C), (8.0E) and (8.0G) is
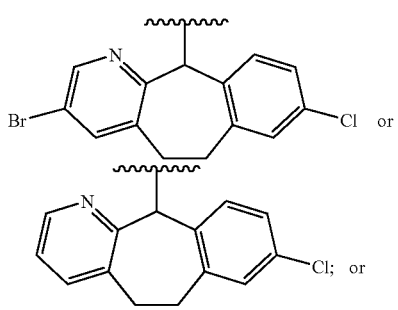
(9) the
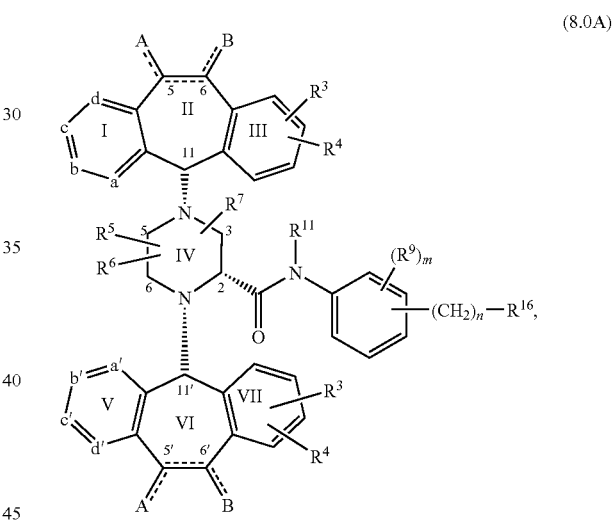
moiety is
and the compound of formula 1.0 is a compound selected from the group consisting of formulas 8.0A, 8.0C, 8.0E, and 8.0G:
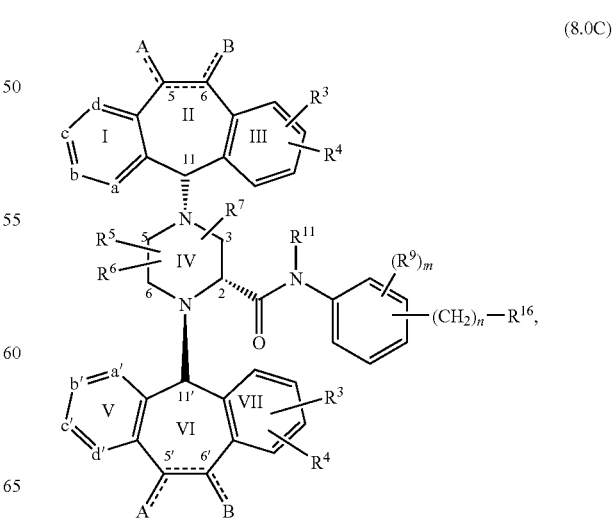

-continued
(8.0E)
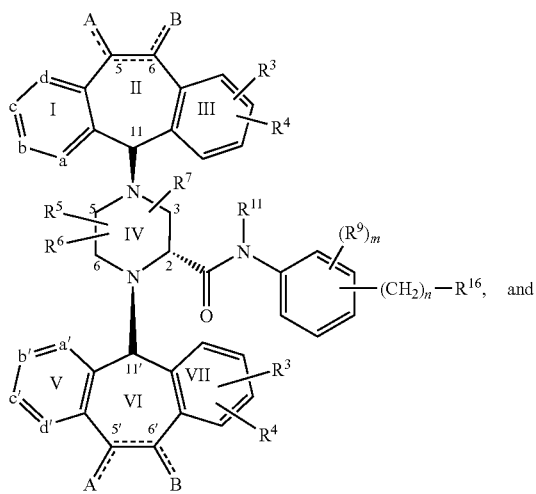
(8.0G)
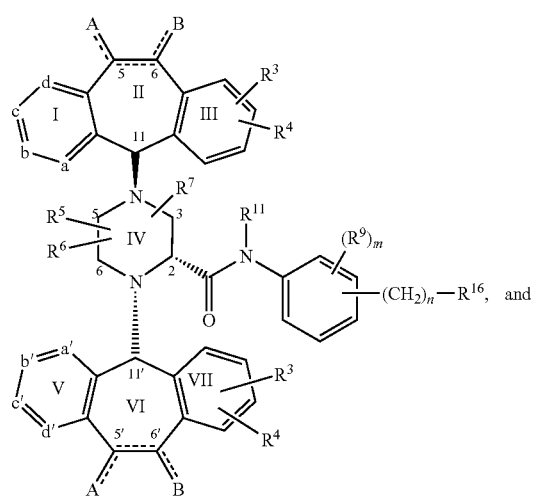
wherein the moiety
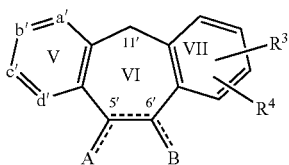
in (8.0A), (8.0C), (8.0E) and (8.0G) is
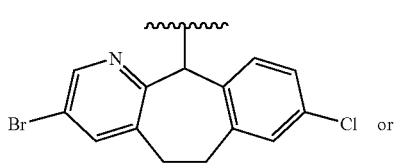
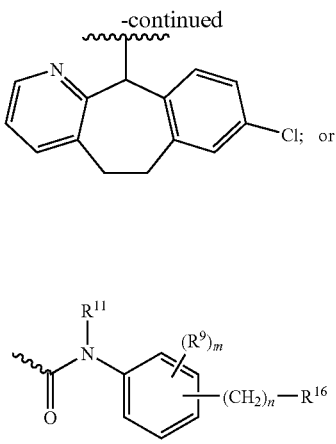
(10) the
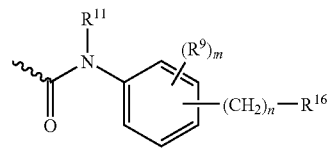
moiety is
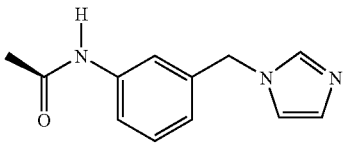
and the compound of formula 1.0 is a compound selected from the group consiting of of formulas 4.0A and 5.0A:
(4.0A)
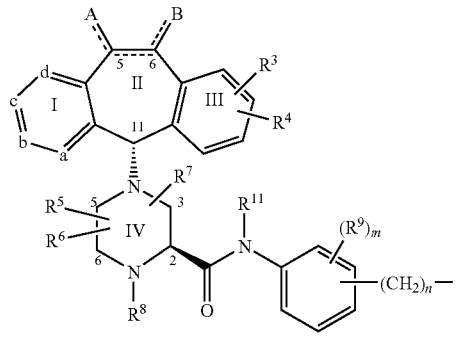
(5.0A)
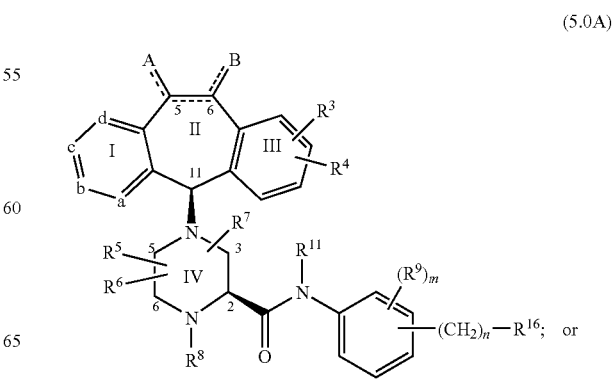

(11) the
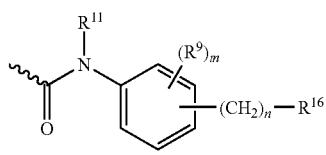
moiety is
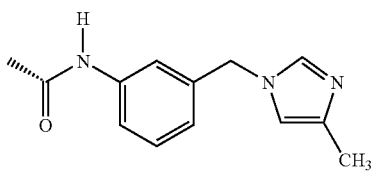
and the compound of formula 1.0 is a compound selected from the group consisting of formulas 7.0A and 7.0B:
(7.0A)
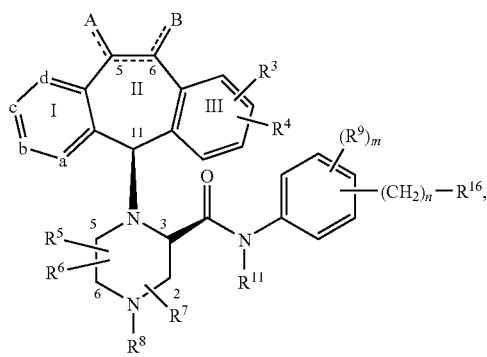
(7.0B)
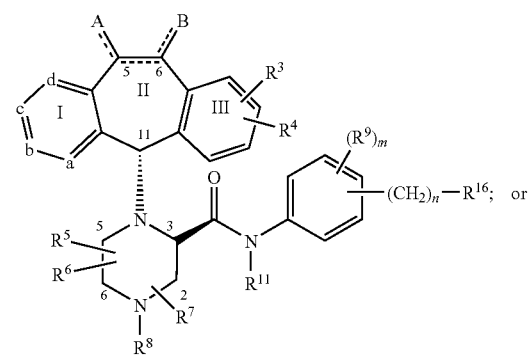
(12) the
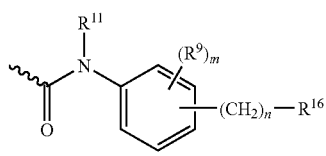
moiety is
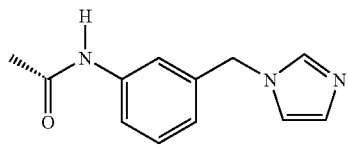
and the compound of formula 1.0 is a compound of formula 7.0:
(7.0)
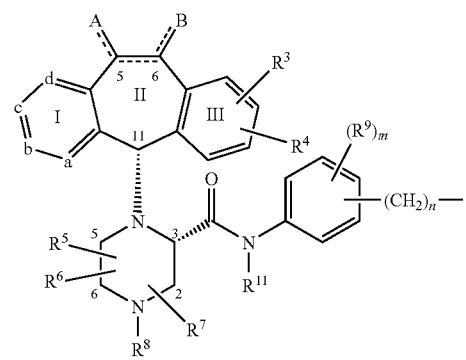
(13) the
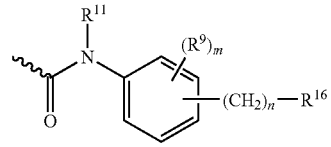
moiety is
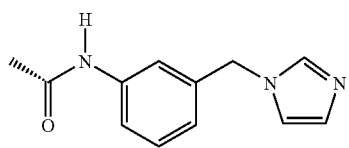
and the compound of formula 1.0 is a compound of formula 7.0C:
(7.0C)
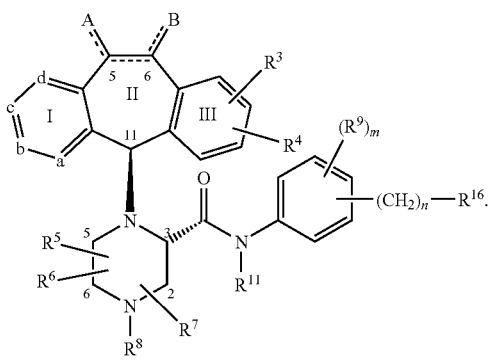

22. The compound of claim 1 wherein $R^8$ is selected from the group consisting of:
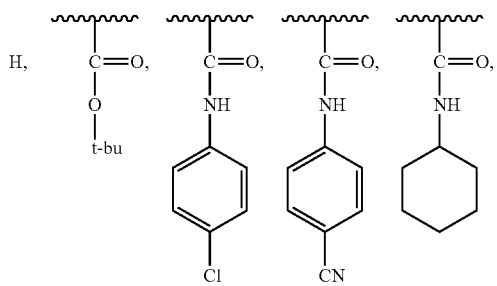
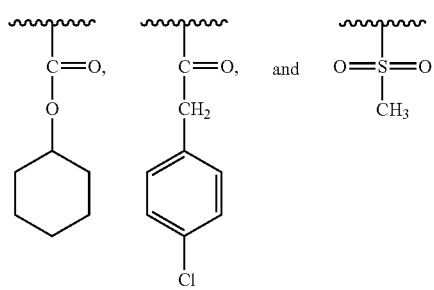
and the compound of formula 1.0 is a compound of formula 4.0:
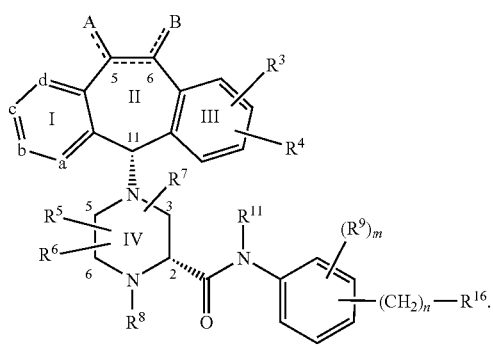
(4.0)
23. The compound of claim 1 wherein $R^8$ is selected from the group consisting of:
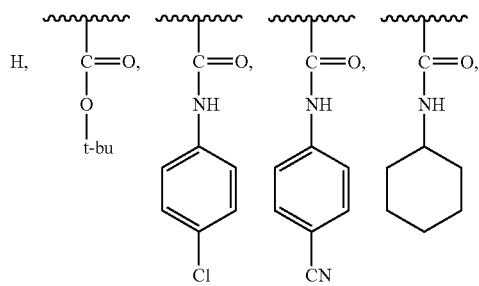
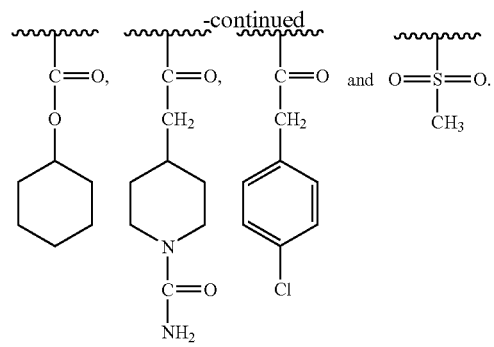
and the moiety
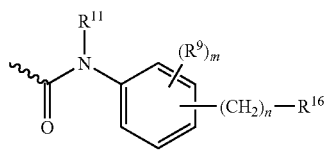
is selected from the group consisting of:
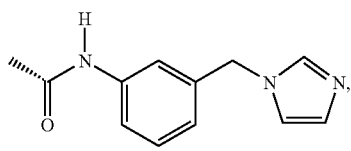
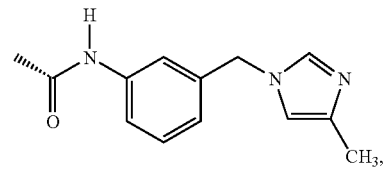
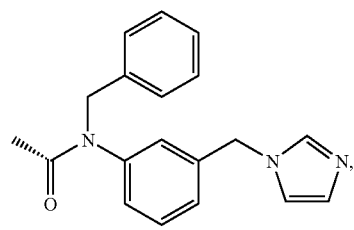
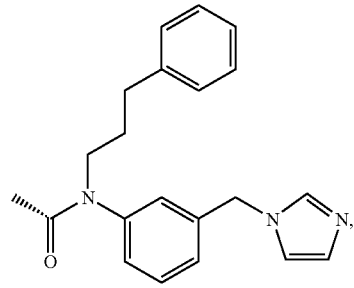

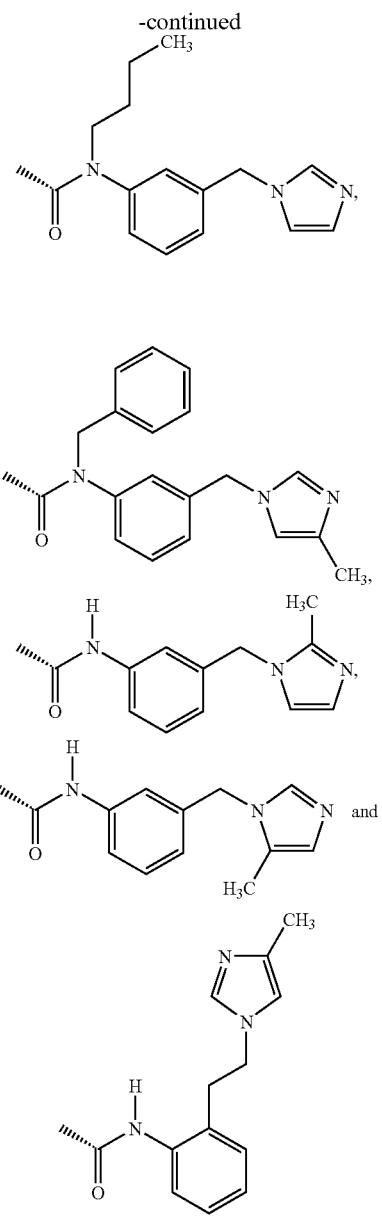
and the compound of formula 1.0 is a compound of formula 4.0:
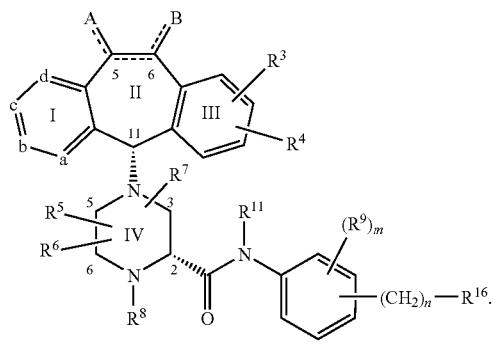
(4.0)
24. The compound of claim 1:
(1) wherein $R^8$ is selected from the group consisting of:
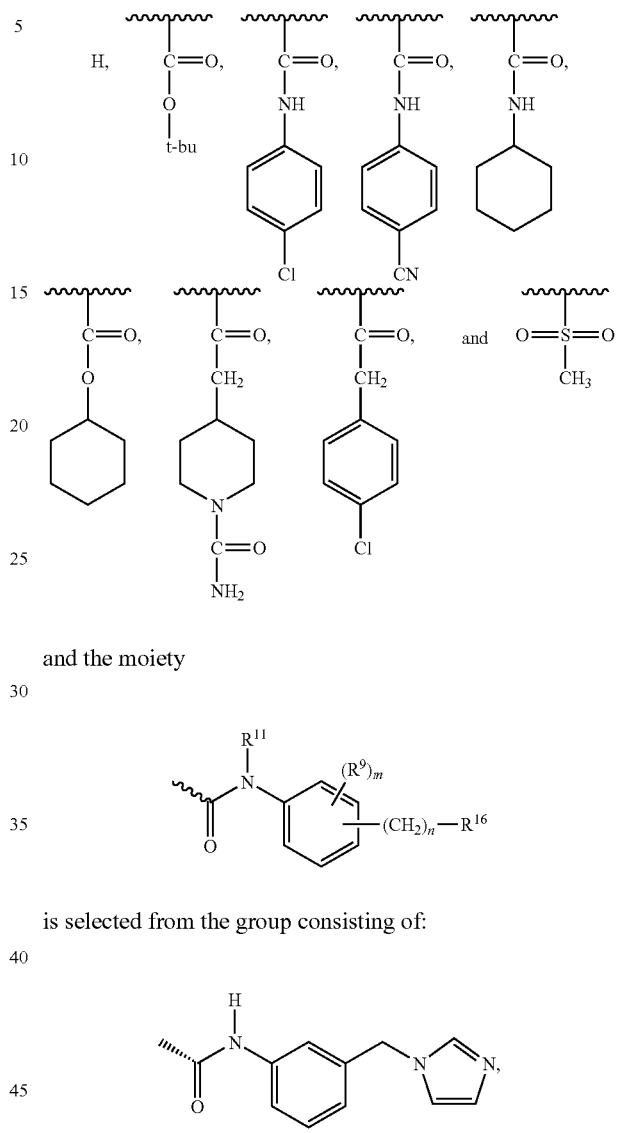
and the moiety
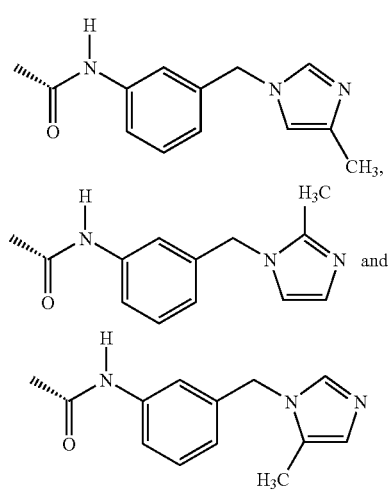
is selected from the group consisting of:

and the compound of formula 1.0 is a compound of formula 4.0:
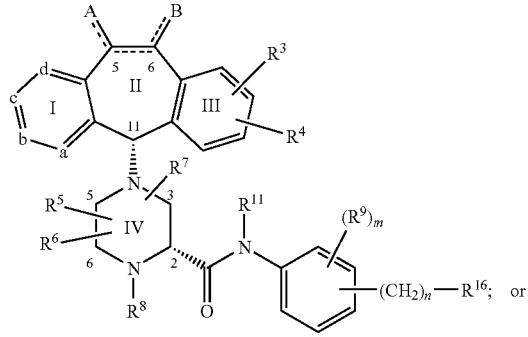
(4.0)
(2) wherein $R^8$ is selected from the group consisting of:
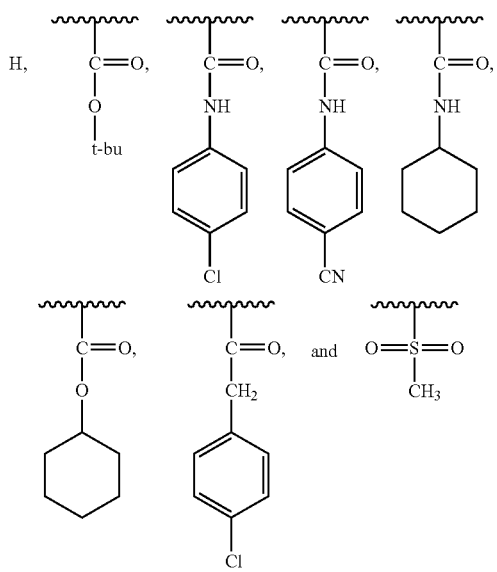
and the moiety
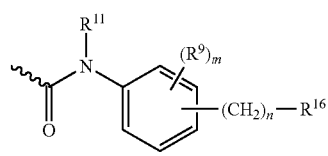
is selected from the group consisting of:
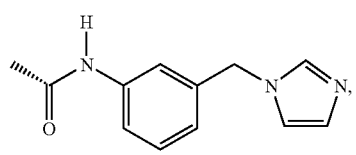
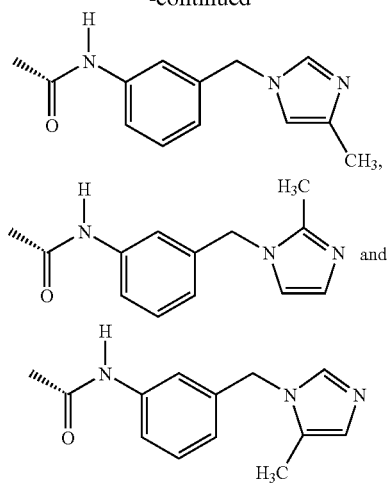
and the compound of formula 1.0 is a compound of formula 4.0:
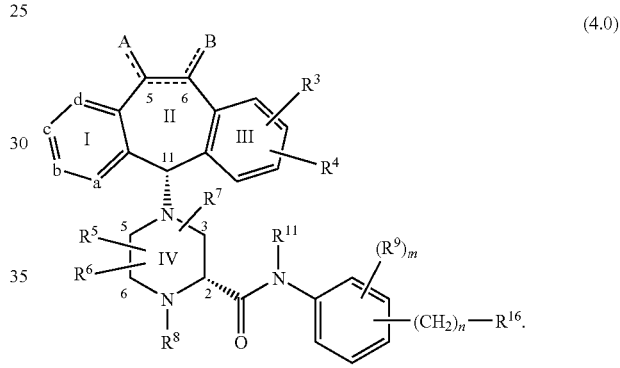
(4.0)
25. The compound of claim 1:
(1) wherein $R^8$ is selected from the group consisting of:
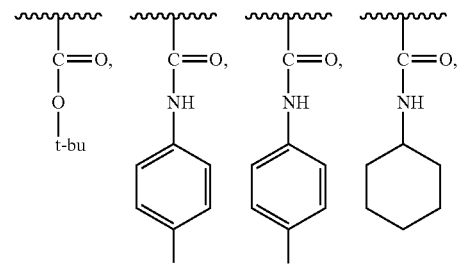
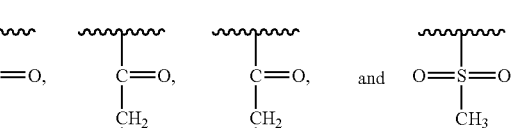
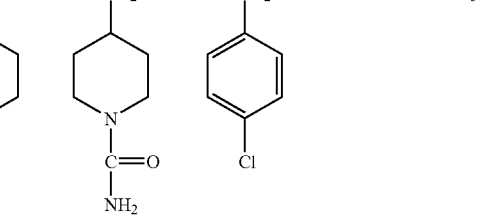

and the compound of formula 1.0 is a compound of formula 5.0:
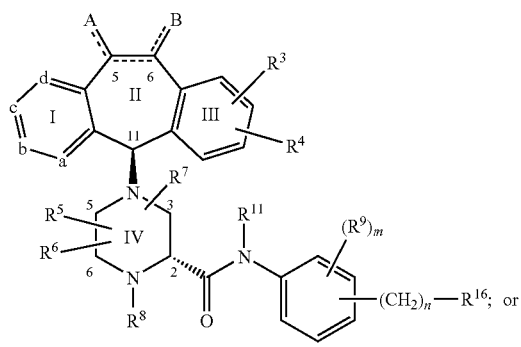
(5.0)
(2) wherein $R^8$ is selected from the group consisting of:
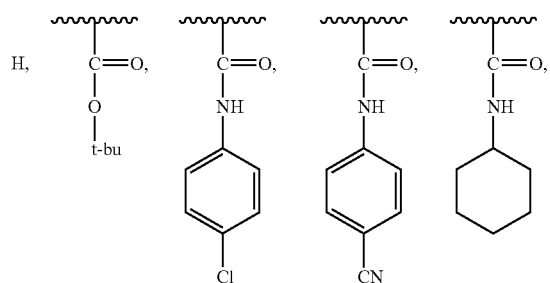
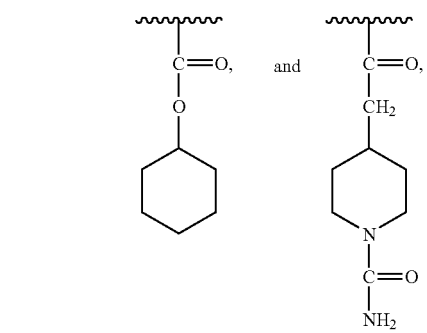
and the compound of formula 1.0 is a compound of formula 5.0:
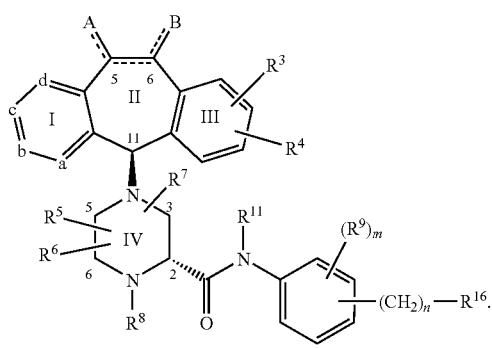
(5.0)
26. The compound of claim 1 wherein $R^8$ is selected from the group consisting of:
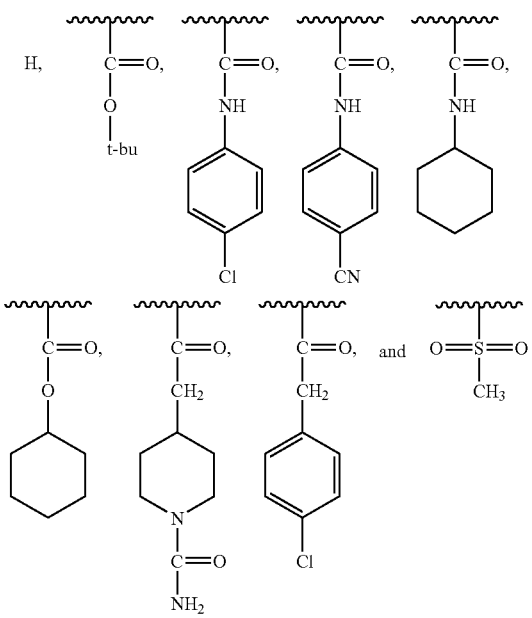
and the moiety
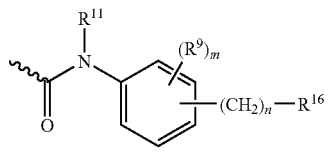
is selected from the group consisting of:
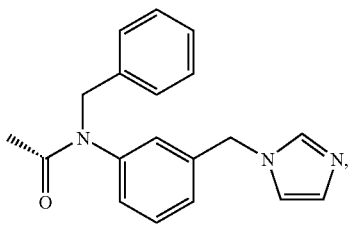
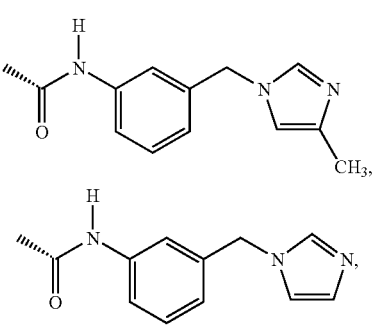

-continued
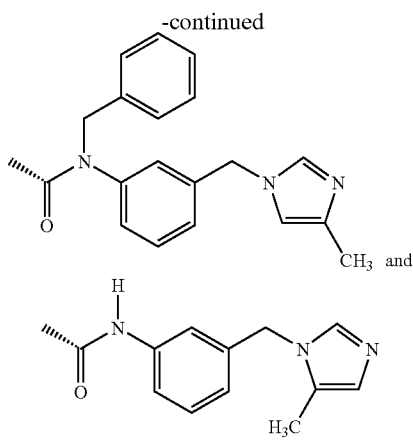
and
and the compound of formula 1.0 is a compound of formula 5.0:
(5.0)
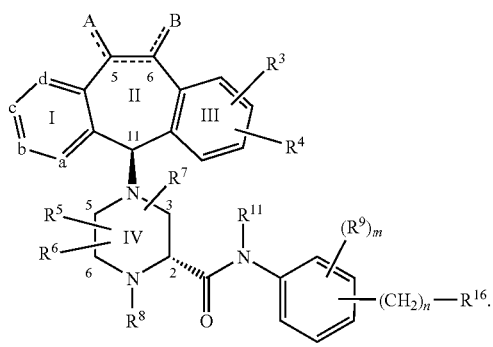
27. The compound of claim 26 wherein:
the moiety
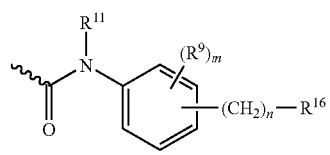
is selected from the group consisting of:
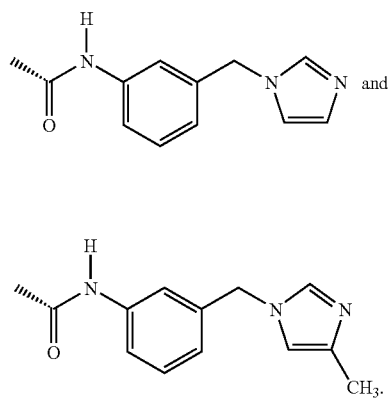
28. The compound of claim 1 wherein $R^8$ is
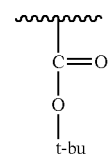
and the moiety
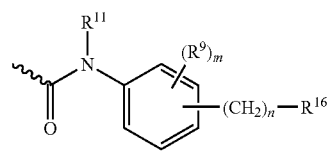
is
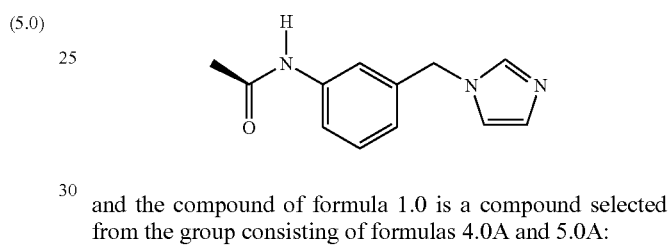
and the compound of formula 1.0 is a compound selected from the group consisting of formulas 4.0A and 5.0A:
(4.0A)
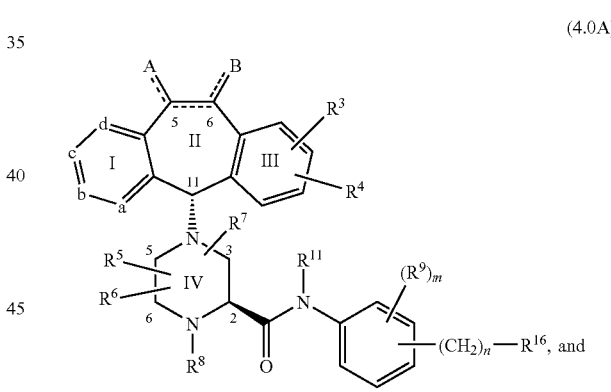
(5.0A)
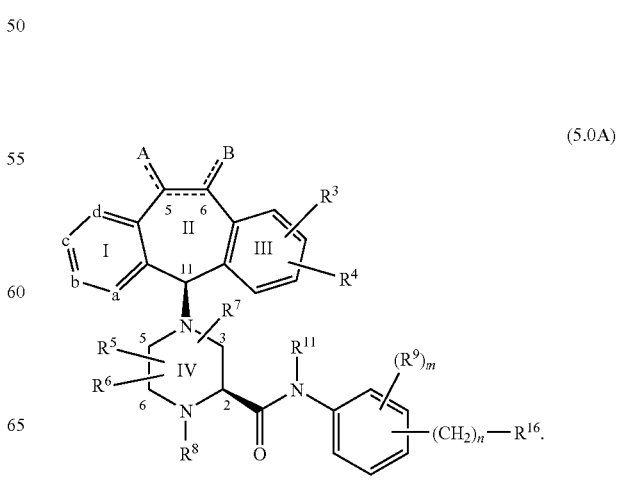

29. The compound of claim 1:

(1) wherein $R^8$ is selected from the group consisting of:

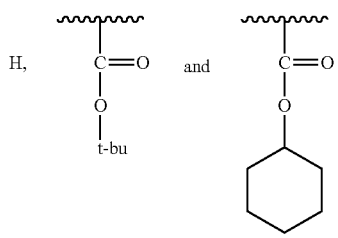

and the moiety

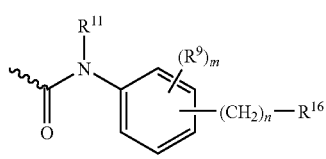

is selected from the group consisting of:

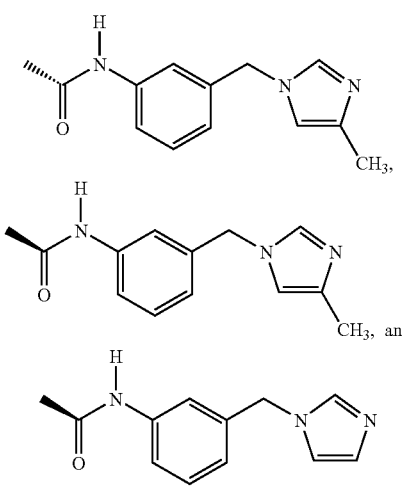

and the compound of formula 1.0 is a compound selected from the group consisting of formulas 7.0A and 7.0B:

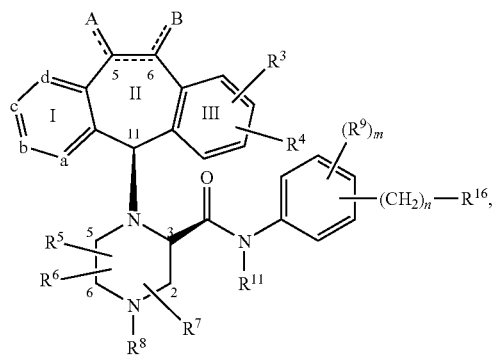

(7.0A)

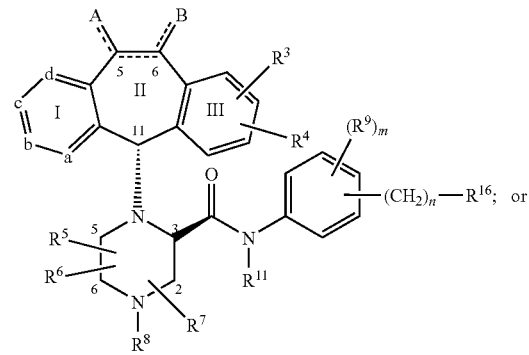

(7.0B)

(2) wherein $R^8$ is selected from the group consisting of:

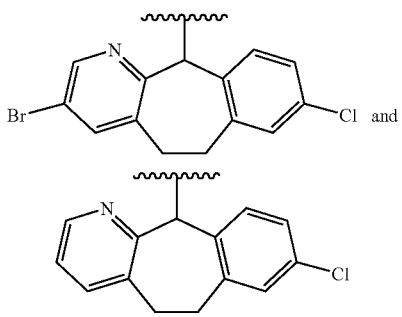

and the moiety

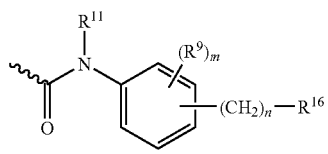

and the compound of formula 1.0 is selected from the group consisting of formulas 8.0B, 8.0D, 8.0F and 8.0H:

(8.0B)
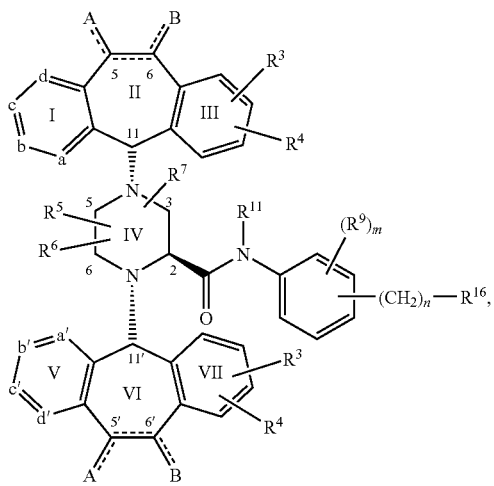
(8.0D)
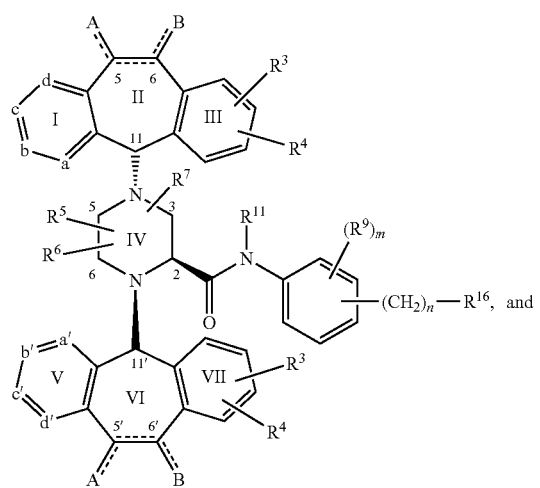
(8.0F)
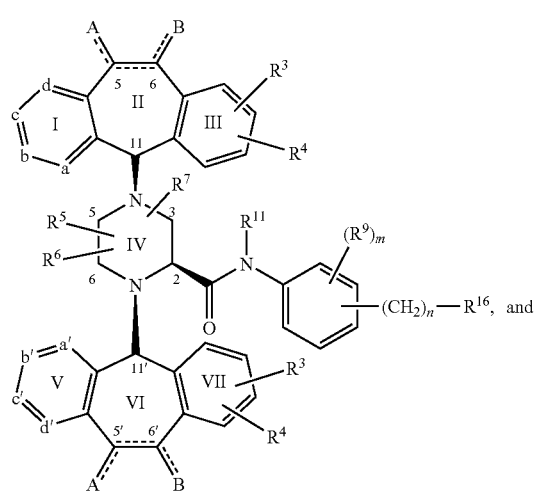
wherein the moiety
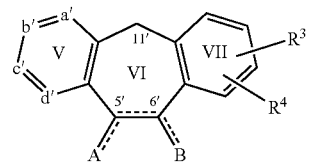
in (8.0B), (8.0D) and (8.0F)
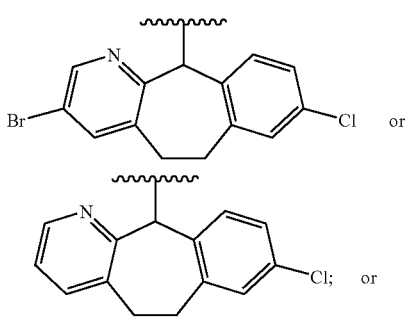
(3) wherein $R^8$ is selected from the group consisting of:
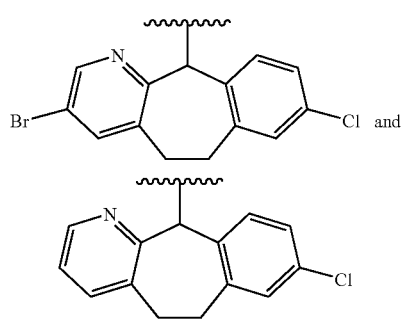
and the moiety
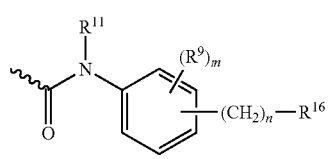
is selected from the group consisting of:
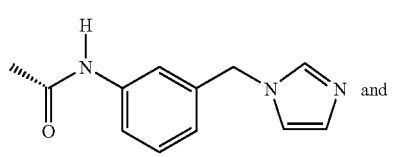
and

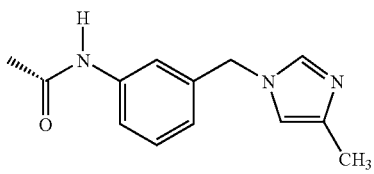
and the compound of formula 1.0 is a compound selected from the group consisting of formulas 8.0A, 8.0C, 8.0E and 8.0G:
(8.0A)
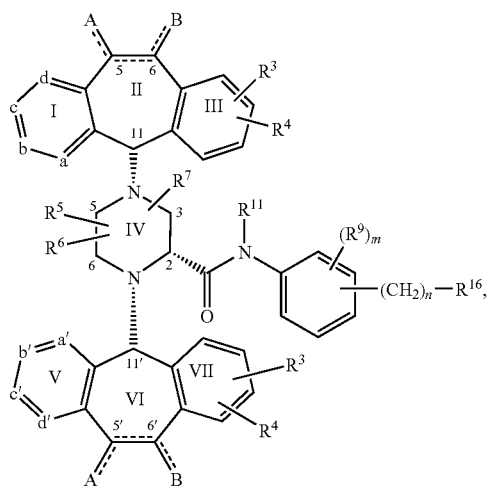
(8.0C)
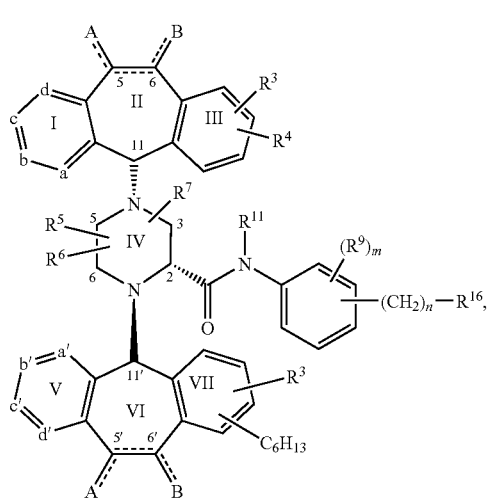
(8.0E)
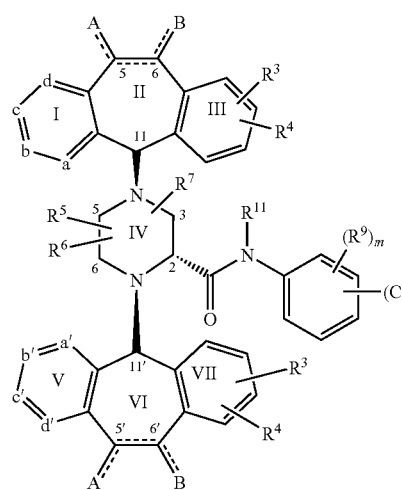
(8.0G)
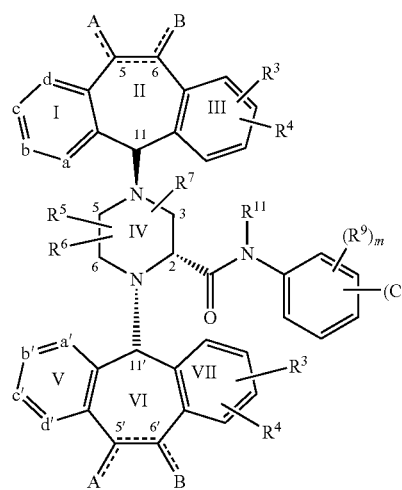
wherein the moiety
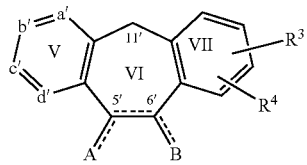
in (8.0A), (8.0C), (8.0E) and (8.0G) is
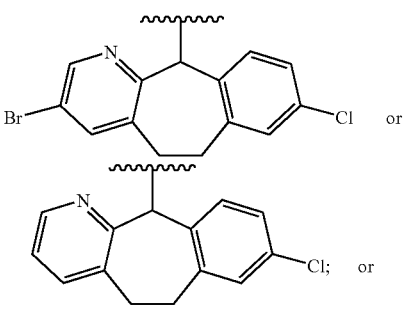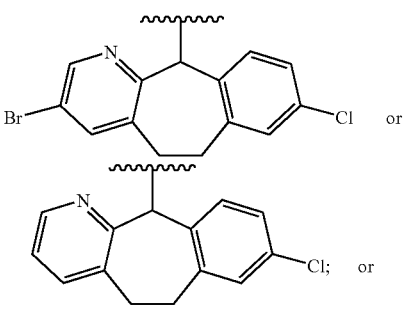

(4) wherein $R^8$ is selected from the group consisting of:

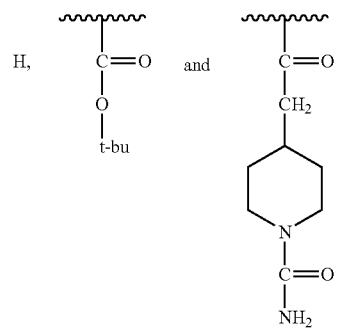

and the moiety

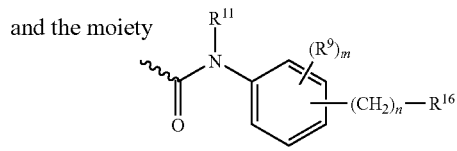

is

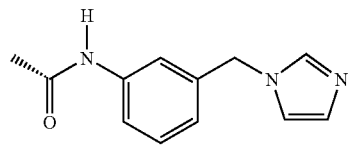

and the compound of formula 1.0 is a compound of formula 7.0:

(7.0)

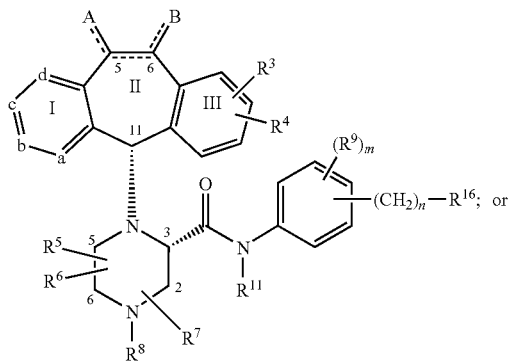

(5) wherein $R^8$ is selected from the group consisting of:

H, C=O (O-t-bu), C=O (O-cyclohexyl), and C=O (CH$_2$-piperidine-N-C(=O)NH$_2$)

and the moiety (with $R^{11}$, N, $(R^9)_m$, $(CH_2)_n$—$R^{16}$)

is (3-imidazolylmethyl-phenyl-NH-C(=O)-)

and the compound of formula 1.0 is a compound of formula 7.0:

(7.0)

[structure 7.0]

30. The compound of claim 1 selected from the group consisting of:

Formula 9.0

[structure with Br, Cl, piperazine, $R^8$, $R^{11}$, $R^{17}$, imidazole]

-continued
Formula 9.0A
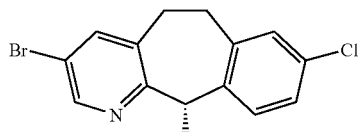
Formula 10.0
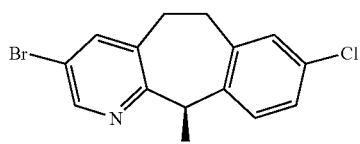
Formula 10.0A
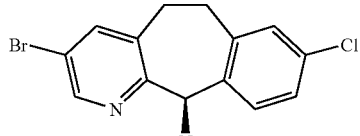
Formula 11.0
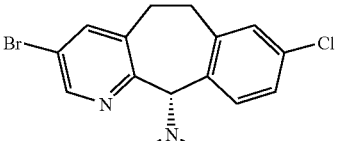
Formula 11.0A
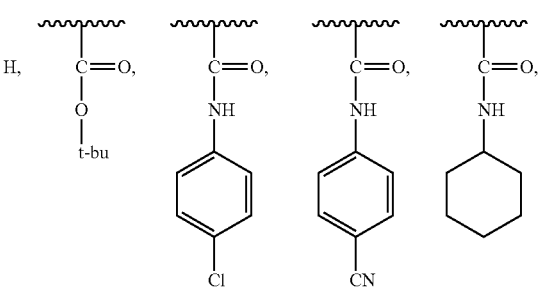
wherein:
R[11] is selected from the group consisting of: H and benzyl, and
R[17] is methyl wherein said methyl is bound to the C-4 position of the imidazolyl ring.
31. The compound of claim 30:
(1) wherein R[8] is selected from the group consisting of:
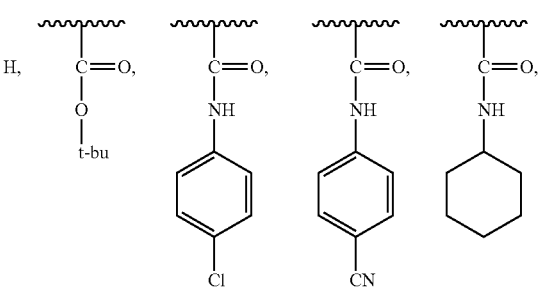
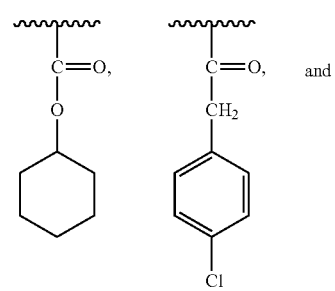
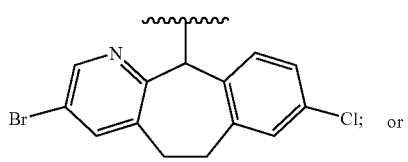
(2) wherein R[8] is selected from the group consisting of:
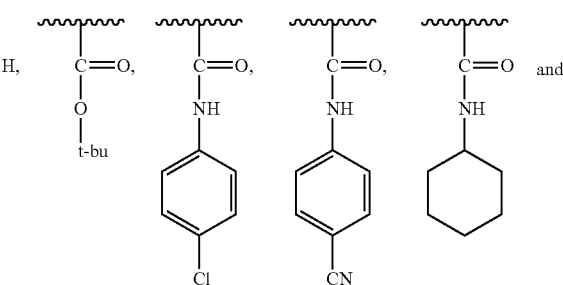
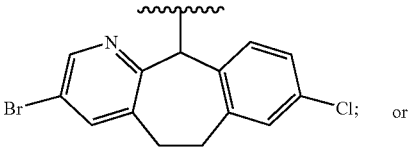

(3) wherein $R^8$ is selected from the group consisting of:
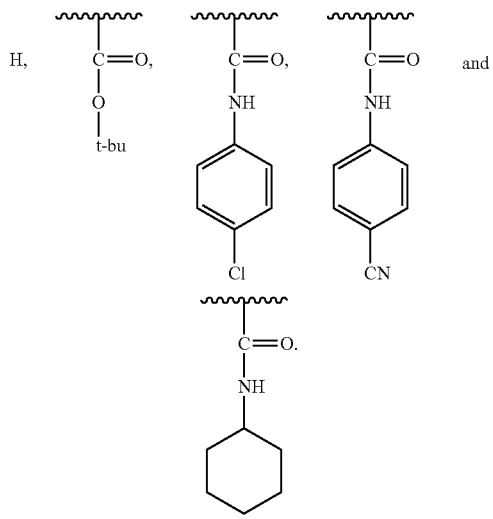
32. The compound of claim 1 having the formula:
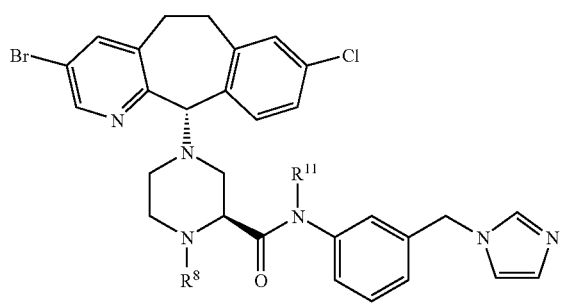
Formula 11.0A
wherein:
$R^8$ is selected from the group consisting of:
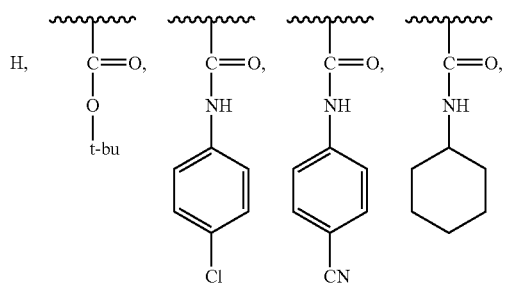
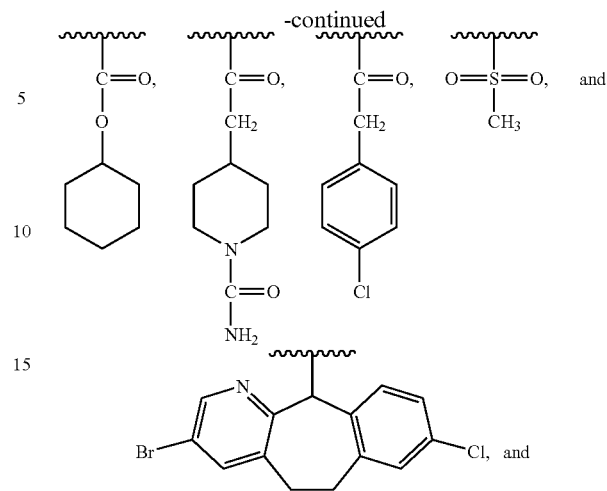
$R^{11}$ is H.
33. The compound of claim 32:
(1) wherein $R^8$ is selected from the group consisting of:
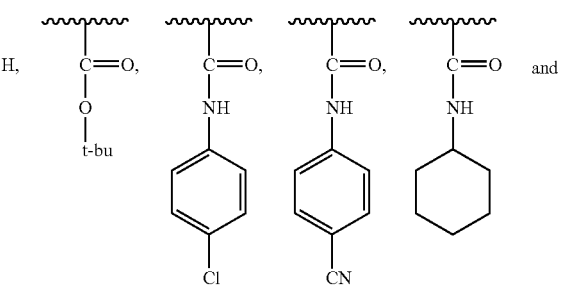
or
(2) wherein $R^8$ is selected from the group consisting of:

-continued

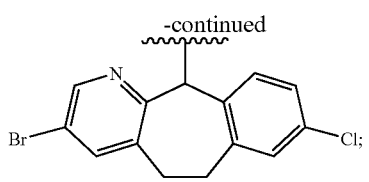

(3) wherein $R^8$ is selected from the group consisting of:

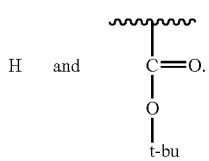 and

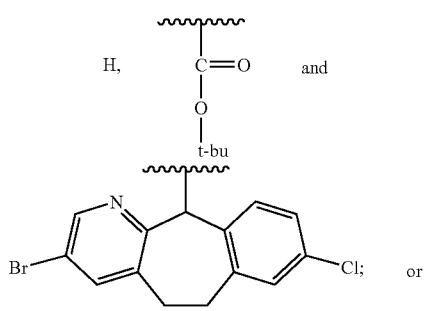

(4) wherein $R^8$ is selected from the group consisting of:

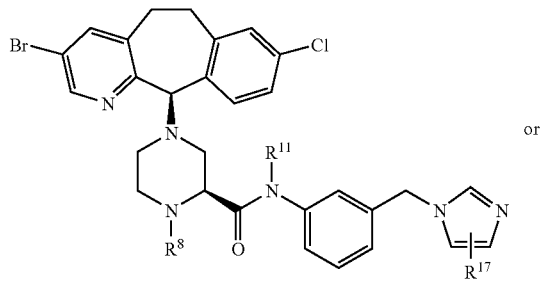

34. The compound of claim 1 having the formula:

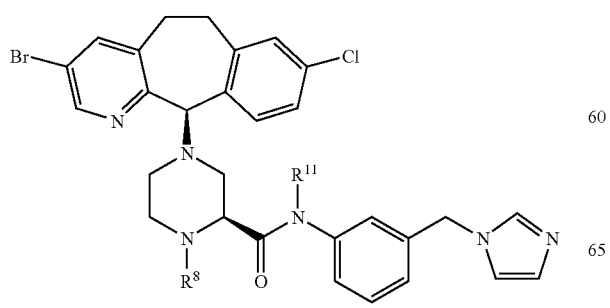

Formula 12.0 or

Formula 12.0A wherein:
$R^8$ is selected from the group consisting of:

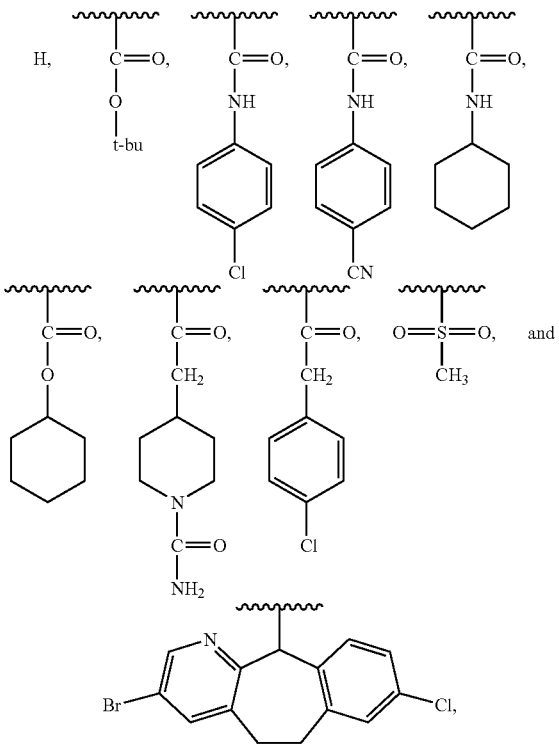

$R^{11}$ is selected from the group consisting of: H and benzyl; and $R^{17}$ is methyl wherein said methyl is bound to the C-4 position of the imidazolyl ring.

35. The compound of claim 34:

(1) wherein $R^8$ is selected from the group consisting of:

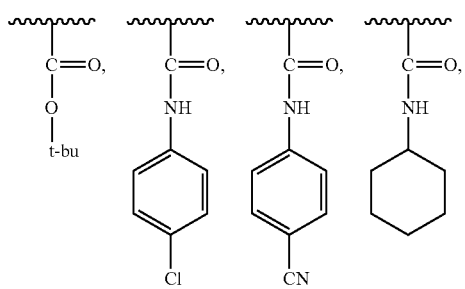

-continued

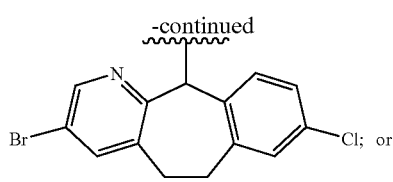

(2) wherein $R^8$ is selected from the group consisting of:

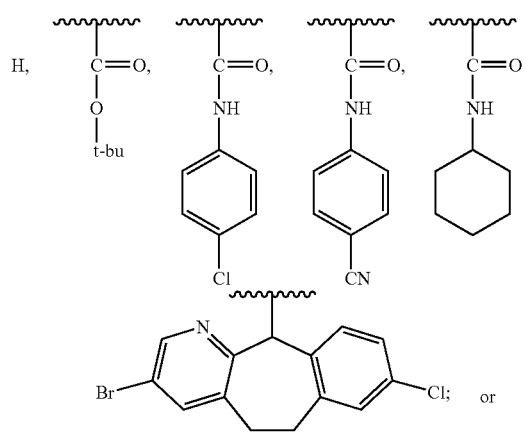

(3) wherein $R^8$ is selected from the group consisting of:

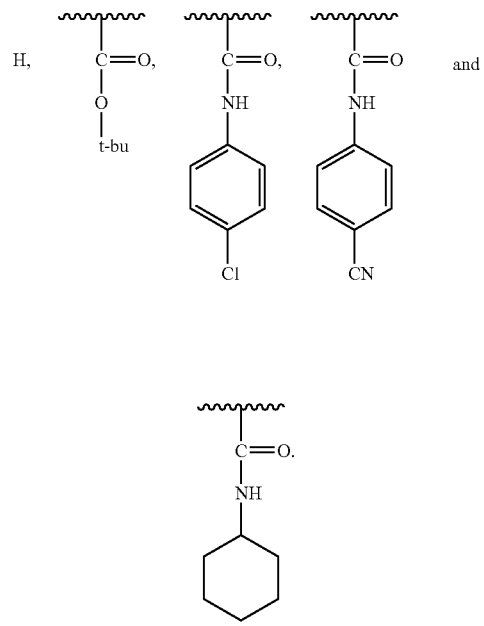

36. The compound of claim 34 wherein $R^{11}$ is H, and $R^8$ is selected from the group consisting of:

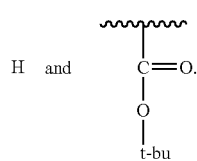

37. The compound of claim 1 having the formula:

Formula 13.0 or

Formula 13.0A wherein:
$R^8$ is selected from the group consisting of:

$R^{11}$ is selected from the group consisting of: H, benzyl, n-butyl and 3-phenylpropyl; and
$R^{17}$ is selected from the group consisting of: methyl wherein said methyl is bound to the C-2, C-4 or C-5 of the imidazolyl ring.

38. The compound of claim 37 wherein $R^8$ is selected from the group consisting of:

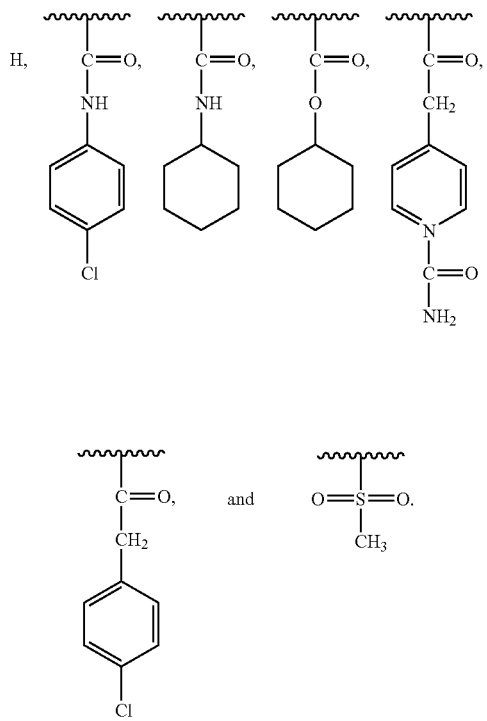

39. The compound of claim 1 having

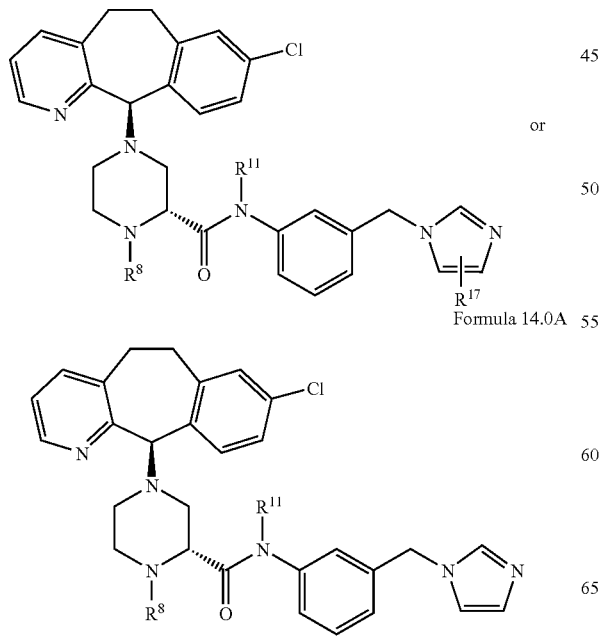

wherein:
$R^8$ is selected from the group consisting of:

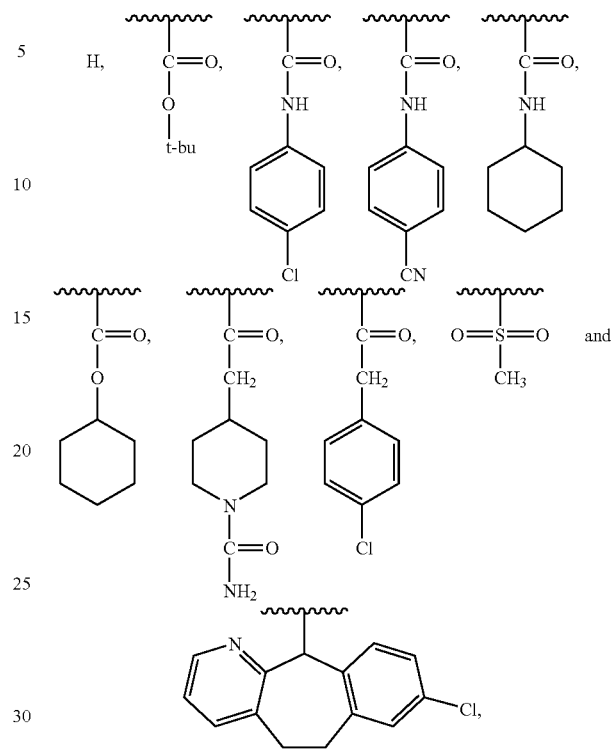

$R^{11}$ is selected from the group consisting of: H, benzyl, n-butyl and 3-phenylpropyl; and $R^{17}$ is selected from the group consisting of: methyl wherein said methyl is bound to the C-2, C-4 or C-5 of the imidazolyl ring.

40. The compound of claim 39 wherein $R^8$ is selected from the group consisting of:

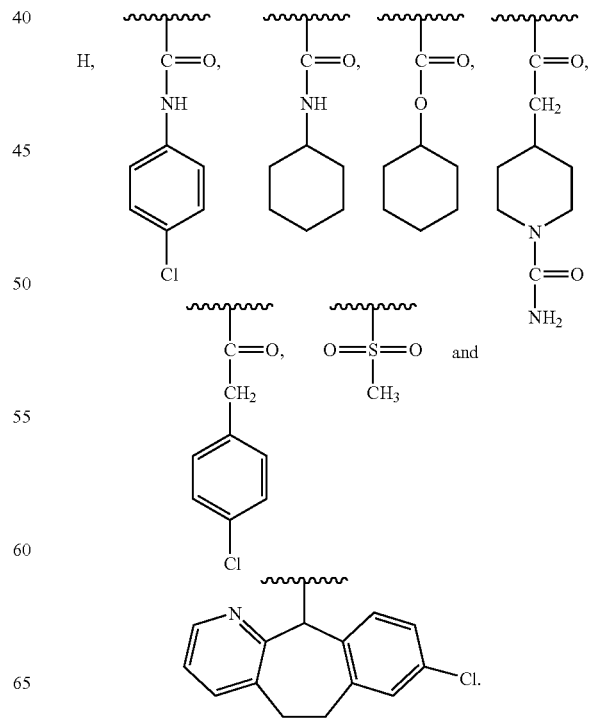

41. The compound of claim 39 wherein $R^{11}$ is selected from the group consisting of: H and benzyl.

42. The compound of claim 41 wherein $R^8$ is selected from the group consisting of:

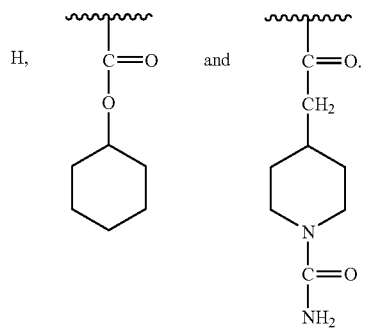

43. The compound of claim 1 selected from the group consisting of:

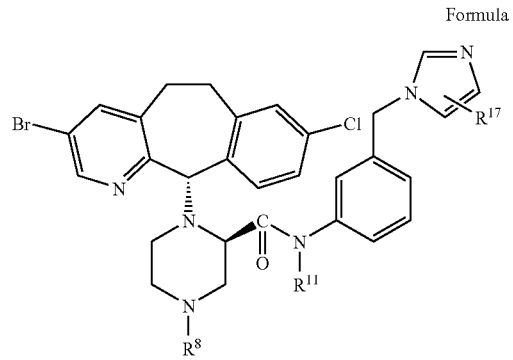

Formula 15.0

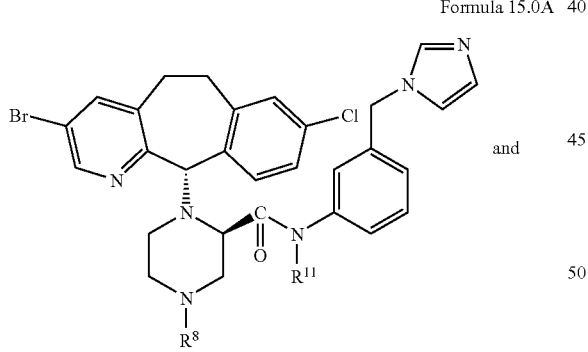

Formula 15.0A

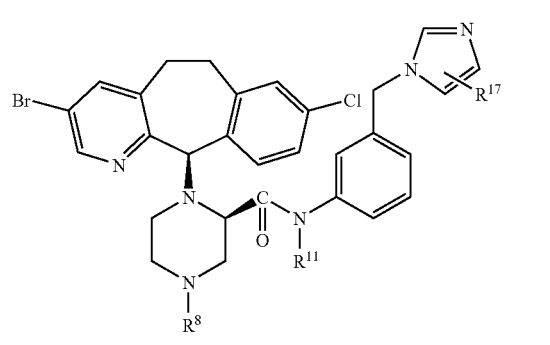

Formula 16.0 wherein:
$R^8$ is selected from the group consisting of:

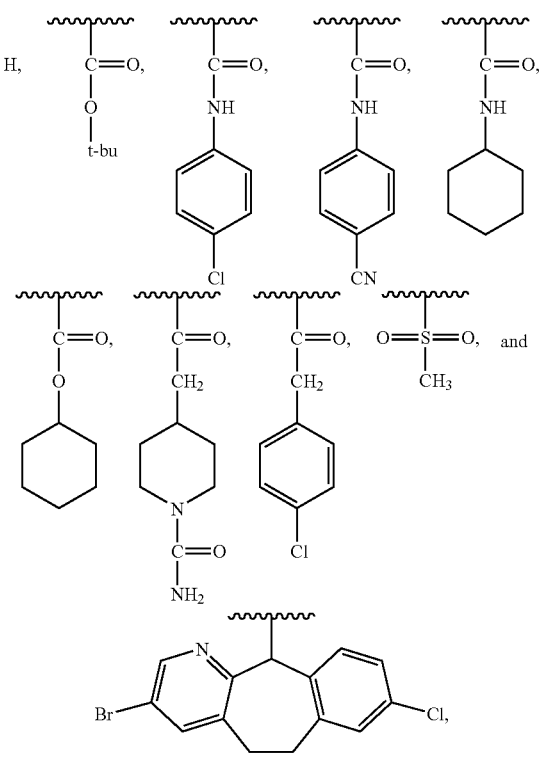

$R^{11}$ is H; and
$R^{17}$ is methyl wherein said methyl is bound to the C-4 of the imidazolyl.

44. The compound of claim 43 wherein said compound is selected from the group consisting of formulas 15.0 and 16.0, and wherein $R^8$ is selected from the group consisting of:

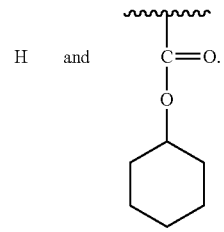

45. The compound of claim 43 wherein said compound is selected from the group consisting of formulas 15.0 and 15.0 A

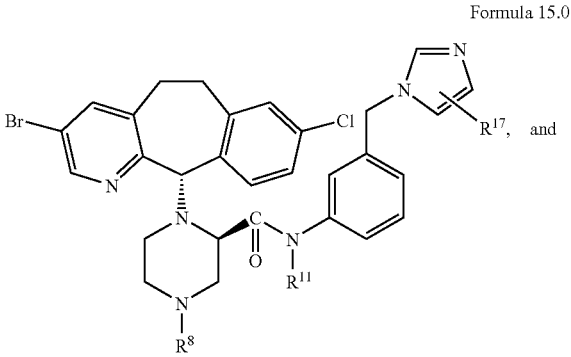

Formula 15.0

Formula 15.0A

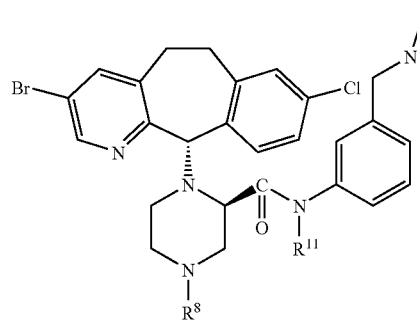

, and wherein R⁸ is:

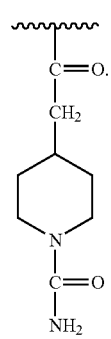

46. The compound of claim 43 wherein said compound is selected from the group consisting of formulas 15.0 and 15.0 A, and wherein R⁸ is selected from the group consisting of:

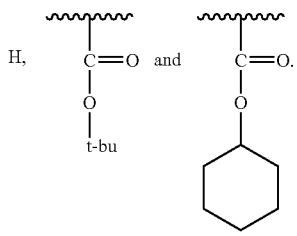

47. The compound of claim 1 having the formula:

Formula 18.0

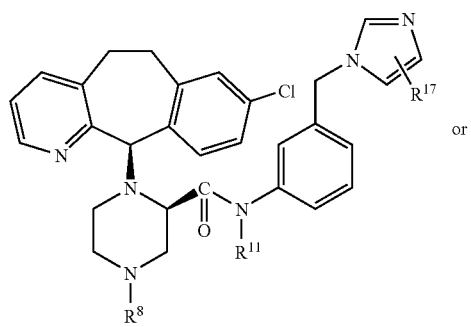

or

Formula 18.0A

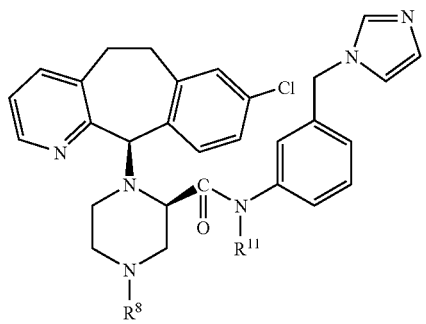

wherein:
R³ is selected from the group consisting of:

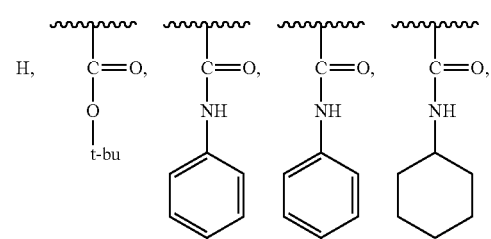

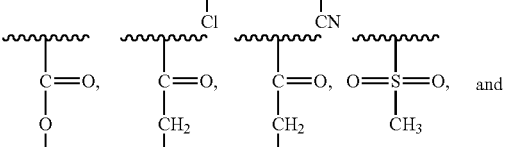

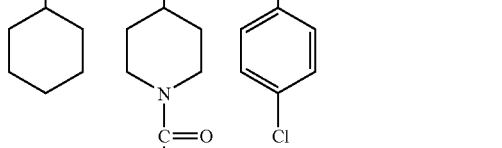

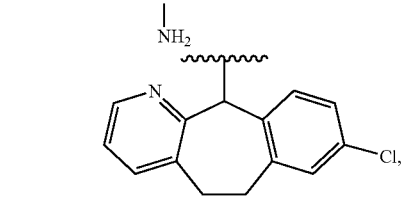

R¹¹ is H; and
R¹⁷ is methyl wherein said methyl is bound to the C-4 of the imidazolyl.

48. The compound of claim 47 wherein R⁸ is selected from the group consisting of:

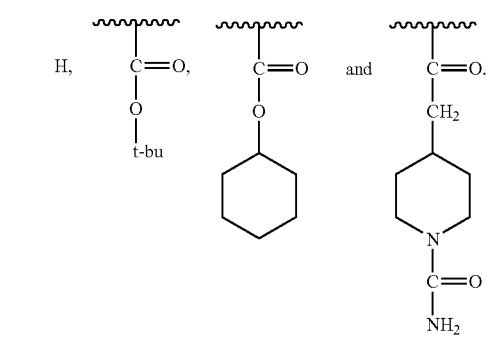

49. The compound of claim 1 having the formula:

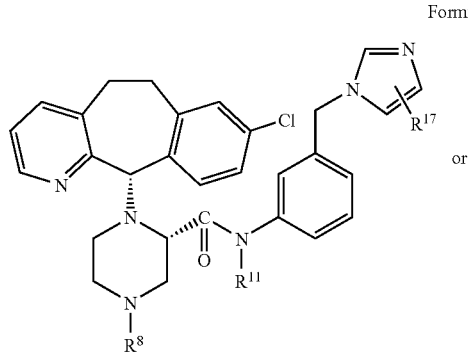

Formula 19.0 or

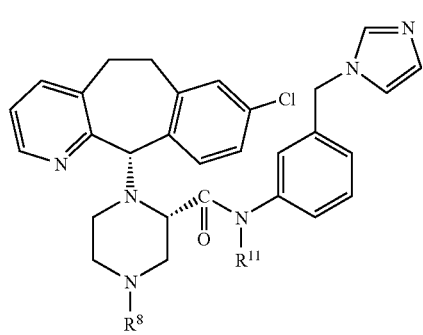

Formula 19.0A wherein:
$R^8$ is selected from the group consisting of:

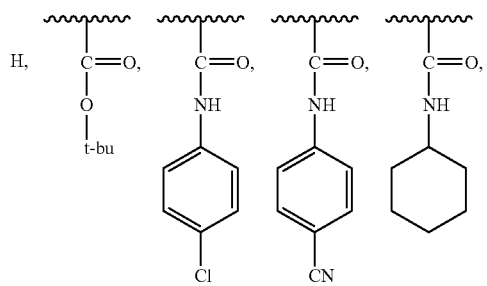

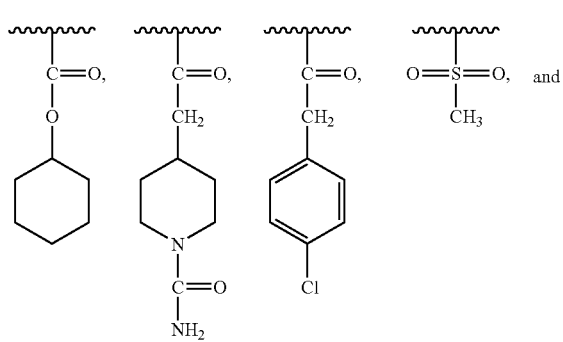

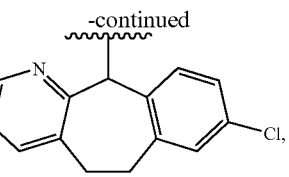

$R^{11}$ is H; and
$R^{17}$ is methyl wherein said methyl is bound to the C-4 of the imidazolyl.

50. The compound of claim 49 wherein $R^8$ is selected from the group consisting of:

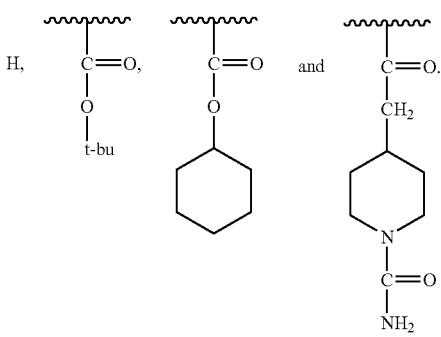

51. The compound of claim 49 wherein $R^8$ is:

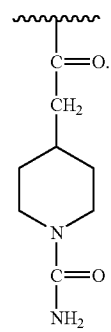

52. The compound of claim 1 wherein said compound is a compound of formula 19.0A:

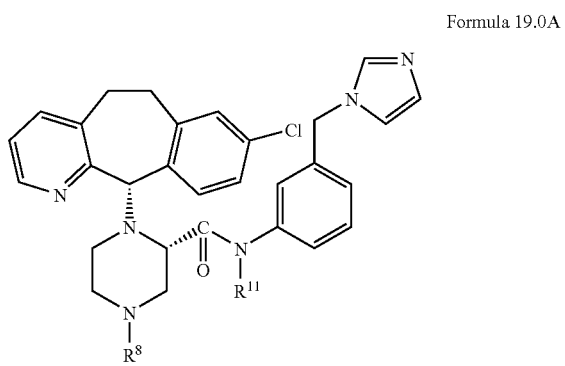

Formula 19.0A wherein:
R[8] is selected from the group consisting of:
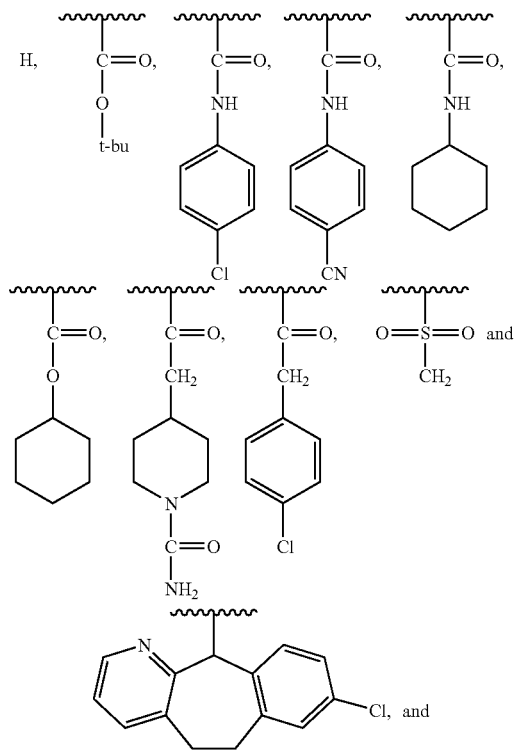
R[8] is H.
53. The compound of claim 52 wherein R[8] is selected from the group consisting of:
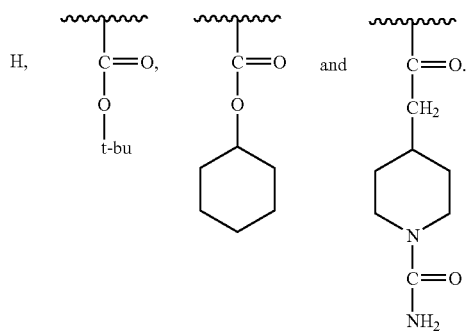
54. The compound of claim 53 wherein R[8] is
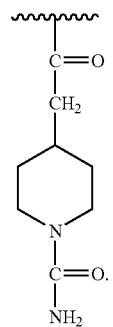
55. The compound of claim 1 having the formula:
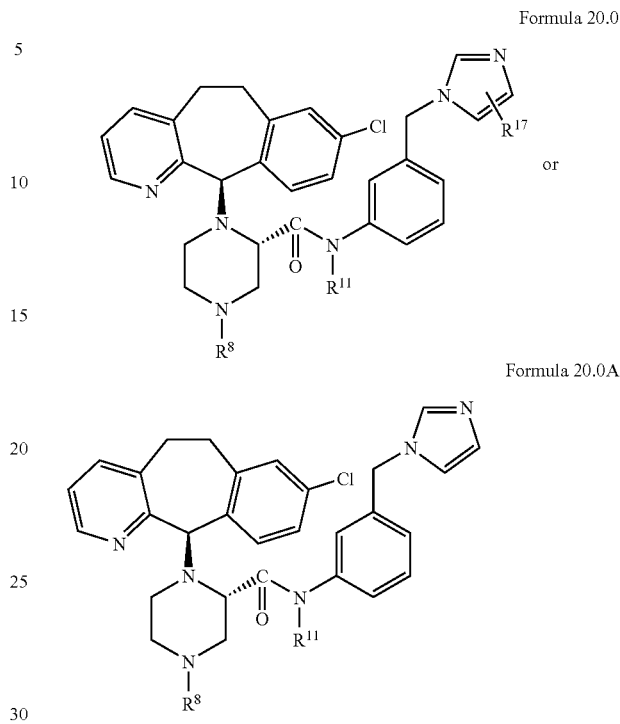
Formula 20.0
Formula 20.0A
wherein
R[8] is selected from the group consisting of:
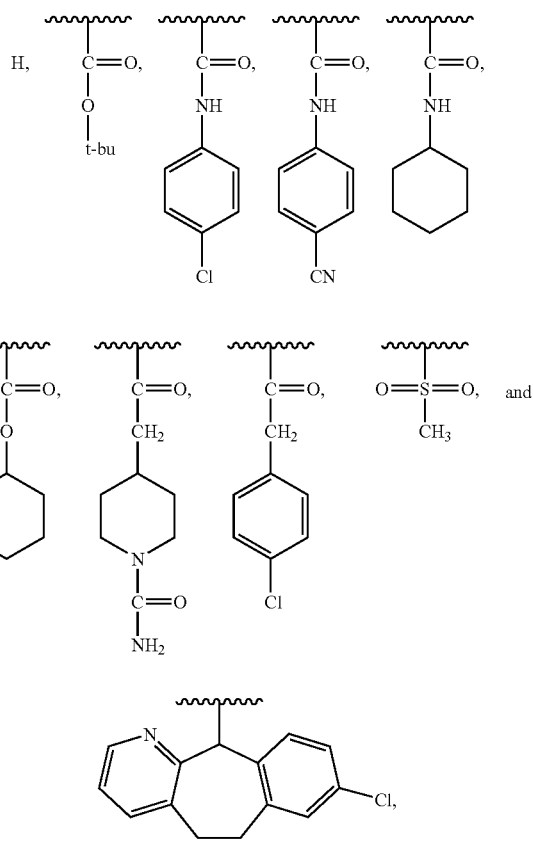

$R^{11}$ is H; and
$R^{17}$ is methyl wherein said methyl is bound to the C-4 of the imidazolyl.

56. The compound of claim 55 wherein $R^8$ is selected from the group consisting of:

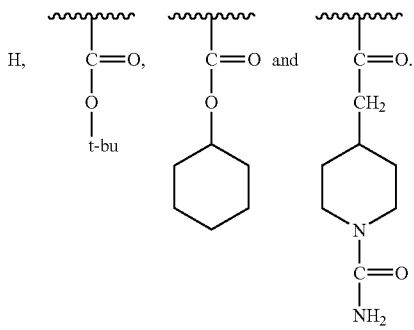

57. The compound of claim 55 wherein said compound is a compound of formula 20.0.A.

58. The compound of claim 56 wherein said compound is a compound of formula 20.0.A.

59. Another embodiment of this invention is directed to compounds of the formula Formula 21.0

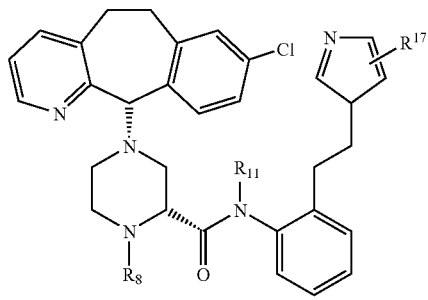

wherein:
$R^8$ is selected from the group consisting of:

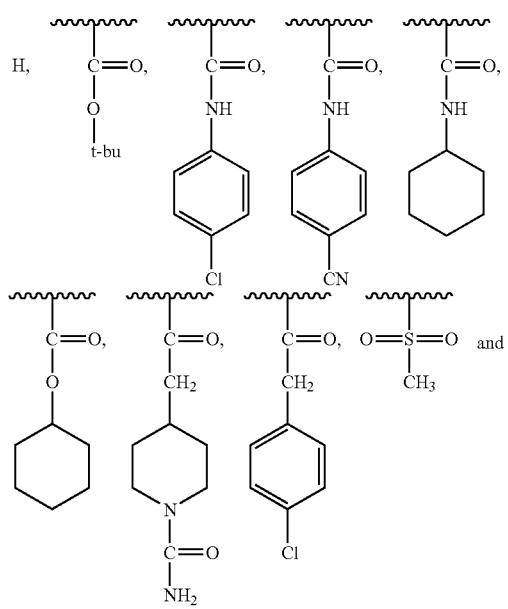

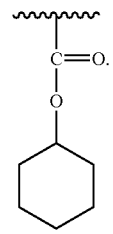

$R^{11}$ is H; and
$R^{17}$ is methyl wherein said methyl is bound to the C-4 of the imidazolyl.

60. The compound of claim 59 wherein $R^8$ is

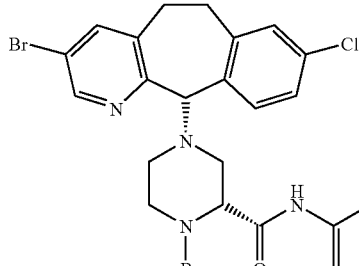

61. The compound of claim 1 selected from the group consisting of comounds:

(1.3)

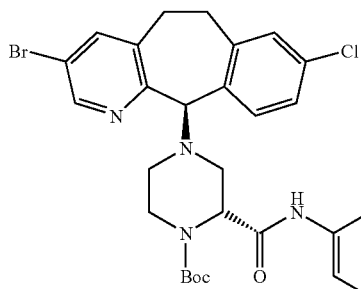

Isomer 1

(1.4)

Isomer 2

(2.1)

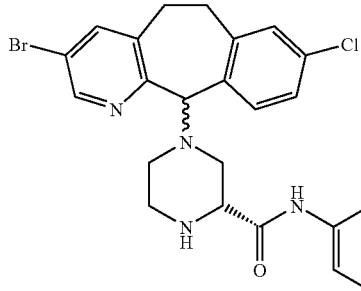

-continued
(3.1)
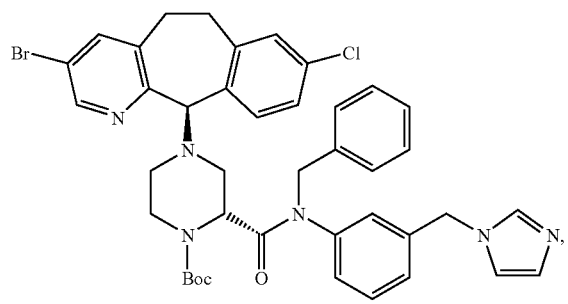
(4.1)
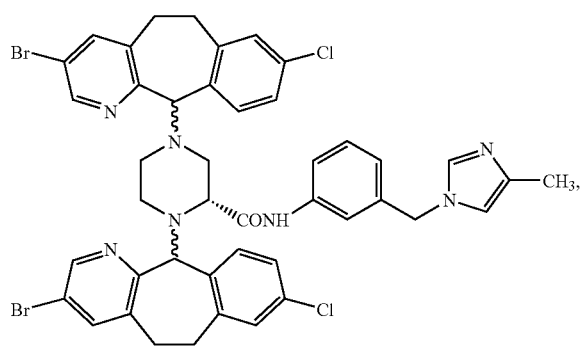
(4.2)
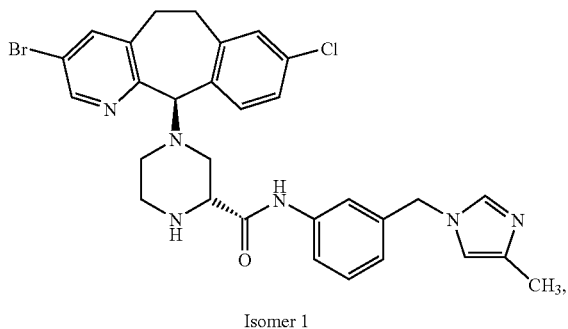
Isomer 1
-continued
(4.3)
Isomer 2
(4.4)
(5.1)
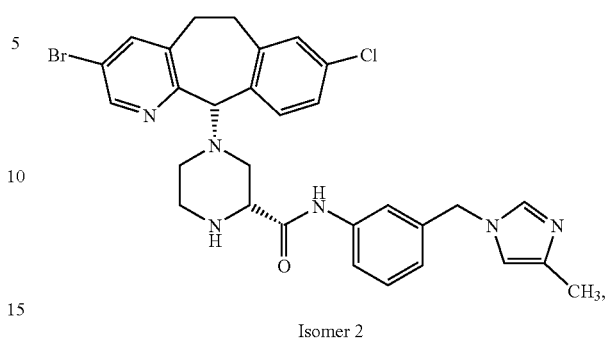
(6.1)
Isomer 1
(7.1)
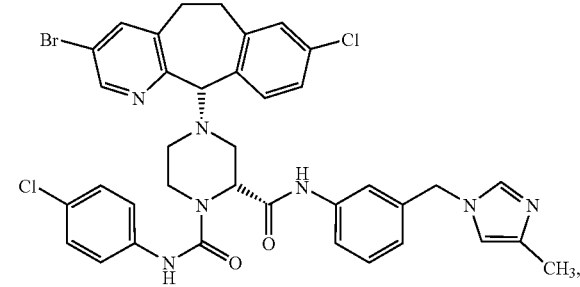

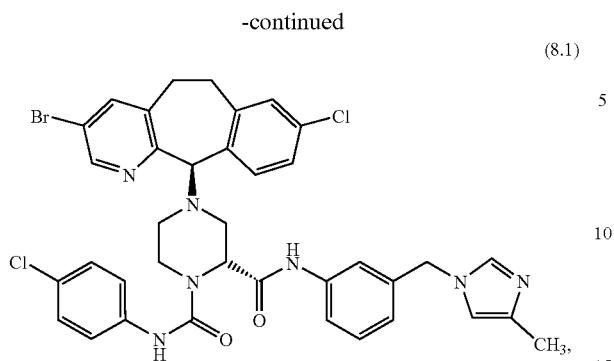
(8.1)
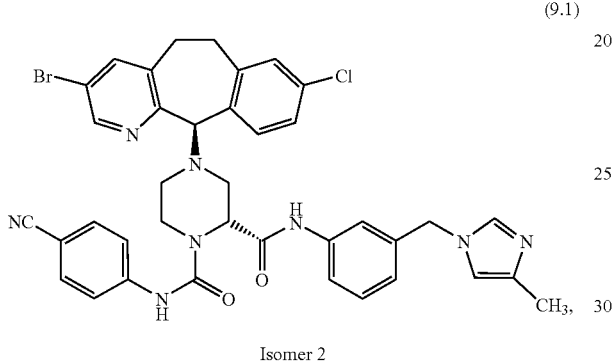
(9.1) Isomer 2
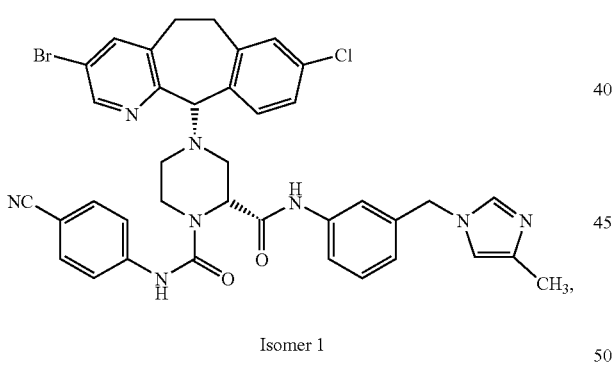
(10.1) Isomer 1
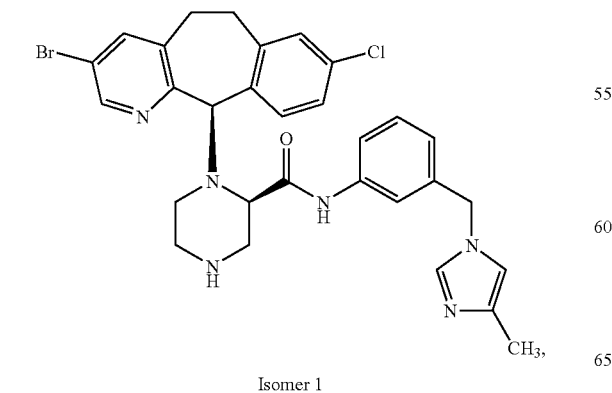
(11.2) Isomer 1
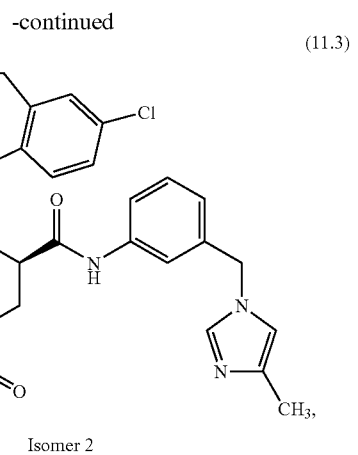
(11.3) Isomer 2
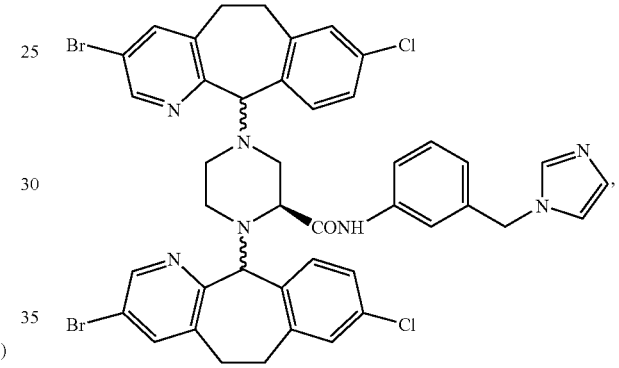
(12.1)
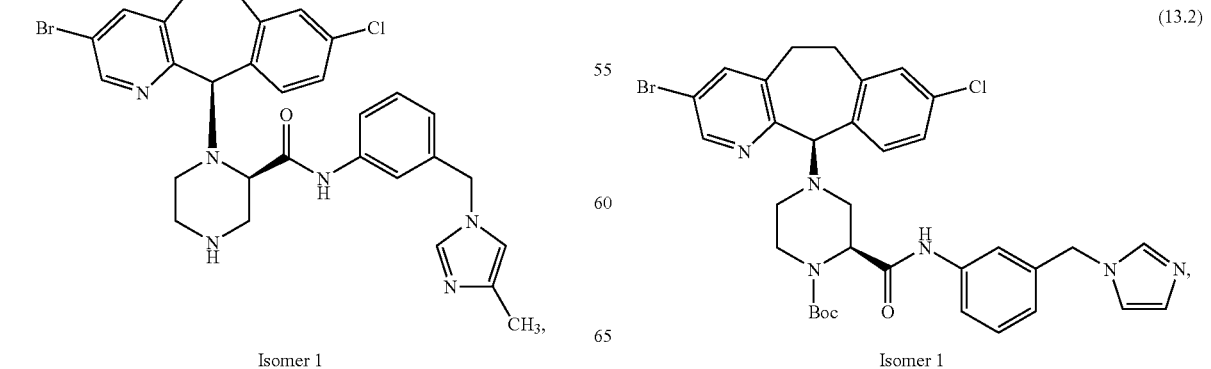
(12.2)
(13.2) Isomer 1

-continued
(13.3)
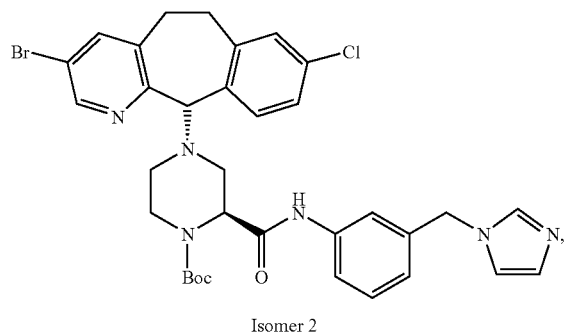
Isomer 2
(14.1)
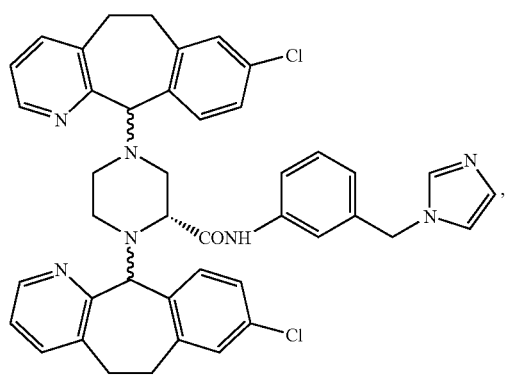
(14.2)
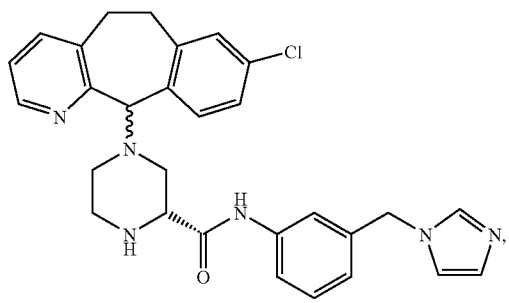
(14.3)
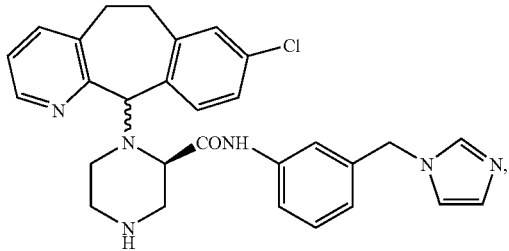
-continued
(15.1)
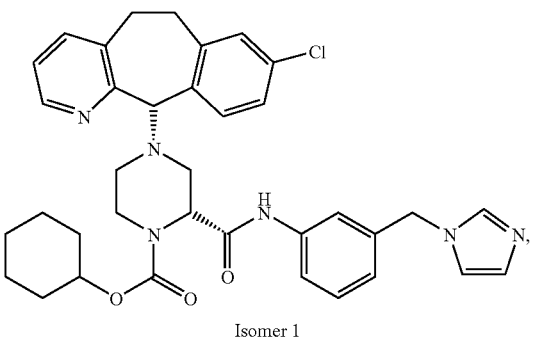
Isomer 1
(15.2)
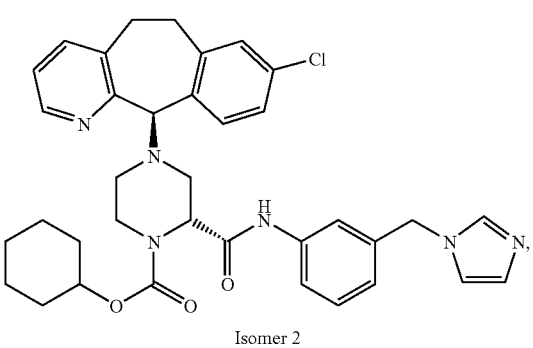
Isomer 2
(16.1)
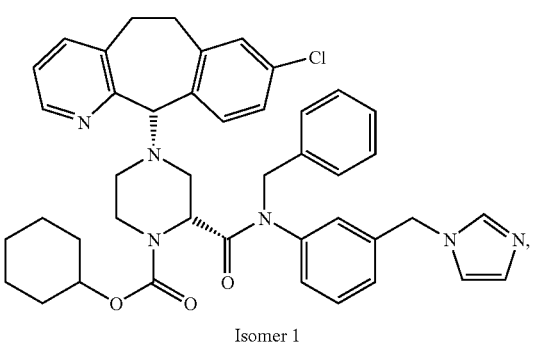
Isomer 1
(17.1)
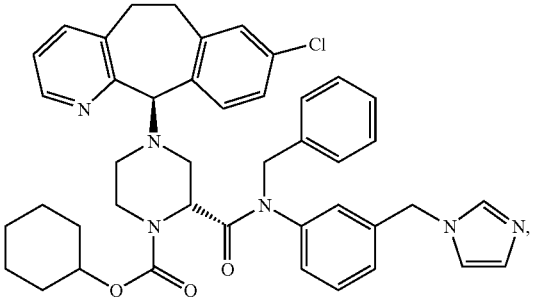

(18.1)
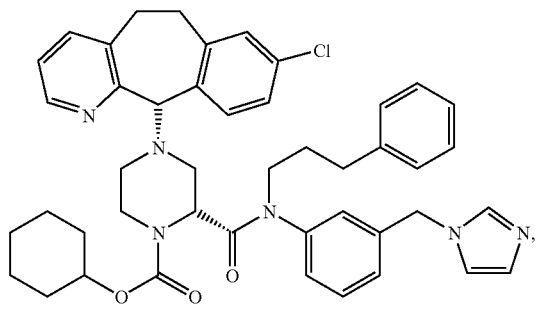
(19.1)
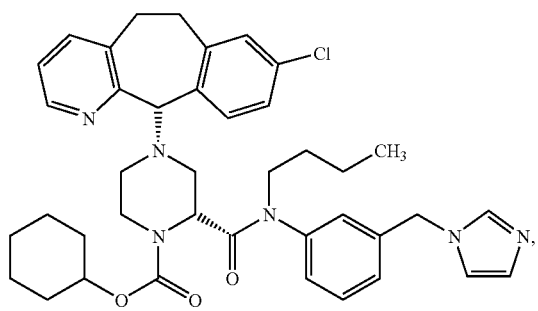
(20.1)
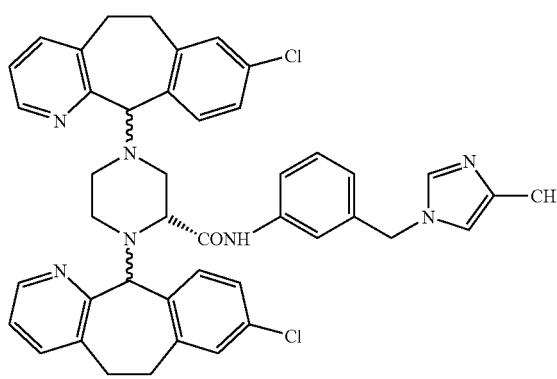
(20.2)
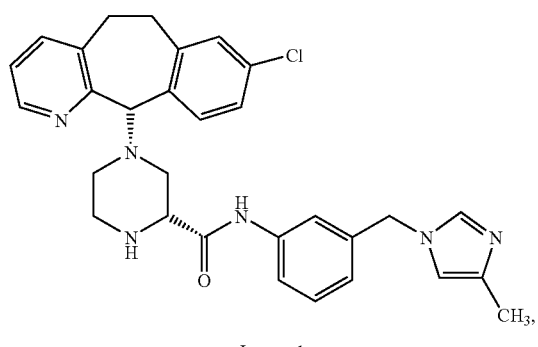
Isomer 1
(20.3)
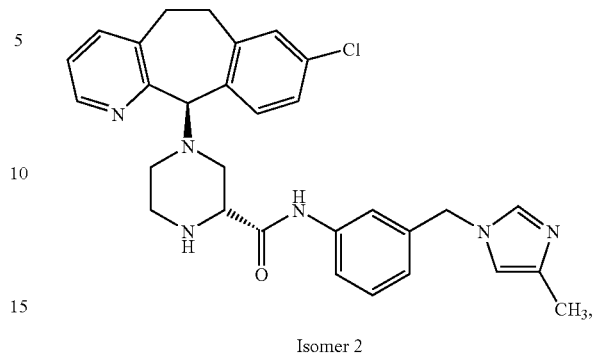
Isomer 2
(20.4)
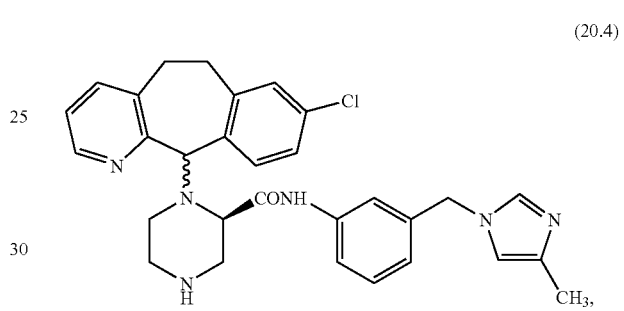
(21.1)
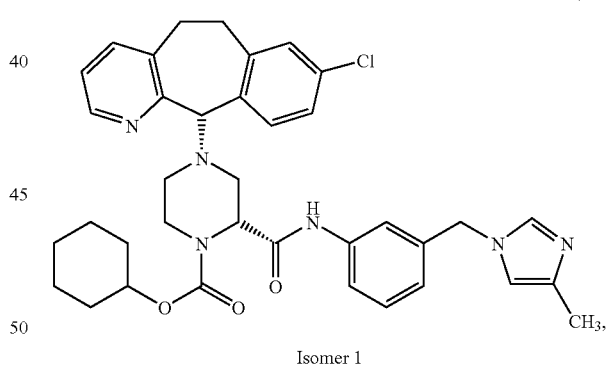
Isomer 1
(22.1)
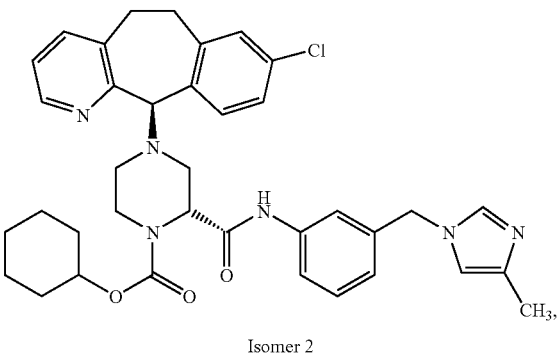
Isomer 2

-continued
(24.1)
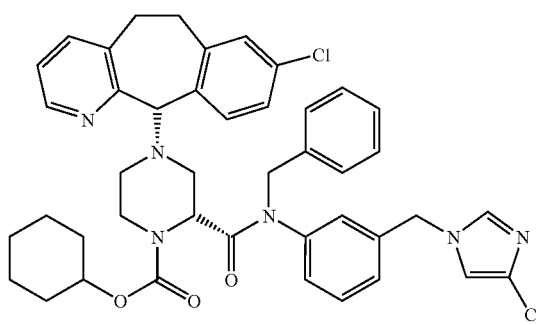
Isomer 1
(25.1)
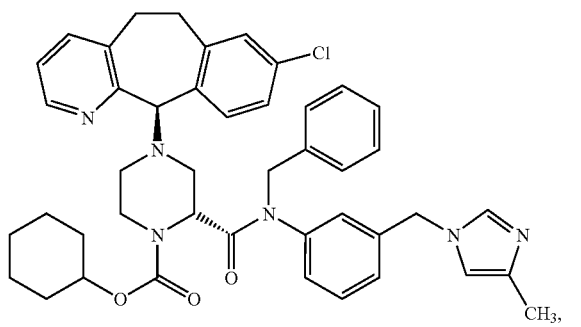
Isomer 2
(26.1)
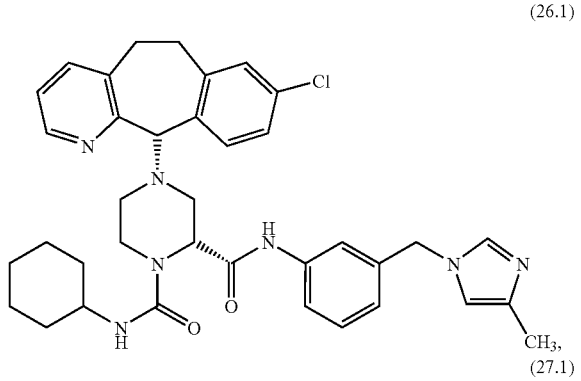
(27.1)
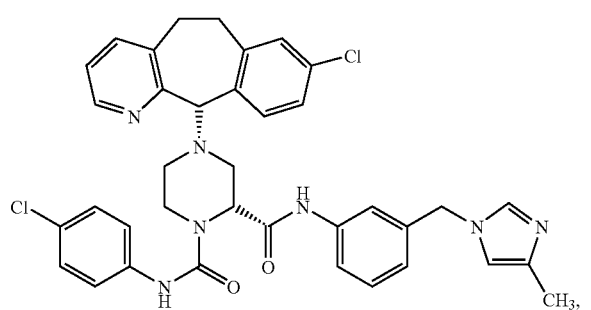
-continued
(28.1)
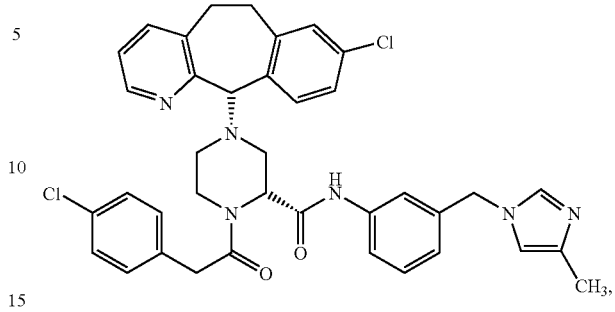
(29.1)
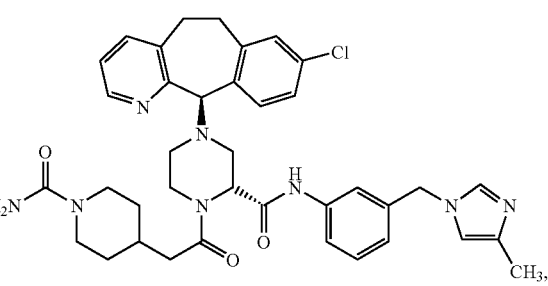
(30.1)
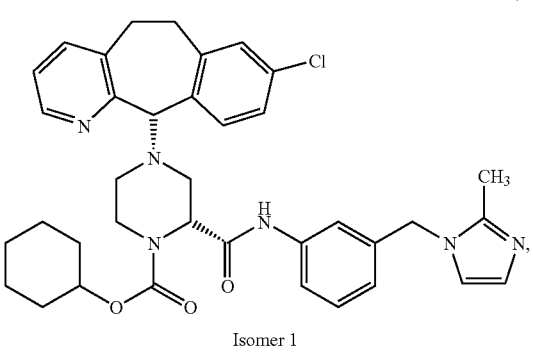
(31.1)
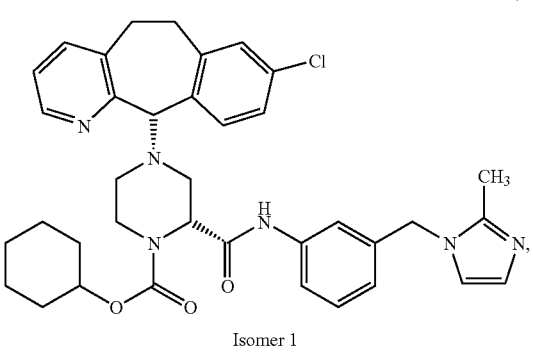
Isomer 1

-continued
(31.2)
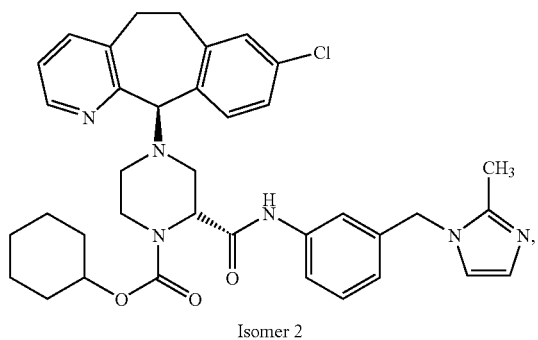
Isomer 2
(32.1)
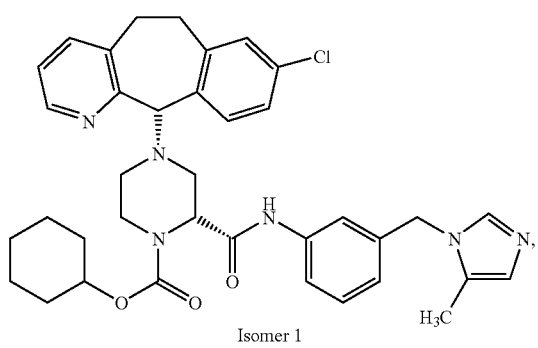
Isomer 1
(32.2)
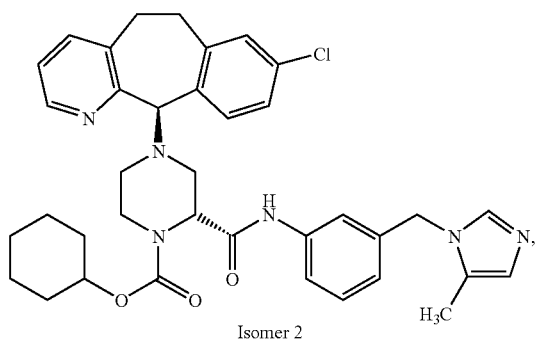
Isomer 2
(33.1)
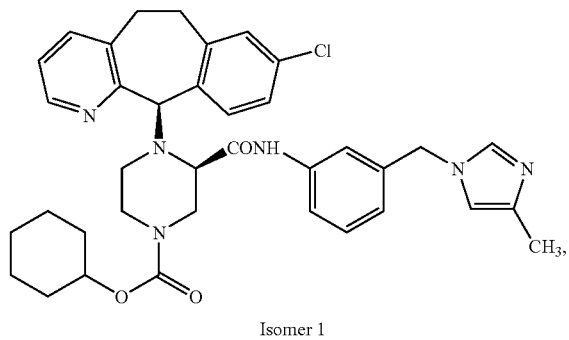
Isomer 1
-continued
(33.2)
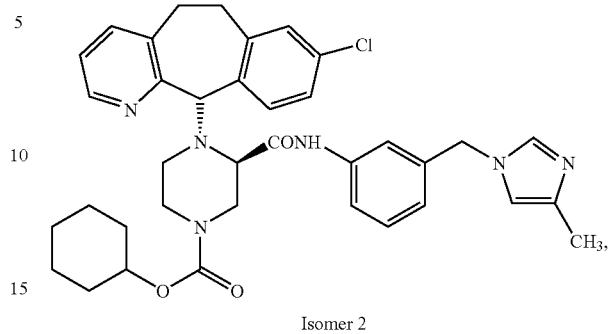
Isomer 2
(34.1)
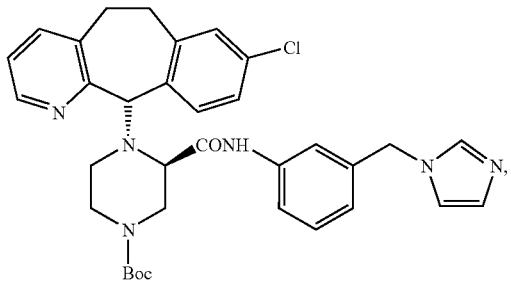
Isomer 1
(34.2)
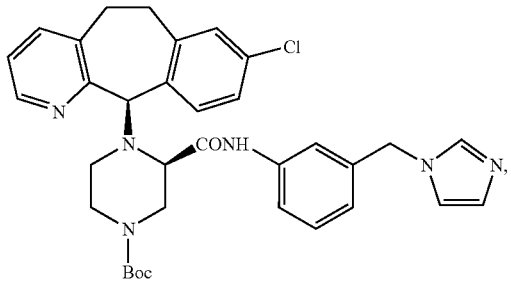
Isomer 2
(35.1)
Isomer 1

-continued
(36.1)
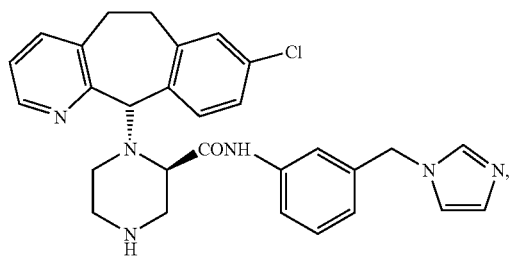
Isomer 2
(37.1)
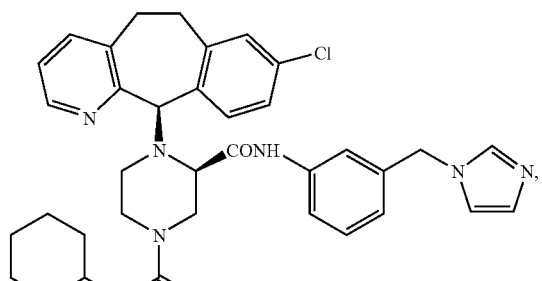
Isomer 2
(38.1)
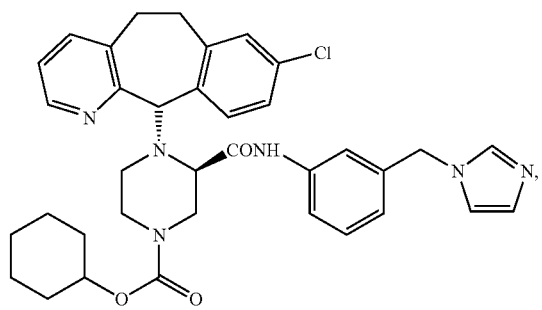
Isomer 1
(39.1)
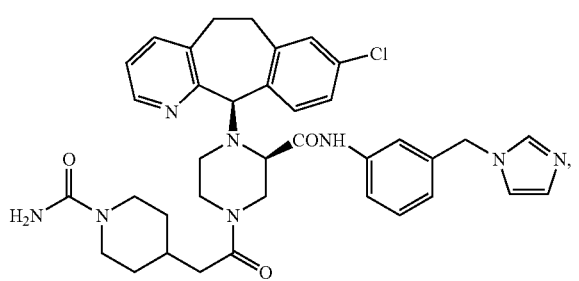
-continued
(40.1)
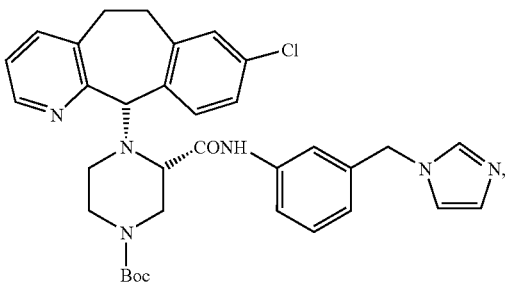
Isomer 1
(40.2)
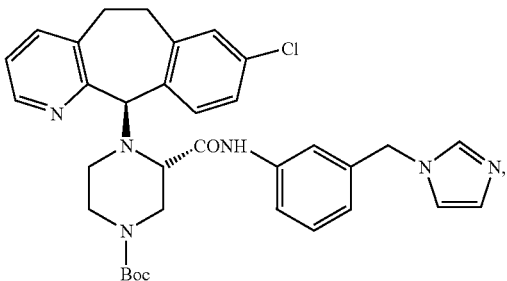
Isomer 2
(41.1)
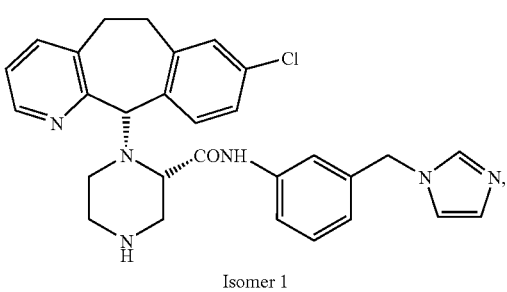
Isomer 1
(42.1)
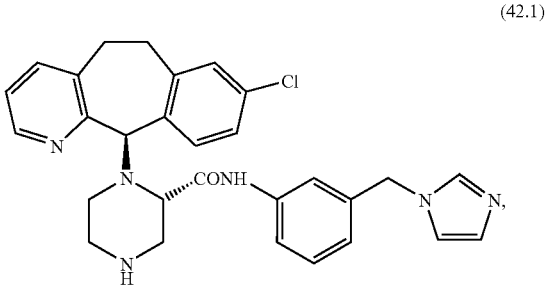
Isomer 2

-continued
(43.1)
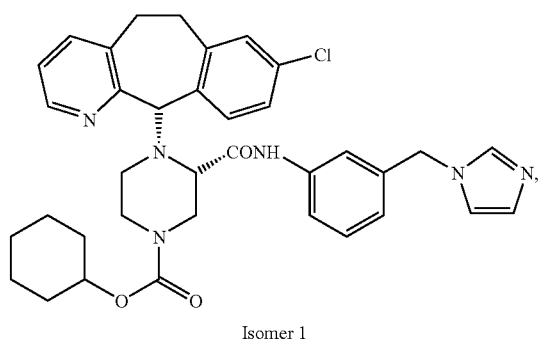
Isomer 1
(44.1)
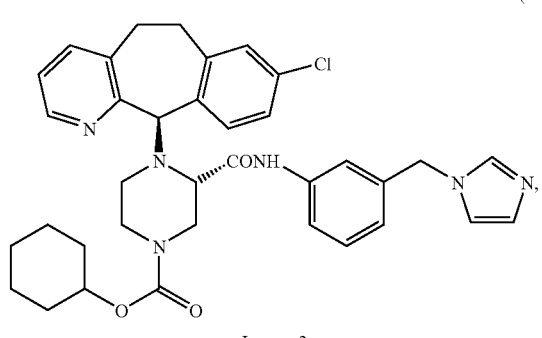
Isomer 2
(45.1)
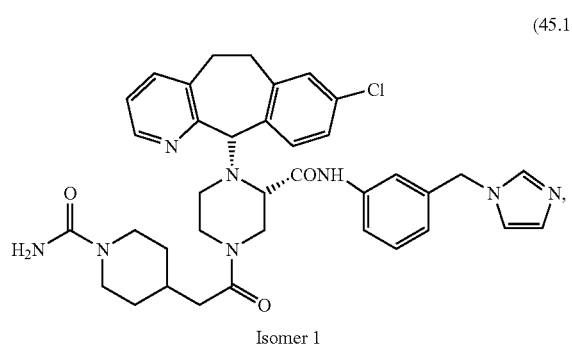
Isomer 1
(46.1)
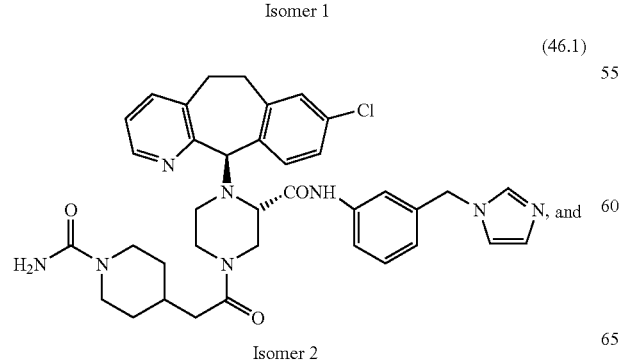
Isomer 2
-continued
(47.1)
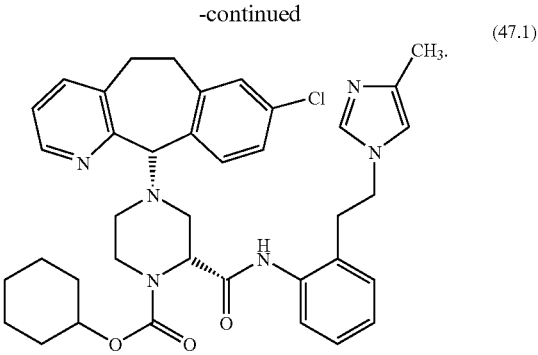
62. The compound of claim 1 selected from the group consisting of compounds:
(1.3)
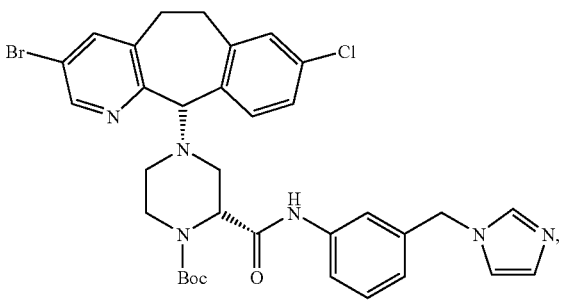
Isomer 1
(1.4)
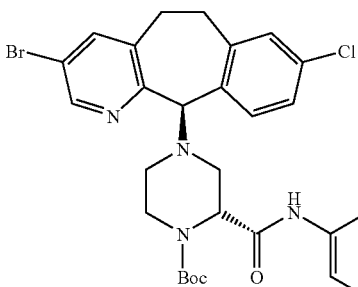
Isomer 2
(15.1)
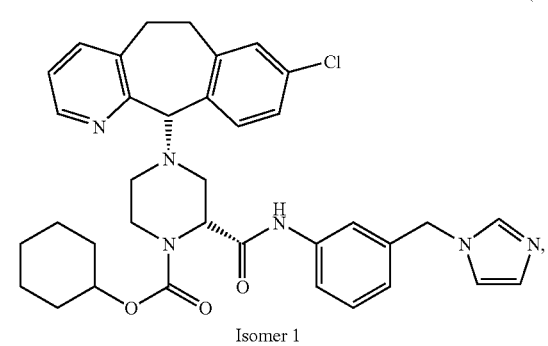
Isomer 1

-continued
(15.2)
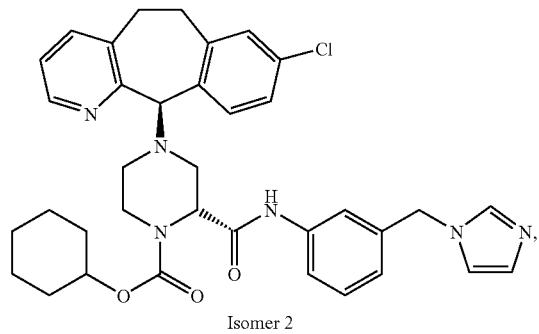
Isomer 2
(21.1)
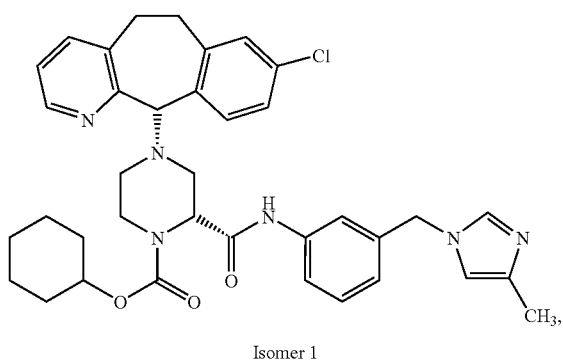
Isomer 1
(22.1)
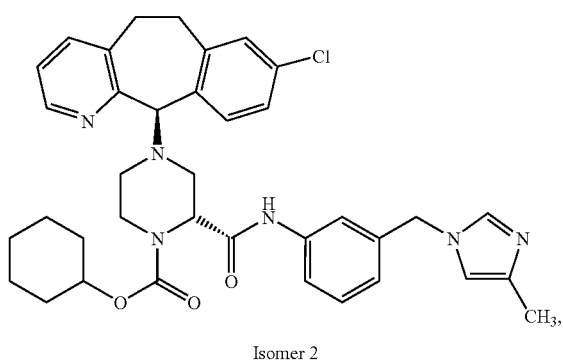
Isomer 2
(26.1)
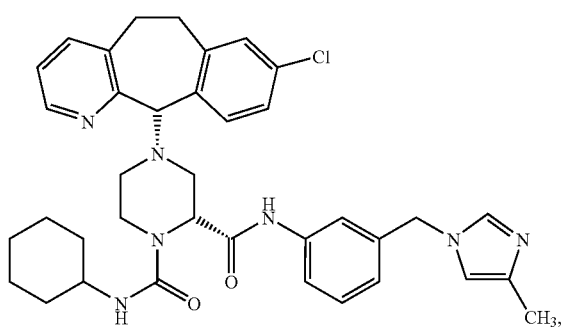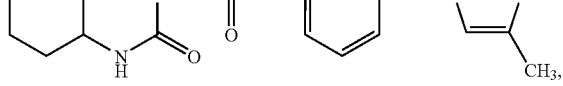
-continued
(28.1)
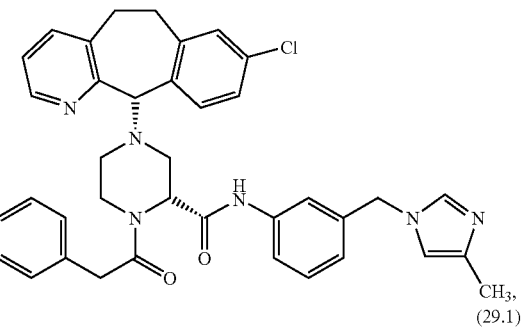
(29.1)
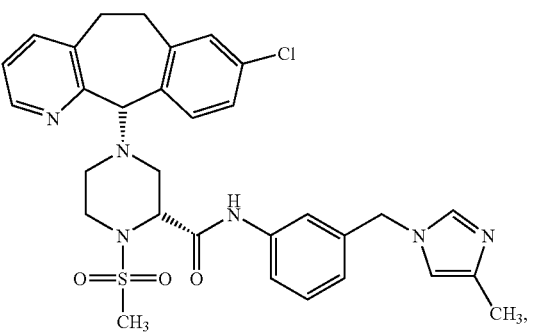
(30.1)
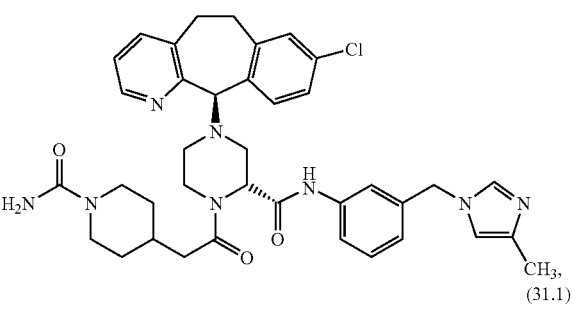
(31.1)
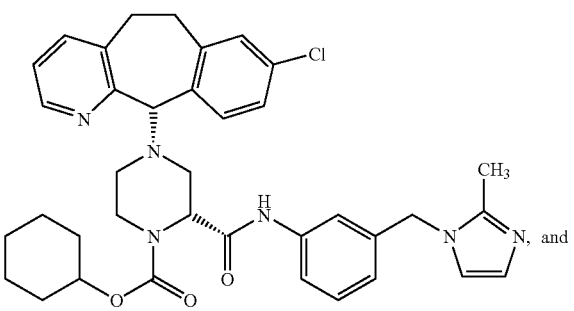
Isomer 1
(31.2)
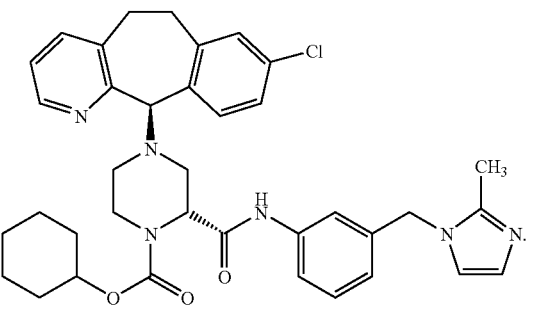
Isomer 2

63. A pharmaceutical composition comprising an effective amount of at least one compound of claim 1 and a pharmaceutically acceptable carrier.

* * * * *